US008198415B2

(12) United States Patent
Rasmussen et al.

(10) Patent No.: US 8,198,415 B2
(45) Date of Patent: Jun. 12, 2012

(54) ANTI-RHESUS D RECOMBINANT POLYCLONAL ANTIBODY

(75) Inventors: Søren Kofoed Rasmussen, Roskilde (DK); Anne Bondgaard Tolstrup, Hillerød (DK); Søren Bregenholt Frederiksen, Søborg (DK); John Haurum, Charlottenlund (DK)

(73) Assignee: Symphogen A/S, Lyngby (DK)

( * ) Notice: Subject to any disclaimer, the term of this patent is extended or adjusted under 35 U.S.C. 154(b) by 709 days.

(21) Appl. No.: 11/632,937

(22) PCT Filed: Jul. 18, 2005

(86) PCT No.: PCT/DK2005/000501
§ 371 (c)(1),
(2), (4) Date: Aug. 30, 2007

(87) PCT Pub. No.: WO2006/007850
PCT Pub. Date: Jan. 26, 2006

(65) Prior Publication Data
US 2009/0017017 A1    Jan. 15, 2009

(30) Foreign Application Priority Data

Jul. 20, 2004  (DK) .................................. 2004 01133
Dec. 22, 2004  (DK) .................................. 2004 01922

(51) Int. Cl.
*C07K 16/00* (2006.01)
(52) U.S. Cl. ................ 530/389.6; 530/387.5; 530/387.1
(58) Field of Classification Search ........................ None
See application file for complete search history.

(56) References Cited

U.S. PATENT DOCUMENTS

| | | | |
|---|---|---|---|
| 5,126,130 A | 6/1992 | Lussenhop et al. | |
| 5,538,848 A | 7/1996 | Livak et al. | |
| 5,789,208 A | 8/1998 | Sharon | |
| 5,876,925 A | 3/1999 | Siegel | |
| 6,255,455 B1 | 7/2001 | Siegel | |
| 6,312,690 B1 | 11/2001 | Edelman et al. | |
| 6,335,163 B1 | 1/2002 | Sharon | |
| 6,610,472 B1 | 8/2003 | Zhu et al. | |
| 2002/0155114 A1 | 10/2002 | Marks et al. | |
| 2006/0275766 A1 | 12/2006 | Haurum et al. | |
| 2007/0141048 A1 | 6/2007 | Oleksiewicz et al. | |

FOREIGN PATENT DOCUMENTS

| | | |
|---|---|---|
| EP | 0 368 684 B1 | 5/1990 |
| EP | 0 383 777 B1 | 8/1990 |
| EP | 0 393 051 B1 | 10/1990 |
| EP | 0 489 771 B1 | 6/1992 |
| EP | 0 576 093 B1 | 12/1993 |
| EP | 1 106 625 A1 | 6/2001 |
| JP | 2001-502887 A | 3/2001 |
| WO | WO 85/02413 A1 | 6/1985 |
| WO | WO 89/02443 A1 | 3/1989 |
| WO | WO 89/02600 A1 | 3/1989 |
| WO | WO 90/11090 A1 | 10/1990 |
| WO | WO 91/03492 A1 | 3/1991 |
| WO | WO 95/20401 A1 | 8/1995 |
| WO | WO 97/49809 A1 | 12/1997 |
| WO | WO 98/06848 A1 | 2/1998 |
| WO | WO 01/58925 A2 | 8/2001 |
| WO | WO 01/58926 A2 | 8/2001 |
| WO | WO 01/59460 A2 | 8/2001 |
| WO | WO 01/89563 A1 | 11/2001 |
| WO | WO 02/44361 A2 | 6/2002 |
| WO | WO 02/052259 A1 | 7/2002 |
| WO | WO 02/055718 A2 | 7/2002 |
| WO | WO 03/102539 A2 | 12/2003 |
| WO | WO 2004/009618 A2 | 1/2004 |
| WO | WO 2004/035169 A2 | 4/2004 |
| WO | WO 2004/061104 A2 | 7/2004 |
| WO | WO 2005/042774 A2 | 5/2005 |
| WO | WO 2006/007853 A2 | 1/2006 |

OTHER PUBLICATIONS

Rudikoff et al. (PNAS 1982, 79:1979-1983).*
Rader et al. (PNAS 1998, 95:8910-8915).*
Office Action mailed Mar. 17, 2010, in U.S. Appl. No. 11/658,021, Rasmussen et al., filed Apr. 18, 2007.
Newkirk, M.M., et al., "Complete Amino Acid Sequences of Variable Regions of Two Human IgM Rheumatoid Factors, BOR and KAS of the Wa idiotypic Family, Reveal Restricted Use of Heavy and Light Chain Variable and Joining Region Gene Segments," *J. Exp. Med.* 166:550-564, The Rockefeller University Press (Aug. 1987).
Ostryanina, N.D., et al., "Multifunctional fractionation of polyclonal antibodies by immunoaffinity high-performance monolithic disk chromatography," *J. Chrom. A* 949:163-171, Elsevier Science B.V. (Mar. 2002).
Williams, B.R. and Sharon, J. "Polyclonal anti-colorectal cancer Fab phase display library selected in one round using density gradient centrifugation to separate antigen-bound and free phage," *Immunol. Lett.* 81:141-148, Elsevier Science B.V. (Apr. 2002).
Bregenholt, S., et al., "Recombinant Human Polyclonal Antibodies: A New Class of Therapeutic Antibodies Against Viral Infections," *Current Pharmaceutical Design* 12:2007-2015, Bentham Science Publishers Ltd. (Jun. 2006).

(Continued)

*Primary Examiner* — Sharon Wen
(74) *Attorney, Agent, or Firm* — Sterne, Kessler, Goldstein & Fox P.L.L.C.

(57) ABSTRACT

The invention relates to a method for manufacturing an anti-RhD recombinant polyclonal antibody composition (anti-RhD rpAb). The method comprises obtaining a collection of cells transfected with a library of anti-RhD antibody expression vectors, wherein each cell in the collection is capable of expressing from a VH and VL comprising nucleic acid segment, one member of the library, which encodes a distinct member of anti-RhD recombinant polyclonal antibody composition and which is located at the same site in the genome of individual cells in said collection. The cells are cultured under suitable conditions for expression of the recombinant polyclonal antibody, which is obtained from the cells or culture supernatant. The nucleic acid segments encoding the anti-RhD rpAb is introduced into the cells by transfection with a library of vectors for site-specific integration. The present method is suitable for manufacturing anti-RhD rpAb, thereby making available a superior replacement of plasma-derived prophylactic and therapeutic immunoglobulin products.

37 Claims, 22 Drawing Sheets

OTHER PUBLICATIONS

Haurum, J. and Bregenholt, S., "Recombinant polyclonal antibodies: Therapeutic antibody technologies come full circle," *IDrugs* 8:404-409, The Thomson Corporation (May 2005).

Logtenberg, T., "Antibody cocktails: next-generation biopharmaceuticals with improved potency," *TRENDS in Biotechnology* 25:390-394, Elsevier Ltd. (Sep. 2007).

Meijer, P.-J., et al., "Isolation of Human Antibody Repertoires with Preservation of the Natural Heavy and Light Chain Pairing," *J. Mol. Biol.* 358:764-772, Elsevier Ltd. (May 2006).

Poulsen, T.R., et al., "Kinetic, Affinity, and Diversity Limits of Human Polyclonal Antibody Responses against Tetanus Toxoid," *J. Immunol.* 179:3841-3850, The American Association of Immunologists, Inc. (Sep. 2007).

Sharon, J., et al., "Recombinant Polyclonal Antibodies for Cancer Therapy," *J. Cell. Biochem.* 96:305-313, Wiley-Liss, Inc. (Oct. 2005).

Tolstrup, A.B., et al., "Development of recombinant human polyclonal antibodies for the treatment of complex human diseases," *Expert. Opin. Biol. Ther.* 6:905-912, Informa UK Ltd. (Sep. 2006).

Wiberg, F.C., et al., "Production of Target-Specific Recombinant Human Polyclonal Antibodies in Mammalian Cells," *Biotechnology and Bioengineering* 94:396-405, Wiley Periodicals, Inc. (Apr. 2006).

Grüntzig, V., et al., "Improved Protocol for T-RFLP by Capillary Electrophoresis," available online at http://rdp8.cme.msu.edu/html/t-rflp_jul02.html (2002).

Judah, J.D., and Nicholls, M.R., "The Separation of Intracellular Serum Albumin from Rat Liver," *Biochem. J.* 123:643-648, Portland Press (1971).

Kenny, J., and Nika, H., "N-terminal Sequence Analysis of Proteins Electroblotted to PVDF Membrane Using Routine 3.1 PVDF Method on the HP G1005A N-terminal Protein Sequencing System," available online at http://www.chem.agilent.com/Library/applications/59653463.pdf (1996).

Mhatre, R., et al., "Purification of antibody Fab fragments by cation-exchange chromatography and pH gradient elution," *J. Chromatogr. A* 707:225-231, Elsevier (1995).

Peixuan, Z., et al., "Typing *Neisseria meningitidis* by Analysis of Restriction Fragment Length Polymorphisms in the Gene Encoding the Class 1 Outer Membrane Protein: Application to Assessment of Epidemics throughout the Last 4 Decades in China," *J. Clin. Microbiol.* 33:458-462, American Society for Microbiology (1995).

Sanger, F., et al., "DNA sequencing with chain-terminating inhibitors," *Proc. Natl. Acad. Sci. U.S.A.* 74:5463-5467, National Academy of Sciences (1977).

Sharon, J., et al., "Recombinant Polyclonal Antibody Libraries," *Comb. Chem. High Throughput Screen.* 3:185-196, Bentham Science Publishers (2000).

Partial European Search Report for European Patent Application No. EP 09 15 1073, completed on Mar. 24, 2009, European Patent Office, The Hague, Netherlands.

Haurum, J.S., "Recombinant polyclonal antibodies: the next generation of antibody therapeutics?" *Drug Discovery Today* 11:655-660, Elsevier Ltd. (Jul. 2006).

Bhat, S., "Galactose to ceramide linkage is essential for the binding of a polyclonal antibody to galactosyl ceramide," *J. Neuroimmunol.* 41:105-110, Elsevier Science Publishers B.V. (1992).

Chen, L., et al., "Expression of a prototypic anti-colorectal cancer polyclonal antibody library in mammalian cells," *Immunol. Lett.* 88:135-140, Elsevier Science B.V. (Aug. 2003).

Tölö, H., et al., "Development of a Highly Purified Multicomponent Leukocyte IFN-α Product," *J. Interferon Cytokine Res.* 21:913-920, Mary Ann Liebert, Inc. (2001).

Office Action mailed Jun. 24, 2009, in U.S. Appl. No. 11/658,021, Rasmussen et al., filed Apr. 18, 2007.

Akatsuka, Y., et al., "Rapid screening of T-cell receptor (TCR) variable gene usage by multiplex PCR: Application for assessment of clonal composition," *Tissue Antigens* 53:122-134, Munksgaard (1999).

Hombach, A., et al., "Isolation of single chain antibody fragments with specificity for cell surface antigens by phage display utilizing internal image anti-idiotypic antibodies," *J. Immunol. Methods,* 218:53-61, Elsevier Science B.V. (1998).

Lee, H.G., "Rapid high-performance isoelectric focusing of monoclonal antibodies in uncoated fused-silica capillaries," *J. Chromatogr. A,* 790:215-223, Elsevier Science B.V. (1997).

Adamczyk, M., et al., "Profiling of polyclonal antibody light chains by liquid chromatography/electrospray ionization mass spectrometry," *Rapid Commun. Mass Spectrom.,* 14:49-51, John Wiley and Sons Ltd. (2000).

Cheng, W.C., et al., "Fractionation of antibodies to the pneumococcal polysaccharides by affinity chromatography," *J Immunol.,* 111:1677-1689, The Williams and Wilkins Co. (1973).

Shirwan, H., et al., "Rejection of cardiac allografts by T cells expressing a restricted repertoire of T-cell receptor Vβ genes," *Immunology,* 90:572-578, Blackwell Scientific Ltd. (1997).

Klitgaard, J.L., et al., "Reduced Susceptibility of Recombinant Polyclonal Antibodies to Inhibitory Anti-Variable Domain Antibody Responses," *J. Immunol.* 177:3782-3790, The American Association of Immunologists, Inc. (Sep. 2006).

Marri, R., "БИОХИМИЯ ЧЕЛОВЕКА [Biochemistry of a human]," vol. 1, pp. 29-31 and 36, Mockba [Moscow], MIR (1993).

Aswad, D.W., et al., "Isoaspartate in peptides and proteins: formation, significance, and analysis," *J. Pharma. Biomed. Anal.* 21:1129-1136, Elsevier Science B.V. (2000).

Barbas III, C.F., et al., "Assembly of combinatorial antibody libraries on phage surfaces: The gene III site," *Proc. Natl. Acad. Sci. USA* 88:7978-7982, National Academy of Sciences (1991).

Bernhard, O.K., et al., "Mass spectrometry analysis of CD4-associating proteins using affinity chromatography and affinity tag-mediated purification of tryptic peptides," *Proteomics* 3:139-146, Wiley-VCH Verlag GmbH & Co. KGaA (2003).

Borth, N., et al., "Efficient Selection of High-Producing Subclones During Gene Amplification of Recombinant Chinese Hamster Ovary Cells by Flow Cytometry and Cell Sorting," *Biotechnol. Bioeng.* 71:266-273, John Wiley & Sons, Inc. (2001).

Bregenholt, S., and Haurum, J., "Pathogen-specific recombinant human polyclonal antibodies: biodefence applications," *Expert Opin. Biol. Ther.* 4:387-396, Ashley Publications Ltd. (Mar. 2004).

Brezinsky, S.C.G., et al., "A simple method for enriching populations of transfected CHO cells for cells of higher specific productivity," *J. Immunol. Methods* 277:141-155, Elsevier Science B.V. (2003).

Bye, J.M., et al., "Germline Variable Region Gene Segment Derivation of Human Monoclonal Anti-Rh(D) Antibodies," *J. Clin. Invest.* 90:2481-2490, The American Society for Clinical Investigation, Inc. (1992).

Chang, T.Y., and Siegel, D.L., "Genetic and Immunological Properties of Phage-Displayed Human Anti-Rh(D) Antibodies: Implications for Rh(D) Epitope Topology," *Blood* 91:3066-3078, The American Society of Hematology (1998).

Chelius, D., and Shaler, T.A., "Capture of Peptides with N-Terminal Serine and Threonine: A Sequence-Specific Chemical Method for Peptide Mixture Simplification," *Bioconjug. Chem.* 14:205-211, American Chemical Society (2003).

Chong, B.E., et al., "Chromatofocusing nonporous reversed-phase high-performance liquid chromatography/electrospray ionization time-of-flight mass spectrometry of proteins from human breast cancer whole cell lysates: a novel two-dimensional liquid chromatography/mass spectrometry method," *Rapid Commun. Mass Spectrom.* 15:291-296, John Wiley & Sons, Ltd. (2001).

Crawford, D.H., et al., "Production of Human Monoclonal Antibody to Rhesus D Antigen," *Lancet* 1:386-388, Lancet Publishing Group (1983).

Cronkhite, R., et al., "Regulation of Idiotope Expression. IV. Genetic Linkage of Two D Region-Dependent T15 Idiotopes to the Igh Allotype," *J. Immunol.* 142:568-574, The American Association of Immunologists (1989).

Endo, Y., et al., "Fractionation of Polyclonal Antibody by Isoelectric Focusing and Chromatofocusing: Separation of High-Affinity Rabbit Clonotype Anti-Thyroxine Antibody," *Anal. Biochem.* 144:41-46, Academic Press (1985).

Gallo, P., "Anion-Exchange Chromatography of Normal and Monoclonal Serum Immunoglobulins," *J. Chromatogr.* 416:53-62, Elsevier Science Publishers B.V. (1987).

George, J.N., "Initial management of adults with idiopathic (immune) thrombocytopenic purpura," *Blood Rev. 16*:37-38, Elsevier Science Ltd. (2002).

Gevaert, K., et al., "Chromatographic Isolation of Methionine-containing Peptides for Gel-free Proteome Analysis," *Mol. Cell. Proteomics 1*:896-903, The American Society for Biochemistry and Molecular Biology, Inc. (2002).

Gevaert, K., et al., "Exploring proteomes and analyzing protein processing by mass spectrometric identification of sorted N-terminal peptides," *Nature Biotechnol. 21*:566-569, Nature America Publishing (2003).

Guo, Z., et al., "Direct fluorescence analysis of genetic polymorphisms by hybridization with oligonucleotide arrays on glass supports," *Nucleic Acids Res. 22*:5456-5465, Oxford University Press (1994).

Gygi, S.P., et al., "Quantitative analysis of complex protein mixtures using isotopecoded affinity tags," *Nature Biotechnol. 17*:994-999, Nature America Publishing (1999).

Harris, R.J., et al., "Assessing Genetic Heterogeneity in Production Cell Lines: Detection by Peptide Mapping of a Low Level Tyr to Gln Sequence Variant in a Recombinant Antibody," *Bio/Technology 11*:1293-1297, Butterworth-Heinemann (1993).

Haurum, J., and Bregenholt, S., "Recombinant polyclonal antibodies: Therapeutic antibody technologies come full circle," *IDrugs 8*:404-409, The Thomson Corporation (May 2005).

Higuchi, R., et al., "Kinetic PCR Analysis: Real-time Monitoring of DNA Amplification Reactions," *Bio/Technology 11*:1026-1030, Butterworth-Heinemann (1993).

Højrup, P., "Proteolytic Peptide Mapping," *Methods Mol. Biol. 251*:227-244, Humana Press Inc. (2004).

Holland, P.M., et al., "Detection of specific polymerase chain reaction product by utilizing the 5'→3' exonuclease activity of *Thermus aquaticus* DNA polymerase," *Proc. Natl. Acad. Sci. USA 88*:7276-7280, National Academy of Sciences (1991).

Huse, K., et al., "Purification of antibodies by affinity chromatography," *J. Biochem. Biophys. Methods 51*:217-231, Elsevier Science B.V. (2002).

Issitt, P.D., and Anstee, D.J., "The Rh Blood Group System," in *Appl. Blood Group Serol.*, Montgomery Scientific Publications, Durham, NC, pp. 315-423 (1998).

Jefferis, R., "Glycosylation of Human IgG Antibodies—Relevance to Therapeutic Applications," *Biopharm.: The Technology & Business of Biopharmaceuticals 14*:19-27, Advanstar Communications Inc. (2001).

Kachman, M.T., et al., "A 2-D Liquid Separations/Mass Mapping Method for Interlysate Comparison of Ovarian Cancers," *Anal. Chem. 74*:1779-1791, American Chemical Society (2002).

Kang, X., and Frey, D.D., "High-performance cation-exchange chromatofocusing of proteins," *J. Chromatogr. A 991*:117-128, Elsevier Science B.V. (2003).

Kozbor, D., and Roder, J.C., "The production of monoclonal antibodies from human lymphocytes," *Immunol. Today 4*:72-79, Elsevier Biomedical Press (1983).

Kumpel, B.M., et al., "Clearance of red cells by monoclonal IgG3 anti-D in vivo is affected by the VF polymorphism of FcγRIIIa (CD16)," *Clin. Exp. Immunol. 132*:81-86, Blackwell Publishing Ltd. (2003).

Liu, W.-T., et al., "Characterization of Microbial Diversity by Determining Terminal Restriction Fragment Length Polymorphisms of Genes Encoding 16S rRNA," *Appl. Environ. Microbiol. 63*:4516-4522, American Society for Microbiology (1997).

Livak, K.J., et al., "Oligonucleotides with Fluorescent Dyes at Opposite Ends Provide a Quenched Probe System Useful for Detecting PCR Product and Nucleic Acid Hybridization," *PCR Methods Appl. 4*:357-362, Cold Spring Harbor Laboratory Press (1995).

Lu, D., et al., "Tailoring in Vitro Selection for a Picomolar Affinity Human Antibody Directed against Vascular Endothelial Growth Factor Receptor 2 for Enhanced Neutralizing Activity," *J. Biol. Chem. 278*:43496-43507, The American Society for Biochemistry and Molecular Biology, Inc. (2003).

Lubman, D.M., et al., "Two-dimensional liquid separations—mass mapping of proteins from human cancer cell lysates," *J. Chromatogr. B 782*:183-196, Elsevier Science B.V. (2002).

Miescher, S., et al., "Sequence and Specificity Analysis of Recombinant Human Fab Anti-Rh D Isolated by Phage Display," *Vox Sang. 75*:278-287, S. Karger AG (1998).

Miescher, S., et al., "CHO expression of a novel human recombinant IgG1 anti-RhD antibody isolated by phage display," *Br. J. Haematol. 111*:157-166, Blackwell Science Ltd. (2000).

Miescher, S., et al., "A single recombinant anti-RhD IgG prevents RhD immunization: association of RhD-positive red blood cell clearance rate with polymorphisms in the FcγRIIA and FcγIIIA genes," *Blood 103*:4028-4035, American Society of Hematology (Jun. 2004).

Mozdzanowski, J., et al., "High-Yield Deblocking of Amino Termini of Recombinant Immunoglobulins with Pyroglutamate Aminopeptidase," *Anal. Biochem. 260*:183-187, Academic Press (1998).

Nowakowski, A., et al., "Potent neutralization of botulinum neurotoxin by recombinant oligoclonal antibody," *Proc. Natl. Acad. Sci. USA 99*:11346-11350, National Academy of Sciences (2002).

Pease, A.C., et al., "Light-generated oligonucleotide arrays for rapid DNA sequence analysis," *Proc. Natl. Acad. Sci. USA 91*:5022-5026, National Academy of Sciences (1994).

Perkins, M., et al., "Determination of the Origin of Charge Heterogeneity in a Murine Monoclonal Antibody," *Pharma. Res. 17*:1110-1117, Plenum Publishing Corporation (2000).

Rasmussen, T., et al., "Quantitation of minimal residual disease in multiple myeloma using an allele-specific real-time PCR assay," *Exper. Hematol. 28*:1039-1045, Elsevier Science Inc. (2000).

Scharf, O., et al., "Immunoglobulin G3 from Polyclonal Human Immunodeficiency Virus (HIV) Immune Globulin Is More Potent than Other Subclasses in Neutralizing HIV Type 1," *J. Virol. 75*:6558-6565, American Society for Microbiology (2001).

Schenerman, M.A., et al., "CMC Strategy Forum Report—Analysis and Structure Characterization of Monoclonal Antibodies," *BioProcess Int. 2*:42-52, PJB Publications (Feb. 2004).

Scott, J.K., and Smith, G.P., "Searching for Peptide Ligands with an Epitope Library," *Science 249*:386-390, American Association for the Advancement of Science (1990).

Selinger, M., "Immunoprophylaxis for rhesus disease—expensive but worth it?," *Br. J. Obstet. Gynaecol. 98*:509-512, Blackwell Scientific Publications (1991).

Sharon, J., et al., "Construction of Polyclonal Antibody Libraries Using Phage Display," *Methods Mol. Biol. 178*:101-112, Humana Press Inc. (2002).

Siegel, D.L., et al., "Section 5: Structural/genetic analysis of mAbs to blood group antigens. Coordinator's report," *Transfus. Clin. Biol. 9*:83-97, Elsevier SAS (2002).

Singh-Gasson, S., et al., "Maskless fabrication of light-directed oligonucleotide microarrays using a digital micromirror array," *Nature Biotechnol. 17*:974-978, Nature American Publishing (1999).

Sittisombut, N., "Human Immunoglobulin Isotypes and Allotypes," in *Weir's Handbook of Experimental Immunology*, ed. 5., Herzenberg L., et al., eds., Oxford: Blackwell, Stanford, CA, 25.1-25.9. (1996).

Stucki, M., et al., "Characterisation of a chromatographically produced anti-D immunoglobulin product," *J. Chromatogr. B 700*:241-248, Elsevier Science B.V. (1997).

Suárez-Álvarez, B., et al., "Characterisation of mouse monoclonal antibodies for pneumolysin: fine epitope mapping and V gene usage," *Immunol. Lett. 88*:227-239, Elsevier Science B.V. (2003).

Wan, M., et al., "Variant Antibody Identification by Peptide Mapping," *Biotechnol. Bioeng. 62*:485-488, John Wiley & Sons, Inc. (1999).

Wang, H., et al., "A protein molecular weight map of ES2 clear cell ovarian carcinoma cells using a two-dimensional liquid separations/ mass mapping technique," *Electrophoresis 23*:3168-3181, Wiley-VCH Verlag GmbH & Co. KGaA (2002).

Wilhelm, J., and Pingoud, A., "Real-Time Polymerase Chain Reaction," *ChemBioChem 4*:1120-1128, Wiley VCH Verlag GmbH & Co. KGaA (2003).

Willcox, B.E., et al., "Production of soluble αβ T-cell receptor heterodimers suitable for biophysical analysis of ligand binding," *Prot. Sci. 8*:2418-2423, Cambridge University Press (1999).

Wu, H., et al., "Cloning, isolation and characterization of human tumor in situ monoclonal antibodies," *Cancer Immunol. Immunother.* *51*:79-90, Springer-Verlag (2002).

Co-pending U.S. Appl. No. 11/633,070, inventors Jensen, A., et al., filed Dec. 4, 2006 (Not Published).

Co-pending U.S. Appl. No. 11/658,021, inventors Rasmussen, L.K., et al., filed Jan. 22, 2007 (Not Published).

Co-pending U.S. Appl. No. 11/792,927, inventors Lantto, J., et al., filed Jun. 13, 2007 (Not Published).

Rasmussen, S.K., et al., "Manufacture of recombinant polyclonal antibodies," *Biotechnol. Lett. 29*:845-854, Springer, New York, NY (Feb. 2007).

Sarantopoulos, S., et al., "A Method for Linking $V_L$ and $V_H$ Region Genes That Allows Bulk Transfer Between Vectors for Use in Generating Polyclonal IgG Libraries," *J. Immunol. 152*:5344-5351 (1994).

Scaradavou, A., et al., "Intravenous Anti-D Treatment of Immune Thrombocytopenic Purpura: Experience in 272 Patients," *Blood 89*:2689-2700 (1997).

Edelman, L., et al., "Obtaining a functional recombinant anti-rhesus (D) antibody using the baculovirus-insect cell expression system," Immunology 91:13-19, Blackwell Science Ltd., London, England, 1997.

\* cited by examiner

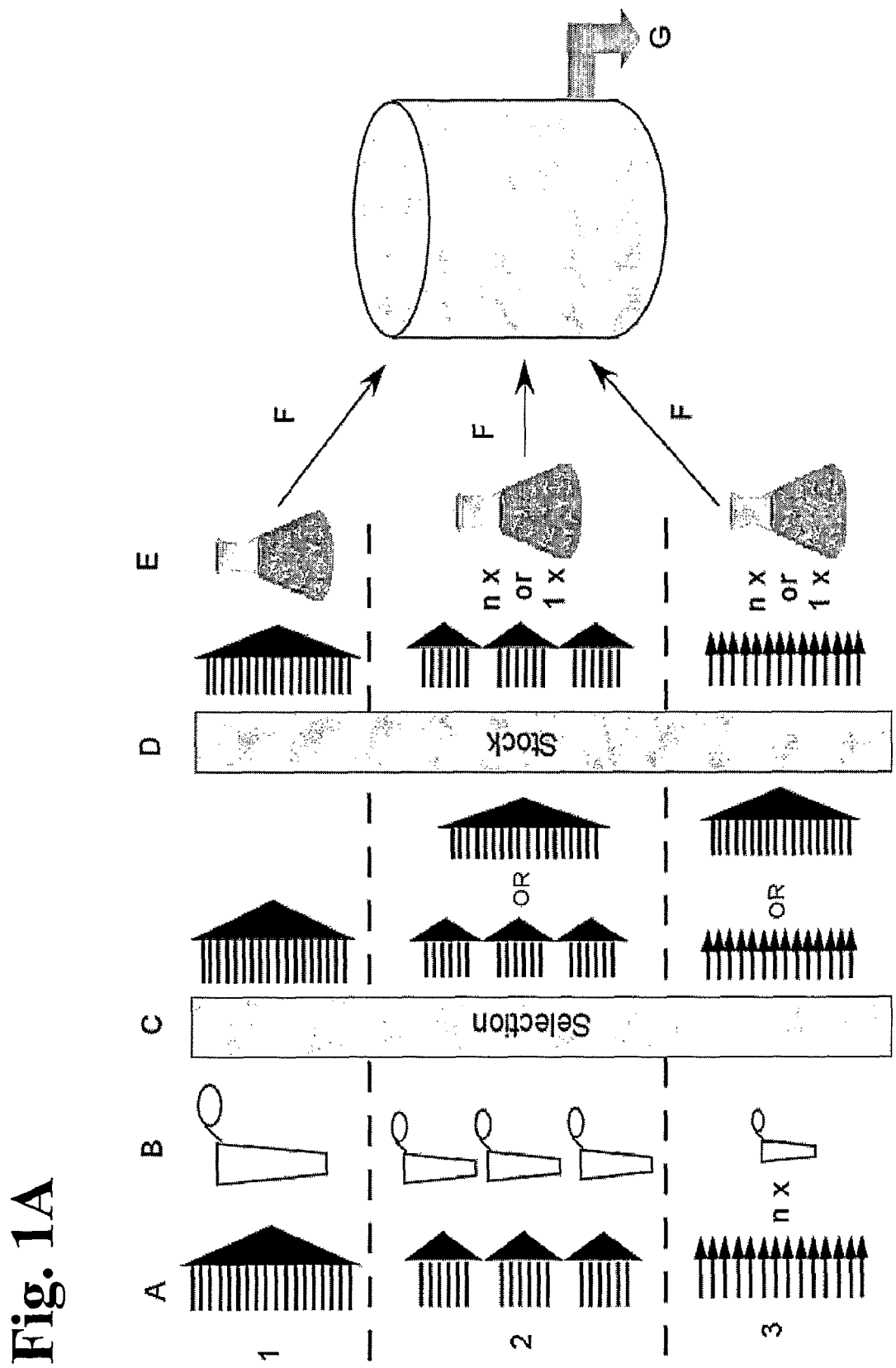

| | | FR1 | CDR1 | FR2 | CDR2 | FR3 | CDR3 | SEQ ID NO: |
|---|---|---|---|---|---|---|---|---|
| | | 1 2 | 3 | 4 | 5 | 6 7 8 | 9 * 10 | |
| | | 12345678901234567890123 | 45678901acdef234 | 567890123456789 | 0123456 | 78901234567890123456789012345678 | 9012345678901234567890 | |
| RhD157.119D11 kappa | (1) | EIVLTQSPATLSLSPGERATLSC | RASQSVSS-----YLA | WYQQKRGQAPRLLIF | NASNRAT | GIPARFSGSGSGTDFTLTISSLEPEDFAVYYC | QQRSSWPPYTFGQGTKLEIKR | 203 |
| RhD189.181E07 Kappa | (1) | EIVMTQSPATLSVSPGERATLSC | RASQSVSS-----NLA | WYQQKPGQAPRLLIY | GASTRAT | GIPARFSGSGSGTEFTLTISSLQSEDFAVYYC | QQYNNWPTLYTFGQGTKLEIKR | 210 |
| RhD324.231F07 Kappa | (1) | EIVLTQSPATLSVSPGERATLSC | RASQSVSS-----NLA | WYQQKPGQAPRLLIY | GASTRAT | GIPARFSGSGSGTEFTLTISSLQSEDFAVYYC | QQYNNWP--RYTFGQGTKLEIKR | 258 |
| RhD201.164H12 Kappa | (1) | EIVLTQSPATLSVSPGERATLSC | RASQSVTS-----NLA | WYQQKPGQAPRLLIY | GASTRAT | GVPARFSGSGSGTEFSLTISSLQSEDFAVYYC | QQYNNWPPIFTFGPGTKLDIKR | 222 |
| RhD303.160B11 Kappa | (1) | EIVLTQSPGTLSLSPGETATLSC | RASQSVSDR----DLA | WYQQKSGQSPRLLMY | GGSTRAP | GIPVRFSGSGSGTEFTLTISSLQSEDFAIYYC | QHYHDWP--PTFGQGTRLEIKR | 249 |
| RhD159.119B09 Kappa | (1) | EIVMTQSPGTLSLSPGERATLSC | RASHTVSSG----YLA | WYQQKPGQAPRLLIY | GASNRAT | GVPDRFGGSGSGTDFTLTISRLEPEDSAVYFC | QQYGTSP-GVTFGQGTRLEIER | 205 |
| RhD191.119E08 Kappa | (1) | EIVLTQSPGTLSSSPGERATLSC | RASQSVTSR----YLA | WYQQKHGQAPRLLIY | GTSTRAT | GIPDRFSGGGSQTDFTLTISRLEPEDFAVYYC | QHYDDSISTYIFGPGTELEIKR | 212 |
| RhD294.119E10 Kappa | (1) | EIVLTQSPGTLSLSPRERATLSC | RANQYVNSN----HLA | WYQQKPGQAPRLLLY | GASRRAT | GIPDRFSGSGTGTDFTLIISRLEPEDFAVYFC | QLYDHSRPMYTFGQGTKLEIKR | 240 |
| RhD202.158E07 Kappa | (1) | EIVLTQSPGTLSLSPGERATLSC | RASQSVSSS----YLA | WYQHKPGQAPRLLIY | GSSNRAT | GIPDRFSGSGSGTDFTVTISRLEPEDFAVYYC | QQYGTA--PYTFGQGTKLEIKR | 223 |
| RhD242.181A03 Kappa | (1) | EIVLTQSPGTLSLSPGERATLSC | RASQSVSSS----YLA | WYQQKPGQAPRLLIY | GASSRAT | GIPDRFSGSGSGTDFTLTISRLEPEDFAVYYC | QQYGSS--RYTFGQGTKLEIKR | 233 |
| RhD295.119B11 Kappa | (1) | EIVLTQSPGTLSLSPGERATLSC | RASQSFSSG----YLA | WYQQKPGQAPRLLIY | GASNRAT | GIPDRFSGSGSGTDFTLTISRLEPEDFAVYYC | QHYGSSP-PLTFGQGTRLEIKR | 241 |
| RhD317.144A02 Kappa | (1) | EIVLTQSPGTLSLSPGERATLSC | RASQSVSSA----FLA | WYQQKPGQAPRLLIY | GASSRAT | GIPDRFSGSGSGTDFTLTISRLEPEDFAVYYC | QQYGSF--SITFGQGTRLEIKR | 254 |
| RhD241.119B05 Kappa | (1) | EIVLTQSPVTLSLSPGERATLSC | RASQSVSSG----YLA | WYQQKPGQAPRLLIY | GTSIRAT | GIPDRFSGSGSGTDFTLTISRLEPEDFAVYYC | QQYGSSP-LYSFGQGTKVDIKR | 232 |
| RhD305.181E06 Kappa | (1) | EIVLTQSPGSLSLSPGERATLSC | RASQSVSSS----YLA | WYQQKPGQAPRLLIY | GPSSRAT | GIPDRFSGSGSGTDFTLTISRLEPEDFAVYYC | QHFGNS---RGTFGQGTKVEIRR | 251 |
| RhD163.119A02 Kappa | (1) | EIVLTQSPGTLSLSPGERATLSC | RASQNPRRN----FLA | WYQQKPGQAPRLLIY | AASTRAT | GIPDRFSGSGSGTDFTLTIDRLEPEDSAVYYC | QVYGSSP-LYTFGQGTKVEMKR | 209 |
| RhD306.223E11 Kappa | (1) | EIVLTQSPGTLSLSPGERVTLSC | RPSRYIASD----YLA | WYQLRPGQAPKLLIY | GASSRAT | GIPDRFSGVGSPTDFTLTISRLEPEDFAMYYC | HYSGGSP-PYPFGQGTRLDIKR | 252 |
| RhD301.160A04 Kappa | (1) | DVVMTQSPLSLPVTPGEPASISC | RSSQSLLHRNGYNYLN | WYLQKPGQSPQLLIY | LGSNRAS | GVPDRFSGSGSGTDFTLKISGVEAEDVAFYYC | MQGLRTP---YTFGQGTKLEIKR | 247 |
| RhD304.164B06 Kappa | (1) | DIQMTQSPSSLSASLGGTVTLTC | RSSQFISR-----YLN | WYQQHPGKVPRLLIS | GASRLQR | GVPSRFTGGGSGTDFTLTIKNVQPDDIATYFC | QHSYRSG--RAFGQGTTVEVKR | 250 |
| RhD158.119B06 Kappa | (1) | DIQMTQSPSPLSASVGDRVSITC | RASRGISN-----SLA | WYQQKPGKVPKLLIY | AASTLQS | GVPSRFSGGGSGTDFTLTISSLQPEDVATYYC | HTYNSAP--FAFGPGTKVDIKR | 204 |
| RhD160.119C07 Kappa | (1) | DIQLTQSPSSLSASVGDRVSITC | RASQGISN-----SLA | WYQQKPGKVPKLLIY | AASTIQS | GVPSRFSGGGSGTDFTLTISSLQPEDVATYYC | QKYNSAP--FAFGPGTKVDIKR | 206 |
| RhD162.119G12 Kappa | (1) | DIQLTQSPSSVSASVGDSVTITC | RASQAVSG-----WVA | WYQQKPGKAPKLLIF | GLSNLED | GVPSRFSGSGSATDFTLTITGLQPEDLATYYC | LQANRFP--LSFGGGTRVEIKR | 208 |
| RhD192.119G06 Kappa | (1) | DIQLTQSPSSVSASVGDRVTITC | RASQGINN-----LLA | WYQQKPGKAPKLLIY | AASNLQS | GVPSRFSGSGSGTDFTLTINSLQPEDFATYYC | QQANSFP--LTFGGGTKVEIKR | 213 |
| RhD161.119E09 Kappa | (1) | DIQMTQSPSFLSASVGDRVTITC | RASQGIRR-----YLA | WFQQKPGKAPKLLIF | SASTLQS | GVPSRFSGSGSGTEFTLTISSLQPEDFATYYC | QQLSSYP-PYTFGQGTKLEIKR | 207 |
| RhD205.160B12 Kappa | (1) | DIQLTQSPSFLSASVGDRVTITC | RASHGISS-----YLA | WYQQKPGKAPNLLIF | PASTLQS | GVPSRFSGSGSGTEFTLTISSLRPEDFATYYC | QQLNSYS-RWAFGQGTKVEVKR | 226 |
| RhD240.125A09 Kappa | (1) | DIQMTQSPSTLSASVGDRVTITC | RASQSISS-----WLA | WYQQKPGKAPKLLVY | KTSSLEG | GVPSRFSGSGSGTEFSLTIFRLQSDDFATYYC | QQYNSFP--YTFGQGTKLEFTR | 231 |
| RhD195.127A07 Kappa | (1) | DIQLTQSPSSLSASVGDRVTITC | RASQNINR-----YLN | WYQHKPGRAPELLIY | AASTLRR | GVPSRFSGSGSGTDFTLTISSLQPEDFATYYC | QQSYSRG---TFGQGTKVEIKR | 216 |
| RhD307.230E11 Kappa | (1) | DIQLTQSPSSLSASVGDRVTITC | RASQYINV--- -YLN | WYQHKAGRAPKLLIY | AASNLQS | GVPFRFIGSGSGTDFTLTISSLQSEDFATYYC | LQSFTVP-R-TFGPGTKVDVKR | 253 |
| RhD243.109A05 Kappa | (1) | DIQLTQSPSSLAASVGDRVIITC | RSGQGIRN-----YLN | WYQQKPGKAPKLLIY | AASFLQS | GVPSRFSGSGSGTDFTLTISSLQPEDFATYNC | QQSYSDP-W-TFGQGTKVEIKR | 234 |
| RhD190.119F05 Kappa | (1) | DIQLTQSPSSLSASVGDRVTITC | RASQSISS-----YLN | WYQQKPGEAPKLLIY | VASTLQS | GAPSRFSGSGSGTDYTLTISSLQ EDSATFYC | QQTYS-P--PYTFGQGTKLEIKR | 211 |
| RhD198.127F10 Kappa | (1) | DIQMTQSPSSLSASVGDRVTITC | RASQSIGN-----YLN | WYQQKPGKAPKLLIS | AASSLQS | GVPSRFSGSGSGTDFTLTISSLHREDYATYYC | QQSYSTP--PYTFGQGTKLEIKR | 219 |
| RhD298.126E10 Kappa | (1) | DIQMTQSPSSLSASVGDRVTITC | RASQSIST-----YLN | WYQQKPGKAPKLLIS | AASSLQS | GVPSRFSGSGSGTDFTLTISSLQREDYAAYYC | QQSYSTP-PYTFGQGTKLEIKR | 244 |
| RhD239.126F09 Kappa | (1) | DIQLTQSPSSLSASVGDRVTITC | RASQSISS-----YLN | WYQQKPGKAPKLLIS | AASSLQS | GVPSRFSGSGSGTDFTLTISSLQREDYATYYC | QQSYSTP-PYTFGQGTKLEIKR | 230 |
| RhD292.109A02 Kappa | (1) | DIQMTQSPSSLSASVGDRVTITC | RASQSISS-----WLN | WYQQKPGKAPNLLIF | AASTIQS | GVPSRFSGSGSGTDFTLTISSLQPEDFATYYC | QQSYSSS-VYTFGQGTKLEIKR | 238 |
| RhD193.126G05 Kappa | (1) | DIQMTQSPSSLSASVGDRVTITC | RASQSISS-----YLN | WYQQNPGKAPKLLIY | GASNLQS | GVPSRFSGSGSGTDFTLTISSLQPEDFATYYC | QQSYSTL-ALTFGGGTKVEIKR | 214 |
| RhD297.126E06 Kappa | (1) | DIQLTQSPSSLSASVGDRVTITC | RASQSISS-----YLN | WYQQNPGKAPKLLIY | GASNLQS | GVPSRFSGSGSGTDFTLTISSLQPEDFATYYC | QQSYSTL-ALTFGGGTKVEIKR | 243 |
| RhD296.126A03 Kappa | (1) | DIQMTQSPSSLSASVGDRVTITC | RASQSISS-----YLN | WYQQKPGKAPKLLIF | AASSLQS | GVPSRFSGSGSGTDFSLTISSLQPEDFATYYC | QQSYSSL-ALTFGGGTKVEIKR | 242 |
| RhD206.160C06 Kappa | (1) | DIQMTQSPSSLSASVGDRVTITC | RASQSIRR-----YLN | WYQKKPGKAPKLLIY | AASSLQS | GVPSRFSGSGSGTDFTLTISSLQPEDFATYYC | QQSYRTQ-GLTFGGGTKVEIKR | 227 |
| RhD244.158B10 Kappa | (1) | DIQMTQSPSSLSASVGDRVIITC | RASQSVNR-----YLN | WYQQKPGKAPKLLIY | AASSLQG | GVPSRFSGSGSGTDFTLTISSLQREDFATYYC | QQSYRTR----TFGQGTKVEIKR | 235 |
| RhD194.126G10 Kappa | (1) | DIQMTQSPSSLSASVGDRVTITC | RASQSIST-----YLN | WYQQKPGKAPKLLIY | AASTLQS | GVPSRFSGSGSGTHFTLTISSLQREDFATYYC | QQTYRTP-TWTFGQGTKVEIKR | 215 |
| RhD196.126H11 Kappa | (1) | DIQMTQSPSSLSASVGDRVTITC | RASQSIST-----YLN | WYQQKPGKAPKLLIY | AASTLQS | GVPSRFSGSGSGTHFTLTISSLQREDFATYYC | QQSYGTP-TWTFGQGTKVEIKR | 217 |
| RhD323.229B07 Kappa | (1) | DIQMTQSPSSLSASVGDRVTITC | RASQSISS-----YLN | WYQQKPGKAPKLLIY | AASTLQS | GVPSRFSGSGSGTDFTLTISSLQPEDFATYYC | QQTYRTP-TWTFGQGTKVEIKR | 257 |
| RhD302.160B10 Kappa | (1) | DIQLTQSPSSLSASVGDRVTITC | RASQSISS-----YLN | WYKQRPGKAPKLLIY | AASTLQS | GVPSRFSGSGSGTDFALTISSLQAEDFATYYC | QQTYST---LWTFGQGTKVEITR | 248 |
| RhD199.164E03 Kappa | (1) | DIQMTQSPSSLSASVGDRVTITC | RASQSISS-----YLN | WYQQKPGKAPKLLIY | AASSLQS | GVPSRFSGSGSGTDFTLTISSLQPEDFATYYC | QQSYSTS-TWTFGQGTKVEIKR | 220 |
| RhD200.164G10 Kappa | (1) | DIQLTQSPSSLSASVGDRVTITC | RASQSISS-----YLN | WYQQKPGKAPKLLIY | AASSLQS | GVPSRFSGSGSGTDFTLTISSLQPEDFATYYC | QQSYSTS--WTFGQGTKVEIKR | 221 |
| RhD293.109A09 Kappa | (1) | DIQMTQSPSSLSASVGDRVTITC | RASQSISS-----YLN | WYQQKPGKAPKLLIY | AASSLQS | GVPSRFSGSGSGIDFTLTISSLQPEDFATYYC | QQSYTTL--WTFGQGTKVEIKR | 239 |
| RhD245.164E06 Kappa | (1) | DIQMTQSPSSLSASVGDGITITC | RASQSVRS-----YLN | WYQQKPGKAPELLIY | AASRLQS | GVPSRFSGSGSGTDFTLTISSLQPEDFATYYC | QHSYSTP-V-TFGQGTKVEVKR | 236 |

*Numbering after amino acid 95 does not follow Clothia.

Fig. 6B

|  | FR1 | CDR1 | FR2 | CDR2 | FR3 | CDR3 | SEQ ID NO: |
|---|---|---|---|---|---|---|---|
|  | 1         2<br>1234567890123456789012 3 | 3<br>4567890 1abc234 | 4<br>5678901234567890 | 5<br>0123456 | 6         7         8<br>7890123456 78ab901234567890 12345678 | 9<br>90123456789012345678 9012 3 |  |
| RhD197.127A08 Lambda (1) | -QTVVTQEPSLTVSPGGTVTLTC | ASSTGAVTIGYYPN | WFQQKPGQAPRALIY | STSKKHS | WTPARFSGSLLG--GKAALTLSGVQPEDEAEYYC | LLFYGG----AQLGVFGGGTKLTVLGQ | 218 |
| RhD203.179F07 Lambda (1) | -QSALTQPASVSGSPGQSITISC | TATSSDIGAINYVS | WYQHHPGKAPKVIIT | DVNKRPS | GVPDRFSGSKSG--NTASLTISGLQPEDEAEYSC | CSYAGNY----GKVPGTGTKVTVLGQ | 224 |
| RhD321.187G08 Lambda (1) | LNEMLTQPHSVSESPGKTVTISC | TRSGSSIASN-YMQ | WYQQRPGSSPTTVIT | EDNRRPS | GVPDRFSGSIDSSSNSASLTISGLKTEDEADYYC | QSYDSNN---NWRSSTHLTVFLGQ | 256 |
| RhD204.128A03 Lambda (1) | LSSELTQDPAVSVALGQTVRITC | QG-DS-LRSY-YAN | WYQQKPGQAPLSVIY | GKNRPS | GIPDRFSGSNSG--NTAFLTITGTQAEDEADYYC | MSRDSSGNYR-ELFGGGTKLTVLGQ | 225 |
| RhD246.179B10 Lambda (1) | LSSELTQDPAVSVTLGQTVRITC | QG-DS-LRHS-YAS | WYQQKPGQAPILVIY | GKNIRPS | GIPDRFSGSTSG--NTASLTITGAQAEDGGDYYC | MSRDTS-TDH-YVTGTGTRVTVVGQ | 237 |
| RhD300.134H09 Lambda (1) | -QTVVTQEPSFSVSPGGTVTLTC | GLSGSVSARYYPS | WYQQTPGQPRTLIH | STNTRSS | GVPDRFSGSILG--NKAALTITGAQADDESDYYC | VLMG----SGIWVTGGGTKLTVLGQ | 236 |
| RhD208.179B11 Lambda (1) | -QTVVTQEPSLTVSPGGTVTLTC | ASSTGSVTSGYYPN | WFQQKPGQAPRPLIS | GTSNKLS | WTPARFSGSLLG--GKAALTVSGVQPEDREAVYYC | LLIYGT---FQFVVGGGTKLTVLGQ | 229 |
| RhD319.187A11 Lambda (1) | -QTVVTQEPSLTVSPGGTVTLTC | ASSTGAVTIGYYPN | WFQQKPGQAPRALIY | STSNKHS | WTPARFSGSLLG--GKAALTLSGVQPEDEAEYYC | LLYYGS---AQHYFGGGTILAVVLGQ | 255 |
| RhD207.127A11 Lambda (1) | -QAVTQEPSLTVSPGGTVTLTC | ASSTGAVTIGYYPN | WFQQKPGQAPRALVH | STSKKHS | WTPARFSGSLLG--GKAALTLSGVQPEDEAEYYC | LLFYGG-AQLGVFGSGTKLTVLGQ | 228 |
| RhD299.127A12 Lambda (1) | -QAVTQEPSLTVSPGGTVTLTC | ASSTGAVTIGYYPN | WFQQKPGQAPRALIY | STSKKHS | WTPARFSGSLLG--GKAALTLSGVQPEDEAEYYC | LLFYGG-AQLGVNGSGTKLTVLGQ | 245 |

*Numbering after amino acid 95 no longer follows Clothia.

ANTI-RHESUS D RECOMBINANT POLYCLONAL ANTIBODY

This application is a National Stage of International Application No. PCT/DK2005/000501, filed Jul. 18, 2005, which claims the benefit of Danish Application No. PA 2004 01133, filed Jul. 20, 2004, and Danish Application No. PA 2004 01992, filed Dec. 22, 2004.

FIELD OF THE INVENTION

The present invention describes the production of an anti-Rhesus D recombinant polyclonal antibody (anti-RhD rpAb), as well as the general approach of generating a polyclonal working cell bank for later production of a desired polyclonal antibody. The invention also relates to libraries encoding anti-RhD rpAb and to cell lines producing anti-RhD rpAb. Further, the application describes pharmacological and diagnostic compositions comprising anti-RhD rpAb and their use in prophylaxis of hemolytic disease of the newborn (HDN), treatment of idiopathic thrombocytopenic purpura (ITP) and prevention of sensitization to the Rhesus D antigen after mistransfusions of RhD(+) blood to RhD(−) individuals.

BACKGROUND OF THE INVENTION

The Rhesus blood group antigens are located on transmembrane erythrocyte proteins encompassing the so-called C, c, E, e and D antigens. Approximately 16% of the Caucasian population is Rhesus D negative (RhD(−)) due to an inherited polymorphism. In addition, multiple genetic and serological variants of RhD exist (divided into category II-VII) of which RhD$^{VI}$ is the most clinically relevant. Since category VI positive red blood cells (RBC) carry fewer of the various epitopes of the D protein than RBC of other categories, RhD$^{VI}$(+) individuals may form alloantibodies against RBC from other RhD positive (RhD(+)) individuals (Issitt, P. D. and Anstee, D. J., 1998. The Rh Blood Group System, Montgomery Scientific Publications, Durham, N.C., pp. 315-423). {Issitt & Anstee 1998 11809/id}

RhD negativity in itself is not associated with any medical conditions, but has important medical implications when a RhD(−) female carries a RhD(+) or RhD$^{VI}$(+) fetus or a RhD$^{VI}$(+) female carries a RhD(+) fetus. Fetomaternal RhD alloimmunization may then occur if fetal erythrocytes enter the maternal circulation, usually perinatally (during delivery), and thereby causes the induction of a maternal anti-RhD antibody response. In subsequent pregnancies RhD-specific IgG-molecules from the mother will cross the placenta into the fetal circulation and mediate lysis of fetal erythrocytes, thereby causing Hemolytic Disease of Newborns (HDN). It has been estimated that on average 20% of RhD(−) women delivering a RhD(+) infant for the second time, and who are not protected appropriately with anti-D prophylaxis, will generate an anti-RhD antibody response. When untreated, approximately 30% of the newborn will have moderate anemia, jaundice, and hepatomegaly, and 20% develop severe anemia and hydrops fetalis, and severely affected newborns are at risk of neonatal death or permanent handicaps.

Polyclonal immunoglobulin preparations against RhD are used worldwide to prevent alloimmunization of pregnant RhD(−) and RhD$^{VI}$(+) women, thereby preventing hemolytic disease of the newborn. Polyclonal immunoglobulin preparations against RhD (anti-D) are currently obtained by pooling of blood plasma obtained from donors who have become hyperimmune, either through natural RhD alloimmunization or through vaccination of RhD negative volunteer males with RhD positive erythrocytes. The efficacy of anti-RhD immunoglobulin preparations for prophylaxis of HDN is well established and has been in routine use for many years. As a result this severe disease has become a rarity.

Nevertheless the underlying cause of the disease, i.e. alloimmunization of pregnant RhD(−) and RhD$^{VI}$(+) women, still remains and thus requires a continual supply of anti-D immunoglobulin preparations.

In addition to the prophylaxis of HDN, anti-D immunoglobulin has also proven useful in the treatment of idiopathic thrombocytopenic purpura (ITP) (George, J. N., 2002. Blood Rev. 16, 37-38). ITP is a hematological disorder, where autoantibodies results in an accelerated platelet clearance in the spleen and liver. Symptoms are decreased platelet levels resulting in bruising and bleeding. In severe cases the spleen is removed. This is however, not possible in infants due to severe side effect, thus alternative treatments like anti-D immunoglobulin are needed. Further, anti-D immunoglobulin is used after mistransfusions of RhD(+) blood to RhD(−) recipients in order to prevent sensitization to the Rhesus D antigen.

The current methods for production of anti-D require, as already mentioned, repeated immunization of an increasingly reluctant pool of donors for the production of high titer antiserum. There are also associated risk factors and technical problems, such as the use of Rhesus positive RBC for repeated immunization carrying the risk of transmission of viral diseases like hepatitis B, AIDS and other as yet unknown viruses. Further, there are problems with batch-to-batch variations. Therefore, an alternative method for production of anti-RhD antibodies is required.

Cellular approaches for generating anti-RhD monoclonal antibodies were first developed as an alternative to hyperimmune serum. These techniques encompassed Epstein Barr Virus transformation of lymphocytes creating B lymphoblastoid cell lines (Crawford et al. 1983. Lancet 1, 386-8). However, these cell lines are unstable and require extensive cloning. Production of human antibodies by the hybridoma technique was also restricted by the lack of a suitable human myeloma cell fusion partner (Kozbor, D. and Roder, J. C., 1983. Immunol. Today. 4, 72).

As substitute for these techniques a molecular approach involving repertoire cloning of $V_H$ and $V_L$ and the construction of phage display libraries was developed (Barbas, C. F. et al. 1991. Proc Natl. Acad. Sci. USA 88, 7978-7982). The phage display technique was also applicable for the isolation of Rhesus D antigen binders. A large number of monoclonal antibodies (mAbs) with Rhesus D antigen binding specificity have been isolated with this technique (WO 97/49809 and Siegel, D. L et al. 2002. Transfus. Clin. Biol. 9, 83-97).

Recent clinical trials with a recombinant anti-RhD$^{VI}$ mAb have shown that it is possible to prevent RhD immunization after a large challenge with RhD(+) RBC (Miescher, S., et al. 2004, Blood 103, 4028-4035). However, the trial also showed that the mAb was less efficient with respect to clearance of the RBC than an anti-D immunoglobulin. The cause of this decreased clearance rate is not known. It is possible that a single antibody is not as efficient as the diversity of antibodies present in the anti-D immunoglobulin product, or that the presence of more than one immunoglobulin isotype i.e. IgG1 and IgG3 {Siegel, Czerwinski, et al. 2002 10320/id} increases RBC clearance.

In addition to the efficiency issue, another issue with respect to HDN prophylaxis is the situation where a RhD$^{VI}$(+) female carries a RhD(+) fetus. In this situation an anti-RhD$^{VI}$ mAb will not be able to prevent alloimmunization of the female. Thus, in order to protect both RhD(−) and RhD$^{VI}$(+)

females, a product with antibodies against Rhesus D category VI antigen as well as antibodies that do not bind category VI antigen but other common Rhesus D antigens is needed.

Another possible issue with mAbs is that they might be immunogenic. Although the mAbs are human, a first time treatment might result in an antibody response from the female treated with the mAb. Theoretically this may happen because the CDR regions of the mAb, which have never been seen by the immune system of the treated individual before, may be recognized as foreign if presented in a sufficiently large dose. Such a reaction will render the anti-RhD mAb useless in repeated prophylactic treatment.

It is possible that some of these potential problems with mAbs could be overcome by mixing monoclonal antibodies. However, this would mean separate production and purification of an undefined number of antibodies, which will be quite costly. Further, different batch properties of the individual monoclonal antibodies of such a mixture may affect the final product.

DISCLOSURE OF CONTRIBUTION

The present invention provides a method for generating a manufacturing cell line which can express an anti-RhD recombinant polyclonal antibody (anti-RhD rpAb) as a single batch.

DESCRIPTION OF THE INVENTION

The present invention provides methods for the consistent manufacturing of anti-RhD recombinant polyclonal antibody (anti-RhD rpAb). It is contemplated that the present invention will open up the possibility for large-scale manufacturing and production of a new class of prophylactic and therapeutic anti-RhD antibody products.

An anti-RhD rpAb of the present invention potentially has some advantages over monoclonal anti-Rhesus D antibodies. First of all every potential Rhesus D epitope will be covered by more than one antibody, thus an anti-RhD rpAb composition can be used in the prophylactic treatment of both RhD(−) and RhD$^{VI}$ females bearing a RhD(+) child. Hence, it will not be necessary to mix mAb from different production and purification batches in order to obtain full prophylactic effect.

Further, in the instance where mAbs should prove to be immunogenic due to the high concentration of one single or a few molecules, an anti-RhD rpAb may be a good alternative. Since an anti-RhD rpAb according to the present invention is composed of between 5 and 56 variant antibody molecules, their individual concentration will be lower, and if one of the antibodies should be depleted due to immunogenicity, there will be plenty of others to cover the Rhesus D antigen, thus prophylaxis will still be efficient.

The production of an anti-RhD rpAb antibody of the present invention can be performed from a single cell line, as a single batch. The generation of a polyclonal manufacturing cell line for the anti-RhD rpAb production will be demonstrated in the detailed description and by a working example.

Definitions

An "antibiotic resistance gene" is a gene encoding a protein that can overcome the inhibitory or toxic effect that an antibiotic has on a cell ensuring the survival and continued proliferation of cells in the presence of the antibiotic.

The term "antibody" describes a functional component of serum and is often referred to either as a collection of molecules (antibodies or immunoglobulin) or as one molecule (the antibody molecule or immunoglobulin molecule). An antibody molecule is capable of binding to or reacting with a specific antigenic determinant (the antigen or the antigenic epitope), which in turn may lead to induction of immunological effector mechanisms. An individual antibody molecule is usually regarded as monospecific, and a composition of antibody molecules may be monoclonal (i.e., consisting of identical antibody molecules) or polyclonal (i.e., consisting of different antibody molecules reacting with the same or different epitopes on the same antigen or even on distinct, different antigens). Each antibody molecule has a unique structure that enables it to bind specifically to its corresponding antigen, and all natural antibody molecules have the same overall basic structure of two identical light chains and two identical heavy chains. Antibodies are also known collectively as immunoglobulins. The terms antibody or antibodies as used herein are also intended to include chimeric and single chain antibodies, as well as binding fragments of antibodies, such as Fab, Fab' or F(ab)$_2$ molecules, Fv fragments or scFv fragments or any other stable fragment, as well as full-length antibody molecules and multimeric forms such as dimeric IgA molecules or pentavalent IgM.

The term "anti-RhD antibody-encoding nucleic acid segment" describes a nucleic acid segment comprising a pair of $V_H$ and $V_L$ genetic elements. The segment may further comprise light chain and/or heavy chain constant region genetic elements, e.g. Kappa or Lambda light chain constant region and/or one or more of the constant region domains CH1, CH2, CH3 or CH4 selected from one of the isotypes IgG1, IgG2, IgG3, IgG4, IgA1, IgA2, IgM, IgD and IgE. The preferred isotypes are IgG1 and/or IgG3. The nucleic acid segment may also comprise one or more promoter cassettes, either facilitating bi-directional or uni-directional transcription of the $V_H$ and $V_L$-encoding sequences. Additional transcriptional or translational elements, such as functional leader sequences directing the gene product to the secretory pathway, poly A signal sequences, UCOE's and/or an IRES may also be present in the segment.

The term "anti-RhD recombinant polyclonal antibody" or "anti-RhD rpAb" describes a composition of recombinantly produced diverse antibody molecules, where the individual members are capable of binding to at least one epitope on the Rhesus D antigen. Preferably, the composition is produced from a single manufacturing cell line. The diversity of the polyclonal antibody is located in the variable regions ($V_H$ and $V_L$ regions), in particular in the CDR1, CDR2 and CDR 3 regions.

The term "bias" is used to denote the phenomenon during recombinant polyclonal antibody production, wherein the composition of an expression library, polyclonal cell line, or polyclonal protein alters over time due to random genetic mutations, differences in proliferation kinetics between individual cells, differences in expression levels between different expression construct sequences, or differences in the cloning efficiency of DNA.

The terms "a distinct member of the anti-RhD rpAb" denotes an individual antibody molecule of the recombinant polyclonal antibody composition, comprising one or more stretches within the variable regions, which are characterized by differences in the amino acid sequence compared to the other individual members of the polyclonal protein. These stretches are in particular located in the CDR1, CDR2 and CDR 3 regions.

As used herein, the term "genome" is not to be taken literally as the normal complement of chromosomes present in a cell, but also extra-chromosomal elements that can be introduced into and maintained in a cell. Such extra-chromosomal elements can include, but are not limited to, mini-chromosomes, YACs (yeast artificial chromosomes), MACs (mouse artificial chromosomes), or HACs (human artificial chromosomes).

The term "head-to-head promoters" refers to a promoter pair being placed in close proximity so that transcription of two genetic elements driven by the promoters occurs in opposite directions (bi-directional transcription). Construction of such a system is described in details in example 3 of U.S. Pat. No. 5,789,208, which is hereby incorporated by reference. A head-to-head promoter can also be constructed with a stuffer composed of irrelevant nucleic acids between the two promoters. Such a stuffer fragment can easily contain more than 500 nucleotides.

The term "hot-spot" as in "hot-spot cell line" refers to a pre-established locus of the genome of the cell that has been selected or generated and characterized for highly efficient transcription of an integrated nucleic acid segment of interest upon integration of the expression vector into that site.

The term "immunoglobulin" commonly is used as a collective designation of the mixture of antibodies found in blood or serum, but may also be used to designate a mixture of antibodies derived from other sources or is used in the term "immunoglobulin molecule".

The term "internal ribosome entry site" or "IRES" describes a structure different from the normal 5' cap-structure on an mRNA. Both structures can be recognized by a ribosome to initiate scanning for an AUG codon to initiate translation. By using one promoter sequence and two initiating AUG's, a first and a second polypeptide sequence can be translated from a single mRNA. Thus, to enable co-translation of a first and a second polynucleotide sequence from a single dicistronic mRNA, the first and second polynucleotide sequence can be transcriptionally fused via a linker sequence including an IRES sequence that enables translation of the polynucleotide sequence downstream of the IRES sequence. In this case, a transcribed dicistronic RNA molecule will be translated from both the capped 5' end and from the internal IRES sequence of the dicistronic RNA molecule to thereby produce both the first and the second polypeptide.

As used herein the term "library" refers to a collection of variant nucleic acid sequences. For example a collection of nucleic acid sequences encoding a diverse population of antibody variable heavy chains and/or variable light chains. Where a member of the variant nucleic acid sequence is comprised of two variant genetic elements, e.g. $V_H$ and $V_L$, it will often be termed a nucleic acid segment. The collection of variant nucleic acid sequences/segments can either be in the form of a pool of such nucleic acid sequences, or it can be a collection of separate nucleic acid sequences (e.g. one unique sequence in each well of a 96 well plate). A library of the present invention typically have at least 3, 5, 10, 20, 50, 1000, $10^4$, $10^5$ or $10^6$ distinct members. In "library of vectors" the variant nucleic acid sequences/segments have been inserted into a vector. However, the terms library and library of vectors can also be used interchangeably.

The term "a library of anti-RhD antibody expression vectors" refers to a collection of variant anti-RhD antibody-encoding nucleic acid sequences inserted into a vector carrying regulatory elements for transcription of the anti-RhD antibodies. The regulatory elements can either be located in the inserted nucleic acid segments or in the vector framework. Preferably the anti-RhD antibody expression vectors also carry at least one recombinase recognition sequences, e.g. a FRT site, it may also carry two different recombinase recognition sequences such as a FRT and a FRT' site.

The term "a majority of the individual cells" refers to a percentage of the cells such as more than 80%, preferably more than 85%, more preferably 90%, 95%, or even 99% or higher.

The term "mass transfer" or "transfer in-mass" is used to describe the transfer of nucleic acid segments of interest from one population of vectors to another population of vectors and doing so for each nucleic acid segments simultaneously without resorting to isolation of the individual segments of interest. Such populations of vectors can be libraries containing for example variable regions, promoters, leaders or enhancing elements of interest. These sequences can then be moved without prior isolation from for example a phage vector to a mammalian expression vector. Especially for antibody sequences this technique ensures that the linkage between $V_H$ and $V_L$ diversity is not lost while moving libraries from, for example, a selection vector (e.g., a phage display vector) to a mammalian expression vector. Hereby the original pairing of $V_H$ and $V_L$ is retained.

As used herein, the term "operably linked" refers to a segment being linked to another segment when placed into a functional relationship with the other segment. For example, DNA encoding a signal sequence is operably linked to DNA encoding a polypeptide if it is expressed as a leader that participates in the transfer of the polypeptide to the endoplasmic reticulum. Also, a promoter or enhancer is operably linked to a coding sequence if it stimulates the transcription of the sequence.

The term "polyclonal antibody" describes a composition of different (diverse) antibody molecules which is capable of binding to or reacting with several different specific antigenic determinants on the same or on different antigens. Usually, the variability of a polyclonal antibody is located in the so-called variable regions of the polyclonal antibody, in particular in the CDR regions. When stating that a member of a polyclonal antibody binds to an antigen, it is herein meant a binding having binding constant that is below 1 mM, preferably below 100 nM, even more preferred below 10 nM.

The term "recombinant polyclonal manufacturing cell line" refers to a mixture/population of protein expressing cells that are transfected with a library of variant nucleic acid segments of interest such that the individual cells, which together constitute the recombinant polyclonal manufacturing cell line, each carry only one transcriptionally active copy of a distinct nucleic acid segment of interest, which encodes one member of the recombinant polyclonal antibody of interest, and that each copy is integrated into the same site of the genome of each cell. The cells constituting the recombinant polyclonal manufacturing cell line are selected for their ability to retain the integrated copy of the distinct nucleic acid segment of interest, for example by antibiotic selection. Cells which can constitute such a manufacturing cell line can be for example bacteria, fungi, eukaryotic cells, such as yeast, insect cells or mammalian cells, especially immortal mammalian cell lines such as CHO cells, COS cells, BHK cells, myeloma cells (e.g., Sp2/0 cells, NS0), NIH 3T3, YB2/0 and immortalized human cells, such as HeLa cells, HEK 293 cells, or PER.C6.

The term "recombinant antibody" is used to describe an antibody molecule or several molecules that is/are expressed from a cell or cell line transfected with an expression vector comprising the coding sequence of the protein which is not naturally associated with the cell. If the antibody molecules are diverse or different, the term "recombinant polyclonal antibody" applies in accordance with the definition of a polyclonal antibody.

The term "recombinase" refers to an enzyme that catalyses recombination between two or more recombination sites or recombination recognition sequences. Recombinases useful in the present invention catalyze recombination at specific recombination sites that are specific nucleic acid sequences recognized by a particular recombinase.

The terms "recombinase recognition site" or "recombination site" describe a nucleic acid sequence which serves as site for both recognition and recombination by a site-specific recombinase enzyme. A recombinase recognition site is generally comprised of short inverted repeat elements (11-13 bp in length) that flank a core sequence (6-8 bp in length). Recombinase recognition sites are also termed recombinase target sites, recombination sites or integration sites and include as examples the FLP-site, loxP-site, attP/attB-sites, six-site, gix-site, R-site and Res-site. Recombinase recognition sites between which a recombinase can catalyze an integration, excision or inversion event are termed matching recombinase recognition sites, for example are two wild type FRT sites considered to match, as well as an attB site and an attP site constitute a matching pair of recombinase recognition sites, whereas, a wildtype FRT site and a mutant FRT site will not necessarily constitute a matching pair of recombinase recognition sites; this will depend on the mutation. These terms are also used interchangeably with the term integration site.

The term "RFLP analysis" refers to "restriction fragment length polymorphism analysis", a method whereby the migratory gel pattern of nucleic acid molecule fragments is analyzed after cleavage with restriction enzymes.

The term "scrambling" describes situations where two or more distinct members of a polyclonal protein, where each member is comprised of two different polypeptide chains, e.g. $V_H$ and $V_L$ chains, is expressed from an individual cell. This situation may arise when the individual cell has integrated into the genome, more than one pair of genetic elements, where each pair of genetic elements encodes a distinct member of the polyclonal protein. In such situations unintended combinations of the polypeptide chains expressed from the genetic elements can be made. "$V_H$-$V_L$ chain scrambling" is an example of the scrambling defined above. The scrambling occurs when unintended combinations of $V_H$ and $V_L$ polypeptides are produced from a cell where two different $V_H$ and $V_L$-encoding nucleic acid segments are integrated into transcriptional active sites in the same cell. Such a scrambled antibody molecule is not likely to retain the original specificity, and thus might not have any therapeutic effect.

The term "selection" is used to describe a method where cells have acquired a certain characteristic that enable the isolation from cells that have not acquired that characteristic. Such characteristics can be resistance to a cytotoxic agent or production of an essential nutrient, enzyme, or color.

The terms "selectable marker gene", "selection marker gene", "selection gene" and "marker gene" are used to describe a gene encoding a selectable marker (e.g., a gene conferring resistance against some cytotoxic drug such as certain antibiotics, a gene capable of producing an essential nutrient which can be depleted from the growth medium, a gene encoding an enzyme producing analyzable metabolites or a gene encoding a colored protein which for example can be sorted by FACS) which is co-introduced into the cells together with the gene(s) of interest.

The term "transfection" is herein used as a broad term for introducing foreign DNA into a cell. The term is also meant to cover other functional equivalent methods for introducing foreign DNA into a cell, such as e.g., transformation, infection, transduction or fusion of a donor cell and an acceptor cell.

As used herein, the term "vector" refers to a nucleic acid molecule into which a nucleic acid sequence can be inserted for transport between different genetic environments and/or for expression in a host cell. A vector capable of integrating into the genome of a host cell at a pre-determined, specific locus in the genome is herein named "a vector for site-specific integration". If the vector carries regulatory elements for transcription of the nucleic acid sequence inserted in the vector (at least a suitable promoter), the vector is herein called "an expression vector". The term "an isotype-encoding vector" refers to a vector carrying nucleic acid sequences encoding an antibody isotype. In the present specification, "phagemid vector" and "phage vector" are used interchangeably. The terms "plasmid" and "vector" are used interchangeably. The invention is intended to include such other forms of vectors, which serve equivalent functions for example plasmids, phagemids and virus genomes or any nucleic acid molecules capable of directing the production of a desired protein in a proper host.

The following style of writing "$V_H$:LC" and "$V_H$:$V_L$" indicate a particular pair of a variable heavy chain sequence with a light chain or a variable light chain sequence. Such particular pairs of $V_H$ and $V_L$ sequences can either be nucleic acid sequences or polypeptides. In the present invention particular $V_H$ and $V_L$ pairs confer binding specificity towards the rhesus D antigen.

Abbreviations: Ab=antibody. Anti-RhD rpAb=anti-Rhesus D recombinant polyclonal antibody. CASY=Cell Counter+Analyzer System. ELISA=Enzyme-Linked Immunosorbent Assay. FRT=Flp Recombinase Target. GFP=Green Fluorescent Proteins. HDN=hemolytic disease of the newborn. ITP=idiopathic thrombocytopenic purpura. LTR=Long Terminal Repeat. mAb=monoclonal antibody. pMCB=polyclonal master cell bank. PVDF=polyvinylidene difluorid. PWCB=polyclonal working cell bank. RBC=red blood cells. RhD=Rhesus D. RhD(−)=Rhesus D negative. RhD(+)=Rhesus D positive. $RhD^{VI}$=Rhesus D category VI antigen. Anti-D=polyclonal immunoglobulin preparation against RhD from hyperimmune donors. SV40 poly A=Simian Virus 40 poly A signal sequence. UCOE=ubiquitous chromatin opening elements. 5' UTR=5' untranslated region of the mRNA.

DESCRIPTION OF THE DRAWINGS

FIG. 1A: Flow chart outlining the generation of a recombinant polyclonal manufacturing cell line and the production of a recombinant polyclonal antibody. 1) Illustrates a bulk transfection strategy; 2) illustrates a semi-bulk transfection strategy and 3) illustrates an individual transfection strategy. A) Illustrates the library of anti-RhD antibody expression vectors (horizontal lines), the arrowheads illustrate the grouping of the vectors. In strategy 1 the vectors are grouped in bulk, in strategy 2 they are grouped in smaller fractions (semi-bulk), whereas in strategy 3 they are kept separate from each other (individual). B) Illustrates the transfection, where the number of tubes depends on the grouping of the vectors constituting the library. C) Illustrates selection of cells that site-specifically have integrated an anti-RhD antibody-encoding nucleic acid segment into the host cell genome, D) Illustrates the generation of a polyclonal anti-RhD antibody library stock, where the selected cells constituting the integrated anti-RhD antibody-encoding nucleic acid segments are stored in a freezer. It is optional to bank individual clones or pool the clones. E) Illustrates the beginning of the manufacturing phase, where clones from the stock are thawed (either individually, from smaller fractions or from a pool). F) Illustrates the stage in the production where the polyclonal cell line is propagated for seeding of a larger bioreactor (intermediate seeding steps are an option although not illustrated). In strategy 2 and 3, this is the stage where the polyclonal cell clone stock no longer is kept as individual clones or semi-bulk fractions, but pooled into a collection of cells, forming a recombinant polyclonal manufacturing cell line (this polyclonal manufacturing cell line may also be stored as a frozen stock). G) Illustrates the final production obtained from the bioreactor manufacturing. Following the production phase, the polyclonal protein composition is harvested for purification and characterization of the product.

Figure 3A:
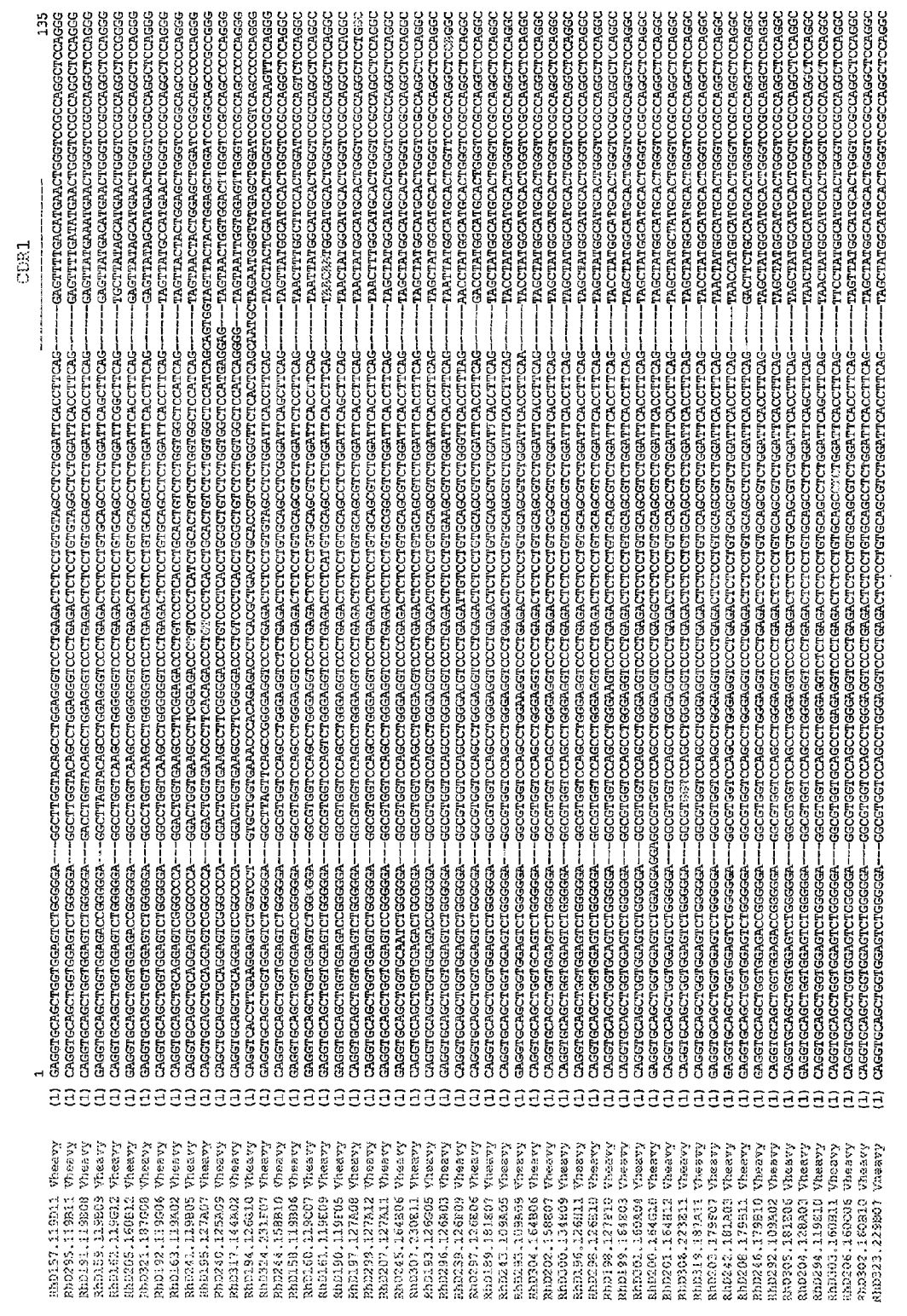
Figure 3B:
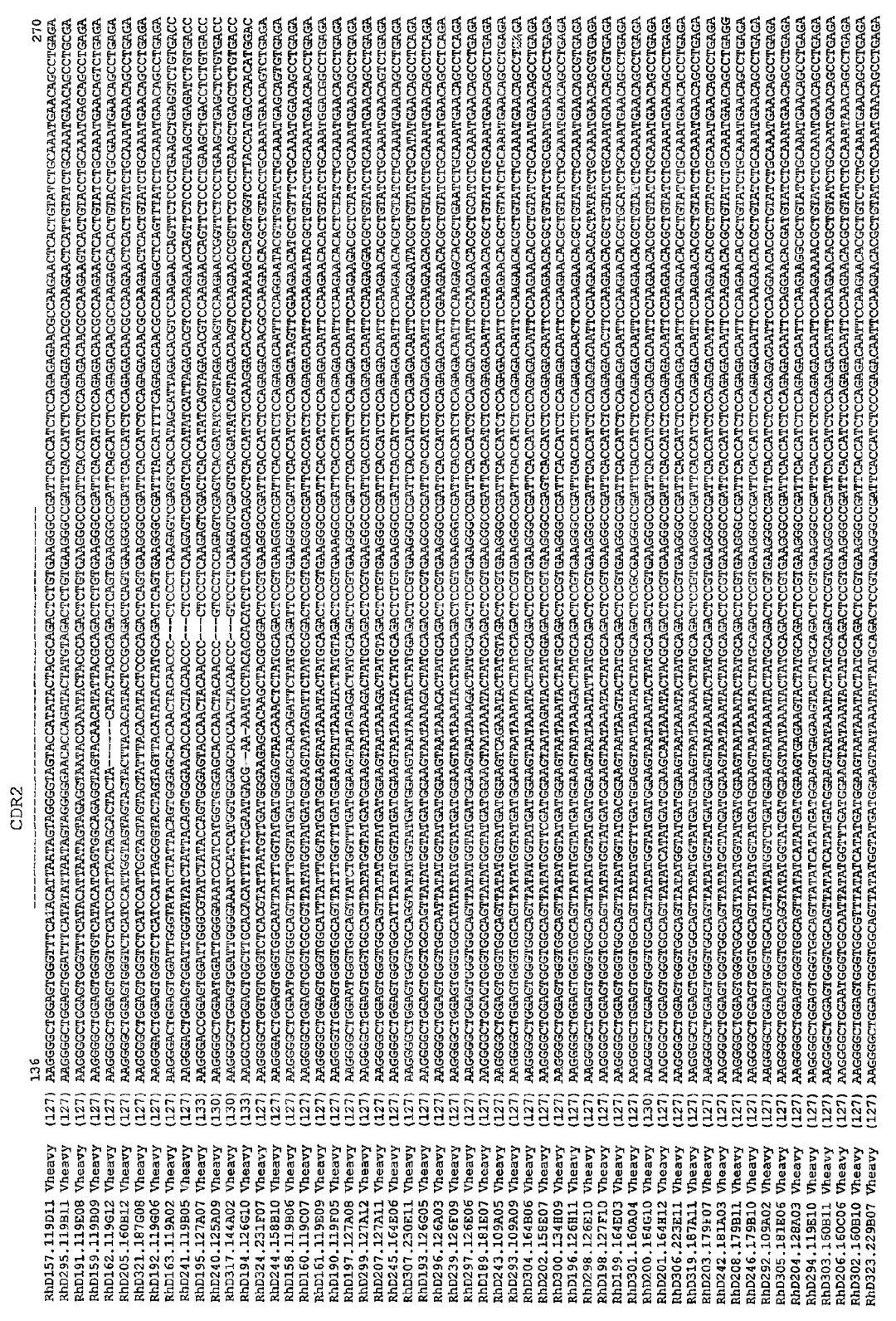
Figure 3C:
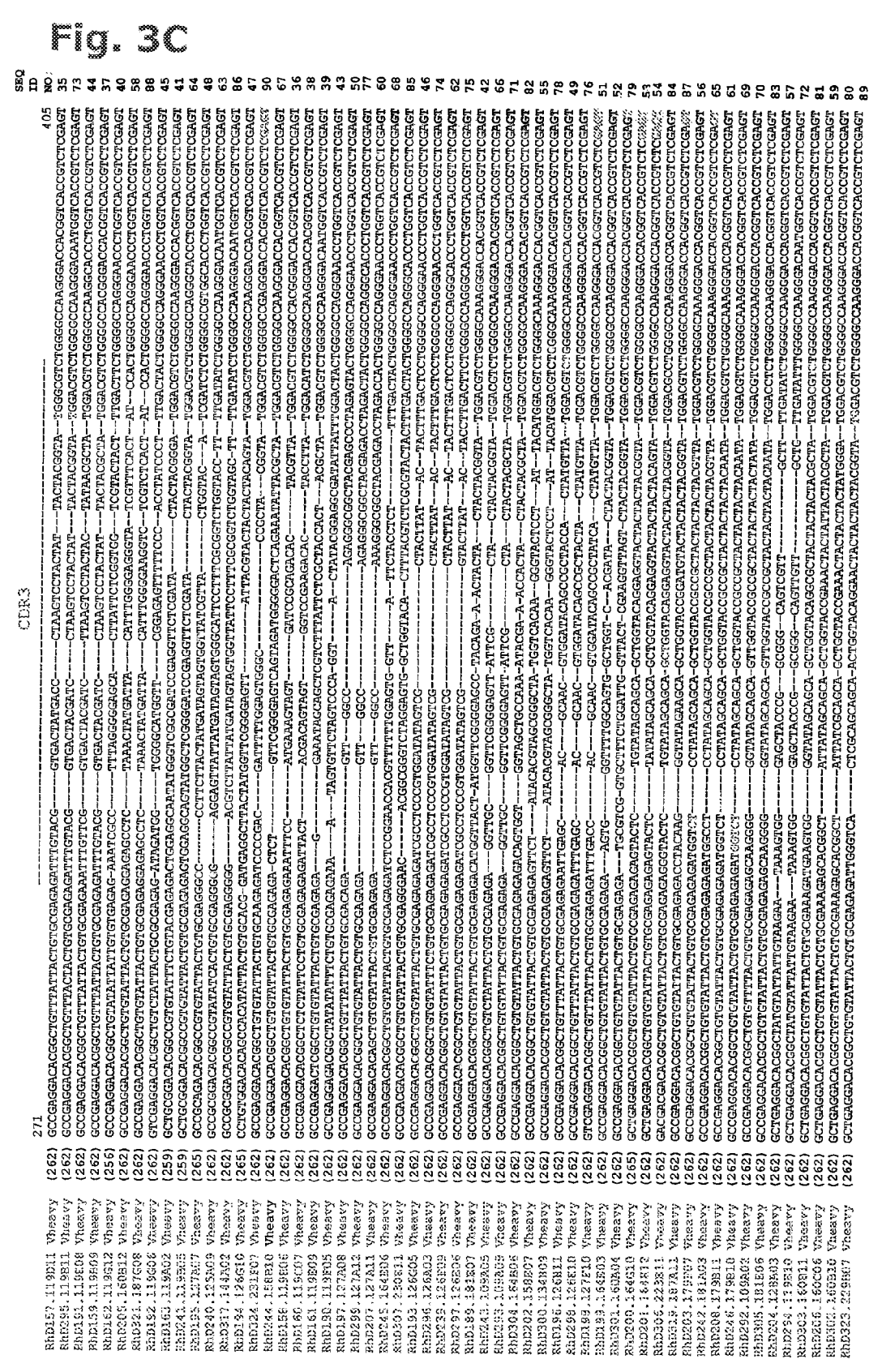

FIG. 3A-C: Alignment of the nucleic acid sequences encoding the variable heavy chain ($V_H$) of the 56 selected RhD clones. The individual clone names are indicated to the right of the alignment, and the position of CDR regions are indicated above the alignments.

Figure 4A:
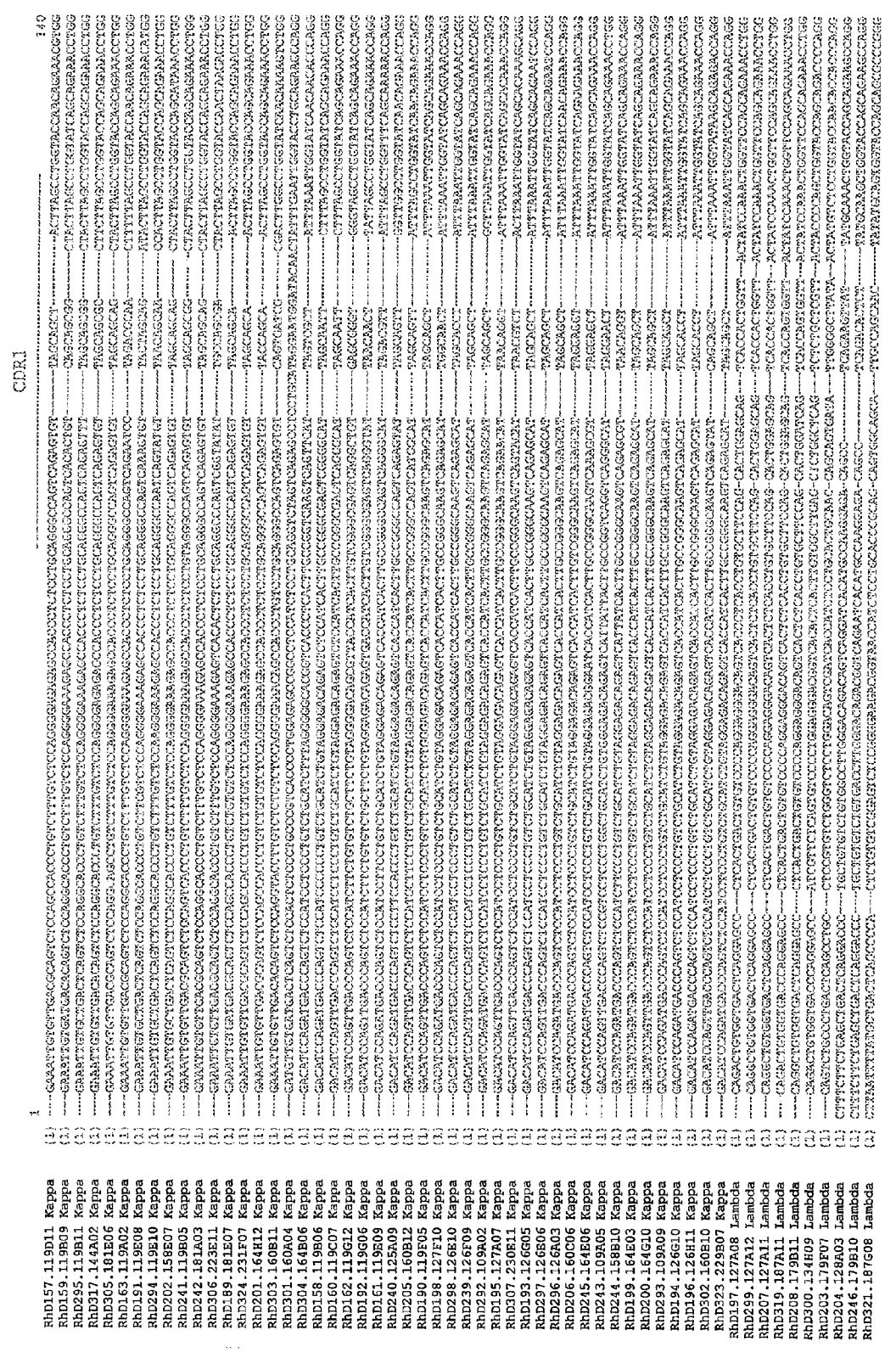
Figure 4B:
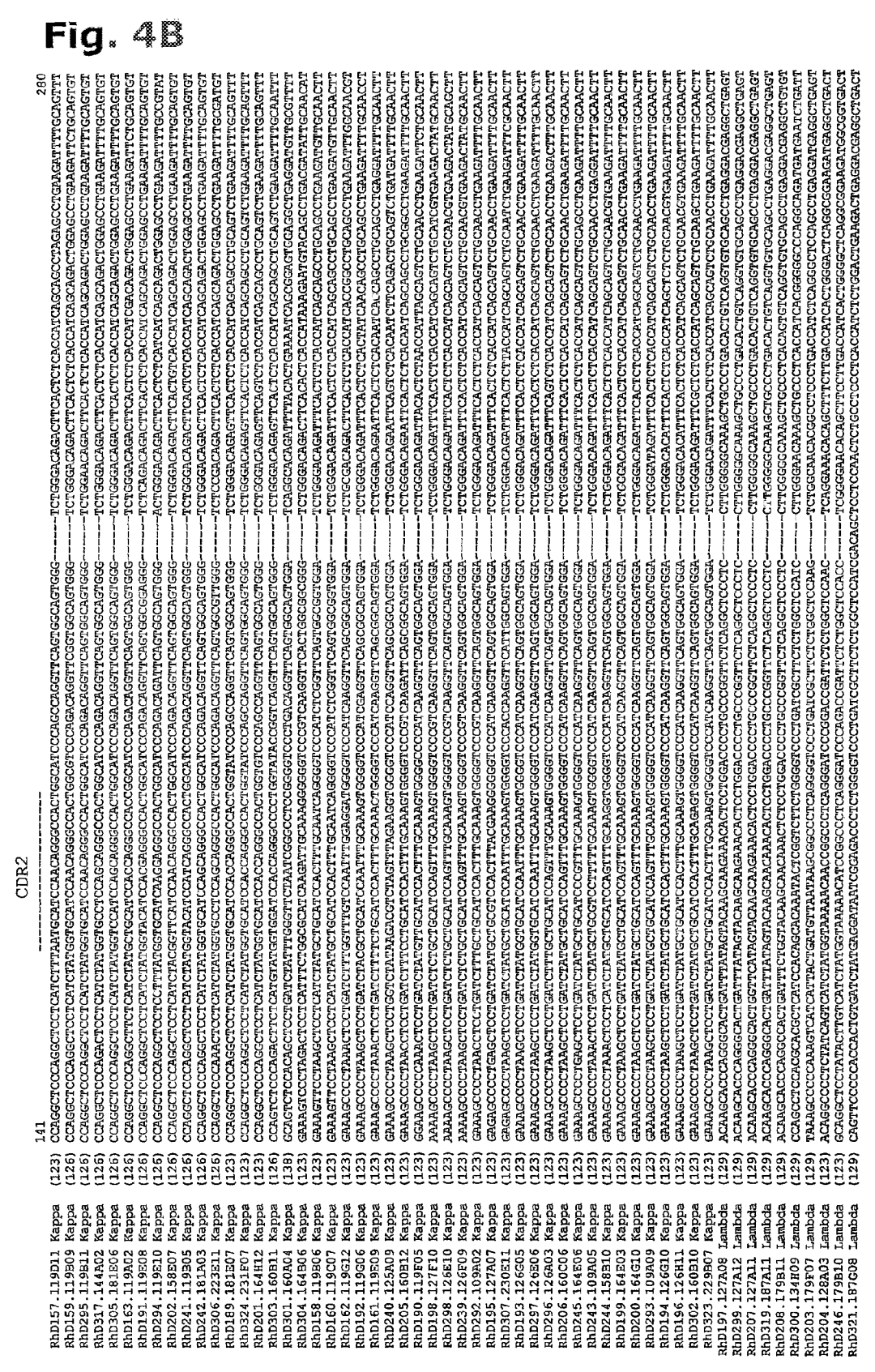
Figure 4C:
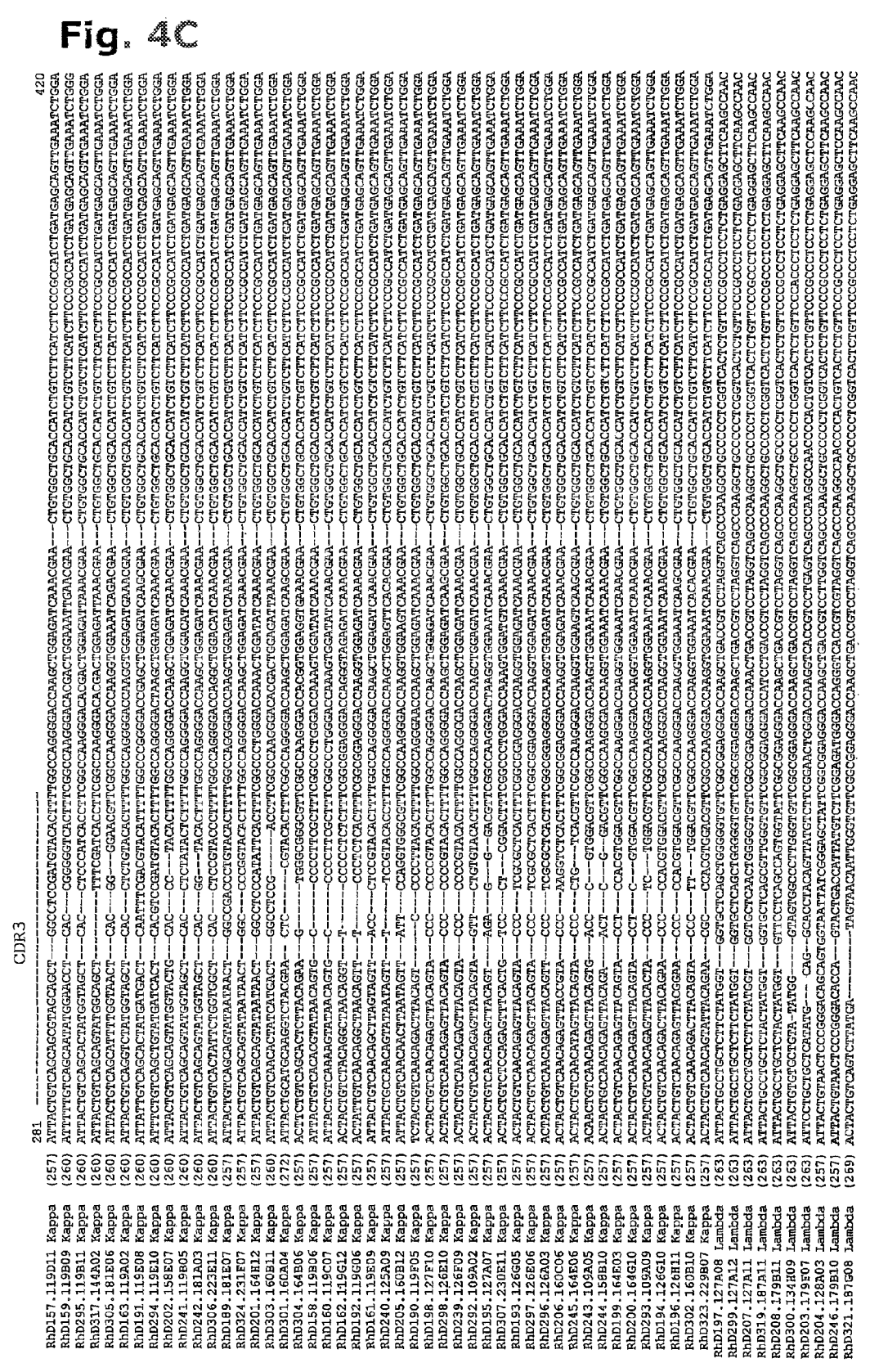
Figure 4D:
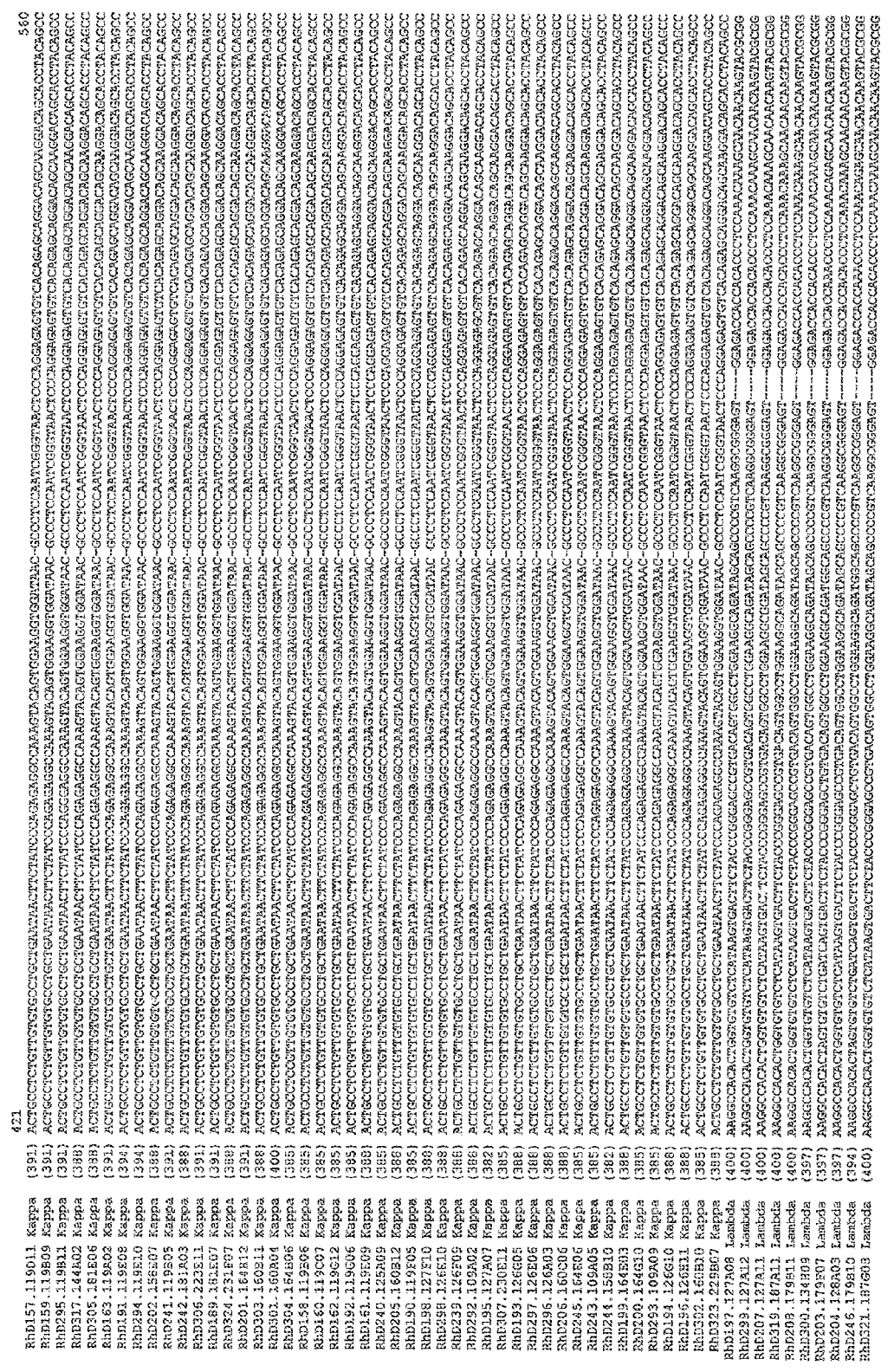
Figure 4E:
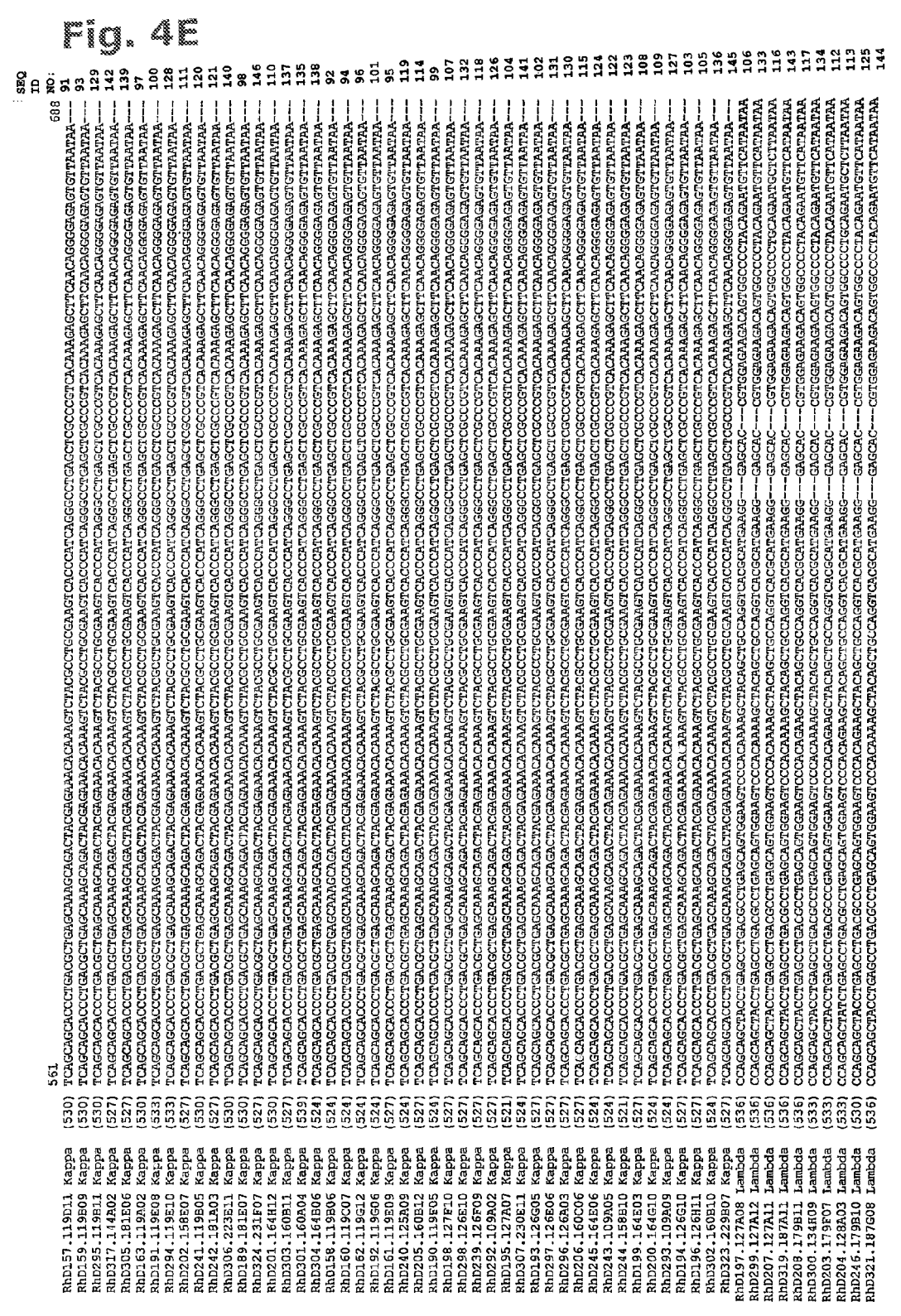

FIG. 4A-E: Alignment of the nucleic acid sequences encoding the entire light chain of the 56 selected RhD clones. The individual clone names together with an indication of whether it is a Kappa or Lambda chain are indicated to the right of the alignment, and the position of CDR regions are indicated above the alignments.

FIG. 5: Alignment of the amino acid sequences corresponding to $V_H$ of the 56 selected RhD clones. The individual clone names are indicated to the right of the alignment, and the position of CDR regions are indicated above the alignments.

FIG. 6A-B: Alignment of the amino acid sequences corresponding to $V_L$ of the 56 selected RhD clones, wherein (A) corresponds to the Kappa chains and (B) to the Lambda chains. The individual clone names are indicated to the right of the alignment, and the position of CDR regions are indicated above the alignments.

DETAILED DESCRIPTION OF THE INVENTION

The Recombinant Polyclonal Protein Expression System

Figure 1B:
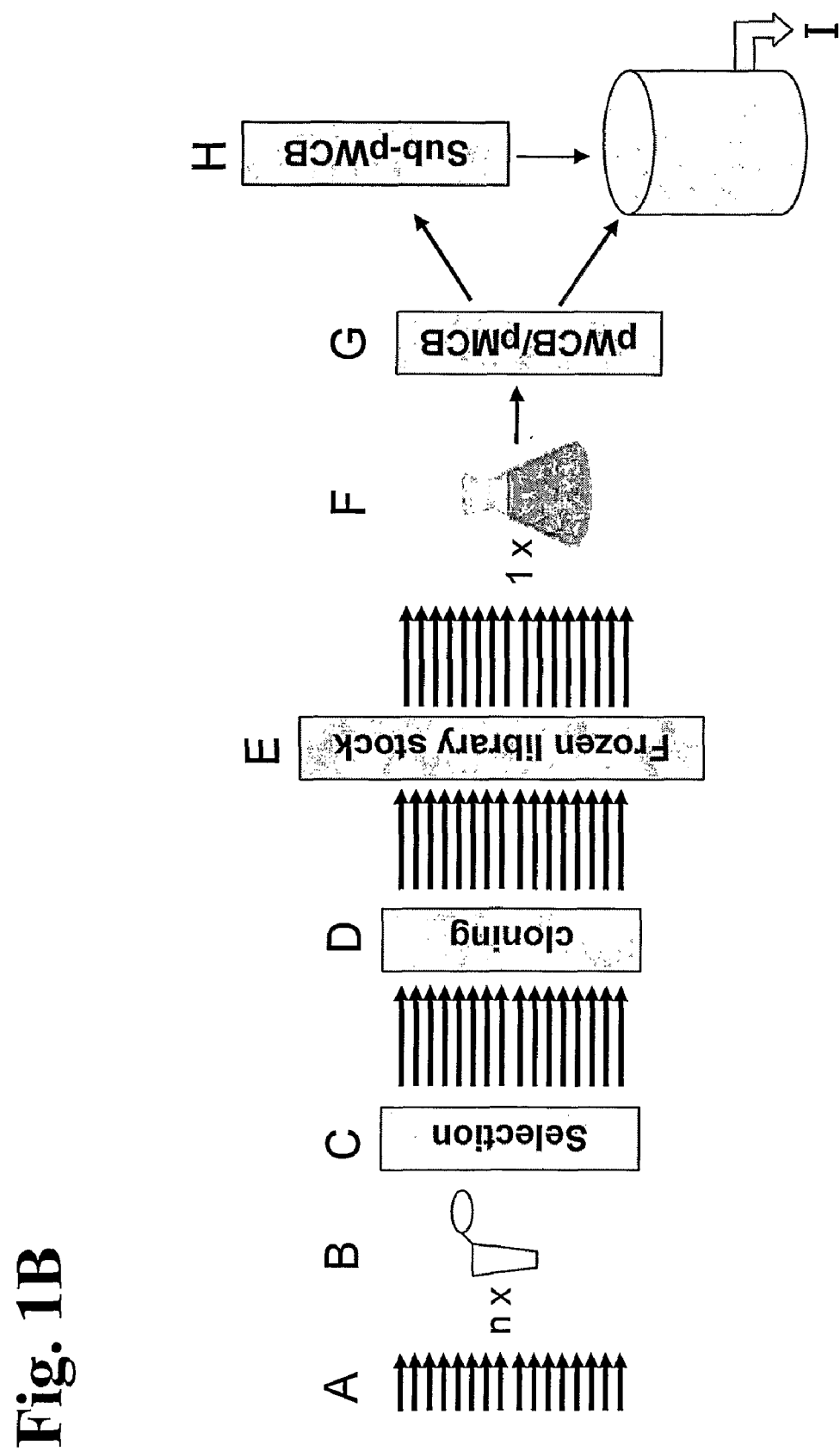
FIG. 1B: Flow chart outlining the generation a pWCB/pMCB and a sub-pWCB from individually transfected host cells and the seeding of a polyclonal manufacturing cell line. A) Illustrates a library comprised of variable region-encoding nucleic acid segments, the arrowheads illustrate the individual members of the library. B) Illustrates the transfection, where each individual member of the library is used to transfect a host cell. The transfection requires as many separate tubes as there are individual members of the library. C) Illustrates selection of cells that have integrated a variable region-encoding nucleic acid segment into their genome in a stable manner, D) Illustrates the selection of individual cell lines that have similar proliferation rates and/or productivity, e.g. by cloning and analysis of single cells sorted by FACS. This step is optional in the generation of a pWCB/pMCB and may also be performed after step E. E) Illustrates the generation of a frozen library stock, constituted of n times individual cell lines each expressing one member of the library comprised of variable region-encoding nucleic acid segments used for transfection. It is optional to bank individual clones into a frozen library stock prior to the generation of a pWCB/pMCB. F) Illustrates the mixing of the individual cell lines, where ampoules from the individual library stock are thawed and expanded in separate cell cultures, followed by the mixing of a predefined number of cells from each culture into a single cell culture. G) Illustrates generation of a pWCB/pMCB by freezing down aliquots from the mixed cell culture in F, thereby generating a collection of vials. H) Illustrates the generation of a sub-pWCB by expanding a single vial from the pMCB and freezing down aliquots with approximately the same number of cells as in the vial from the pMCB. I) Illustrates the generation of a polyclonal manufacturing cell line from a seed train (intermediate seeding steps which are not illustrated) initiated either from the pWCB or the sub-pWCB.

The present invention provides a recombinant polyclonal antibody expression system for the consistent manufacturing of anti-RhD recombinant polyclonal antibody (anti-RhD rpAb) from one or a few cell lines.

One of the major advantages of the manufacturing method of the present invention is that all the members constituting the anti-RhD rpAb can be produced in one or a few bioreactors or equivalents thereof. Further, the anti-RhD rpAb composition can be purified from the reactor as a single preparation without having to separate the individual members constituting the anti-RhD rpAb during the process. In contrast, if one wanted to mimic an anti-RhD rpAb composition by mixing purified anti-RhD monoclonal antibodies (anti-RhD mAbs) (as for example proposed in WO 97/49809) it would require the separate manufacturing in a bioreactor, of each anti-RhD mAb to be included in the composition and most likely the antibodies would be purified individually as well. Such a production of an anti-RhD mAb mixture would be very costly, and time and space consuming compared to the method of the present invention for producing an anti-RhD recombinant polyclonal. Thus, the method as described in WO 97/49809 would naturally result in a practical limit to the number of anti-RhD mAbs that could be included in such a mixture, whereas the technology as described herein generally can produce a polyclonal antibody with as many individual members as desired. Further, the individual members of an anti-RhD rpAb of the present invention are produced under exact same conditions (in the same manufacturing reactor), thus uniform posttranslational modifications are ensured compared to a mixture of anti-RhD mAbs where slight production differences from batch to batch may change the product properties.

In order to obtain a recombinant polyclonal manufacturing cell line which is capable of expressing anti-RhD rpAb without significant loss of the diversity characterizing the polyclonality during the production period, the individual cells within the mixture of cells composing the polyclonal manufacturing cell line will need to be as uniform as possible.

Conventional monoclonal antibody expression techniques using random integration are undesirable for the production of a recombinant polyclonal antibody, since the random nature of the process will cause the number and positions of the integrated nucleic acid sequences to vary from cell to cell. Thus, if recombinant polyclonal antibody is produced by such traditional protocols, it is likely to result in a heterogeneous cell culture with variable expression rates of individual members of the polyclonal protein, and genetic instability due to positional effects of the integrated nucleic acid segment. This will most likely result in a biased expression of the members constituting the polyclonal protein.

Introduction of the anti-RhD antibody-encoding nucleic acid segment into a predefined genomic site is therefore desirable, this can in principle be achieved by homologous recombination. However, owing to the dominance of illegitimate recombination events, homologous recombination is very inefficient and may also result in introduction of several copies of variant anti-RhD antibody-encoding nucleic acid segments into the genome of a single cell.

To circumvent these problems the expression system of the present invention uses site-specific integration into the genome of the individual host cells. The system of the present invention encompasses a library of anti-RhD antibody expression vectors for site-specific integration comprising the variant nucleic acid segments encoding the anti-RhD rpAb. Individual nucleic acid segments from the library are inserted into individual cells at the same pre-established chromosomal location by site-specific integration at a predefined recombination recognition site or by a recombinase-mediated cassette exchange procedure, thereby generating a cell line, wherein the individual cells expresses a distinct member of the anti-RhD rpAb. As described below, multiple integrations might occur in some of the cells constituting the recombinant polyclonal manufacturing cell line. This, however, is not considered to pose a problem as long as a majority of the individual cells express a single distinct member of the anti-RhD rpAb. Preferably this is achieved by ensuring a single integrant in the genome of the majority of the individual cells or if there are more integrants, ensuring that only one is transcribed.

Recombinases such as Cre, Flp, beta-recombinase, Gin, Pin, PinB, PinD, R/RS, Tn3 resolvase, XerC/D integrase/recombinase, lambda integrase, or phage φC31 integrase can be used. Suitable recombinases for integration into the chromosomal location can be provided either (i) by expression from the cell's own genome into which said nucleic acid segment is introduced, (ii) by being operatively encoded by the vector inserted into the cell, (iii) through expression from a second nucleic acid molecule, or (iv) as a protein. In a preferred embodiment, the anti-RhD antibody-encoding nucleic acid segment contained in an individual vector of the library is integrated into a locus that mediates high-level transcription and expression of the anti-RhD antibody nucleic acid segment, a so-called "hot-spot".

The host cell line used is preferably a mammalian cell line comprising those typically used for biopharmaceutical protein expression, e.g., CHO cells, COS cells, BHK cells, myeloma cells (e.g., Sp2/0 cells, NS0), YB2/0, NIH 3T3, and immortalized human cells, such as HeLa cells, HEK 293 cells, or PER.C6. In the present invention CHO cells were used. However, a person of ordinary skill in the art would easily be able to substitute CHO cells with other mammalian cells as described, or even utilize other types of cells, including plant cells, yeast cells, insect cells, fungi and bacteria. Thus, the choice of cell type is not intended to be limiting to the invention. In a preferred embodiment, a mammalian cell line containing a pre-characterized hot-spot, mediating high expression levels of the anti-RhD rpAb is used for the manufacture. In an even more preferred embodiment, the mammalian cell line contains a single recombinase recognition site located in a pre-identified hot-spot.

In a further embodiment of the present invention, variant anti-RhD antibody-encoding nucleic acid segments are integrated in a site-specific manner utilizing the same chromosomal integration site in the host cells. Such incorporation into a single specific site minimizes positional effects otherwise seen with random integration or integration into multiple sites in a genome. Further, scrambling among $V_H$ and $V_L$ chains is not likely to occur when using a single specific site for integration.

In a host cell line comprising a site-specific integration system, the individual transfected host cells are expressing the same overall antibody apart from the differences observed in the variable region of the antibody. Therefore, a majority of cells within such a pool of cells should display similar characteristics with respect to productivity and genetic stability and hence this technology offers the possibility of a controlled production of an anti-RhD rpAb.

In addition to the variability of the $V_H$ and $V_L$ regions, in particular the CDR regions, the constant regions may also be varied with respect to isotype. This implies that one particular $V_H$ and $V_L$ pair may be produced with varying constant heavy chain isotypes, e.g. the human IgG1, IgG2, IgG3, IgG4, IgA1, IgA2, IgM, IgD and IgE. Thus, an anti-RhD rpAb may comprise antibody molecules that are characterized by sequence differences between the individual antibody molecules in the variable region (V region) as well as in the constant region. The anti-RhD rpAb composition can be composed of antibodies with any heavy chain isotype mentioned above or combinations thereof. Preferred anti-RhD rpAb compositions contain IgG1 constant regions, IgG3 constant regions or IgG1 and IgG3 constant regions. In a preferred embodiment of the present invention each or some of the $V_H$ and $V_L$ pairs are expressed with a human IgG1, IgG3, IgA1 and/or IgA2 constant heavy chain.

In order to provide a library of anti-RhD antibody-encoding nucleic acid segments a number of methods known in the art may be utilized. A first library comprising $V_H$ and $V_L$-encoding segments may either be generated by combinatorial techniques (e.g. EP 0 368 684) or techniques maintaining the cognate pairing (pairs of variable region-encoding sequences derived from the same cell, described in WO 05/042774 claiming the priority of the unpublished patent application DK 200400782). Further, $V_H$ and $V_L$-encoding segment libraries may be generated by incorporating isolated CDR gene fragments, into an appropriate framework (e.g. Soderlind, E. et al., 2000. Nat. Biotechnol. 18, 852-856), or by mutation of one or more anti-RhD $V_H$ and $V_L$-encoding sequences. This first library is screened for $V_H$ and $V_L$-encoding nucleic acid segments producing antibodies or fragments with binding specificity towards RhD, thereby generating a library of anti-RhD Ab-encoding nucleic acid segments. In particular with combinatorial libraries the screening is preceded by an enrichment step for example a so-called biopanning step. Known biopanning technologies are phage display (Kang, A. S. et al. 1991. Proc Natl Acad Sci USA 88, 4363-4366), ribosome display (Schaffitzel, C. et al. 1999. J. Immunol. Methods 231, 119-135), DNA display (Cull, M. G. et al. 1992. Proc Natl Acad Sci USA 89, 1865-1869), RNA-peptide display (Roberts, R. W., Szostak, J. W., 1997. Proc Natl Acad Sci USA 94, 12297-12302), covalent display (WO 98/37186), bacterial surface display (Fuchs, P. et al. 1991. Biotechnology 9, 1369-1372), yeast surface display (Boder, E. T., Wittrup, K. D., 1997. Nat Biotechnol 15, 553-557) and eukaryotic virus display (Grabherr, R., Ernst, W., 2001. Comb. Chem. High Throughput. Screen. 4, 185-192). FACS and magnetic bead sorting are also applicable for enrichment (panning) purposes using labeled antigen. The screening for Rhesus D binders are generally performed with immunodetection assays such as agglutination, FACS, ELISA, FLISA and/or immunodot assays.

Following screening, the generated sub-library of $V_H$ and $V_L$-encoding nucleic acid segments, generally needs to be transferred from the screening vector to an expression vectors suitable for site-specific integration and expression in the desired host cell. It is important that the sequences encoding the individual $V_H$:$V_L$ pairs are maintained during the transfer. This can either be achieved by having the individual members of the sub-library separate and moving $V_H$ and $V_L$-encoding sequences one by one. Alternatively, the vectors constituting the sub-library are pooled, and the sequences encoding the $V_H$:$V_L$ pairs are moved as segments, keeping the $V_H$ and $V_L$-encoding sequences together during the transfer. This process is also termed mass transfer, and enables an easy transfer of all the selected $V_H$:$V_L$ pairs from one vector to another.

In a further embodiment of the present invention, an anti-RhD recombinant polyclonal antibody composition comprises a defined subset of individual antibodies, based on the common feature that they exhibit binding to at least one epitope on the Rhesus D antigen e.g. epD1, epD2, epD3, epD4, epD5, epD6/7, epD8 and/or epD9, but not or very weakly to Rhesus C, c, E, e antigens. Preferably the anti-RhD rpAb composition is composed of at least one antibody which bind to epD3, epD4 and epD9 (RhD category VI antigen binding antibody) and further antibodies which at least in combination binds to the remaining epitopes epD1, epD2, epD5, epD6/7 and epD8, e.g. an antibody against RhD category II or III antigen, or a RhD category IV or V antigen binding antibody combined with an antibody against category VII antigen. Typically an anti-RhD rpAb composition has at least 5, 10, 20, 50, 100 or 500 distinct variant members. The preferred number of variant members range between 5 and 100, even more preferred between 5 and 50 and most preferred between 10 and 25.

A further embodiment of the present invention is a recombinant polyclonal manufacturing cell line, comprising a collection of cells transfected with a library of anti-RhD polyclonal antibody-encoding nucleic acid segments, wherein each cell in the collection is capable of expressing one member of the library, which encodes a distinct member of an anti-RhD rpAb or fragment and which is located at the same site in the genome of individual cells in said collection, wherein said nucleic acid segment is not naturally associated with said cell in the collection.

In an additional embodiment the variant nucleic acid segments encoding the anti-RhD rpAb are all derived from naturally occurring sequences, for example isolated from a donor, either as combinatorial $V_H$:$V_L$ pairs or as cognate pairs, and not derived by mutation.

Compositions of cells that contain variant nucleic acids located at a single specific site in the genome within each cell have been described in WO 02/44361. This document discloses the use of the cells to identify molecules having desirable properties, but the reference does not deal with the provision of a production system or with the provision of polyclonal antibody characterized by a specific binding to an antigen.

The Host Cell

A suitable host cell comprises, in a region of its genome, one or more suitable recombination sites, i.e., nucleic acid sequences recognizable by one or more recombinase enzymes, hence also termed recombinase recognition sequences. To be able to select for integrants, (i.e., cells having an integrated copy of an anti-RhD antibody-encoding nucleic acid segment in an integration site) the recombination site is operably linked to a first selection gene (e.g., an antibiotic resistance gene) situated 3' (downstream) to the recombination site. Furthermore, a weak promoter (e.g., a truncated SV40 early promoter) and a transcription start codon may be situated 5' (upstream) to the recombination site that constitutes an integral part of the resistance marker-coding region. Thus, the transcription start codon initiates the start of transcription of the selection gene in the host cell before transfection with the library of anti-RhD antibody expression vectors encoding the anti-RhD rpAb. Preferably, the host cell line only has one recombination site, and if it has more than one recombinase recognition sequence, these should be non-homologous as described in the section "The vector for site-specific integration", and only allow for a single integration into the genome.

Host cells for site-specific integration as described above can be generated from any cell which can integrate DNA into their chromosomes or retain extra-chromosomal elements such as mini-chromosomes, YACs (Yeast artificial chromosomes), MACs (Mouse artificial chromosomes), or HACs (Human artificial chromosomes). MACs and HACs are described in detail in WO 97/40183, hereby incorporated by reference. Preferably mammalian cells such as CHO cells, COS cells, BHK cells, myeloma cells (e.g., Sp2/0 or NS0 cells), fibroblasts such as NIH 3T3, and immortalized human cells, such as HeLa cells, HEK 293 cells, or PER.C6, are used. However, non-mammalian eukaryotic or prokaryotic cells, such as plant cells, insect cells, yeast cells, fungi, *E. coli* etc., can also be employed.

In one embodiment of the present invention, the cell line which is to be used as starting material is sub-cloned by performing a so-called limiting dilution of the cell line down to a single cell level, followed by growing each single cell to a new population of cells prior to transfection with the library of vectors of interest. Such sub-cloning can also be performed later in the process of selecting the right cell line, if desired.

The host cells for site-specific integration may be obtained by transfection with a randomly integrating plasmid comprising a weak promoter (e.g., a truncated SV40 early promoter), a transcription start codon, a recombination site situated 3' to the start codon. Preferably, the integrating plasmid also comprises a marker gene coupled to a first selection gene. One example of such an integrating plasmid is the pFRT/LacZeo2 from Invitrogen (Carlsbad, Calif.). The marker gene can be used to evaluate the relative strength of expression at the genomic location used for inserting a nucleic acid sequence of interest. A marker gene, (e.g., beta-galactosidase (LacZ), green fluorescent protein (GFP) or a cell surface marker) can be linked to the first selection gene in a gene fusion or transcriptionally linked by an IRES (internal ribosomal entry site) such that co-expression of the first selection gene and marker gene occurs. The use of a selection gene that establishes a survival pressure on the cells (e.g. drug resistance or nutritional depletion) combined with a marker allowing for evaluation of the relative expression levels from cell line to cell line is an efficient method to ensure high producing cells which maintain the integrated plasmid within the genome. Cells with the recombination sequence inserted at a spot with particularly active transcription will lead to high expression of the marker gene e.g. GFP or LacZ. High expressers can be selected by fluorescence activated cell sorting (FACS) and cloned. At this point it should also be analyzed whether the integrant is a single integrant. This can be performed by real-time PCR and Southern blotting. The preparation of cells having an FRT site at a pre-determined location in the genome was described in e.g. U.S. Pat. No. 5,677,177.

Another method for evaluating relative expression levels from cells transfected with an integrating plasmid is to perform an additional integration-excision step on the cells generated as described above. This pool of selected cells are transfected again, with a plasmid encoding a recombinase corresponding to the recombination site of the integrating plasmid and a second plasmid containing a second selection marker without a start codon, the coding region of which is preceded by a recombination sequence likewise corresponding to the first integrating plasmid. This second plasmid also contains the coding sequence for a fluorescent marker protein (e.g., GFP (or equivalent fluorescent proteins) driven by a suitable promoter. The recombinase mediates integration of this plasmid into the host cell genome where a similar recombination sequence previously has been inserted by the integrating plasmid. Cells with the recombination sequence inserted at a spot with particularly active transcription will lead to high expression of the fluorescent protein. High expressers are selected by fluorescence activated cell sorting (FACS) and cloned. Clones with consistently high expression and containing one copy of the inserted plasmid are transfected with the recombinase and selected by the first selection marker, identifying cells where the second plasmid sequence has been removed by the recombinase, making the first selection marker work again. These cells still contain the first recombination sequence inserted at a transcriptional hot-spot and can now be used for the expression of genes of interest.

Cell lines, which achieve high expression of the marker gene upon integration of a single copy of the plasmid, are used for transfection with the anti-RhD antibody expression library. The recombination site in the host cell is preferably located in a gene or region of particularly active expression, i.e., in a so-called hot-spot.

The Vector for Site-Specific Integration

A suitable vector comprises a suitable recombination site linked to a suitable selection gene different from the selection gene used for construction of the host cell. Suitable selection genes for use in mammalian cell expression include, but are not limited to, genes enabling for nutritional selection, such as the thymidine kinase gene (TK), glutamine synthetase gene (GS), tryptophan synthase gene (trpB) or histidinol dehydrogenase gene (hisD). Further, selection markers are antimetabolite resistance genes conferring drug resistance, such as the dihydrofolate reductase gene (dhfr) which can be selected for with hypoxanthine and thymidine deficient medium and further selected for with methotrexate, the xanthine-guanine phosphoribosyltransferase gene (gpt), which can be selected for with mycophenolic acid, the neomycin phosphotransferase gene (neo) which can be selected for with G418 in eukaryotic cells and neomycin or kanamycin in prokaryotic cells, the hygromycin B phosphotransferase (hyg, hph, hpt) gene which can be selected for with hygromycin, the puromycin N-acetyl-transferase gene (pac) which can be selected for with puromycin or the Blasticidin S deaminase gene (Bsd) which can be selected for with blasticidin. Finally, genes encoding proteins that enables sorting e.g. by flow cytometry can also be used as selection markers, such as green fluorescent protein (GFP), the nerve growth factor receptor (NGFR) or other membrane proteins, or beta-galactosidase (LacZ).

In one aspect of the present invention, the selectable gene is neither preceded by a promoter nor equipped with a translation initiating codon. The promoter and ATG codon is provided at the selected site-specific recombination site. If the vector is integrated at a location other than the selected recombination site in the genome of the host cell, no expression of this second selection gene can occur due to lack of promoter and initiation codon. If integration occurs at the selected recombination site in the genome of the host cell, the second selection gene is expressed and expression of the first selection gene is lost.

Integration may e.g., be carried out using a so-called FRT site/Flp recombinase recognition sequence (5'-gaagttcctattc-cgaagttcctattctctagaaagtataggaacttc-3' (SEQ ID NO 1) or variants thereof) in the genome and on the vector for site-specific integration together with the Flp recombinase or mutants thereof from *Saccharomyces cerevisiae*. However, other recombinase systems may equally well be used, including those of Cre recombinase and a variety of lox sites such as loxP from bacteriophage P1 or variants or mutants thereof, e.g., lox66, lox71, lox76, lox75, lox43, lox44 and lox511 (C. Gorman and C. Bullock, Curr. Opinion in Biotechnology 2000, 11: 455-460) or by using phage integrase ɸC31 or lambda integrase, which carries out recombination between the attP site and the attB site (A. C. Groth et al. PNAS 2000, 97: 5995-6000). Further recombinase systems that could be utilized in the present invention are, but are not limited to, the β-recombinase-six system from bacterial plasmid pSM19035 (Rojo and Alonso 1995), the Gin-gix system from bacteriophage Mu (Crisona et al 1994), the R-RS system from *Zygosaccharomyces rouxii* (Onouchi et al 1995), or Tn3 resolvase which recognize res recombination sites (Stark et al 1994) or the XerC/D system from *E coli* (Blakely and Sherratt 1994).

A further variant of the site-specific recombination system, termed recombinase cassette mediated exchange (RMCE), uses non-homologous recombination sites. In such a system, two non-identical recombination sites are introduced into the host genome for the generation of specific target sites. Recombination sites corresponding to those flanking the target site also flank the construct containing the gene of interest. Such a system has been described in WO 99/25854, which is hereby incorporated by reference in its entirety. The use of non-homologous recombination sites was shown to suppress excision of the gene of interest from the chromosome. The non-identical recombination sites can be composed of any of the recombination sites described above as long as the corresponding recombinases are provided and the sites cannot recombine with each other. For example, non-identical recombination sites could consist of a FRT site and a mutant FRT site utilizing a Flp recombinase for integration (Schlake and Bode 1994, Biochemistry 33, 12746-12751), a loxP site and a mutant non-compatible loxP site utilizing the Cre recombinase (Langer et al 2002, Nucleic Acids Res. 30, 3067-3077) or a FRT site and a loxP site utilizing Flp and Cre recombinases for the integration (Lauth et al 2002, Nucleic Acids Res. 30, 21, e115).

Further, a system using two different FRT sites has been described in Verhoeyen et al., Hum. Gene Ther. 2001 12, 933-44. In this approach the integrating plasmid is transferred to the host cells by retroviral infection. The plasmid consists of a combination of a reporter gene and a first selection marker gene as well as the retroviral elements required for infection. The retroviral 3'LTR contains two different FRT sites. A non functional second selection marker gene, which lacks a promoter and the translation initiating codon is located 3' to these sites. During the process of retroviral infection the 3'LTR sequence is copied to the 5'LTR. This results in the flanking of the reporter gene and the first selection marker gene by two different FRT sites on each side. The sequence between the outer FRT sites can be exchanged against an anti-RhD antibody-encoding nucleic acid segment under the control of a strong promoter. The cassette containing the anti-RhD antibody-encoding nucleic acid segment is flanked by the same set of FRT sites. The reaction is catalyzed by the Flp recombinase. In the transfected exchange plasmid an IRES element and a translation initiating codon are located further downstream of the nucleic acid segment. After replacement of the integrated cassette the non functional selection marker gene located in the 3' LTR sequence outside the FRT sites is activated by the translation initiating codon provided by the cassette constituting the anti-RhD antibody-encoding nucleic acid segment. The exchange status can further be enriched if a negative selection marker (e.g. thymidine kinase) is present in the integrating vector.

The integrating vector can also be transferred to the host cells by standard transfection. In this case the integrating cassette is flanked by an FRT site at the 5' end and a different FRT' site at the 3' end. The ATG-deficient second resistance marker gene is positioned further downstream of the 3' FRT' site. The exchange for an anti-RhD antibody-encoding nucleic acid segment proceeds as described for the retroviral system.

Another system that prevents excision of the anti-RhD antibody-encoding nucleic acid segment after its site-specific integration into the chromosome is the ɸC31 integrase, also mentioned above. This system has been described thoroughly in patent applications WO 01/07572 and WO 02/08409, hereby incorporated by reference in their entirety.

Preferably the integrating vector is an isotype-encoding vector, where the constant regions (preferably including introns) are present in the vector prior to insertion of the $V_H$ and $V_L$ comprising segment from the screening vector. The constant regions present in the vector can either be the entire heavy chain constant region ($CH_1$ to $CH_3$ or to $CH_4$) or the constant region encoding the Fc part of the antibody ($CH_2$ to $CH_3$ or to $CH_4$). The light chain Kappa or Lambda constant region may also be present prior to transfer. The choice of the number of constant regions present, if any, depends on the screening and transfer system used. The heavy chain constant regions can be selected from the isotypes IgG1, IgG2, IgG3, IgG4, IgA1, IgA2, IgM, IgD and IgE. Preferred isotypes are IgG1 and/or IgG3.

Figure 7:
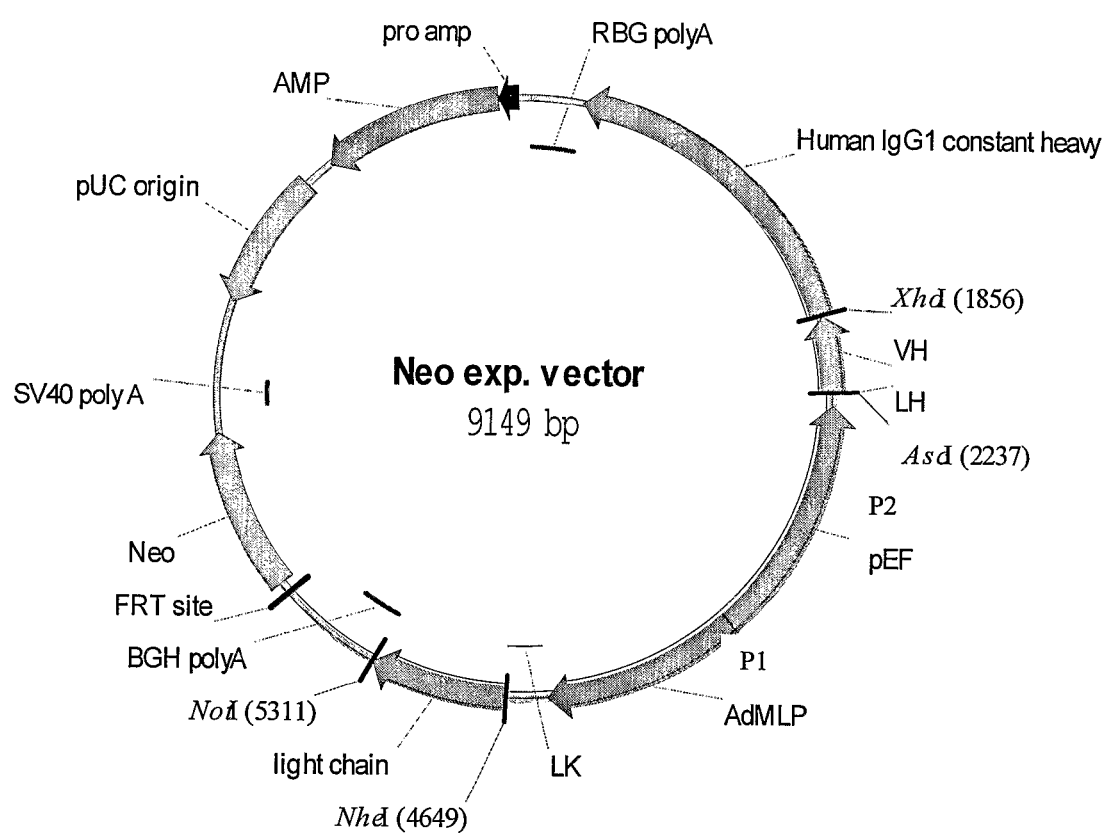
FIG. 7: Neo exp. vector: Schematic representation of the mammalian expression vector used to facilitate site-specific integration into the genome of a host cell of the anti-RhD antibody-encoding nucleic acid segments. The vector comprises the following elements: pro amp and AMP=promoter and ampicillin resistance gene. pUC origin=pUC origin of replication. Restriction enzyme sites: XhoI, AscI, NheI and NotI. P1/P2=promoter set driving the expression of the light chain and IgG heavy chain, respectively. LH=heavy chain leader sequence. VH=Sequence coding for the variable heavy chain of an anti-RhD Ab. Human IgG1 constant heavy=Sequences coding for the human constant IgG1 heavy chain. RBG polyA=Rabbit β-globin polyA signal sequence. BGH polyA=Bovine Growth Hormone polyA signal sequence. LK=kappa chain leader sequence. Light chain=Sequence coding for the light chain of an anti-RhD Ab. FRT site=Flp recombinase recognition sequence. Neomycin=Neomycin resistance gene. SV40 polyA=Simian virus 40 polyA signal sequence.

Further, the vector for site-specific integration of the anti-RhD antibody-encoding nucleic acid segment contains suitable promoters or equivalent sequences directing high levels of expression of each of the $V_H$ and $V_L$ chains. Preferably the promoters are of mammalian origin. The $V_H$ and $V_L$-encoding sequences are placed as pairs in the vector used for integration (one pair per vector molecule), thereby ensuring that they will be kept together throughout the integration process. Preferably, the promoters are located within the anti-RhD antibody-encoding nucleic acid segment. For bi-directional expression a head-to-head promoter configuration in the expression vector is used (FIG. 7). For unidirectional expression two promoters, one in front of the $V_H$ genetic element and one in front of the $V_L$ genetic element, or one promoter in front of $V_H$ or $V_L$ combined with an IRES sequence between the heavy and light genetic elements, can be used to achieve expression.

A nucleic acid sequence encoding a functional leader sequence can be included in the expression vector to direct the gene product to the endoplasmic reticulum or a specific location within the cell such as an organelle. A strong polyadenylation signal sequence can be situated 3' of the heavy chain and light chain-encoding sequences. The polyadenylation signal ensures termination and polyadenylation of the nascent RNA transcript and is correlated with message stability.

The expression vector for site-specific integration can carry additional transcriptional regulatory elements, such as enhancers or UCOE (ubiquitous chromatin opening elements) for increased expression at the site of integration. Enhancers are nucleic acid sequences that interact specifically with cellular proteins involved in transcription. The UCOE opens chromatin or maintains chromatin in an open state and facilitates reproducible expression of an operably-linked gene (described in more detail in WO 00/05393, hereby incorporated by reference in its entirety). When one or more of the regulatory elements described in the above are integrated into the chromosome of a host cell they are termed heterologous regulatory elements.

Establishing an Expression System for High-Level Expression of a Polyclonal Protein Methods for introducing a nucleic acid sequence into a cell are known in the art. These methods typically include the use of a DNA vector to introduce the sequence of interest into the cell, the genome or an extra-chromosomal element. Transfection of cells may be accomplished by a number of methods known to those skilled in the art, including calcium phosphate precipitation, electroporation, microinjection, liposome fusion, RBC ghost fusion, protoplast fusion, and the like.

For the transfection of a host cell line, a library of anti-RhD antibody expression vectors, wherein each individual vector comprises one single copy of a nucleic acid segment, encoding a distinct member of the anti-RhD rpAb, is used. This library of anti-RhD antibody expression vectors collectively encodes the anti-RhD rpAb. Suitable vectors for site-specific integration were described in the previous section. The individual vectors constituting the library of anti-RhD antibody-encoding nucleic acid segments can either be mixed together into a single composition, or the individual vectors encoding an individual member of the anti-RhD rpAb can be kept in separate compositions or in mixtures of approximately 5 to 50 individual vectors of the library in a composition.

The generation of a recombinant polyclonal manufacturing cell line and the production of a recombinant polyclonal antibody from such a cell line can be obtained by several different transfection and manufacturing strategies. These strategies are outlined in FIG. 1A and described in more detail below.

One way of generating the recombinant polyclonal manufacturing cell line, is to use a library of vectors mixed together into a single composition for the transfection of the host cell line. This method is termed bulk transfection or transfection in bulk (all the individual members of the library are transfected into the host cell line in one tube). Generally, the vector and host cell design previously described will ensure that a polyclonal cell line will be obtained upon appropriate selection. In such a cell line a majority of the individual cells have integrated one copy of a nucleic acid segment, encoding a distinct member of the anti-RhD rpAb from the library of anti-RhD antibody expression vectors into the genome. The single copy of the nucleic acid segment is integrated into a single specific site of the genome of each cell in the collection of cells, thereby generating a polyclonal cell line comprised of individual cells expressing individual members of the anti-RhD rpAb. Preferably a frozen stock of the polyclonal cell line is generated before initiation of the anti-RhD rpAb manufacturing.

Another way of generating the recombinant polyclonal manufacturing cell line is to split the library of anti-RhD antibody expression vectors into fractions, containing approximately 5 to 50 individual vectors of the library before transfection. Preferably, a fraction of the library constitutes 10 to 15 individual vectors. Each composition is then transfected into an aliquot of host cells. This method is termed semi-bulk transfection. The number of aliquots transfected will depend on the size of the library and the number of individual vectors in each fraction. If the library for example constitutes 50 distinct variant members, which are split into fractions containing 10 distinct variant members in a composition, 5 aliquots of host cells would need to be transfected with a library composition constituting a distinct fraction of the original library. The aliquots of host cells are selected for site-specific integration. Preferably, the distinct aliquots are selected separately. However, they can also be pooled before selection. To obtain the desired polyclonal cell line for manufacturing, the aliquots can be mixed before generating the frozen stock, immediately after they have been retrieved from the stock or after a short proliferation time. Optionally, the aliquots of cells are kept separate throughout production, and the polyclonal antibody composition is assembled by combining the products of each aliquot rather than the aliquots of cells before production.

A third way of generating the recombinant polyclonal manufacturing cell line, is a high throughput method in which host cells are transfected separately using the individual vectors constituting the library of anti-RhD antibody expression vectors. This method is termed individual transfection. The individually transfected host cells are preferably selected for site-specific integration separately. However, they can also be pooled before selection. The individual cell clones generated upon selection may be analyzed with respect to proliferation time and integration pattern and preferably, those with similar growth rates and a single site-specific integrant are used to generate a frozen library stock. The individual cell clones can be mixed to obtain the desired polyclonal cell line before generating the stock, immediately after they have been retrieved from the stock, or after a short proliferation time. Alternatively, the individually transfected host cells are mixed even earlier, namely before selection is performed.

A shared feature in the manufacturing strategies outlined in the above is that all the individual members constituting the anti-RhD rpAb can be produced in one, or a limited number of bioreactors, with approximately 5 to 10 as the maximum. The only difference is the stage at which one chooses to generate the collection of cells that constitutes the recombinant polyclonal manufacturing cell line.

The host cell line to be used for expression and production of an anti-RhD rpAb has at least one nucleic acid sequence recognizable by a recombinase enzyme. The preparation of such a host cell line was described in the section "The host cell".

The vector for site-specific integration is preferably integrated in a predefined genomic locus that mediates high-level expression, a so-called hot-spot.

If expression levels need to be increased, gene amplification can be performed using selection for a DHFR gene or a glutamine synthetase (GS) gene. This requires the use of vectors comprising such a selection marker.

The following description is one example of how to obtain a recombinant polyclonal antibody manufacturing cell line, where scrambling of the chains is minimal if existing at all.

Nucleic acid segments containing a universal promoter cassette for constitutive expression having two promoters placed in opposite transcriptional direction, such as a head-to-head construction surrounded by the variable heavy chain and the whole of the kappa light chain is constructed, allowing transfer of the whole construct into a vector for site-specific integration said vector comprising a FRT site and a neomycin resistance gene and the heavy chain constant region. It is contemplated that a promoter cassette for inducible expression can also be used. Furthermore, the promoters can be placed head-to-tail for unidirectional transcription. CHO-Flp-In cells (Invitrogen, Carlsbad, Calif.) which stably express the lacZ-Zeocin fusion gene, are used for the experiment, rendering the cells resistant to the antibiotic Zeocin. The cells are maintained in a suitable media medium containing Zeocin. The cells are co-transfected in bulk with a plasmid expressing the Flp recombinase and the library of anti-RhD antibody expression vectors for site-specific integration encoding the anti-RhD rpAb and a different selection marker (neomycin). After transfection, the cells are cultivated in the presence of neomycin. Cells that exhibit resistance to neomycin are then preferably adapted to growth in suspension as well as serum free conditions, this can be performed in one or two steps and with or without selection pressure. Alternatively, the cells are adapted to grow in suspension under serum free conditions prior to transfection of the cells. When the polyclonal cell line has been adapted to the appropriate conditions scaling up can be initiated using different culture systems, such as conventional small culture flasks, Nunc multilayer cell factories, small high yield bioreactors (MiniPerm, INTEGRA-CELLine, wavebags, BelloCell) and spinner flasks to hollow fiber- and bioreactors. The suitable production time and choice of final bioreactor size are dependent on the desired yield of protein from the batch and expression levels from the cell line. Times might vary from a couple of days up to three month. The cells are tested for antibody production using ELISA. The expressed anti-RhD rpAb is isolated from the supernatant. The anti-RhD rpAb is purified and characterized. Examples of purification and characterization procedures are described later.

Clonal Diversity/Polyclonality

One of the characteristics of a polyclonal antibody is that it is constituted of a number of individual antibody molecules where each antibody molecule is homologous to the other molecules of the polyclonal antibody, but also has a variability that is characterized by differences in the amino acid sequence between the individual members of the polyclonal antibody. These differences are normally confined to the variable region in particular the CDR regions, CDR1, CDR2 and CDR3. This variability of a polyclonal antibody can also be described as diversity on the functional level, e.g., different specificity and affinity with respect to different antigenic determinants on the same or different antigens located on one or more targets. In a recombinant polyclonal antibody the diversity constitutes a sub-set of the diversity observed in a donor derived immunoglobulin product. Such a sub-set is carefully selected and characterized with respect to its ability to bind desired target antigens, in this particular case the Rhesus D antigen.

One of the concerns with respect to production of a recombinant polyclonal antibody may be whether the clonal diversity is maintained in the final product. The clonal diversity may be analyzed by RFLP or sequencing of (RT)-PCR products from the cells expressing the anti-RhD rpAb. The diversity can also be analyzed on protein level by functional tests (e.g., ELISA) on the anti-RhD rpAb produced by the cell line, by anti-idiotypic antibodies to individual members or by chromatographic methods.

Clonal bias, if it exists, can be estimated by comparing the clonal diversity of the initial library, used for transfection, with the diversity found in the pool of cells (polyclonal cell line) expressing the anti-RhD rpAb.

Clonal diversity of an anti-RhD rpAb can be assessed as the distribution of individual members of the polyclonal composition. This distribution can be assessed as the total number of different individual members in the final polyclonal antibody composition compared to the number of different encoding sequences originally introduced into the cell line during transfection. In this case sufficient diversity is considered to be acquired when at least 50% of the encoding sequences originally used in the transfection can be identified as different individual members of the final anti-RhD rpAb. Preferably at least 75% of the anti-RhD antibody-encoding sequences used for transfection can be identified as antibodies in the final composition. Even more preferred at least 85% to 95%, and most preferred a 100% of the anti-RhD antibody-encoding sequences used for transfection can be identified as antibodies in the final composition.

The distribution of individual members of the anti-RhD rpAb composition can also be assessed with respect to the mutual distribution among the individual members. In this case sufficient clonal diversity is considered to be acquired if no single member of the composition constitutes more than 75% of the total number of individual members in the final anti-RhD rpAb composition. Preferably, no individual member exceeds more that 50%, even more preferred 25% and most preferred 10% of the total number of individual members in the final polyclonal composition. The assessment of clonal diversity based on the distribution of the individual members in the polyclonal composition can be performed by RFLP analysis, sequence analysis or protein analysis such as the approaches described later on for characterization of a polyclonal composition.

Clonal diversity may be reduced as a result of clonal bias which can arise a) during the cloning process, b) as a result of variations in cellular proliferation, or c) through scrambling of multiple integrants. If such biases arise, each of these sources of a loss of clonal diversity is easily remedied by minor modifications to the methods as described herein.

In order to limit bias introduced by cloning of the variable domains into the appropriate vectors, the transfer of the genes of interest from one vector to another may be designed in such a way that cloning bias is limited. Mass transfer techniques and a careful selection of the *E. coli* strain used for amplification can reduce the cloning bias. Another possibility is to perform an individual transfer of each polynucleotide encoding an individual member of the polyclonal antibody, between screening vectors and vectors for site-specific integration.

It is possible that variations in cellular proliferation rates of the individual cells in the cell line could, over a prolonged period of time, introduce a bias into the anti-RhD rpAb expression, increasing or reducing the presence of some members of the anti-RhD rpAb expressed by the cell line. One reason for such variations in proliferation rates could be that the population of cells constituting the starting cell line used for the initial transfection is heterogeneous. It is known that individual cells in a cell line develop differently over a prolonged period of time.

To ensure a more homogeneous starting material, subcloning of the cell line prior to transfection with the library of interest may be performed using a limiting dilution of the cell line down to the single cell level and growing each single cell to a new population of cells (so-called cellular sub-cloning by limiting dilution). One or more of these populations of cells are then selected as starting material based on their proliferation and expression properties.

Further, the selection pressure used to ensure that only cells that have received site-specific integrants will survive, might affect proliferation rates of individual cells within a polyclonal cell line. This might be due to the favoring of cells that undergo certain genetic changes in order to adapt to the selection pressure. Thus, the choice of selection marker might also influence proliferation rate-induced bias. If this occurs, different selection markers should be tested. In cases where selection is based on a substance that is toxic to the cells, the optimal concentration should be tested carefully, as well as whether selection is needed throughout the entire production period or only in the initial phase.

An additional approach to ensure a well defined cell population is to use fluorescence activated cell sorting (FACS) after the transfection and selection procedures. Fluorescence labeled antibodies can be used to enrich for highly productive cells derived from a pool of cells transfected with IgG constructs (Brezinsky et al. J. 2003. Immunol Methods 277, 141-155). This method can also be used to sort cells expressing similar levels of immunoglobulin, thereby creating a homogenous cell population with respect to productivity. Likewise, by using labeling with the fluorescent dye 5,6-carboxylfluorescein diacetate succinimidyl ester (CFSE) cells showing similar proliferation rates can be selected by FACS methods. Further, differences in expression levels of the individual members of the anti-RhD rpAb may also introduce a bias into the final product over a prolonged period of time.

If the polyclonal cell line is generated by mixing separately transfected clones after selection (the $3^{rd}$ approach in FIG. 1A), the following selection criteria may be set up for the individual clones at the cell culture level prior to mixing: proliferation rates have to be between 24 and 32 hours, the productivity should exceed 1.5 pg antibody per cell per day, and the culture should show a homogenous cell population assessed by an intra cellular staining method. If desired a more homogenous cell population for each individual clone can be obtained with the surface staining method described by Brezinsky prior to mixing the individual clones by gating on a particular area of the population in connection with the FACS analysis.

Even if a proliferation rate-induced, or productivity-induced bias occurs, the loss or over-representation of individual members might not necessarily be critical, depending on the diversity requirements of the final anti-RhD rpAb product.

In cells with site-specific single integrants, the cells will only differ in the sequence of the variable regions of the antibodies to be expressed. Therefore, the different cellular effects imposed by variation in integration site and gene regulatory elements are eliminated and the integrated segments have minimal effects on the cellular proliferation rate. Neither scrambling nor multiple integrations is likely to cause problems in the proliferation rate of the manufacturing cell line, since these are rare events. Random integrations generally occur with an efficiency of approximately $10^{-5}$, whereas site-specific integration occurs with an efficiency of approximately $10^{-3}$. If multiple integrations should unexpectedly pose a problem, an alternative is to repeat the transfection with the library of anti-RhD antibody expression vectors, because the likelihood that the event will reoccur is very small, as described above.

Considering statistics, bulk transfection of a large number of cells also constitutes a way to circumvent an undesired clonal bias. In this approach, a host cell line is transfected in bulk with the library of anti-RhD antibody expression vectors. Such a library constitutes many copies of each distinct member of the library. These copies should preferably be integrated into a large number of host cells. Preferably at least 100, 1000, 10000 or 100000 individual cells are transfected with copies of distinct members of the library of variant nucleic acid segments. Thus, if a library of distinct variant nucleic acid segments is composed of 1000 distinct members which are each integrated into 1000 individual cells, $10^6$ clones containing a site-specifically integrated anti-RhD antibody-encoding segment should arise from the transfection. In this manner the gausian curve of individual cell doubling rates should influence the general population only in very small degrees. This will increase the probability of keeping the clonal composition constant, even if a low percentage of the manufacturing cells should exhibit aberrant growth and/or expression properties.

Alternatively the semi-bulk transfection or individual transfection methods previously described may be used.

Establishment of a Polyclonal Working Cell Bank (pWCB)

The section "Establishing an expression system for high-level expression of a polyclonal protein" describes three alternative ways of establishing a polyclonal manufacturing cell line. The section describes the generation of a frozen library stock which is constituted of a collection of cells, obtained by bulk or semi-bulk transfection, where each individual cell in the library stock is capable of expressing an individual member from a library of anti-RhD antibody expression vectors. Preferably, the clonal diversity requirements already described is fulfilled by the collection of cells, such that essentially all members of the library can be expressed from a frozen library stock ampoule, when thawed and expanded to establish a polyclonal manufacturing cell line. In the bulk transfection and semi-bulk transfection approaches the frozen library stock, can also be considered as a polyclonal working cell bank (pWCB), in that a single vial from the frozen library stock can be thawed and expanded into a polyclonal manufacturing cell line.

Alternatively, in the previously described third approach for the generation of a recombinant polyclonal manufacturing cell line, the frozen library stock is composed of separate cell lines, which have been individually transfected with an individual member of a library of anti-RhD antibody expression vectors. The transfectants are selected for stable expression of the integrated vector-derived nucleic acid segment from their genome. Preferably, the nucleic acid segments are integrated site-specifically into one or more sites in the genome of the transfectants, and even more preferred in a single site of the genome. The transfected cells obtained e.g. from clonal colonies upon selection may either be isolated and maintained as single clones or pooled to generate a pool of clones expressing the same anti-RhD antibody. In the present invention a single clone of cells as well as pool of clones expressing the same antibody is termed an individual cell line. Thus, if the library of anti-RhD antibody expression vectors constituted 25 individual members, the frozen library stock, in this third approach, would be composed of 25 individual cell lines (not a mixture of cell lines) each expressing an individual member from the library of anti-RhD antibody expression vectors.

Hence, one vial from this library stock will result in the generation of a monoclonal anti-RhD antibody if used for manufacturing.

The present invention exemplifies a library of anti-RhD antibody expression vectors. However, the generation of a frozen library stock is independent of the antigen specificity of the polyclonal protein produced from a library comprised of variable region-encoding nucleic acid segments and may be used with any other library comprised of antibody $V_H$ and $V_L$-encoding nucleic acid segments, or T cell receptor (TcR) α and β-, or γ and δ-encoding nucleic acid segments. A library comprised of variable region-encoding nucleic acid segments can in addition to the variable regions also encode one or more constant regions. Thus, a library comprised of antibody $V_H$ and $V_L$-encoding nucleic acid segments may result in Fv, scFv, Fab molecules or full-length antibody molecules, and a library comprised of TcR variable region-encoding segments may result in molecules composed of TcR variable domain fragments, soluble TcRs or full-length TcRs.

In situations where the frozen library stock is composed of individual cell lines it will be appropriate to generate a pWCB which can be used for the establishment of the polyclonal manufacturing cell line by thawing and expanding the contents of a single ampoule. The individual cell lines used to generate such a pWCB are either obtained from i) a single clone or ii) a pool of clones (a pool of single colonies obtained after selection). The clones have been obtained from host cells individually transfected with, and selected for stable expression of an individual member of a library comprising variable region-encoding nucleic acid segments, such as antibody $V_H$ and $V_L$-encoding segments or TcR α and β-, or γ and δ-encoding segments. Selection for stable expression is performed by procedures known in the art, e.g. using selection marker genes. In a preferred embodiment of the present invention the individual cell lines are obtained from cloned or subcloned cells, e.g. by subjecting a cell line originating from i) or ii) (see previous description) to limiting dilution or single cell FACS analysis and selection, or by selecting high expression clones e.g. using a robot like the ClonePix FL (see below). The individual cell lines used to generate the pWCB as described above may be pre-stored in a frozen library stock of individual cell lines, from which an ampoule of each individual cell line is thawed and expanded prior to the generation of a pWCB. Preferably, the individual cell lines express full-length antibodies with properties that differ from the properties of the antibodies produced by the other members of the pWBC, e.g. different antigen specificity, different affinity, different variable or CDR regions and/or different constant regions.

Each cell line used to generate the pWCB, produces a different member of a polyclonal protein. Preferably, each distinct member of the polyclonal protein binds a particular antigen. Additionally, it is preferred that each distinct member is produced from a single specific site in the genome of each host cell. A pWCB is generated by mixing a predefined number of cells from each individual cell line. Preferably, the cells are mixed in equal numbers (a 1:1 ratio), although other ratios also may be desired (see later). The mixture of cells is frozen down in aliquots, in that they are distributed into a number of vials with a defined number of cells in each vial. These vials are frozen and stored as the pWCB for later manufacturing purposes. Preferably, the number of vials constituting the pWCB exceeds 10, 25, 50, 75, 100, 200, 500 or 1000 vials. The individual vials in a pWCB may be thawed at different points in time generating different batches of the polyclonal manufacturing cell line which are capable of producing a polyclonal protein with essentially the same composition from batch to batch (See Example 5).

In an alternative approach of the present invention, the polyclonal manufacturing cell line may be expanded from a sub-pWCB, which is derived from a pWCB. The sub-pWCB is generated by thawing a single vial from a pWCB and expanding the cells for a number of generations sufficient to produce a total number of cells which can be frozen down in a new series of aliquots (the sub-pWCB), with approximately the same number of cells in each sub-pWCB aliquot as in the pWCB vial originally used to generate the sub-pWCB. The advantage of this approach is that the pWCB now serves as a master cell bank as known from other recombinant protein production protocols. Thus, in this approach the pWCB may also be termed a polyclonal master cell bank (pMCB). When the sub-pWCB has been exhausted, it is possible to generate a new sub-pWCB from an aliquot of the pWCB/pMCB. This approach will therefore require a significantly lower amount of work than would be required to expand the individual cell lines from the frozen library stock and mixing a new pWCB. Further, in the event that the sub-pWCB is exhausted, the chance of producing further batches of the polyclonal manufacturing cell line, which are capable of producing a polyclonal protein with essentially the same composition from batch to batch is increased. The principle of generating a pWCB/pMCB and a sub-pWCB from individually transfected host cells is illustrated in FIG. 1B.

The advantage of producing a pWCB or pMCB by mixing individual cell lines which have been obtained by individual transfection, compared to the direct generation of a pWCB of pMCB by bulk transfection or semi-bulk transfection, is that it is possible to perform additional analysis and selections of the individually transfected cell lines prior to generation of the pWBC or pMCB. This may ensure a more stable polyclonal manufacturing cell line which fulfills the diversity requirements already described. In the following pWCB is to be understood as pWCB or pMCB.

In an additional embodiment of the present invention, individual cell lines which have been selected for stable expression of an individual member of a library of variable region-encoding nucleic acid segments as described above, are further characterized with respect to their proliferation rates and/or productivity prior to generation of a pWCB. In a preferred embodiment cell lines with similar proliferation rates or productivity are selected for the generation of a pWCB. Even more preferred, cell lines with similar productivity as well as similar proliferation rates are selected for the generation of the pWCB. Preferably, the cell lines are adapted to serum free suspension culture prior to the characterization of proliferation rates and/or productivity. Alternatively, the parental cells used for transfection are adapted to serum free suspension culture prior to transfection.

Proliferation rates can be assessed by methods known in the art, for example as described in example 2 of the current invention. Proliferation rates for mammalian cell lines should be between 18 and 100 hours, preferably between 22 and 40 hours and most preferred between 24 and 32 hours. The productivity should exceed 0.5 pg protein per cell per day (pg/(cell*day)), preferably it should exceed 1, 1.5, 3, 5 or 8 pg/(cell*day). Further, the cell line should show a homogenous cell population with respect to expression when assessed by an intra-cellular staining method. If desired a more homogeneous cell population for each individual cell line can be obtained by cloning e.g. by the FACS sorting methods described below.

In further embodiments of the present invention, the individual cell lines are FACS sorted to identify cells with a homogeneous expression level, after the transfection and selection procedures. The possibility of sorting for individual high-expressing clones or a sub-pool of cells with high expression levels by gating on a particular area of the population in connection with the FACS analysis is therefore an additional embodiment of the present invention. The generation of cloned cells by FACS analysis and selection is particularly useful when the individual cell lines are generated from a pool of clones.

Fluorescence labeled antibodies can be used to sort for cells expressing high levels of the desired protein e.g. antibody or TcR, thereby creating a homogeneous cell population with respect to productivity. This technique is based on the observation that secreted proteins can be detected on the surface of the cell secreting them, and the amount of surface protein apparently corresponds to the expression levels of the individual cell. The high producing cells can therefore be single cell sorted upon staining with a labeled antibody, followed by analysis by FACS. The technique has been described by Brezinsky (Brezinsky et al. J. 2003. Immunol Methods 277, 141-155).

An alternative sorting technique is based on the coupling of a ligand, with specificity to the protein expressed from the cells, to the surface of the cells. For example an anti-Fc antibody or an anti-idiotype antibody can be coupled to the surface of the protein secreting cell population via biotin. The antibodies secreted by an individual cell are then captured by the anti-Fc antibodies on the surface of that cell. Following this, the high producing cells can be sorted by FACS upon staining with a labeled antibody. This technique has been described in EP 667896.

To obtain cell lines with a homogeneous high expression levels, single cells having a high expression level are analyzed based on the FACS profile obtained by one of the described techniques. The individual cell clones are then expanded and potentially analyzed with respect to proliferation rates and productivity as described above. Alternatively, a sub-pool of cells having the highest expression level as identified by the FACS profile is collected by sorting. The sub-pool of cells from the individual cell line can likewise be analyzed with respect to proliferation rates and productivity if desired.

In an alternative embodiment of this invention, a robot such as the ClonePixFL robot (Genetix, UK) is used to select clones exhibiting high expression levels and/or similar growth properties. This is done as follows: The colonies obtained after transfection and selection are grown in a semi-solid medium which allows for detection of high-producing colonies by capturing the secreted protein product in the immediate proximity of the colony. The production level from each colony is determined by means of immunofluorescence labeling of the protein expressed by the cells followed by image software selection of the best clones based on pre-determined selection criteria such as expression level and growth properties. Furthermore, the size (reflecting the cell proliferation rate) of each colony can be assessed by the robot using light detection imaging. Colonies with the desired production and/or growth properties are then isolated by the robot and transferred to 96-well plates for further propagation.

Preferably, individual cell lines with similar productivity are selected for the generation of the pWCB. In a preferred embodiment individual cell lines constituting the pWCB are generated from cloned cells, e.g. obtained by single cell sorting, limiting dilution or robot picking, with a high expression level or from a pool of cells with high expression level.

In the present invention, both individual cell lines obtained from a single colony of cells isolated after transfection and selection as well as individual cell lines obtained from a clone obtained e.g. by single cell FACS sorting, are termed cloned cell lines. In a preferred embodiment such cloned cell lines are used to generate the pWCB.

In further embodiments of the present invention, the individual cell lines are mixed at different ratios upon generation of a pWCB. The individual cell lines can be mixed according to predetermined criteria based on the properties of the individual cell lines and/or individual protein member expressed by said cell line, e.g. specific productivity or binding affinity. For example, individual cell lines expressing certain antibodies binding particularly critical antigens or epitopes can be supplied in excess of the remaining member cell lines of the pWCB, e.g. in 2-fold, 3-fold, 5-fold or 10-fold higher amounts. One member cell line may for example be added in a 2:1 ratio over all the other members, e.g. $4 \times 10^6$ cells of member 1 and $2 \times 10^6$ cells of each of the remaining member cell lines.

In a preferred embodiment of the present invention, a pWCB for production of an Anti-RhD rpAb is generated. Even more preferred such a pWCB is generated such that cell lines which produce antibodies with reactivity against a RhD category VI antigen constitute at least 5%, 8%, 10%, 12%, 15%, 20% or 25% of the total amount of cells included in the pWCB.

This approach of differentiated ratios of the individual cell lines in the pWCB may also be adopted to circumvent differences in proliferation rates and productivity among the individual cell lines, in particular if these have not been selected for similarity in these traits. Hence, if one or more of the individual cell lines have a slower proliferation rate, i.e. longer doubling times, compared to other members of the polyclonal working cell bank which are characterized by a faster proliferation rate, but this slower proliferation rate is not associated with a particular high productivity, this particular member(s) may be added to the pWCB in an increased amount to compensate for its slow growth. For example may a cell line with a proliferation rate of 50 hours be added in a 2:1 ration if the remaining cell lines constituting the pWCB have proliferation rates between 22 and 30 hours. Likewise, the ratio of cell lines with short doubling times may be reduced to ensure that these will not take over during manufacturing. Further, the ratios of the individual cell lines in a pWCB may be adjusted upon analysis of the polyclonal protein products produced from the polyclonal manufacturing cell lines generated from the pWCB. Such adjustments may for example be made based on IEX profiles or equivalent characterization tools. If such an analysis shows that one or more particular protein members are produced in an increased amount compared to the remaining members, a new pWCB may be generated, wherein the ratio of the cell lines producing these particular protein members are reduced. And visa versa, if a particular member is produced in a low amount, a pWCB with an increased ratio of the cell line producing this member may be generated.

Purification of an Anti-RhD rpAb from Culture Supernatant

Isolation of anti-RhD rpAb from culture supernatants is possible using various chromatographic techniques that utilize differences in the physico-chemical properties of proteins, e.g. differences in molecular weight, net charge, hydrophobicity, or affinity towards a specific ligand or protein. Proteins may thus be separated according to molecular weight using gel filtration chromatography or according to net charge using ion-exchange (cation/anion) chromatography or alternatively using chromatofocusing.

Affinity chromatography combined with subsequent purification steps such as ion-exchange chromatography, hydrophobic interactions and gel filtration has frequently been used for the purification of IgG (polyclonal as well as monoclonal) from different sources e.g., ascites fluid, cell culture supernatants and serum. Affinity purification, where the separation is based on a reversible interaction between the anti-RhD antibodies and a specific ligand coupled to a chromatographic matrix, is an easy and rapid method, which offers high selectivity, usually high capacity and concentration into a smaller volume. Specific ligands in the form of peptides capable of binding to anti-RhD antibodies may be obtained according to the method described in EP 1 106 625 using peptide phage display. Protein A and protein G, two bacterial cell surface proteins, have high affinity for the $F_c$ region, and have, in an immobilized form, been used for many routine applications, including purification of polyclonal IgG and its subclasses from various species and absorption and purification of immune complexes.

Following affinity chromatography, downstream chromatography steps, e.g. ion-exchange and/or hydrophobic interaction chromatography, can be performed to remove host cell proteins, leaked Protein A, and DNA. With the protein A affinity and cation exchange chromatography it has been observed that pH-values above 5 may cause precipitation of the anti-RhD rpAb. Thus buffers should be adjusted carefully with appropriate buffering agents, e.g. Tris or acetate.

Gel filtration, as a final purification step, can be used to remove contaminant molecules such as dimers and other aggregates, and transfer the sample into storage buffer. Depending on the source and expression conditions it may be necessary to include an additional purification step to achieve the required level of antibody purity. Hydrophobic interaction chromatography or ion-exchange chromatography are thus frequently used, in combination with Protein A and gelfiltration chromatography, to purify antibodies for therapeutic use.

In order to purify other classes of antibodies, alternative affinity chromatography media have to be used since proteins A and G do not bind IgA and IgM. An immuno-affinity purification can be used (anti-IgA or anti-IgM monoclonal antibodies coupled to solid phase) or, alternatively, multistep purification strategies including ion-exchange and hydrophobic interaction can be employed.

Structural Characterization of Anti-RhD rpAb

Structural characterization of polyclonal antibodies requires high resolution due to the complexity of the mixture (clonal diversity, heterogeneity and glycosylation). Traditional approaches such as gel filtration, ion-exchange chromatography or electrophoresis may not have sufficient resolution to differentiate among the individual antibodies in the anti-RhD rpAb. Two-dimensional polyacrylamide gel electrophoresis (2D-PAGE) has been used for profiling of complex protein mixtures followed by mass spectrometry (MS) or liquid chromatography (LC)-MS (e.g., proteomics). 2D-PAGE, which combines separation on the basis of a protein's charge and mass, has proven useful for differentiating among polyclonal, oligoclonal and monoclonal immunoglobulin in serum samples. However, this method has some limitations. Chromatographic techniques, in particular capillary and LC coupled to electrospray ionization MS are increasingly being applied for the analysis of complex peptide mixtures. LC-MS has been used for the characterization of monoclonal antibodies and recently also for profiling of polyclonal antibody light chains. The analysis of very complex samples requires more resolving power of the chromatographic system, which can be obtained by separation in two dimensions (or more). Such an approach is based on ion-exchange in the first dimension and reversed-phase chromatography (or hydrophobic interaction) in the second dimension optionally coupled to MS.

Functional Characterization of Anti-RhD rpAb

An anti-RhD rpAb antibody can for example be characterized functionally through comparability studies with anti-D immunoglobulin products or anti-RhD mAbs. Such studies can be performed in vitro as well as in vivo.

In vitro functional characterization methods of anti-RhD rpAb could for example be phagocytosis assays ($^{51}$Cr-based or FACS based), antibody dependent cellular cytotoxicity (ADCC) and rosetting assay. Briefly described the assays are performed as follows:

ADCC Assay ($^{51}$Cr Based):

Human PBMC are used as effector cells and RhD negative and positive RBC (0 in the AB0 system) are used as targets. First, the RBC (RhD(+) and RhD(−)) are $^{51}$Cr labelled, washed and then sensitized with anti-RhD antibodies (e.g. anti-RhD rpAb, anti-D or anti-RhD mAb) in various dilutions. The effector cells (PMBC) are added to the sensitized RBC (ratio of 20:1) and incubation is performed overnight. Cells are spun down and the supernatants from the wells are transferred to a Lumaplate (PerkinElmer). Controls for spontaneous release are included (RBC with $^{51}$Cr only) and for total release (addition of Triton-X-100 to $^{51}$Cr-labeled RBC). The Lumaplate is dried and counted in a Topcounter (PerkinElmer).

Phagocytosis Assay ($^{51}$Cr Based):

Phagocytosis can be measured in combination with the ADCC assay. After harvesting the supernatant in the ADCC assay, the remaining supernatant is removed and the red blood cells are lysed by addition of a hypotonic buffer. The cells are washed and the supernatant is removed. PBS+1% Triton-X-100 is added to all wells and fixed amounts are transferred to a Lumaplate, dried and counted as before.

Phagocytosis Assay (FACS Based):

This assay is based on adherence of the phagocytic cells. The human leukemic monoblast cell line U937 can be used for this assay. U937 cells are differentiated using 10 nM PMA. Two days later 60% of the medium is removed and replaced by medium without PMA. The cell membrane of red blood cells (RhD(+) and RhD(−)) are stained with PKH26 (PE) according to the manufactures protocol (Sigma). The RBC's are sensitized with anti-RhD antibodies in various dilutions and excess antibodies are removed by washing. On day three, the non-adherent cells U937 cell are removed by washing and sensitized RBC (RhD(+) and RhD(−)) are added to the wells. The plates are incubated overnight in the incubator. Non-phagocytozed RBC are washed away by several steps. Attached but not phagocytozed RBC are lysed by addition of hypotonic buffer followed by additional washing. The U937 cells detached from the wells by incubation with trypsin. Cells are analyzed on the FACS.

Rosetting Assay

A rosetting assay is merely an Fc receptor binding assay. Sensitized red blood cells are incubated with differentiated U937 cells prepared as described above. RBC (RhD (−) and RhD(+)) are sensitized with anti-RhD antibodies in various dilutions and excess antibodies are removed by washing before they are mixed with U937 cells. Incubation is performed for one hour and non-bound RBC are washed away. The percentage of cells with two or more RBC attached to the surface is counted.

An in vivo functional characterization of anti-RhD antibodies is described by Miescher (Miescher, S., et al. 2004, Blood 103, 4028-4035), an involves injection of RhD(+) cells into RhD(−) individuals followed by administration of anti- RhD antibody. RBC clearance and anti-RhD antibody sensation of the donors was analyzed.

Therapeutic Compositions

In an embodiment of the invention, a pharmaceutical composition comprising anti-RhD rpAb or anti-RhD recombinant polyclonal Fab or another anti-RhD recombinant polyclonal fragment as active ingredient is intended for the prophylaxis of hemolytic disease of the newborn, treatment of idiopathic thrombocytopenic purpura (ITP) or prevention of sensitization to the Rhesus D antigen after mistransfusions of RhD(+) blood to RhD(−) individuals.

The pharmaceutical composition further comprises a pharmaceutically acceptable excipient.

Anti-RhD rpAb or polyclonal fragments thereof may be administered within a pharmaceutically-acceptable diluent, carrier, or excipient, in unit dosage form. Conventional pharmaceutical practice may be employed to provide suitable formulations or compositions to administer to female mothers or patients. In a preferred embodiment the administration is prophylactic. Any appropriate route of administration may be employed, for example, administration may be parenteral, intravenous, intra-arterial, subcutaneous, intramuscular, intraperitoneal, intranasal, aerosol, suppository, or oral administration. For example, therapeutic formulations may be in the form of, liquid solutions or suspensions; for oral administration, formulations may be in the form of tablets or capsules chewing gum or pasta, and for intranasal formulations, in the form of powders, nasal drops, or aerosols.

The pharmaceutical compositions of the present invention are prepared in a manner known per se, for example, by means of conventional dissolving, lyophilizing, mixing, granulating or confectioning processes. The pharmaceutical compositions may be formulated according to conventional pharmaceutical practice (see for example, in Remington: The Science and Practice of Pharmacy (20th ed.), ed. A. R. Gennaro, 2000, Lippincott Williams & Wilkins, Philadelphia, Pa. and Encyclopedia of Pharmaceutical Technology, eds. J. Swarbrick and J. C. Boylan, 1988-1999, Marcel Dekker, New York, N.Y.).

Solutions of the active ingredient, and also suspensions, and especially isotonic aqueous solutions or suspensions, are preferably used, it being possible, for example in the case of lyophilized compositions that comprise the active ingredient alone or together with a carrier, for example mannitol, for such solutions or suspensions to be produced prior to use. The pharmaceutical compositions may be sterilized and/or may comprise excipients, for example preservatives, stabilizers, wetting and/or emulsifying agents, solubilizers, salts for regulating the osmotic pressure and/or buffers, and are prepared in a manner known per se, for example by means of conventional dissolving or lyophilizing processes. The said solutions or suspensions may comprise viscosity-increasing substances, such as sodium carboxymethylcellulose, carboxymethylcellulose, dextran, polyvinylpyrrolidone or gelatin.

The injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, pills, or capsules, which may be coated with shellac, sugar or both. It is also possible for them to be incorporated into plastics carriers that allow the active ingredients to diffuse or be released in measured amounts.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, tablets, pills, or capsules The formulations can be administered to human individuals in therapeutically or prophylactic effective amounts (e.g., amounts which prevent, eliminate, or reduce a pathological condition) to provide therapy for a disease or condition. The preferred dosage of therapeutic agent to be administered is likely to depend on such variables as the type and extent of the disorder, the overall health status of the particular patient, the formulation of the compound excipients, and its route of administration.

Therapeutic Uses of the Compositions According to the Invention

The pharmaceutical compositions according to the present invention may be used for the treatment, amelioration or prophylaxis of a disease in a mammal. Conditions that can be treated or prevented with the present pharmaceutical compositions include prevention of hemolytic disease of the newborn, treatment of idiopathic thrombocytopenic purpura (ITP) or prevention of sensitization to the Rhesus D antigen after mistransfusions of RhD(+) blood to RhD(−) individuals.

One aspect of the present invention is a method for disease treatment, amelioration or prophylaxis in an animal, wherein an effective amount of anti-RhD rpAb or fragment is administered.

A further embodiment of the present invention is the use of an anti-RhD recombinant polyclonal antibody or polyclonal antibody fragment for the preparation of a composition for the prophylaxis of hemolytic disease of the newborn or treatment of idiopathic thrombocytopenic purpura (ITP).

Diagnostic Use and Environmental Detection Use

Another embodiment of the invention is directed to diagnostic kits. Kits according to the present invention comprise an anti-RhD rpAb prepared according to the invention which protein may be labeled with a detectable label or non-labeled for non-label detection. The kit may be used to identify RhD (+) individuals, or individuals with a particular Rhesus D category. Identification of the later can be achieved by having a anti-RhD rpAb composition which only react with that particular Rhesus D category.

EXAMPLES

The following examples describe how anti-RhD rpAb is expressed and produced in a high-producer cell line, where $V_H$ and $V_L$ comprising nucleic acid segments or vector(s) have been inserted by site-specific integration into a pre-characterized chromosomal "hot-spot" site.

In the examples, CHO cells were utilized as host cell. The advantages thereof include the availability of suitable growth medium, their ability to grow efficiently to a high density in culture, and their ability to express mammalian proteins such as antibodies in a biologically active form.

In general, transformation of E. coli and transfection of mammalian cells according to the subject invention will be performed according to conventional methods.

The following examples illustrate the invention, but should not be viewed as limiting the scope of the invention.

Example 1

Production of an Anti-Rhesus D Recombinant Polyclonal Antibody

Donors

Donors were enrolled at Aalborg Sygehus Nord. A total of eight RhD(−) women were immunized with RhD(+) erythrocytes derived from RhD(+) individuals. The donors had a varying history of the immunizations with respect to the number of boosts and the origin of RhD(+) erythrocytes for the immunization. The immunization history of the different donors is given in the table 1.

TABLE 1

| Donor # | # of boost | # of boosts from different origin |
|---|---|---|
| 1 | 3 | 2 |
| 2 | 6 | 2 |
| 3 | 2 | 1 |
| 4 | 4 | 4 |
| 5 | 2 | 2 |
| 6 | 3 | 2 |
| 7 | 2 | 2 |
| 8 | 2 | 2 |

Mononuclear cells were harvested by leukopheresis 5-7 days after the last boost. The cells were pelleted and immediately transferred to the cell lysis solution from a commercially available RNA preparation kit (NucleoSpin RNA L, Machery-Nagel, cat. no. 740 962.20). After lysis of the cells, the suspension was frozen before further processing.

Generation of Anti-Rhesus D Fab Display Library

The material obtained from each donor was kept separate throughout the procedure of library generation and panning. The cell lysates were thawed and RNA was prepared according to kit instructions (NucleoSpin RNA L). The integrity of the RNA was analyzed by agarose gel electrophoresis, thus verifying that the 18S/28S ribosomal RNAs were not degraded.

RNA was subjected to cDNA synthesis in an oligo(dT) primed reaction using approximately 10 μg total RNA in a reaction using ThermoScript (Invitrogen), according to the manufacturer's instructions. The cDNA was used as template in PCR reactions using the following primers:

$V_H$ Forward Primers (XhoI Site in Bold):

| J region | SEQ ID | Primer sequence |
|---|---|---|
| JH1/2 | 2 | GGAGGCGCTC GAGACGGTGA CCAGGGTGCC |
| JH3 | 3 | GGAGGCGCTC GAGACGGTGA CCATTGTCCC |
| JH4/5 | 4 | GGAGGCGCTC GAGACGGTGA CCAGGGTTCC |
| JH6 | 5 | GGAGGCGCTC GAGACGGTGA CCGTGGTCCC |

$V_H$ Reverse Primers (AscI Site in Bold):

| V gene family | SEQ ID | Primer sequence |
|---|---|---|
| 1B/7A | 6 | CCAGCCGGGG CGCGCCCAGR TGCAGCTGGT GCARTCTGG |
| 1C | 7 | CCAGCCGGGG CGCGCCSAGG TCCAGCTGGT RCAGTCTGG |
| 2B | 8 | CCAGCCGGGG CGCGCCCAGR TCACCTTGAA GGAGTCTGG |
| 3B | 9 | CCAGCCGGGG CGCGCCSAGG TGCAGCTGGT GGAGTCTGG |
| 3C | 10 | CCAGCCGGGG CGCGCCGAGG TGCAGCTGGT GGAGWCYGG |
| 4B | 11 | CCAGCCGGGG CGCGCCCAGG TGCAGCTACA GCAGTGGGG |
| 4C | 12 | CCAGCCGGGG CGCGCCCAGS TGCAGCTGCA GGAGTCSGG |
| 5B | 13 | CCAGCCGGGG CGCGCCGARG TGCAGCTGGT GCAGTCTGG |
| 6A | 14 | CCAGCCGGGG CGCGCCCAGG TACAGCTGCA GCAGTCAGG |

$C_\kappa$ Forward Primer (NotI Site in Bold):

| SEQ ID | Primer sequence |
|---|---|
| 15 | ACCGCCTCCA CCGGCGGCCG CTTATTAACA CTCTCCCCTG TTGAAGCTCT T |

$V_\kappa$ Reverse Primers (NheI Site in Bold):

| V gene family | SEQ ID | Primer sequence |
|---|---|---|
| 1B | 16 | CAACCAGCGC TAGCCGACAT CCAGWTGACC CAGTCTCC |
| 2 | 17 | CAACCAGCGC TAGCCGATGT TGTGATGACT CAGTCTCC |
| 3B | 18 | CAACCAGCGC TAGCCGAAAT TGTGWTGACR CAGTCTCC |
| 4B | 19 | CAACCAGCGC TAGCCGATAT TGTGATGACC CACACTCC |
| 5 | 20 | CAACCAGCGC TAGCCGAAAC GACACTCACG CAGTCTCC |
| 6 | 21 | CAACCAGCGC TAGCCGAAAT TGTGCTGACT CAGTCTCC |

$C_\lambda$ Forward Primer (NotI Sit in Bold):

| λ family | SEQ ID | Primer sequence |
|---|---|---|
| 2 | 22 | ACCGCCTCCACCGGCGGCCGCTTATTATGAACATTCTGTAGGGCCACTG |
| 7 | 23 | ACCGCCTCCACCGGCGGCCGCTTATTAAGAGCATTCTGCAGGGGCACTG |

$V_\lambda$ Reverse Primers (NheI in Bold):

| V gene family | SEQ ID | Primer sequence |
|---|---|---|
| 1A | 24 | CAACCAGCGC TAGCCCAGTC TGTGCTGACT CAGCCACC |
| 1B | 25 | CAACCAGCGC TAGCCCAGTC TGTGYTGACG CAGCCGCC |
| 1C | 26 | CAACCAGCGC TAGCCCAGTC TGTCGTGACG CAGCCGCC |
| 2 | 27 | CAACCAGCGC TAGCCCARTC TGCCCTGACT CAGCCT |
| 3A | 28 | CAACCAGCGC TAGCCCTTTC CTATGWGCTG ACTCAGCCACC |
| 3B | 29 | CAACCAGCGC TAGCCCTTTC TTCTGAGCTG ACTCAGGACCC |
| 4 | 30 | CAACCAGCGC TAGCCCACGT TATACTGACT CAACCGCC |
| 5 | 31 | CAACCAGCGC TAGCCCAGGC TGTGCTGACT CAGCCGTC |
| 6 | 32 | CAACCAGCGC TAGCCCTTAA TTTTATGCTG ACTCAGCCCCA |
| 7/8 | 33 | CAACCAGCGC TAGCCCAGRC TGTGGTGACY CAGGAGCC |
| 9 | 34 | CAACCAGCGC TAGCCCWGCC TGTGCTGACT CAGCCMCC |

Figure 2:
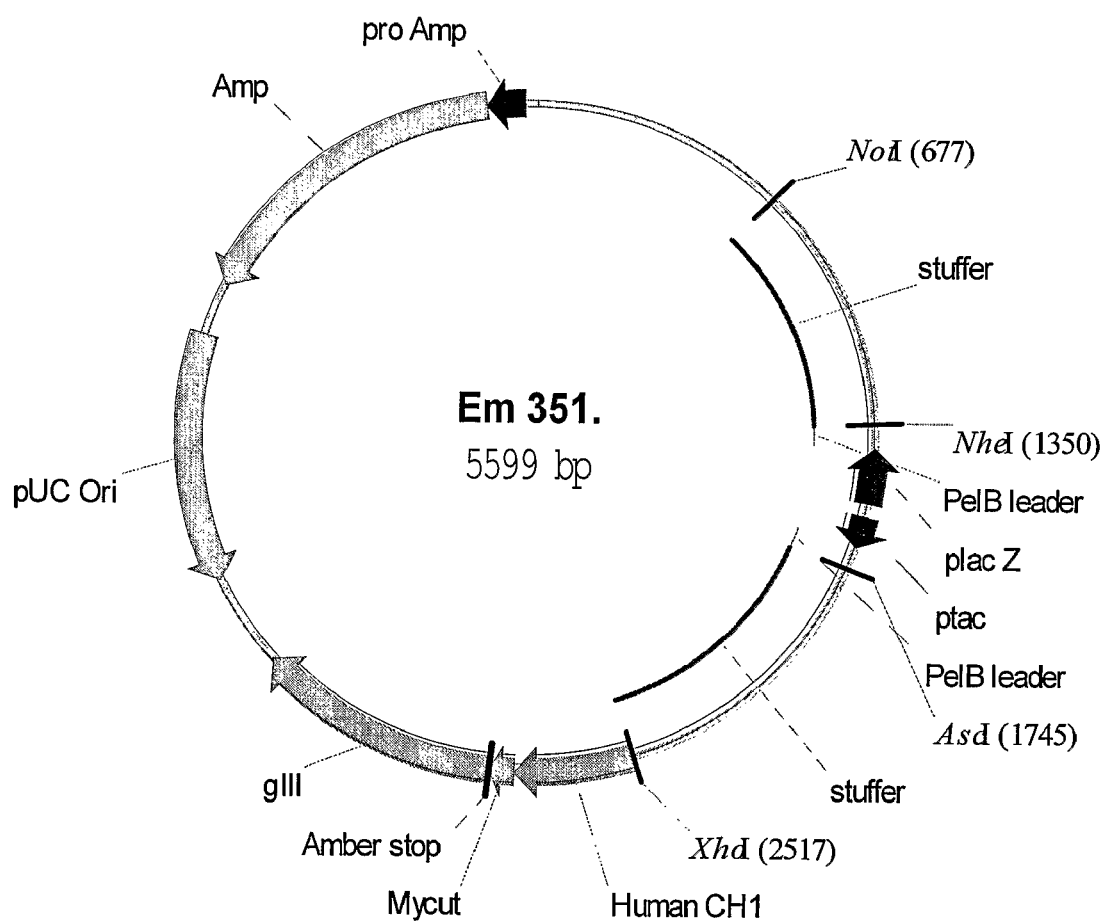
FIG. 2: Phage display vector: Em351, an *E. coli* vector used to generate an anti-RhD Fab phage display library by inserting heavy chain variable region and the light chain fragments amplified from a suitable donor into the vector at the indicated AscI/XhoI and NheI/NotI restriction sites, respectively. The vector comprises the following elements: pro Amp and Amp=promoter and ampicillin resistance gene. pUC Ori=origin of replication. Human CH1=sequence encoding human immunoglobulin gamma 1 heavy chain domain 1. Stuffer=irrelevant sequence inserts which are cut out during insertion of the heavy and light chain fragments. p tac and p lac Z=bacterial promoters. PeIB=modified bacterial PeIB leaders for targeting expression of the Fab to the periplasmic space of the *E. coli*. Mycut=proteinase recognition site. Amber stop=amber stop codon. gIII=phage M13 truncated geneIII (from bp 198 to the C-terminal).

PCR was performed with individual primer pairs amounting to 36 $V_H$ reactions, 6 Kappa reactions and 22 Lambda reactions. All $V_H$, Kappa, and Lambda PCR products were pooled separately and following purification using NucleoSpin columns (Machery-Nagel, cat. no. 740 590.250), the products were digested prior to cloning ($V_H$: AscI/XhoI, Kappa and Lambda: NheI/NotI) followed by a gel purification step of the bands of interest (PerfectPrep Gel Cleanup kit, Eppendorf, cat. no. 0032 007.759). The light chains (Kappa and Lambda separately) were inserted into a NheI/NotI treated Em351 phage display vector (FIG. 2), by ligation and amplified in *E. coli* XL1 Blue (Stratagene). Plasmid DNA constituting the light chain library was isolated from the *E. coli* cells selected over night on Carbenicillin agar plates (two libraries for each donor, Kappa and Lambda, respectively). This library DNA was subjected to digest with AscI/XhoI, and after gel purification, the $V_H$ PCR products (subjected to digest with the same enzymes and gel purified) were ligated into the two light chain libraries from each donor and amplified in *E. coli* TG1 cells (Stratagene) using Carbenicillin selection on agar plates. After overnight growth, bacteria were scraped off the plates, and glycerol stocks were prepared for proper library storage. A plasmid DNA preparation containing the combinatorial variable heavy chain-light chain ($V_H$:LC) library was also performed to secure the library for the future. The combinatorial libraries contained in the TG1 cells (two from each donor) were now ready for phage display and panning. The sizes of the combinatorial libraries (16 in total) were $10^6$ or larger.

Enrichment for Phages Displaying Rhesus D Antigen Binding Fab Fragments

Phages displaying Fabs on their surface were generated as follows: 50 mL 2×YT/1% glucose/100 μg/mL Carbenicillin was inoculated with TG1 cells containing the combinatorial $V_H$:$V_L$ library to obtain an $OD_{600}$ of approximately 0.08. The culture was shaking for 1½ h, and helper phage was added (VSCM13). The culture was incubated at 37° C. for ½ h without shaking and for ½ h with shaking. The bacteria were pelleted (3200×g, 10 minutes, 4° C.), and re-suspended in 50 mL 2×YT/100 μg/mL Carbenicillin/70 μg/mL Kanamycin, and the culture was shaken overnight at 30° C. The phages were precipitated from the culture supernatant by adding ⅕ volume of 20% PEG/1.5 M NaCl, incubating on ice for 30 minutes, and centrifugation at 8000×g for 30 minutes at 4° C. Precipitated phages were resuspended in PBS and used directly for panning.

Panning for Rhesus D antigen binding Fab fragments was performed in a two-step procedure. $10^8$ RhD(−) red blood cells (RBC) were washed three times in PBS (centrifugation at 2000×g, 45 sec), and re-suspended in 150 μl panning buffer (2% skim milk in 0.85×PBS). Fifty μl freshly prepared phages were added to the RhD(−) cells (re-suspended in panning buffer) in order to perform a negative selection step, and incubated for 1 h on an end-over-end rotator at 4° C. Following the one hour incubation, the cells were pelleted by centrifugation (2000×g, 45 sec), and the phage-containing supernatant was incubated with $2\times10^7$ RhD(+) RBC (washed three times in PBS). The phage:RhD(+) RBC mix was incubated for one hour on an end-over-end rotator at 4° C. Unbound phages were removed by washing five times with 1 mL panning buffer, and five times with PBS. Bound phages were eluted by addition of 200 μl $H_2O$ (which lyses the cells). One hundred μl of the eluate was added to exponentially growing TG1 cells, the remainder was stored at −80° C. TG1 cells infected with eluated phages were plated on Carb/glu agar dishes and incubated overnight at 37° C. The following day, the colonies were scraped off the plates, and 10 mL culture medium was inoculated for preparation of phages for the second round of panning. The second round of panning was performed as described for the first round.

Enrichment for Phages Displaying Rhesus D Category VI Antigen Binding Fab Fragments In a separate set of pannings, selections were performed in order to retrieve clones with reactivity towards the RhD category VI antigen. The negative selection was performed on RhD(−) blood as described, and the positive selection was performed on $RhD^{VI}$ positive erythrocytes. The procedure was otherwise as described above.

Screening for Anti-RhD Binding Fabs

After each round of panning single colonies were picked for analysis of their binding properties to red blood cells in agglutination assays. Briefly, single colonies were inoculated into 2×YT/100 μg/mL carbenicillin/1% glucose and shaken overnight at 37° C. The next day, DeepWell plates were inoculated using 900 μl 2×YT/100 μg/mL carbenicillin/0.1% glucose and 10 μl overnight culture. The plates were shaken for two hours at 37° C., before Fab induction was performed with addition of 300 μl 2×YT/100 μg/mL carbenicillin/0.25 mM IPTG per well. The plate was shaken overnight at 30° C.

The following day, the bacteria were pelleted by centrifugation (3200×g, 4° C., 10 minutes), and re-suspended in 100 μl of 0.8 M NaCl, 0.2×PBS, 8 mM EDTA, and incubated for 15 minutes on ice in order to perform a periplasmic extraction of the Fab fragments. The plate was transferred to −20° C. and finally the suspension was thawed and centrifugation was performed for 10 minutes at 4° C. and 3200×g. The periplasmic extract was used in ELISA assays for analysis of Fab content and in agglutination assays to evaluate the binding potential of the individual Fab fragments.

The agglutination assay was performed as follows: RhD(−) and RhD(+) RBC were mixed in a 1:1 ratio, and washed 3 times in PBS. After the final wash, the cell mix was re-suspended in 1% BSA in PBS at a density of 10% cells, 50 μl was added to each well of a 96-plate. Periplasmic extracts were added to the wells. As a positive control Rhesogamma P immunoglobulin (Aventis) was used according to the manufacturer's instructions. The plates were incubated for one hour at room temperature with gentle shaking. The cells were washed three times with PBS, before the secondary antibody was added (goat anti-human Fab/FITC conjugate, Sigma F5512) in a 1:100 dilution. The plates were left for agglutination for one hour at room temperature without shaking. Fab fragments positive in the agglutination assay was determined by visual inspection, and recorded by taking a picture. Quantization of the binding activity of the Fab fragments was performed by FACS analysis of the agglutination samples.

When performing screening for clones with reactivity towards RhD$^{VI}$+ erythrocytes, such cells were used in conjunction with RhD(−) cells in a procedure otherwise identical to that described above.

Selection of Diverse Anti-RhD Fab-Encoding Sequences

A total of 1700 RhD antigen binding clones were identified. All the positive clones were submitted for DNA sequencing. From these 56 clones were selected based on their unique set of heavy chain CDR sequences. For multiple clones which used the same heavy chain with different light chains, the clone which showed the highest binding activity in the FACS assay was selected. Thereby a sub-library comprised of pairs of variable heavy chain ($V_H$) and light chain (LC)-encoding sequences, representing a broad diversity with high RhD antigen specificity, was selected from all the positive clones.

The binding activity of these 56 clones was re-confirmed in agglutination assays, to ensure no false positive clones were selected.

The selected clones were further analyzed with respect to mutations due to for instance inter-family cross-priming, since such mutations may lead to overall structural changes of the expressed antibody possibly creating new epitopes and thereby result in an increased immunogenicity of the final product. Clones with such mutations were repaired as described in the following section relating to $V_H$:LC transfer from the phagemid vector to the mammalian expression vector.

Figure 5:
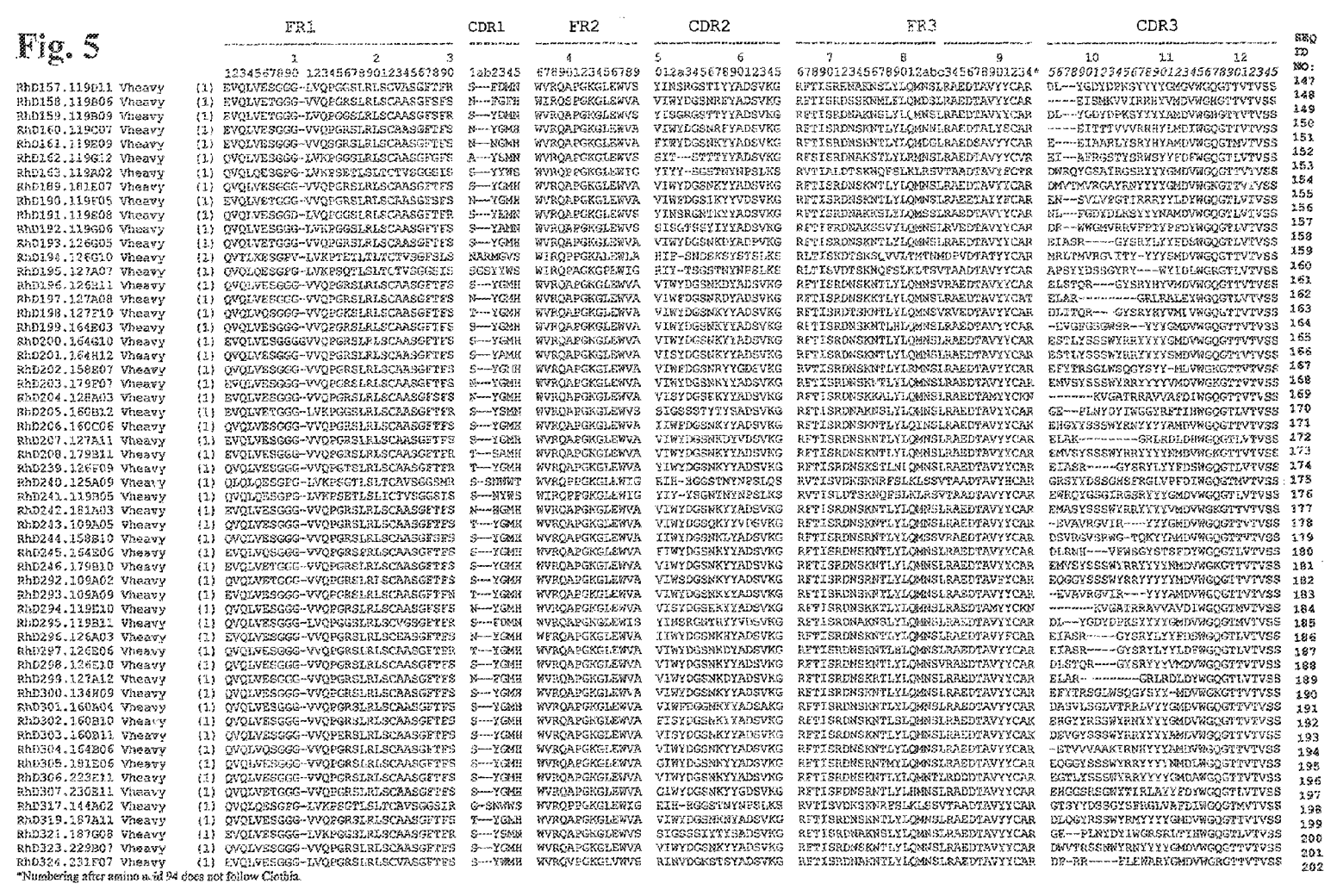

Alignments of the corrected nucleic acid sequences for the $V_H$ and light chains (LC) are shown in FIG. 3 to 6, respectively. Further alignments of the $V_H$ and $V_L$ polypeptide chains are shown in FIGS. 5 and 6, respectively. The polypeptide alignments were performed and numbered according to structural criteria defined by Chothia (Chothia et al. 1992 J. Mol. Biol. 227, 776-798; Tomlinson et al. 1995 EMBO J. 14, 4628-4638 and Williams et al. 1996 J. Mol. Biol., 264, 220-232). The figures further indicate the position of the three CDR regions within the variable regions. The CDR region positions within the amino acid sequences are summarized in table 2. The numbering of the CDR3 regions in the polypeptide alignments (FIGS. 5 and 6) does not follow Chothia (transition marked with an asterisk in the figures). In order to enable identification of the CDR3 region with respect to amino acid position, a continued numbering has been assigned after the asterisk. The CDR3 region sequence for each individual clone can be derived from the figures based on this numbering.

TABLE 2

|  | $V_H$ a.a. position | $V_L$ Kappa a.a. position | $V_L$ Lambda a.a. position |
| --- | --- | --- | --- |
| Figure | 5 | 6A | 6B |
| CDR1 | 31-35 | 24-34 | 25-35 |
| CDR2 | 50-65 | 50-56 | 53-57 |
| CDR3 | 95-125 | 89-110 | 90-113 |

The pairs of variable heavy chain and complete light chain which have been screened as Fabs and selected for their ability to bind RhD antigen can be identified by their identical clone numbers. All the 56 $V_H$:LC pairs are listed by clone number, the nucleic acid (nuc.) SEQ IDs and the amino acid (a.a.) SEQ IDs in table 3.

TABLE 3

| Clone Name | $V_H$ nuc. SEQ ID | LC nuc. SEQ ID | $V_H$ a.a. SEQ ID | LC a.a. SEQ ID |
| --- | --- | --- | --- | --- |
| RhD157.119D11 | 35 | 91 | 147 | 203 |
| RhD158.119B06 | 36 | 92 | 148 | 204 |
| RhD159.119B09 | 37 | 93 | 149 | 205 |
| RhD160.119C07 | 38 | 94 | 150 | 206 |
| RhD161.119E09 | 39 | 95 | 151 | 207 |
| RhD162.119G12 | 40 | 96 | 152 | 208 |
| RhD163.119A02 | 41 | 97 | 153 | 209 |
| RhD189.181E07 | 42 | 98 | 154 | 210 |
| RhD190.119F05 | 43 | 99 | 155 | 211 |
| RhD191.119E08 | 44 | 100 | 156 | 212 |
| RhD192.119G06 | 45 | 101 | 157 | 213 |
| RhD193.126G05 | 46 | 102 | 158 | 214 |
| RhD194.126G10 | 47 | 103 | 159 | 215 |
| RhD195.127A07 | 48 | 104 | 160 | 216 |
| RhD196.126H11 | 49 | 105 | 161 | 217 |
| RhD197.127A08 | 50 | 106 | 162 | 218 |
| RhD198.127F10 | 51 | 107 | 163 | 219 |
| RhD199.164E03 | 52 | 108 | 164 | 220 |
| RhD200.164G10 | 53 | 109 | 165 | 221 |
| RhD201.164H12 | 54 | 110 | 166 | 222 |
| RhD202.158E07 | 55 | 111 | 167 | 223 |
| RhD203.179F07 | 56 | 112 | 168 | 224 |
| RhD204.128A03 | 57 | 113 | 169 | 225 |
| RhD205.160B12 | 58 | 114 | 170 | 226 |
| RhD206.160C06 | 59 | 115 | 171 | 227 |
| RhD207.127A11 | 60 | 116 | 172 | 228 |
| RhD208.179B11 | 61 | 117 | 173 | 229 |
| RhD239.126F09 | 62 | 118 | 174 | 230 |
| RhD240.125A09 | 63 | 119 | 175 | 231 |
| RhD241.119B05 | 64 | 120 | 176 | 232 |
| RhD242.181A03 | 65 | 121 | 177 | 233 |
| RhD243.109A05 | 66 | 122 | 178 | 234 |
| RhD244.158B10 | 67 | 123 | 179 | 235 |
| RhD245.164E06 | 68 | 124 | 180 | 236 |
| RhD246.179B10 | 69 | 125 | 181 | 237 |
| RhD292.109A02 | 70 | 126 | 182 | 238 |
| RhD293.109A09 | 71 | 127 | 183 | 239 |
| RhD294.119E10 | 72 | 128 | 184 | 240 |
| RhD295.119B11 | 73 | 129 | 185 | 241 |
| RhD296.126A03 | 74 | 130 | 186 | 242 |
| RhD297.126E06 | 75 | 131 | 187 | 243 |
| RhD298.126E10 | 76 | 132 | 188 | 244 |
| RhD299.127A12 | 77 | 133 | 189 | 245 |
| RhD300.134H09 | 78 | 134 | 190 | 246 |
| RhD301.160A04 | 79 | 135 | 191 | 247 |
| RhD302.160B10 | 80 | 136 | 192 | 248 |
| RhD303.160B11 | 81 | 137 | 193 | 249 |
| RhD304.164B06 | 82 | 138 | 194 | 250 |

TABLE 3-continued

| Clone Name | V$_H$ nuc. SEQ ID | LC nuc. SEQ ID | V$_H$ a.a. SEQ ID | LC a.a. SEQ ID |
|---|---|---|---|---|
| RhD305.181E06 | 83 | 139 | 195 | 251 |
| RhD306.223E11 | 84 | 140 | 196 | 252 |
| RhD307.230E11 | 85 | 141 | 197 | 253 |
| RhD317.144A02 | 86 | 142 | 198 | 254 |
| RhD319.187A11 | 87 | 143 | 199 | 255 |
| RhD321.187G08 | 88 | 144 | 200 | 256 |
| RhD323.229B07 | 89 | 145 | 201 | 257 |
| RhD324.231F07 | 90 | 146 | 202 | 258 |

Transfer of the Selected V$_H$ and Light Chain-Encoding Sequences to a Mammalian Expression Vector.

Due to the mutations resulting from, for instance, inter-family cross-priming it was necessary to repair of a large number of the selected sequences. This was done in connection with exchange of expression system from phage display to mammalian expression. For this reason the transfer was performed separately for each individual clone.

The transfer and repair was performed as follows: First the V$_H$-encoding sequence situated in the Em351 vector was re-amplified by PCR using the high fidelity polymerase, Phusion (Finnzymes) and a proper set of correcting primers. The V$_H$ PCR fragment was digested with AscI and XhoI and subjected to gel purification. The Neo exp. vector (FIG. 7) was digested with the corresponding enzymes and gel purified thereby removing the nucleic acid sequence situated between the leader sequence and the heavy chain constant regions. The corrected V$_H$ fragment and the Neo exp. vector were ligated and amplified in E. coli Top10 cells. Plasmid DNA of the V$_H$ containing Neo exp. vector was isolated from the E. coli cells selected over night on Carbenicillin.

Following transfer of the V$_H$-encoding sequence the corresponding LC sequence was re-amplified by PCR using the high fidelity polymerase, Phusion (Finnzymes) and a proper set of correcting primers. The LC PCR fragment was digested with NheI and NotI and subjected to gel purification. The V$_H$ containing Neo exp. vector was digested with the corresponding enzymes and gel purified thereby removing the nucleic acid sequence situated between the kappa leader sequence and the BGHpolyA signal sequence. The corrected LC fragment and the V$_H$ containing Neo exp. vector were ligated and amplified in E. coli Top10 cells. Glycerol stocks were prepared for each individual clone, and a high quality plasmid preparation suitable for transfection of mammalian cells was prepared from the bacterial cultures as well.

By performing the transfer separately for each clone the V$_H$:LC pairs originally selected by phage display were regenerated in the mammalian expression vector. In the instances where repair was not necessary the nucleic acid segment was transferred without performing PCR prior to the digestion with the appropriate restriction enzymes.

The mammalian expression vectors generated by the transfer described are suitable for expressing a full-length anti-RhD recombinant polyclonal antibody. Although the vectors are kept separate at this point it is still considered as a library of anti-RhD antibody expression vectors.

Transfection and Selection of Mammalian Cell Lines

The Flp-In CHO cell line (Invitrogen) was used as starting cell line for establishment of a recombinant polyclonal manufacturing cell line. However, to obtain a more homogenous cell line the parental Flp-In CHO cell line was sub-cloned. Briefly, the parental cell line was sub-cloned by limited dilution and several clones were selected and expanded. Based on growth behavior one clone, CHO-Flp-In (019), was selected as production cell line.

All the 56 plasmid preparations were transfected individually into the CHO-Flp-In (019) cell line as follows: the CHO-Flp-In (019) cells were cultured as adherent cells in F12-HAM with 10% fetal calf serum (FCS). 2.5×10$^6$ cells were transfected with plasmid representing one clone using Fugene6 (Roche). Cells were trypsinated 24 hours after transfection and transferred to 3×T175 flasks. Selection pressure, in this case 450 µg/ml Neomycin, was added 48 hours after transfection. Approximately two weeks later clones appeared. Clones were counted and cells were trypsinated and hereafter cultured as pools of clones expressing one of the 56 specific anti-Rhesus-D antibodies.

Adaptation to Serum Free Suspension Culture

The individual adherent anti-Rhesus-D antibody CHO-Flp-In (019) cell cultures were trypsinated, centrifuged and transferred to separate shaker flasks with 8×10$^5$ cells/ml in appropriate serum free medium (Excell302, JRH Biosciences).

Growth and cell morphology were followed over several weeks. When cells showed good and stable growth behavior and had doubling time below 32 hours 50 aliquots of each culture with 10×10$^6$ cells/tube were frozen down (56×50 aliquots).

Characterization of Cell Lines

All the individual cell lines were characterized with respect to antibody production and proliferation. This was performed with the following assays:

Production:

The production of recombinant antibodies in the individual cultures were followed over time by Kappa or Lambda specific ELISA. ELISA plates were coated overnight with goat-anti-human Kappa (Caltag) or goat-anti-human Lambda (Caltag) antibodies in carbonate buffer, pH 9.6. Plates were washed 6 times with washing buffer (1×PBS and 0.05% Tween 20) and blocked for 1 hour with washing buffer with 2% milk. Samples were added to wells and plates were incubated for 1 hour. Plates were washed 6× and secondary antibodies (goat-anti-human IgG (H+L) HRPO, Caltag) were added for 1 hour followed by 6× wash. ELISA was developed with TMB substrate and reaction stopped by addition of H$_2$SO$_4$. Plates were read at 450 nm.

Further, intracellular FACS staining, using fluorescently tagged antibodies was used to measure the production of recombinant antibodies in the cell culture system. 5×10$^5$ cells were washed in cold FACS PBS (1×PBS ad 2% FCS) and centrifuged. Cells were fixed in CellFix (BD-Biosciences) for 20 min and hereafter washed in saponin buffer (1×PBS and 0.2% Saponin). The suspension was centrifuged and fluorescently tagged antibody (Goat F(ab')$_2$ Fragment, Anti-human IgG(H+L)-PE, Beckman Coulter) was added for 20 min on ice. Cells were washed twice in saponin buffer and resuspended in FACS buffer and analyzed by FACS. This intracellular staining was used to determine the general expression level as well as to determine the homogeneity of the cell population in relation to expression of recombinant antibodies.

Proliferation:

Aliquots of cell suspension were taken three times a week and cell number, cell size, degree of clumping and percentage of dead cells were determined by CASY® (Cell Counter+Analyzer System from Schärfe System GmbH) analysis. The doubling time for the cell cultures was calculated by cell number derived form CASY® measurements.

Establishment of a Manufacturing Cell Line for Anti-Rhesus D Recombinant Polyclonal Antibody Production Ten cell lines each expressing a distinct recombinant anti-Rhesus-D antibody (RhD157.119D11, RhD158.119B06, RhD159.119B09, RhD161.119E09, RhD163.119A02, RhD190.119F05, RhD191.119E08, RhD192.119G06, RhD197.127A08 and RhD204.128A03) were selected to constitute the recombinant polyclonal manufacturing cell line. The Rhd197 and RhD204 were lambda clones whereas all the others were kappa clones.

After the cell cultures expressing the individual anti-Rhesus antibodies were fully adapted to serum free suspension culture in shaker flasks they were mixed in equal cell number, thereby generating a polyclonal CHO-Flp-In (019) cell line. The mixed cell culture was centrifuged and frozen down in aliquots of $10 \times 10^6$ cells/tube.

Two tubes (3948 FCW065 and 3949 FCW065) were thawed and cultured individually for 11 weeks in 1000 ml shaker flasks containing 100 ml Excell302 medium with neomycin.

The supernatant was harvested and filtered prior to purification of the anti-RhD rpAb.

Clonal Diversity

The clonal diversity was assayed both on the protein level as well as on the mRNA level. The supernatant sample used to analyze the antibody composition was taken after 9 weeks of cultivation, whereas the cell sample used to analyze the mRNA composition was taken at the harvest after 11 weeks of cultivation.

Antibody Composition:

The anti-RhD rpAb expressed from the polyclonal CHO-Flp-In (019) cell line is an IgG1 isotype antibody. Anti-RhD rpAb was purified from both aliquots (3948 and 3949) using a column with immobilized Protein A. The individual antibodies interacted with immobilized Protein A at pH 7.4, whereas contaminating proteins were washed from the column. The bound antibodies were subsequently eluted from the column at low pH value (pH 2.7). The fractions containing antibodies, determined from absorbance measurements at 280 nm, were pooled and dialyzed against 5 mM sodium acetate pH 5.

Figure 8:
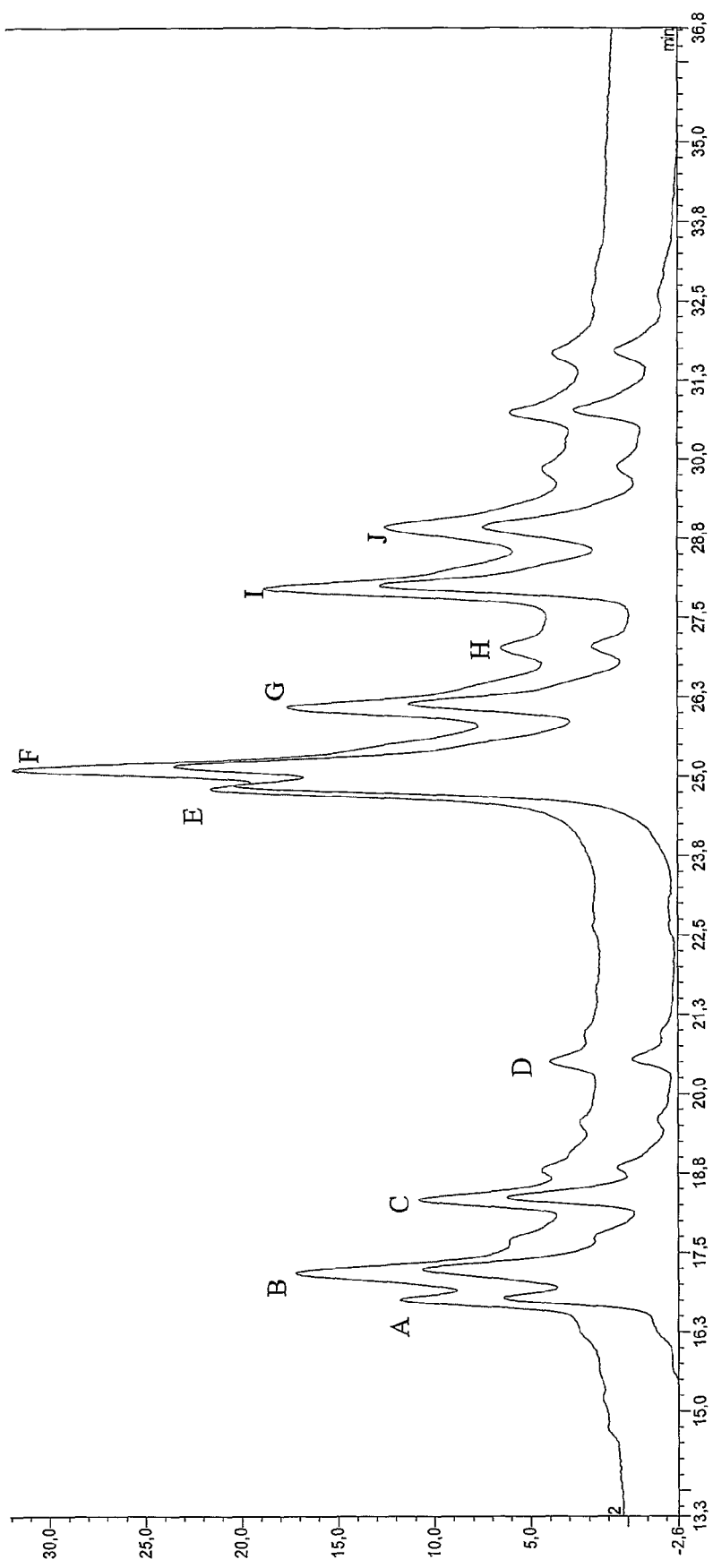
FIG. 8: Cation exchange chromatograms of anti-RhD rpAb composition from aliquots 3948 and 3949 after 9 weeks cultivation. The lower diagram corresponds to aliquot 3949 and the upper one to aliquot 3948. The Y-axis of the top diagram has been displaced in order to separate it from the lower diagram. Peaks A-J comprise antibodies differing in net charge and individual antibodies appearing charge heterogeneous.

The anti-RhD rpAb compositions obtained from aliquot 3948 and 3949 (FCW065) after 9 weeks of cultivation were analyzed using cation exchange chromatography. The Protein A purified anti-RhD rpAb was applied onto a PolyCatA column (4.6×100 mm) in 25 mM sodium acetate, 150 mM sodium chloride, pH 5.0 at a flow rate of 60 ml h$^{-1}$ operated at room temperature. The antibody components were subsequently eluted using a linear gradient from 150-350 mM sodium chloride in 25 mM sodium acetate, pH 5.0 at a flow rate of 60 ml h$^{-1}$. The antibody components were detected spectrophotometrically at 280 nm. The chromatogram (FIG. 8) was subsequently integrated and the area of the individual peaks A-J was subsequently used to quantitate antibody components (table 4). The total area of the peaks was set to 100%. The chromatograms from the two aliquots showed an identical peak distribution, as well as similar concentrations of the components in each peak. From these results it can be concluded that aliquots of the same polyclonal cell line grown under identical conditions will produce anti-RhD rpAb with a similar clonal diversity.

The individual members of the anti-RhD rpAb were allocated to one or more particular peaks (summarized in table 4). The allocation is based on chromatograms obtained for antibody products from each individual clone. No individual chromatogram was obtained for antibodies produced from RhD158.119B06, thus this clone was not assigned to any of the peaks. However it is considered likely that peak D constitute RhD158.119B06, the clone may also be represented in some of the other peaks due to heterogeneity. In particular the antibody product from clone RhD197.127A08 has a high degree of heterogeneity. Clone RhD190.119F05 should have been visible at 15.3 min. However, it was not detectable, indicating that this clone has been lost from the recombinant polyclonal manufacturing cell line. The loss of clone RhD190.119F05 corresponds to a 10% reduction of diversity which is considered acceptable with respect to diversity of the final anti-RhD rpAb composition.

TABLE 4

| Peak | Quantity 3948 (% area) | Quantity 3949 (% area) | Clone name | Comment |
|---|---|---|---|---|
| A | 5.1 | 5.1 | RhD157.119D11 | Clone is also present in peak B |
| B | 12.0 | 10.2 | RhD157.119D11 RhD159.119B09 RhD192.119G06 | This peak represent at least three different clones |
| C | 5.2 | 5.3 | RhD191.119E08 | |
| D | 1.2 | 0.8 | (RhD158.119B06) | Not actually allocated to this peak, but it is likely to be. May also be represented in other peaks. |
| E | 10.9 | 14.4 | RhD204.128A03 | |
| F | 24.3 | 23.0 | RhD197.127A08 | This clone split into several peaks, due to heterogeneity. |
| G | 13.6 | 12.5 | RhD197.127A08 | |
| H | 3.3 | 4.0 | RhD197.127A08 | |
| I | 14.0 | 13.7 | RhD161.119E09 | |
| J | 10.5 | 10.5 | RHD163.119A02 RhD190.119F05 | The clone has been lost | mRNA Composition:

The clonal diversity within the polyclonal CHO-Flp-In (019) cell line after 11 weeks of cultivation was estimated by RT-PCR-RFLP analysis. Briefly, a cell suspension corresponding to 200 cells were subjected to a freeze-thaw procedure and these lysates were used as template in a RT-PCR using One-STEP RT-PCR kit (Qiagen) with primers amplifying the light chain. The primer sequences were:

```
forward primer
5'-CGTTCTTTTTCGCAACGGGTTTG     (SEQ ID 259)

reverse primer
5'-AAGACCGATGGGCCCTTGGTGGA     (SEQ ID 260)
```

Figure 9:
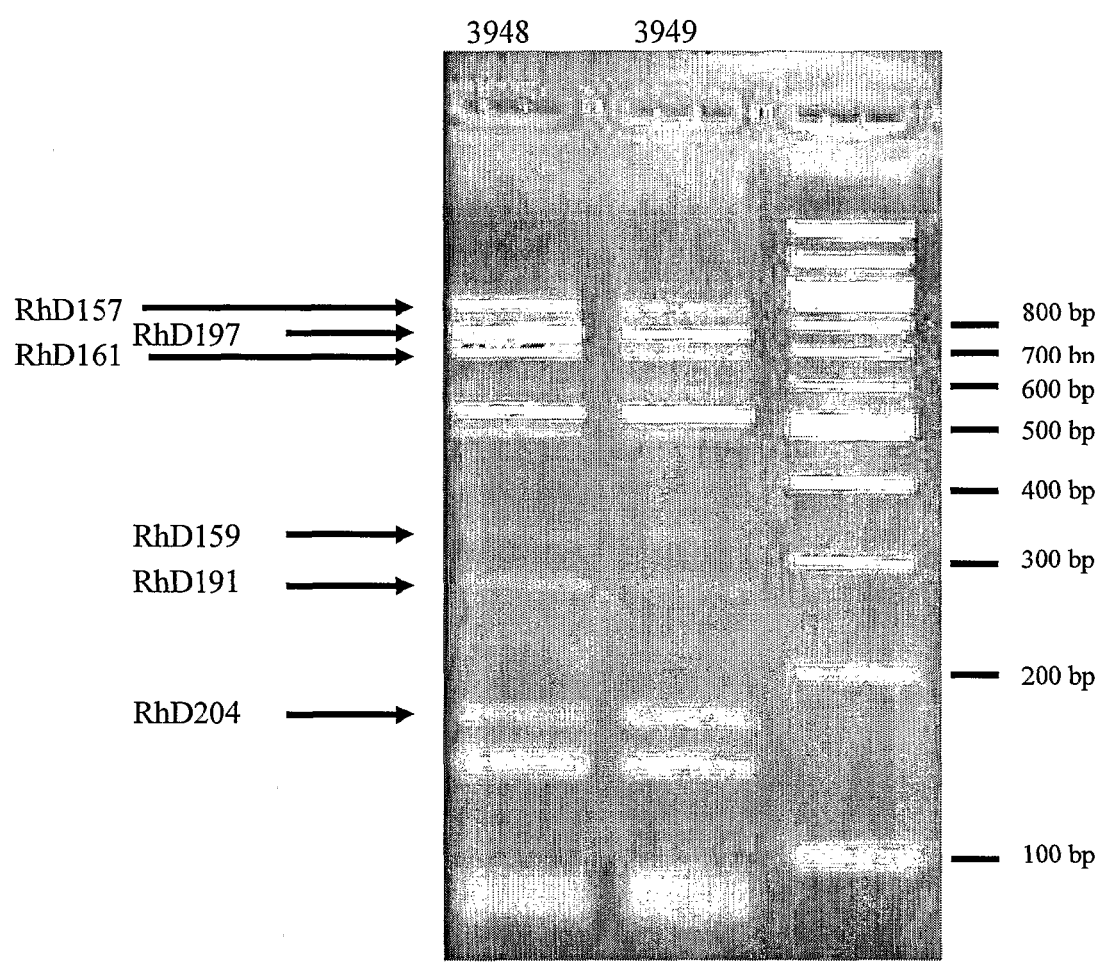
FIG. 9: Gel picture showing HinfI RFLP analysis on RT-PCR product derived from polyclonal cell line aliquots 3948+ and 3949+ (FCW065) producing anti-RhD rpAb after 11 weeks cultivation. Bands which can be assigned to specific clones are identified.

The RT-PCR products were digested with HinfI and analyzed by agarose gel electrophoresis, visualizing the restriction product with ethidium bromide staining (FIG. 9).

The expected size of the restriction fragments obtained by HinfI digestion of the RT-PCR amplified light chains are shown for each individual clone in table 5. Six unique fragment sizes on the gel, which could be assigned to specific Rhesus D antibody producing clones, are indicated in bold. Not all unique fragments could be identified on the gel, these are indicated in italic. This does, however not necessarily mean that these clones are not represented in the culture, the fragments may either not have been separated sufficiently from other fragments to be identifiable, or their concentration is to weak compared to the stronger bands. This may be more pronounced for shorter fragments, since they bind a smaller number of ethidium bromide molecules and therefore are less visible.

TABLE 5

| RhD # | 157 | 158 | 159 | 161 | 163 | 190 | 191 | 192 | 197 | 204 |
|---|---|---|---|---|---|---|---|---|---|---|
| HinfI fragment size | 825 | 671 | 505 | 696 | 505 | 502 | *475* | 671 | 743 | *521* |
| | 138 | 138 | 320 | 138 | *166* | *191* | 268 | *149* | 138 | 167 |
| | 76 | 126 | 138 | 126 | *154* | 138 | 138 | 138 | 85 | 138 |
| | | 76 | 77 | 76 | 138 | 126 | 85 | 76 | 76 | 88 |
| | | 22 | | | 76 | 76 | 76 | | | |

The two aliquots (3948 and 3949) of the same polyclonal cell line, show a similar expression pattern in the gel, although the intensity of the bands are not completely identical, this also indicates that aliquots of the same polyclonal cell line grown under identical conditions will produce anti-RhD rpAb with a similar clonal diversity.

Summary

The present experiment succeeded in generating a library of anti-Rhesus D antibody expression vectors comprising 56 variant anti-Rhesus D-encoding nucleic acid segments (Table 3).

Plasmids containing individual members of the library were used to transfect the CHO-Flp-In (019) cell line, generating 56 individual cell lines capable of expressing a specific anti-RhD antibody.

10 of these cell lines were mixed in order to generate a anti-RhD rpAb manufacturing cell line, which after 9 weeks cultivation still maintained 90% of the initial diversity. After 11 weeks of cultivation mRNA from six different clones could be unambiguously identified and several other clones are likely to be represented in the band an approximately 500 bp.

The fact that two aliquots of the polyclonal CHO-Flp-In (019) cell lines showed similar results with respect to clonal diversity, illustrated that reproducible results can be obtained.

Example 2

Generation of a Working Cell Bank for Larger Scale Production

Twenty seven cell cultures were selected to constitute the polyclonal cell line (RhD157.119D11, RhD159.119B09, RhD160.119C07, RhD161.119E09, RhD162.119G12, RhD163.119A02, RhD189.181E07, RhD191.119E08, RhD192.119G06, RhD196.126H11, RhD197.127A08, RhD199.164E03, RhD201.164H12, RhD202.158E07, RhD203.179F07, RhD207.127A11, RhD240.125A09, RhD241.119B05, RhD244.158B10, RhD245.164E06, RhD293.109A09, RhD301.160A04, RhD305.181E06, RhD306.223E11, RhD307.230E11, RhD319.187A11 and RhD324.231F07).

In addition to the high degree of diversity among the individual clones, the clone selections were also based on growth and production characteristics of the individual cell cultures.

Included in the selection criteria at the cell culture level were:
I. Doubling time; had to be between 24 and 32 hours
II: Intracellular staining; had to show a homogenous cell population
III: Productivity; had to exceed 1.5 pg per cell per day The 27 different cell cultures will be equally mixed in regard to cell number and this mix will constitute the working cell bank for a pilot plant production of anti-RhD rpAb.

Example 3

The present example illustrates the characterization of a polyclonal cell culture with eight members over time. The clonal diversity of the culture was assessed at the genetic level using RFLP analysis and at the protein level using a chromatographic technique in one dimension.

The polyclonal cell line of the present example was constituted of the following eight members: RhD191.119E08, RhD196.126H11, RhD201.164H12, RhD203.179F07, RhD244.158B10, RhD306.223E11, RhD319.187A11 and RhD324.231F07

In the example they will simply be written as follows RhD191, RhD201, RhD203, RhD244, RhD306, RhD319 and RhD324.

RFLP Analysis to Estimate Clone Diversity in Polyclonal Cell Cultures

The distribution of the individual clones in a polyclonal cell culture expressing eight different anti-Rhesus D antibodies was estimated by terminal RFLP (T-RFLP) analysis of RT-PCR products derived from the polyclonal cell line. In the T-RFLP procedure the forward and/or reverse primer(s) are fluorescently labeled and therefore a proportion of the restriction fragments generated from the amplicons will contain the label. The labeled fragments can subsequently be separated by capillary electrophoresis and detected by fluorescence. The analysis can be performed both on the light chain and the variable region of the heavy chain-encoding sequences, depending on the primers applied.

Briefly, a cell suspension corresponding to 200 cells was washed one time in PBS and subjected to a freeze-thaw procedure generating lysates used as template in a RT-PCR amplification using a One-Step RT-PCR kit (Qiagen) and suitable primers.

The RT-PCR was carried out on a standard thermal cycler with the following conditions:

| Reverse transcription | 55° C. for 30 min |
|---|---|
| Denature | 95° C. for 15 min |
| Start cycle loop (35 cycles) | |
| Denature | 95° C. for 30 sec |
| Anneal | 60° C. for 30 sec |
| Elongate | 72° C. for 5 min |

-continued

| End cycle loop | |
| --- | --- |
| Elongate | 72° C. for 15 min |
| Finish | 8° C. forever |

For analysis of the light chain the following primers were used for the RT-PCR amplification. The reverse primer was 6-carboxyflorescein (FAM) labeled and the primer sequences were as follows:

```
VL Forward primer:
5'-TCTCTTCCGCATCGCTGTCT

CL Reverse primer:
5'-FAM-AGGAAAGGACAGTGGGAGTGGCAC
```

Twenty μl of the RT-PCR product was digested with 1 U of NheI, 1 U of PstI and 1 U of HinfI (all from New England Biolabs) in NEB1 for 2 hours.

The labeled fragments were detected by fluorescence capillary electrophoresis on an ABI3700 (Applied Biosystems) at Statens Serum Institute, Copenhagen, DK.

The expected fragments for each of the anti-RhD antibody producing cell clones are shown in Table 6 and the FAM labeled fragments are indicated in bold.

TABLE 6

| RhD # | 191 | 196 | 201 | 203 | 244 | 306 | 319 | 324 |
| --- | --- | --- | --- | --- | --- | --- | --- | --- |
| NheI/PstI/HinfI fragment size | 475 | 696 | 516 | 422 | 690 | 682 | 761 | 513 |
| | 210 | 138 | 166 | 318 | 138 | 138 | 138 | 166 |
| | 138 | 76 | 138 | 138 | 76 | 76 | 138 |
| | 76 | 67 | 76 | 76 | 67 | 67 | 67 | 76 |
| | 67 | 59 | 76 | 67 | 41 | 59 | | 76 |
| | 58 | | 67 | 18 | 18 | 17 | | 67 |
| | 18 | | | | | | | |

Figure 10:
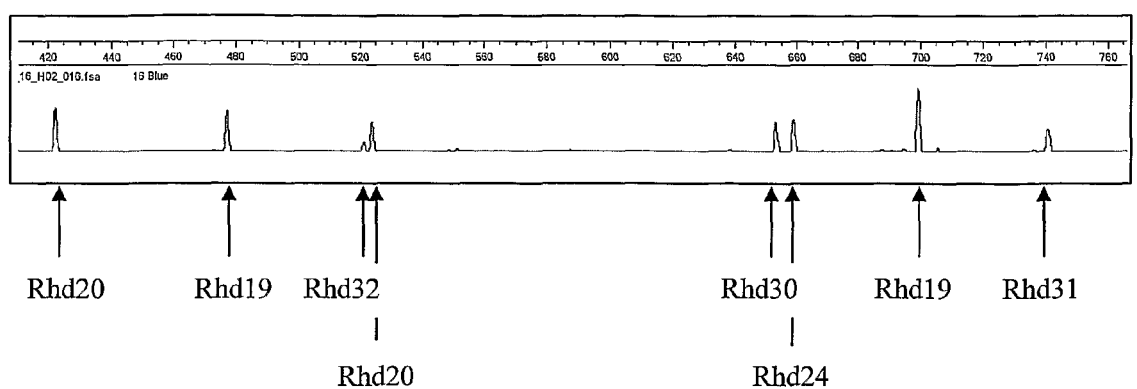
FIG. 10: T-RFLP patterns of anti-Rhesus D antibody light chains from a polyclonal cell culture expressing anti-RhD rpAb with eight different anti-Rhesus D antibodies. The eight different anti-Rhesus D clones have been assigned to the peaks indicated by arrows.

The T-RFLP pattern is shown in FIG. 10 and all eight anti-Rhesus D antibody producing clones have been assigned to specific peaks. Under the assumption that there was no template/primer competition during the RT-PCR, the relative peak area will correspond to the relative amount of mRNA transcribed from each antibody light chain gene represented in the polyclonal cell line.

For analysis of the heavy chain variable region within the same polyclonal cell line the RT-PCR amplification was carried out with VH-specific primers. The primer sequences were as follows:

```
VH Forward primer:
5'-FAM CGTAGCTCTTTTAAGAGGTG

VH Reverse primer:
5'-HEX-ACCGATGGGCCCTTGGTGGA
```

Twenty μl of the RT-PCR product was digested with 1 U of RsaI and 1 U of NdeI (all from New England Biolabs) in NEB2 for 2 hours.

The labeled fragments were detected by fluorescence capillary electrophoresis on an ABI3700. The analysis was performed by Statens Serum Institute, Copenhagen, DK.

The expected T-RFLP patterns are shown in Table 7, where the FAM labeled fragments are shown in bold and the HEX (6-Carboxy-2',4,4',5,7,7'-hexachlorofluorescein succinimidyl ester) labeled fragments are underscored.

TABLE 7

| RhD # | 191 | 196 | 201 | 203 | 244 | 306 | 319 | 324 |
| --- | --- | --- | --- | --- | --- | --- | --- | --- |
| RsaI/NdeI Fragment size | 203 | <u>429</u> | 186 | 350 | <u>435</u> | 328 | 232 | 266 |
| | <u>166</u> | | 142 | <u>88</u> | | <u>79</u> | 118 | <u>157</u> |
| | 63 | | <u>79</u> | | | 22 | <u>79</u> | |
| | | | 22 | | | 9 | 9 | |
| | | | 9 | | | | | |

The polyclonal cell line was cultivated over 5 weeks and once a week samples were taken for T-RFLP analyses. The analysis was performed on the variable heavy chain, but could have been performed on the light chain as well if desired.

Figure 12:
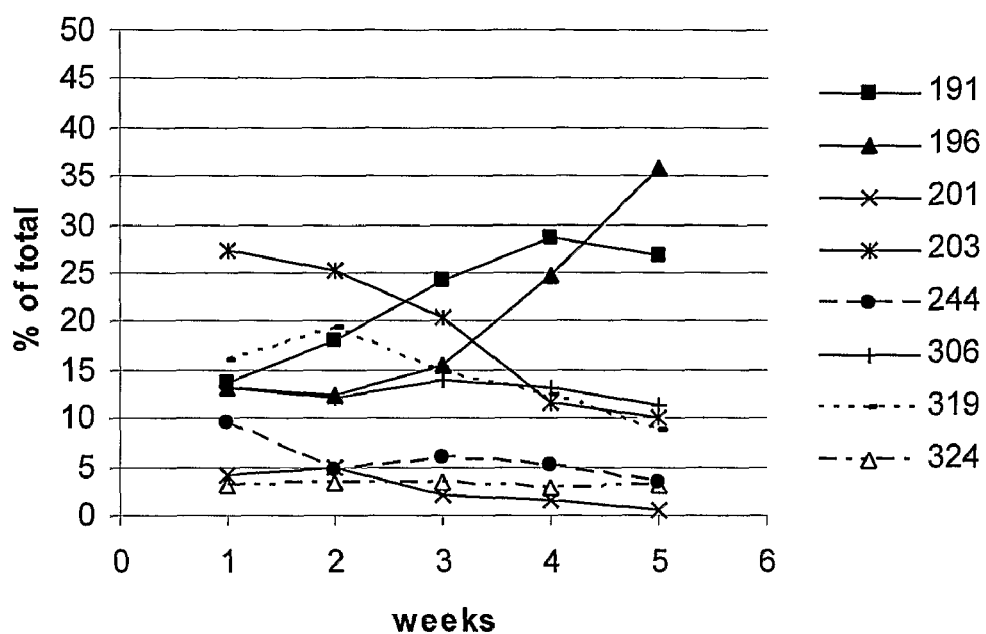
FIG. 12: cDNA distribution estimated by T-RFLP of eight different anti-Rhesus D heavy chain-encoding sequences from a polyclonal cell culture which was cultivated for five weeks.

After capillary electrophoresis of the restriction fragments, the relative peak areas were integrated and used to estimate the clonal diversity of the polyclonal cell culture. The relative quantities over time are shown in FIG. 12.

Based on these results, it seems that RhD196 increase whereas RhD203 seems to decrease over time. The quantities of the other clones are quite stable during the cultivation period and all eight cDNA could be detected after five weeks of cultivation.

By performing T-RFLP on both light chain and heavy chain as well as on both mRNA and DNA it should be possible to obtain a precise fingerprint of the clonal diversity within the polyclonal cell culture, for example in cells at the limit of in vitro cell age or at any given time point during cultivation.

The technique can therefore be used to monitor the stability of the clonal diversity in a cell culture over time during antibody production. The technique can also be applied to monitor the batch-to-batch consistency for example of different ampoules frozen down from the same pWCB or in cells harvested after two or more manufacturing runs.

Figure 13:
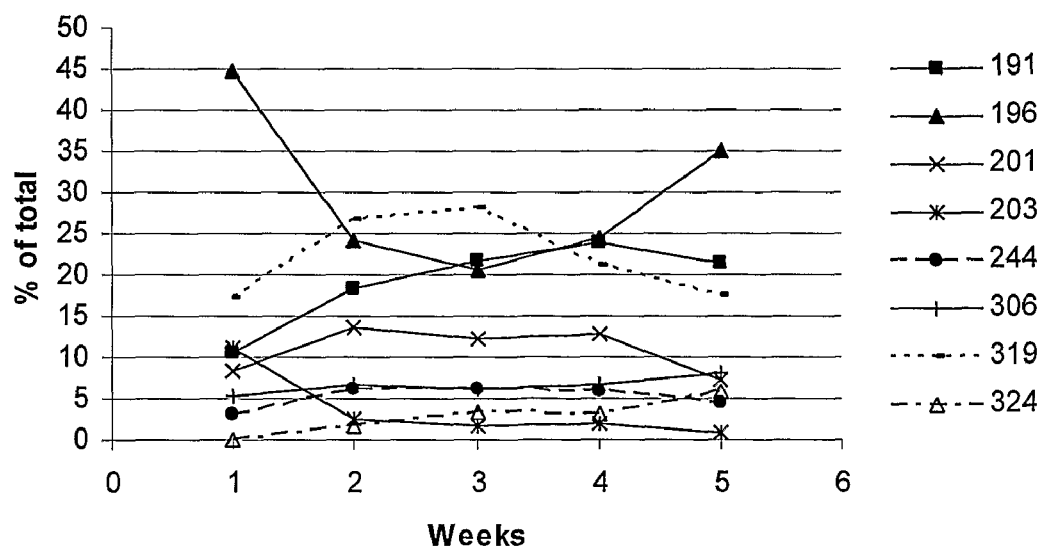
FIG. 13: Shows the relative content (%) of an anti-RhD rpAb with eight different antibodies analyzed using cation-exchange chromatography. Integrated chromatographic peaks were assigned to individual antibodies from the retention times and peak patterns obtained from single antibodies analyzed individually using cation-exchange chromatography under identical conditions.

Cation-Exchange Chromatographic Analysis to Estimate Clonal Diversity in a Polyclonal Cell Culture The polyclonal antibody produced from the same polyclonal cell culture as used in the T-RFLP analysis described above was analyzed using cation-exchange chromatography. The protein A purified recombinantly produced polyclonal antibody was applied onto a PolyCatA column (4.6×100 mm) in 25 mM sodium acetate, 150 mM sodium chloride, pH 5.0 at a flow rate of 60 ml h$^{-1}$ operated at room temperature. The antibody components were subsequently eluted using a linear gradient from 150-350 mM sodium chloride in 25 mM sodium acetate, pH 5.0 at a flow rate of 60 ml h$^{-1}$. The antibody components were detected spectrophotometrically at 280 nm and the chromatogram was subsequently integrated and the area of individual peaks was then used to quantitate antibody components. The relative quantities over time are shown in FIG. 13.

Summary

The results obtained at the genetic level by the RFLP analysis and at the protein level by cation-exchange chromatography are comparable. FIGS. 12 and 13 clearly illustrate that most of the individual clones in the polyclonal cell line as well as the individual antibodies of the polyclonal antibody expressed from the cell line follow the same trends during the 5 weeks of cultivation. Thus, analyses at the genetic as well as at protein level are good equivalents for assessing the compositional diversity of a cell line at the genetic level and of the recombinant polyclonal protein produced from the cell line.

Example 4

The present example illustrates the characterization of a polyclonal cell culture with twenty-five members over time. The clonal diversity of the culture was assessed at the genetic level using T-RFLP analysis and at the protein level using a chromatographic technique in one dimension.

The polyclonal cell line of the present example was constituted of the twenty five members indicated in Table 8. Further, the growth characteristics of the individual clones are shown in Table 8.

TABLE 8

| Clone name | Doubling time (h) | Productivity pg/(cell*day)[a] | Clone name | Doubling time | Productivity pg/(cell*day) |
|---|---|---|---|---|---|
| RhD157.119D11 | 25.6 | 4 | RhD207.127A11 | 34.4 | 3.8 |
| RhD159.119B09 | 26.1 | 1.4 | RhD240.125A09 | 29.6 | 3.6 |
| RhD160.119C07 | 25.4 | 3.8 | RhD241.119B05 | 32.8 | 4.1 |
| RhD162.119G12 | 27.7 | 5.9 | RhD245.164E06 | 28 | 1.5 |
| RhD189.181E07 | 27.8 | 3.2 | RhD293.109A09 | 30.7 | 7.1 |
| RhD191.119E08 | 30.8 | 1.2 | RhD301.160A04 | 29.7 | 5.1 |
| RhD192.119G06 | 25.4 | 1.2 | RhD305.181E06 | 31 | 6.7 |
| RhD196.126H11 | 32 | 8.7 | RhD306.223E11 | 30.9 | 1.7 |
| RhD197.127A08 | 30.1 | 1.6 | RhD317.144A02 | 27 | 10.4 |
| RhD199.164E03 | 27.3 | 2.9 | RhD319.187A11 | 28 | 5.6 |
| RhD201.164H12 | 27.6 | 10.6 | RhD321.187G08 | 31 | 2.7 |
| RhD202.158E07 | 28.8 | 3.1 | RhD324.231F07 | 31.2 | 6.4 |
| RhD203.179F07 | 31.5 | N.A[c] | | | |

[a] Data represent the average of two ELISA measurements
[b] RhD$^{VI}$ reactive
[c] Data not available In the following the clone names are generally only identified by their first three digits, e.g. RhD157.119D11 is written as RhD157.

T-RFLP Analysis of the Variable Part of the Heavy Chain Genes Derived from a Polyclonal Cell Culture Expressing Twenty-Five Different Anti-Rhesus D Antibodies Over a 5 Weeks Cultivation Period.

The polyclonal cell culture examined in the present example was composed of a mixture of cell cultures expressing twenty-five different anti-Rhesus D antibodies (generated as described in Example 1). The polyclonal cell culture was cultivated over 5 weeks and once a week samples were taken for T-RFLP analyses.

The RT-PCR was carried out with the VH-specific primers described in Example 3 and restriction fragmentation was carried out likewise.

Figure 11:
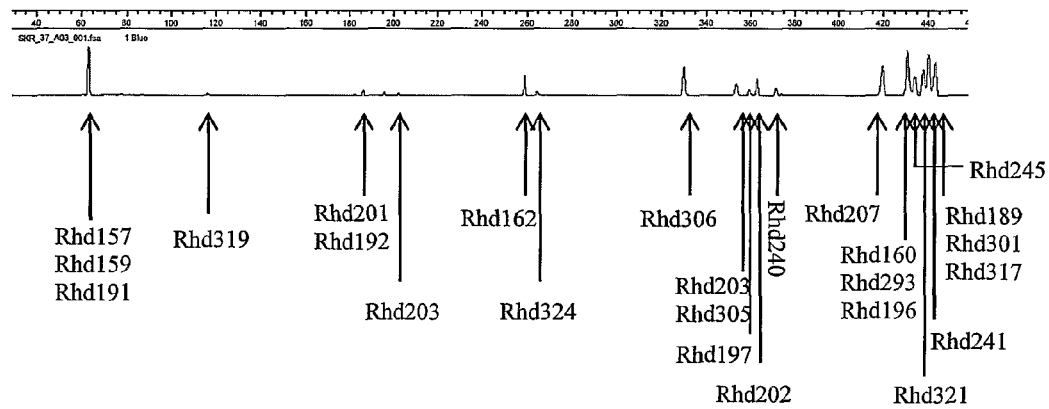
FIG. 11: T-RFLP patterns of anti-Rhesus D antibody heavy chain variable regions from a polyclonal cell culture expressing anti-RhD rpAb with twenty-five different anti-Rhesus D antibodies at a given time point. The twenty-five different anti-Rhesus D clones have been assigned to the peaks indicated by arrows.

T-RFLP of the twenty-five different anti-Rhesus D-encoding sequences will, if all genotypes are present, result in seventeen different FAM labeled fragments. Some fragments will represent up to three different genotypes whereas others will represent a single genotype. The expected sizes of FAM labeled fragments are shown in Table 9 together with the relative quantities of the different FAM labeled fragments over time. Further, one example of a T-RFLP profile is shown in FIG. 11.

TABLE 9

| RhD # | RsaI/NdeI FAM fragment size (bp) | Group | Week1 Area % | Week2 Area % | Week3 Area % | Week4 Area % | Week5 Area % |
|---|---|---|---|---|---|---|---|
| Rhd157 | 63 | 1 | 9.5 | 5.0 | 5.3 | 4.8 | 4.6 |
| Rhd159 | 63 | 1 | | | | | |
| Rhd191 | 63 | 1 | | | | | |
| Rhd319 | 118 | 2 | 0.8 | 0.2 | 0.2 | 0.2 | 0.0 |
| Rhd201 | 186 | 3 | 1.5 | 0.8 | 0.9 | 1.1 | 0.7 |
| Rhd192 | 187 | 3 | | | | | |
| Rhd199 | 203 | 4 | 0.9 | 0.3 | 0.3 | 0.4 | 0.4 |
| Rhd162 | 260 | 5 | 7.4 | 3.6 | 1.7 | 1.0 | 0.0 |
| Rhd324 | 266 | 6 | 1.0 | 0.8 | 0.6 | 0.5 | 0.0 |
| Rhd306 | 328 | 7 | 10.3 | 8.0 | 7.2 | 7.9 | 7.8 |
| Rhd203 | 350 | 8 | 6.0 | 3.4 | 3.8 | 5.9 | 8.9 |
| Rhd305 | 350 | 8 | | | | | |
| Rhd197 | 356 | 9 | 5.1 | 1.8 | 1.7 | 1.8 | 1.3 |
| Rhd202 | 359 | 10 | 3.8 | 4.3 | 5.6 | 5.2 | 3.7 |
| Rhd240 | 369 | 11 | 3.3 | 1.8 | 1.3 | 0.8 | 0.0 |
| Rhd207 | 414 | 12 | 11.7 | 10.5 | 10.1 | 9.9 | 11.1 |
| Rhd160 | 426 | 13 | 11.3 | 17.1 | 17.5 | 18.1 | 17.2 |
| Rhd293 | 426 | 13 | | | | | |
| Rhd196 | 426 | 13 | | | | | |
| Rhd245 | 429 | 14 | 6.5 | 7.1 | 8.3 | 11.0 | 16.8 |
| Rhd321 | 432 | 15 | 6.8 | 9.4 | 8.3 | 7.5 | 4.9 |
| Rhd241 | 435 | 16 | 4.8 | 13.7 | 12.5 | 7.2 | 4.0 |
| Rhd189 | 438 | 17 | 9.4 | 12.3 | 14.8 | 16.8 | 18.7 |
| Rhd301 | 438 | 17 | | | | | |
| Rhd317 | 438 | 17 | | | | | |

It was possible to separate the restriction fragments to an extent that allowed information to be obtained for twelve individual clones of the twenty-five clones constituting the cell line.

The remaining fractions could potentially be subjected to sequencing in order to obtain more information on the remaining clones.

Figure 14:
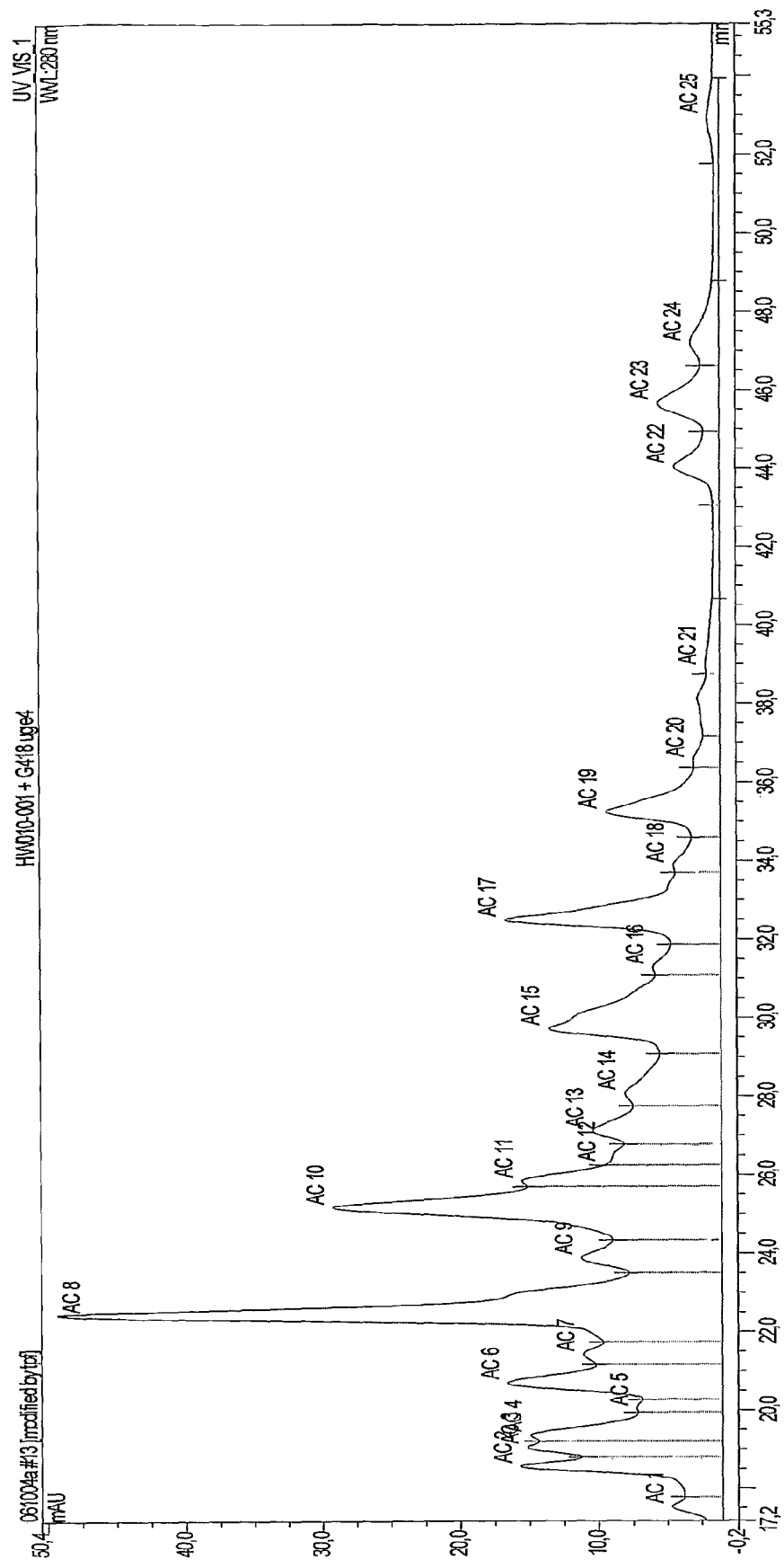
FIG. 14: Cation-exchange chromatogram of an anti-RhD rpAb with twenty-five individual members from a sample obtained after 4 weeks cultivation. Peaks AC1 to 25 comprise antibodies differing in net charge and individual antibodies appearing charge heterogeneous.

Cation-Exchange Chromatographic Analysis to Estimate Clonal Diversity in a Polyclonal Cell Culture Expressing Twenty-Five Different Anti-Rhesus D Antibodies The polyclonal antibody produced from the same polyclonal cell culture as used in the T-RFLP analysis described above, was analyzed using cation-exchange chromatography. The protein A purified recombinantly produced polyclonal antibody was applied onto a PolyCatA column (4.6×100 mm) in 25 mM sodium acetate, 150 mM sodium chloride, pH 5.0 at a flow rate of 60 ml h$^{-1}$ operated at room temperature. The antibody components were subsequently eluted using a linear gradient from 150-350 mM sodium chloride in 25 mM sodium acetate, pH 5.0 at a flow rate of 60 ml h$^{-1}$. The antibody components were detected spectrophotometrically at 280 nm and the chromatogram was subsequently integrated and the area of individual peaks was used to quantitate the different antibody components. FIG. 14 shows the chromatogram produced from the sample obtained a week 4, the antibody containing peaks being numbered from 1 to 25. It is pure concurrence that the chromatogram contains an identical number of peaks as the number of individual antibodies in the polyclonal antibody analyzed. Table 10 show the relative content in percent of the total antibody components (AC1 to 25), as well as the representation of the individual antibodies in each antibody component (peak). The assignment of individual antibodies to the integrated chromatographic peaks was based on the retention times and peak patterns obtained from monoclonal antibodies analyzed using cation-exchange chromatography under identical conditions.

TABLE 10

| Peak | RhD# Ab represented | Week 1 Rel. Area % | Week 2 Rel. Area % | Week 3 Rel. Area % | Week 4 Rel. Area % | Week 5 Rel. Area % |
|---|---|---|---|---|---|---|
| AC 1 | 293, 319 | 2.06 | 2.3 | 1.7 | 1.06 | 0.81 |
| AC 2 | 157, 293 | 3.63 | 3.83 | 3.97 | 3.89 | 3.06 |
| AC 3 | 157, 192 | 2.66 | 2.8 | 2.89 | 2.83 | 2.34 |
| AC 4 | 159, 189, 199 | 6.11 | 5.52 | 5.1 | 4.1 | 2.99 |
| AC 5 | 319 | 2.18 | 1.94 | 1.33 | 1.08 | 1.26 |
| AC 6 | 241, 191 | 6.01 | 6.4 | 6.32 | 5.42 | 4.1 |
| AC 7 | 189, 192, 199, 201 | 3.89 | 4.21 | 3.38 | 2.95 | 2.63 |
| AC 8 | 160 | 12.1 | 15.77 | 18.71 | 17.59 | 15.56 |
| AC 9 | 203, 191 | 2.65 | 3.89 | 3.69 | 3.99 | 4.14 |
| AC 10 | 162, 202 | 6.78 | 10.22 | 13.52 | 12.29 | 9.75 |
| AC 11 | 203, 306, 301 | 2.86 | 3.63 | 4.35 | 3.66 | 3.92 |
| AC 12 | 245 | 1.43 | 1.63 | 1.5 | 2.27 | 2.02 |
| AC 13 | 301, 321 | 2.5 | 3.35 | 3.92 | 4.16 | 3.64 |
| AC 14 | 305 | 2.44 | 2.61 | 3.12 | 4.23 | 6.07 |
| AC 15 | 196, 197, 240, 305, 321 | 8.33 | 7.22 | 7.36 | 8.49 | 4.01 |
| AC 16 | 197 | 3.82 | 2.71 | 2.15 | 1.86 | 7.86 |
| AC 17 | 196, 240, 324 | 7.57 | 5.12 | 4.86 | 6.89 | 7.79 |
| AC 18 | 197, 321 | 2.27 | 1.44 | 1.51 | 1.39 | 2.83 |
| AC 19 | 196, 240 | 3.8 | 2.63 | 2.87 | 3.98 | 6.35 |
| AC 20 | 317 | 4.58 | 1.39 | 0.77 | 0.71 | 0.86 |
| AC 21 | 317 | 2.86 | 0.59 | 0.36 | 0.83 | 0.42 |
| AC 22 | 207 | 2.07 | 2.61 | 1.58 | 1.65 | 1.93 |
| AC 23 | 207 | 3.33 | 3.87 | 2.56 | 2.41 | 2.87 |
| AC 24 | 207 | 2.46 | 3.48 | 1.73 | 1.52 | 1.92 |
| AC 25 | Unknown | 1.58 | 0.83 | 2 | 0.75 | 0.87 |

Cation-exchange chromatography separates individual antibody members from a polyclonal antibody based on differences in net charge between the individual members and in addition separates forms of individual antibodies that appear charge heterogeneous. Several antibodies were therefore represented in a single peak, e.g. AC 1 containing RhD293 and RhD319 (see Table 10) and some individual antibodies were further represented in several chromatographic peaks, e.g. RhD319 which is present both in AC1 and 5 (see Table 10).

Peaks which contain more than one individual antibody could be subjected to additional protein chemical characterization techniques, such as quantitative analysis with anti-idiotype peptides, proteolytic peptide mapping, N-terminal sequencing or a second dimension chromatography.

Summary

The present example illustrates the combined use of T-RFLP analyses and cation-exchange chromatography for assessing the distribution of the primary transcripts and of antibody components, respectively, over a period of cultivation. The T-RFLP analysis allows for unique identification of 12 individual clones of the 25 clones expressed in the polyclonal cell line and in the present example it is illustrated that these 12 clones could be detected during 4 weeks cultivation with the T-RFLP analysis. Potentially, more clones could be identified by sequence analysis of fragments representing more than one clone. The distribution of antibody components was analyzed using cation-exchange chromatography and in the present example it is seen that the distribution of the 25 analyzed components is relatively stable during cultivation Although unique identification of all individual antibodies is difficult due to the inherent charge heterogeneous nature of the expressed antibodies it was demonstrated in the present example that antibody component 8 representing the RhD160 antibody showed the highest antibody level during the cultivation period in accordance with the high T-RFLP values obtained for group 13 representing the RhD160, 293, and 196 clones. Furthermore, the RhD 207 component, which could be uniquely identified by T-RFLP as well as by cation-exchange chromatography, showed T-RFLP levels of 10-11% and slightly lower levels of 5.5-10% obtained at antibody level. Overall, the two techniques together demonstrate a relatively stable production at the mRNA and antibody level during cultivation; however, potential discrepancies between the two techniques could also be seen, illustrated by the apparent loss of transcription of some clones at weeks 5 of cultivation contrasting the results obtained at the antibody level. Thus, the present example justifies the complementary use of both techniques to define cultivation intervals within which stable production of complex polyclonal protein can be obtained.

Example 5

The present example demonstrates the generation of pWCB containing anti-RhD rpAb with 25 individual members and provides confirmation of a minimal batch-to-batch variation of rpAb products purified from different vials from the pWCB.

Generation of the pWCB

To generate a pWCB containing anti-RhD rpAb with 25 individual members, one vial of each of 25 banked monoclonal anti-RhD antibody production cell lines (RhD157, 159, 160, 162, 189, 191, 192, 196, 197, 199, 201, 202, 203, 207, 240, 241, 245, 293, 301, 305, 306, 317, 319, 321, 324) were thawed in ExCell 302 medium containing 4 mM glutamine and expanded for 3 weeks in the same medium supplemented with 500 µg/ml G418 and anti-clumping agent diluted 1:250. Equal numbers of cells ($2 \times 10^6$) from each culture were then carefully mixed together, and frozen in liquid nitrogen ($5 \times 10^7$ cells/vial) using standard freezing procedures.

Cultivation in Bioreactors

Vials from the pWCB were thawed in T75 flasks (Nunc, Roskilde, Denmark) and expanded in spinner flasks (Techne, Cambridge, UK). 5 L bioreactors (Applikon, Schiedam, Netherlands) were inoculated with $0.6 \times 10^6$ cells/ml in 1.5 L. During the reactor runs, cells were fed on a daily basis with ExCell 302 medium supplemented with concentrated feed solution, glutamine and glucose to a final volume of 4.5 L. The bioreactor runs were terminated after 16-17 days. The three batches are termed Sym04:21, Sym04:23 and Sym04:24. The batches were cultured at different points in time.

Analysis of Batch-to-Batch Variation

The recombinant polyclonal antibody samples were purified by affinity chromatography using HiTrap™ rProtein A columns (GE Healthcare, UK).

The purified recombinant polyclonal antibody samples were analyzed using cation-exchange chromatography employing a PolyCAT A column (4.6×100 mm, from PolyLC Inc., MA, US) in 25 mM sodium acetate, 150 mM sodium chloride, pH 5.0 at a flow rate of 60 ml/h (room temperature). The antibody peaks were subsequently eluted using a linear gradient from 150 mM to 350 or 500 mM NaCl in 25 mM sodium acetate, pH 5.0 at a flow rate of 60 ml/h. The antibody peaks were detected spectrophotometrically at 280 nm. The chromatograms were integrated and the area of individual peaks used for quantification. As already mentioned some of the individual antibodies displayed charge heterogeneity and two antibodies may contribute to the same peak in the IEX chromatogram.

Table 11 show the relative content in percent of the total antibody components (AC). In the present example the relative area has been calculated for 35 AC, whereas Example 4 only calculated the relative area for 25 AC. This difference is strictly due to a different assignment of the peaks in the chromatogram and not to actual differences in the profile as such.

TABLE 11

| Peak | Average Rel. Area % | Standard deviation |
|---|---|---|
| AC 1 | 1.71 | 0.35 |
| AC 2 | 2.36 | 0.13 |
| AC 3 | 4.40 | 0.78 |
| AC 4 | 3.58 | 0.78 |
| AC 5 | 5.83 | 0.60 |
| AC 6 | 2.11 | 0.25 |
| AC 7 | 4.16 | 0.33 |
| AC 8 | 4.21 | 0.59 |
| AC 9 | 3.41 | 0.97 |
| AC 10 | 14.22 | 2.91 |
| AC 11 | 4.24 | 0.79 |
| AC 12 | 2.98 | 0.47 |
| AC 13 | 2.31 | 0.16 |
| AC 14 | 2.44 | 0.26 |
| AC 15 | 9.17 | 0.52 |
| AC 16 | 5.08 | 0.43 |
| AC 17 | 1.98 | 0.26 |
| AC 18 | 3.04 | 0.26 |
| AC 19 | 1.79 | 0.16 |
| AC 20 | 1.39 | 0.07 |
| AC 21 | 1.32 | 0.15 |
| AC 22 | 2.60 | 0.23 |
| AC 23 | 1.59 | 0.25 |
| AC 24 | 0.62 | 0.12 |
| AC 25 | 1.12 | 0.06 |
| AC 26 | 1.31 | 0.04 |
| AC 27 | 0.58 | 0.12 |
| AC 28 | 1.30 | 0.25 |
| AC 29 | 1.05 | 0.39 |
| AC 30 | 0.66 | 0.24 |
| AC 31 | 0.70 | 0.44 |
| AC 32 | 1.64 | 0.10 |
| AC 33 | 2.30 | 0.16 |
| AC 34 | 1.77 | 0.24 |
| AC 35 | 1.03 | 0.44 |

Table 11 shows that the reproducibility between the harvested antibody products from the three batches was high. The variation in the size of individual antibody peaks was within 20% for most antibody components, whereas the variation for some of the smallest peaks was slightly larger.

Example 6

The present example demonstrates that different batches of an anti-RhD rpAb with 25 individual members (same composition as in Example 4) bind to RhD-positive erythrocytes with similar potency and show comparable biological activity with respect to the relevant effector mechanisms: Antibody-dependent cellular cytotoxicity (ADCC) and phagocytosis.

Preparation of Red Blood Cells

Red blood cells (RBC) were prepared from whole blood obtained from healthy donors after informed consent at the Blood Bank, Aalborg Hospital, DK, by washing the blood three times in PBS (Gibco, Invitrogen, United Kingdom) containing 1% bovine serum albumin (BSA, Sigma-Aldrich, Germany). The erythrocytes were resuspended and stored at 4° C. as a 10% solution in ID-Cellstab (DiaMed, Switzerland).

Preparation of PBMC

Buffy coats containing blood from healthy donors were obtained from the Blood Bank at the National Hospital, Copenhagen, Denmark and peripheral blood mononuclear cells (PBMC) were purified on Lymphoprep (Axis-Shield, Norway).

Potency Assay

Figure 15:
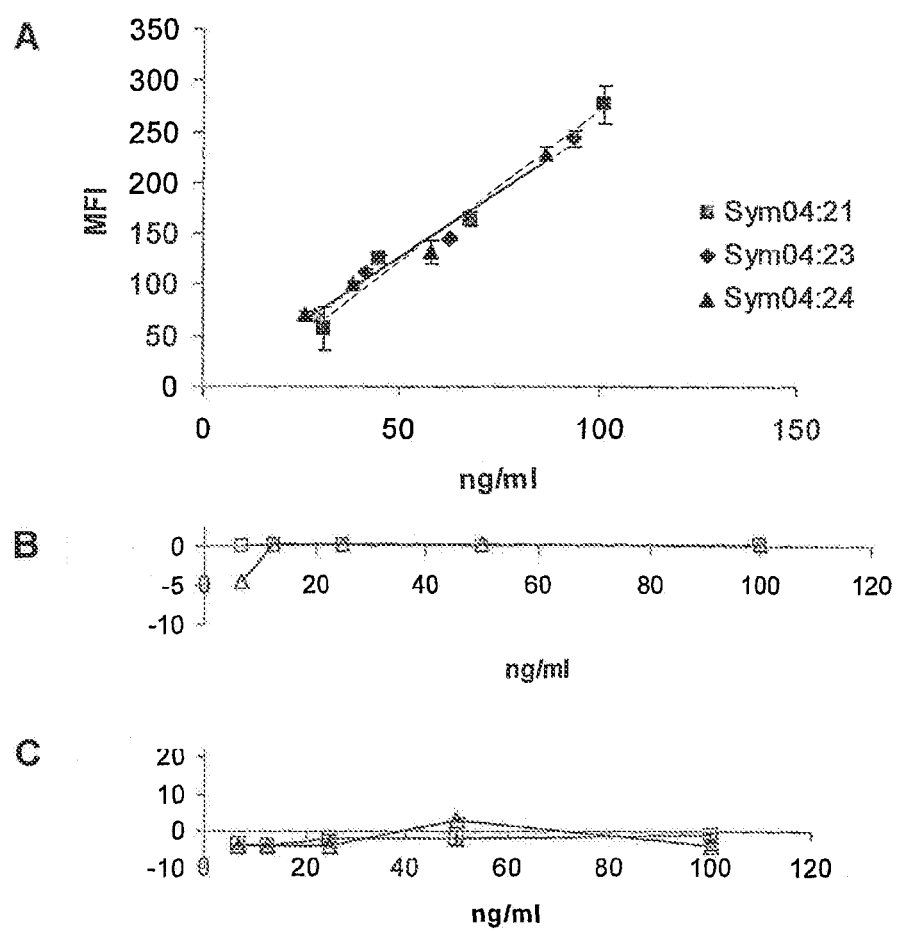
FIG. 15: (A) Shows a comparison of the potency of three batches, Sym04:21, Sym04:23, and Sym04:24, of anti-RhD pAb with 25 individual members, produced by fed batch cultivation in 5 L scale. Binding of pAb to RhD-positive erythrocytes was measured by FACS and the mean fluorescence intensity (MFI) is shown as a function of pAb concentration in ng/ml. Further, the functional activity of an anti-RhD pAb with 25 individual members was measured on Sym04:21 and Sym04:24 in a combined ADCC/phagocytosis assay. (B) Shows the ADCC results as percentage of specific lysis of RhD-positive and RhD-negative erythrocytes as a function of pAb concentration in ng/ml. (c) Shows the percentage of phagocytosis of RhD-positive and RhD-negative erythrocytes as a function of pAb concentration in ng/ml.

The potency assay was adopted from the European Pharmacopoeia 4 (section 2.7.13 method C). The binding capacity of an anti-RhD rpAb with 25 individual members was measured using RhD-positive erythrocytes at $5 \times 10^4$ cells/µl in PBS, 1% BSA. Anti-RhD rpAb batches, Sym04:21, Sym04:23, and Sym04:24, were obtained from individual 5 L fed batch bioreactor runs. Dilutions (1½-fold) of the Anti-RhD rpAb batches were made in PBS, 1% BSA in triplicate in 96 well plates (Becton Dickinson Labware, NJ, USA). Fifty µl of the anti-RhD rpAb dilutions were mixed with 50 µl of erythrocytes and incubated at 37° C. for 40 min. The cells were washed twice (300×g, 2 min) in PBS, 1% BSA. Eighty µl of phycoerythrin-conjugated goat anti-human IgG, (Beckman Coulter, Calif., USA) diluted 1:20 in PBS, 1% BSA was added to each sample and left at 4° C. for 30 min. The samples were washed in PBS, 10% BSA and in FacsFlow (Becton Dickinson, Belgium) (300×g, 2 min), and resuspended in 200 μl FACSFlow. The samples were run on a FACSCalibur (Becton Dickinson, Calif., USA) and data analysis performed using CellQuest Pro and Excel. The three individual Anti-RhD rpAb batches displayed essentially identical binding potency to RhD-positive erythrocytes (FIG. 15A)

Combined ADCC and Phagocytosis Assay

This assay was adapted from Berkman et al. 2002. Autoimmunity 35, 415-419. Briefly, RhD positive (RhD+) and RhD negative (RhD−) red blood cells (RBC) were labeled with radioactive Chromium. For $Cr^{51}$ labeling, $1 \times 10^8$ RhD+ and RhD− RBC, respectively, were centrifuged (600×g for 10 min) and 100 μl Dulbeccos' modified eagles medium (DMEM) and 200 μl sodium chromate (0.2 μCi) (GE Healthcare, UK) were added to each tube before incubation for 1.5 hours at 37° C. The suspension was washed twice in 50 ml PBS and resuspended in 1 ml complete DMEM (containing 2 mM glutamine, 1% Penicillin-Streptomycin and 10% fetal calf serum) (Invitrogen, CA, US). Cells were adjusted to $4 \times 10^6$ cells/ml and 50 μl/well were added to 96-well cell culture plates (Nunc). Fifty μl of two-fold dilutions of Anti-RhD rpAb from batch Sym04:21 or Sym04:24, was then added to each well, except control wells. Control wells were supplied with complete DMEM and used for either spontaneous lysis/retention or maximum lysis.

The PBMC were adjusted to $2 \times 10^7$ cells/ml, and 100 μl were added to each well and incubated at 37° C. overnight. One hundred μl % Triton-X-100 (Merck, Germany) was added to the maximum lysis control wells. The plates were centrifuged (600×g for 2 min) and 50 μl of the supernatant was transferred to ADCC Lumaplates (Perkin Elmer, Belgium).

Following transfer of the supernatants, the cell culture plates were centrifuged (300×g for 2 min) and 50 μl supernatant from the maximum lysis wells were transferred to another LumaPlate (phagocytosis LumaPlate). In the cell culture plate, the supernatant was removed from the remaining wells and lysis buffer (140 mM $NH_4Cl$, 17 mM Tris-HCl) was added, followed by 5 min incubation at 37° C. $NH_4Cl$ lyses the RBC, but leaves the PBMC fraction and thereby the phagocytozed RBC intact. After RBC lysis, the plates were centrifuged (4° C., 2 min, 300 g), pellets were washed twice in PBS, and resuspended in 100 μl PBS. One hundred μl % Triton-X-100 was added to the wells to lyse the phagocytic PBMC, and 50 μl of the lysate was transferred to the phagocytosis LumaPlates. The Lumaplates were dried overnight at 40° C. and counted in a TopCount NXT (Packard, Conn., USA). All data were imported into Excell and analyzed as described by Berkman et al. 2002. Autoimmunity 35, 415-419. Briefly, the computations were performed as follows:

ADCC: Immune lysis (%)=(mean test $Cr^{51}$ released−mean spontaneous $Cr^{51}$ released)/(total $Cr^{51}$ in target erythrocytes−machine background)×100

Phagocytosis: Immune phagocytosis (%)=(mean test $Cr^{51}$ retention−mean spontaneous $Cr^{51}$ retention)/(total $Cr^{51}$ in target erythrocytes−machine background)×100

All data were normalized to the combined maximum plateau values

The functional activity of anti-RhD rpAb from the two consecutive reactor runs showed nearly identical functional activity in both in vitro assays (FIGS. 15B and 15C) reflecting the high consistency between the batches.

Example 7

The present example demonstrates that the clonal diversity of an anti-RhD rpAb with 25 individual members (same composition as in Example 4) is maintained during downstream processing (DSP). Cation-exchange chromatographic analysis is used to estimate clonal diversity during DSP of the recombinant polyclonal antibody.

Down-Stream Processing

Figure 16:
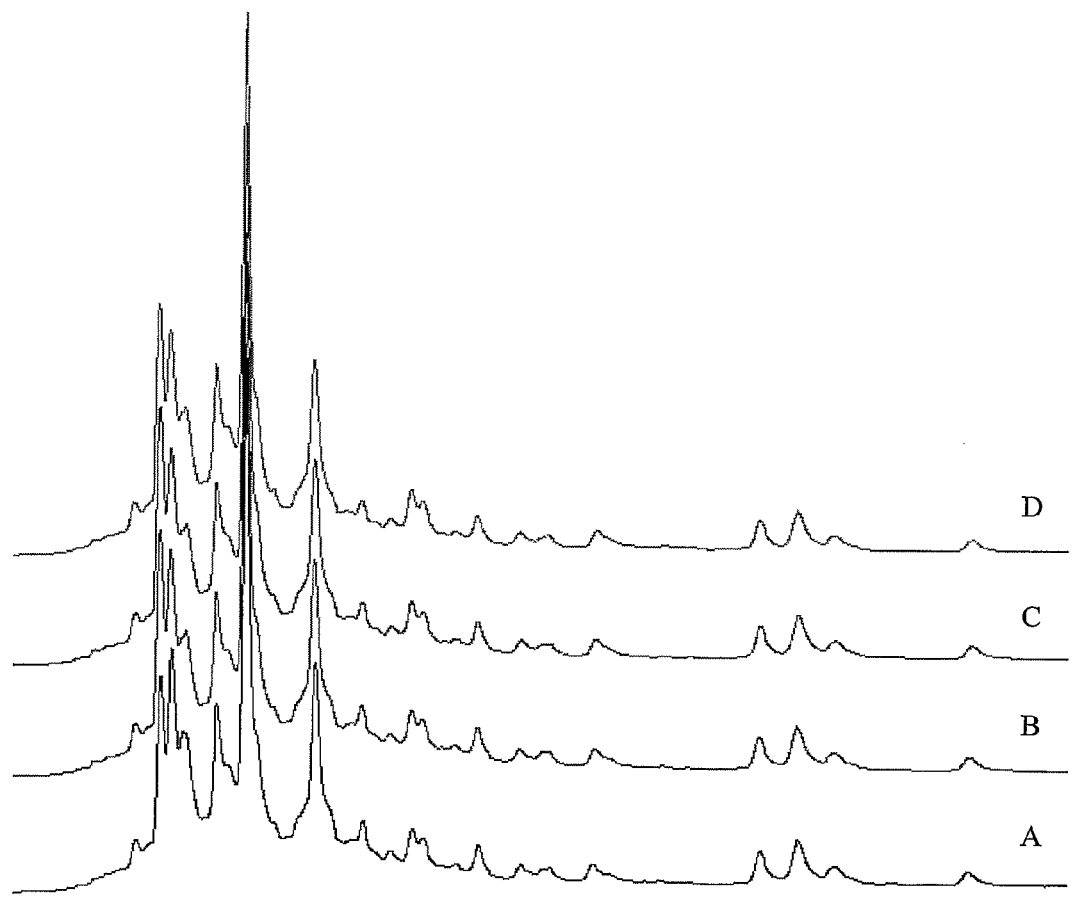
FIG. 16: Cation-exchange chromatography profiles showing samples taken at different stages during down-stream processing of an anti-RhD rpAb sample containing 25 individual members represented by material collected following capture elution (A), Sephadex G-25 (B), DEAE-Sepharose (C), and MEP Hypercel (D)

An anti-RhD rpAb sample, containing 25 individual members, from a developmental bioreactor run was purified using the following DSP steps:

1. capture of the antibodies using a MAbSelect column
2. virus inactivation at pH 3
3. buffer exchange using a Sephadex G-25 column
4. anion-exchange chromatography using a DEAE-Sepharose column
5. virus filtration using a Planova 15N filter, and
6. hydrophobic charge induction chromatography using a MEP Hypercel column
7. ultra filtration/diafiltration using a Millipore biomax filter Analysis of Clonal Diversity After Individual DSP Steps Cation-exchange chromatography was used to analyze the clonal diversity during DSP of a recombinant polyclonal antibody composition. Samples taken after step 1, 3, 4 and 6 during DSP of a anti-RhD rpAb was applied onto a PolyCatA column (4.6×100 mm) in 25 mM sodium acetate, 150 mM sodium chloride, pH 5.0 at a flow rate of 60 ml h$^{-1}$ operated at room temperature. The antibody components were subsequently eluted using a linear gradient from 150-500 mM sodium chloride in 25 mM sodium acetate, pH 5.0 at a flow rate of 60 ml h−1. The antibody components were detected spectrophotometrically at 280 nm and the chromatograms were compared (FIG. 16) to detect the potential loss of clonal diversity during DSP. In the present example it was demonstrated, using cation-exchange chromatography that the clonal diversity is essentially unchanged during DSP of a recombinant polyclonal antibody.

The invention claimed is:

1. An anti-RhD recombinant polyclonal antibody comprising:
   a) a variable heavy chain ($V_H$) sequence selected from the group consisting of SEQ ID NOs: 147-202; and
   b) a light chain (LC) sequence selected from the group consisting of SEQ ID NOs: 203-258.

2. The anti-RhD recombinant polyclonal antibody according to claim 1, wherein said antibody specifically binds to an RhD category VI antigen selected from the group consisting of epD3, epD4 and epD9 or a Rhesus D antigen epitope selected from the group consisting of epD1, epD2, epD5, epD6/7 and epD8.

3. The anti-RhD recombinant polyclonal antibody according to claim 1, wherein said antibody comprises a sequence selected from the group consisting of:
   a) the $V_H$ sequence of SEQ ID NO: 147 and the LC sequence of SEQ ID NO: 203;
   b) the $V_H$ sequence of SEQ ID NO: 148 and the LC sequence of SEQ ID NO: 204;
   c) the $V_H$ sequence of SEQ ID NO: 149 and the LC sequence of SEQ ID NO: 205;
   d) the $V_H$ sequence of SEQ ID NO: 151 and the LC sequence of SEQ ID NO: 207;
   e) the $V_H$ sequence of SEQ ID NO: 153 and the LC sequence of SEQ ID NO: 209;
   f) the $V_H$ sequence of SEQ ID NO: 155 and the LC sequence of SEQ ID NO: 211;
   g) the $V_H$ sequence of SEQ ID NO: 156 and the LC sequence of SEQ ID NO: 212;
   h) the $V_H$ sequence of SEQ ID NO: 157 and the LC sequence of SEQ ID NO: 213;
   i) the $V_H$ sequence of SEQ ID NO: 162 and the LC sequence of SEQ ID NO: 218; and
   j) the $V_H$ sequence of SEQ ID NO: 169 and the LC sequence of SEQ ID NO: 225.

4. The anti-RhD recombinant polyclonal antibody according to claim 1, wherein said antibody comprises a sequence selected from the group consisting of:
   a) the $V_H$ sequence of SEQ ID NO: 147 and the LC sequence of SEQ ID NO: 203;
   b) the $V_H$ sequence of SEQ ID NO: 149 and the LC sequence of SEQ ID NO: 205;
   c) the $V_H$ sequence of SEQ ID NO: 150 and the LC sequence of SEQ ID NO: 206;
   d) the $V_H$ sequence of SEQ ID NO: 152 and the LC sequence of SEQ ID NO: 208;
   e) the $V_H$ sequence of SEQ ID NO: 154 and the LC sequence of SEQ ID NO: 210;

f) the V_H sequence of SEQ ID NO: 156 and the LC sequence of SEQ ID NO: 212;
g) the V_H sequence of SEQ ID NO: 157 and the LC sequence of SEQ ID NO: 213;
h) the V_H sequence of SEQ ID NO: 161 and the LC sequence of SEQ ID NO: 217;
i) the V_H sequence of SEQ ID NO: 162 and the LC sequence of SEQ ID NO: 218;
j) the V_H sequence of SEQ ID NO: 164 and the LC sequence of SEQ ID NO: 220;
k) the V_H sequence of SEQ ID NO: 166 and the LC sequence of SEQ ID NO: 222;
l) the V_H sequence of SEQ ID NO: 167 and the LC sequence of SEQ ID NO: 223;
m) the V_H sequence of SEQ ID NO: 168 and the LC sequence of SEQ ID NO: 224;
n) the V_H sequence of SEQ ID NO: 172 and the LC sequence of SEQ ID NO: 228;
o) the V_H sequence of SEQ ID NO: 175 and the LC sequence of SEQ ID NO: 231;
p) the V_H sequence of SEQ ID NO: 176 and the LC sequence of SEQ ID NO: 232;
q) the V_H sequence of SEQ ID NO: 180 and the LC sequence of SEQ ID NO: 236;
r) the V_H sequence of SEQ ID NO: 182 and the LC sequence of SEQ ID NO: 238;
s) the V_H sequence of SEQ ID NO: 183 and the LC sequence of SEQ ID NO: 239;
t) the V_H sequence of SEQ ID NO: 191 and the LC sequence of SEQ ID NO: 247;
u) the V_H sequence of SEQ ID NO: 195 and the LC sequence of SEQ ID NO: 251;
v) the V_H sequence of SEQ ID NO: 196 and the LC sequence of SEQ ID NO: 252;
w) the V_H sequence of SEQ ID NO: 198 and the LC sequence of SEQ ID NO: 254;
x) the V_H sequence of SEQ ID NO: 199 and the LC sequence of SEQ ID NO: 255;
y) the V_H sequence of SEQ ID NO: 200 and the LC sequence of SEQ ID NO: 256; and
z) the V_H sequence of SEQ ID NO: 202 and the LC sequence of SEQ ID NO: 258.

5. The anti-RhD recombinant polyclonal antibody according to claim 1, wherein said antibody specifically binds to an RhD category VI antigen selected from the group consisting of epD3, epD4 and epD9.

6. The anti-RhD recombinant polyclonal antibody according to claim 1, wherein said antibody specifically binds to a Rhesus D antigen epitope selected from the group consisting of epD1, epD2, epD5, epD6/7 and epD8.

7. The anti-RhD recombinant polyclonal antibody according to claim 1, wherein said antibody comprises the VH sequence of SEQ ID NO: 147 and the LC sequence of SEQ ID NO: 203.

8. The anti-RhD recombinant polyclonal antibody according to claim 1, wherein said antibody comprises the VH sequence of SEQ ID NO: 148 and the LC sequence of SEQ ID NO: 204.

9. The anti-RhD recombinant polyclonal antibody according to claim 1, wherein said antibody comprises the VH sequence of SEQ ID NO: 149 and the LC sequence of SEQ ID NO: 205.

10. The anti-RhD recombinant polyclonal antibody according to claim 1, wherein said antibody comprises the VH sequence of SEQ ID NO: 150 and the LC sequence of SEQ ID NO: 206.

11. The anti-RhD recombinant polyclonal antibody according to claim 1, wherein said antibody comprises the VH sequence of SEQ ID NO: 151 and the LC sequence of SEQ ID NO: 207.

12. The anti-RhD recombinant polyclonal antibody according to claim 1, wherein said antibody comprises the VH sequence of SEQ ID NO: 152 and the LC sequence of SEQ ID NO: 208.

13. The anti-RhD recombinant polyclonal antibody according to claim 1, wherein said antibody comprises the VH sequence of SEQ ID NO: 153 and the LC sequence of SEQ ID NO: 209.

14. The anti-RhD recombinant polyclonal antibody according to claim 1, wherein said antibody comprises the VH sequence of SEQ ID NO: 154 and the LC sequence of SEQ ID NO: 210.

15. The anti-RhD recombinant polyclonal antibody according to claim 1, wherein said antibody comprises the VH sequence of SEQ ID NO: 155 and the LC sequence of SEQ ID NO: 211.

16. The anti-RhD recombinant polyclonal antibody according to claim 1, wherein said antibody comprises the VH sequence of SEQ ID NO: 156 and the LC sequence of SEQ ID NO: 212.

17. The anti-RhD recombinant polyclonal antibody according to claim 1, wherein said antibody comprises the VH sequence of SEQ ID NO: 157 and the LC sequence of SEQ ID NO: 213.

18. The anti-RhD recombinant polyclonal antibody according to claim 1, wherein said antibody comprises the VH sequence of SEQ ID NO: 161 and the LC sequence of SEQ ID NO: 217.

19. The anti-RhD recombinant polyclonal antibody according to claim 1, wherein said antibody comprises the VH sequence of SEQ ID NO: 162 and the LC sequence of SEQ ID NO: 218.

20. The anti-RhD recombinant polyclonal antibody according to claim 1, wherein said antibody comprises the VH sequence of SEQ ID NO: 164 and the LC sequence of SEQ ID NO: 220.

21. The anti-RhD recombinant polyclonal antibody according to claim 1, wherein said antibody comprises the VH sequence of SEQ ID NO: 166 and the LC sequence of SEQ ID NO: 222.

22. The anti-RhD recombinant polyclonal antibody according to claim 1, wherein said antibody comprises the VH sequence of SEQ ID NO: 167 and the LC sequence of SEQ ID NO: 223.

23. The anti-RhD recombinant polyclonal antibody according to claim 1, wherein said antibody comprises the VH sequence of SEQ ID NO: 168 and the LC sequence of SEQ ID NO: 224.

24. The anti-RhD recombinant polyclonal antibody according to claim 1, wherein said antibody comprises the VH sequence of SEQ ID NO: 169 and the LC sequence of SEQ ID NO: 225.

25. The anti-RhD recombinant polyclonal antibody according to claim 1, wherein said antibody comprises the VH sequence of SEQ ID NO: 172 and the LC sequence of SEQ ID NO: 228.

26. The anti-RhD recombinant polyclonal antibody according to claim 1, wherein said antibody comprises the VH sequence of SEQ ID NO: 175 and the LC sequence of SEQ ID NO: 231.

27. The anti-RhD recombinant polyclonal antibody according to claim 1, wherein said antibody comprises the VH sequence of SEQ ID NO: 176 and the LC sequence of SEQ ID NO: 232.

28. The anti-RhD recombinant polyclonal antibody according to claim 1, wherein said antibody comprises the VH sequence of SEQ ID NO: 180 and the LC sequence of SEQ ID NO: 236.

29. The anti-RhD recombinant polyclonal antibody according to claim 1, wherein said antibody comprises the VH sequence of SEQ ID NO: 182 and the LC sequence of SEQ ID NO: 238.

30. The anti-RhD recombinant polyclonal antibody according to claim 1, wherein said antibody comprises the VH sequence of SEQ ID NO: 183 and the LC sequence of SEQ ID NO: 239.

31. The anti-RhD recombinant polyclonal antibody according to claim 1, wherein said antibody comprises the VH sequence of SEQ ID NO: 191 and the LC sequence of SEQ ID NO: 247.

32. The anti-RhD recombinant polyclonal antibody according to claim 1, wherein said antibody comprises the VH sequence of SEQ ID NO: 195 and the LC sequence of SEQ ID NO: 251.

33. The anti-RhD recombinant polyclonal antibody according to claim 1, wherein said antibody comprises the VH sequence of SEQ ID NO: 196 and the LC sequence of SEQ ID NO: 252.

34. The anti-RhD recombinant polyclonal antibody according to claim 1, wherein said antibody comprises the VH sequence of SEQ ID NO: 198 and the LC sequence of SEQ ID NO: 254.

35. The anti-RhD recombinant polyclonal antibody according to claim 1, wherein said antibody comprises the VH sequence of SEQ ID NO: 199 and the LC sequence of SEQ ID NO: 255.

36. The anti-RhD recombinant polyclonal antibody according to claim 1, wherein said antibody comprises the VH sequence of SEQ ID NO: 200 and the LC sequence of SEQ ID NO: 256.

37. The anti-RhD recombinant polyclonal antibody according to claim 1, wherein said antibody comprises the VH sequence of SEQ ID NO: 202 and the LC sequence of SEQ ID NO: 258.

\* \* \* \* \*

UNITED STATES PATENT AND TRADEMARK OFFICE
CERTIFICATE OF CORRECTION

| | | |
|---|---|---|
| PATENT NO. | : 8,198,415 B2 | Page 1 of 1 |
| APPLICATION NO. | : 11/632937 | |
| DATED | : June 12, 2012 | |
| INVENTOR(S) | : Rasmussen et al. | |

It is certified that error appears in the above-identified patent and that said Letters Patent is hereby corrected as shown below:

On the Title Page:

Item (30), Foreign Application Priority Data section, please replace
"(DK).................2004 01922" with --(DK).................2004 01992--.

Signed and Sealed this
Eleventh Day of September, 2012

David J. Kappos
*Director of the United States Patent and Trademark Office*

SEQUENCE LISTING

<160> NUMBER OF SEQ ID NOS: 260

<210> SEQ ID NO 1
<211> LENGTH: 48
<212> TYPE: DNA
<213> ORGANISM: Saccharomyces cerevisiae

<400> SEQUENCE: 1

```
gaagttccta ttccgaagtt cctattctct agaaagtata ggaacttc        48
```

<210> SEQ ID NO 2
<211> LENGTH: 30
<212> TYPE: DNA
<213> ORGANISM: Artificial
<220> FEATURE:
<223> OTHER INFORMATION: Synthetic primer sequence

<400> SEQUENCE: 2

```
ggaggcgctc gagacggtga ccagggtgcc                             30
```

<210> SEQ ID NO 3
<211> LENGTH: 30
<212> TYPE: DNA
<213> ORGANISM: Artificial
<220> FEATURE:
<223> OTHER INFORMATION: Synthetic primer sequence

<400> SEQUENCE: 3

```
ggaggcgctc gagacggtga ccattgtccc                             30
```

<210> SEQ ID NO 4
<211> LENGTH: 30
<212> TYPE: DNA
<213> ORGANISM: Artificial
<220> FEATURE:
<223> OTHER INFORMATION: Synthetic primer sequence

<400> SEQUENCE: 4

```
ggaggcgctc gagacggtga ccagggttcc                             30
```

<210> SEQ ID NO 5
<211> LENGTH: 30
<212> TYPE: DNA
<213> ORGANISM: Artificial
<220> FEATURE:
<223> OTHER INFORMATION: Synthetic primer sequence

<400> SEQUENCE: 5

```
ggaggcgctc gagacggtga ccgtggtccc                             30
```

<210> SEQ ID NO 6
<211> LENGTH: 39
<212> TYPE: DNA
<213> ORGANISM: Artificial
<220> FEATURE:
<223> OTHER INFORMATION: Synthetic primer sequence

<400> SEQUENCE: 6

```
ccagccgggg cgcgcccagr tgcagctggt gcartctgg                   39
```

<210> SEQ ID NO 7
<211> LENGTH: 39
<212> TYPE: DNA
<213> ORGANISM: Artificial
<220> FEATURE:
<223> OTHER INFORMATION: Synthetic primer sequence

<400> SEQUENCE: 7

```
ccagccgggg cgcgccsagg tccagctggt rcagtctgg                   39
```

<210> SEQ ID NO 8
<211> LENGTH: 39
<212> TYPE: DNA
<213> ORGANISM: Artificial
<220> FEATURE:

-continued

<223> OTHER INFORMATION: Synthetic primer sequence

<400> SEQUENCE: 8
ccagccgggg cgcgcccagr tcaccttgaa ggagtctgg                          39

<210> SEQ ID NO 9
<211> LENGTH: 39
<212> TYPE: DNA
<213> ORGANISM: Artificial
<220> FEATURE:
<223> OTHER INFORMATION: Synthetic primer sequence

<400> SEQUENCE: 9
ccagccgggg cgcgccsagg tgcagctggt ggagtctgg                          39

<210> SEQ ID NO 10
<211> LENGTH: 39
<212> TYPE: DNA
<213> ORGANISM: Artificial
<220> FEATURE:
<223> OTHER INFORMATION: Synthetic primer sequence

<400> SEQUENCE: 10
ccagccgggg cgcgccgagg tgcagctggt ggagwcygg                          39

<210> SEQ ID NO 11
<211> LENGTH: 39
<212> TYPE: DNA
<213> ORGANISM: Artificial
<220> FEATURE:
<223> OTHER INFORMATION: Synthetic primer sequence

<400> SEQUENCE: 11
ccagccgggg cgcgcccagg tgcagctaca gcagtgggg                          39

<210> SEQ ID NO 12
<211> LENGTH: 39
<212> TYPE: DNA
<213> ORGANISM: Artificial
<220> FEATURE:
<223> OTHER INFORMATION: Synthetic primer sequence

<400> SEQUENCE: 12
ccagccgggg cgcgcccags tgcagctgca ggagtcsgg                          39

<210> SEQ ID NO 13
<211> LENGTH: 39
<212> TYPE: DNA
<213> ORGANISM: Artificial
<220> FEATURE:
<223> OTHER INFORMATION: Synthetic primer sequence

<400> SEQUENCE: 13
ccagccgggg cgcgccgarg tgcagctggt gcagtctgg                          39

<210> SEQ ID NO 14
<211> LENGTH: 39
<212> TYPE: DNA
<213> ORGANISM: Artificial
<220> FEATURE:
<223> OTHER INFORMATION: Synthetic primer sequence

<400> SEQUENCE: 14
ccagccgggg cgcgcccagg tacagctgca gcagtcagg                          39

<210> SEQ ID NO 15

```
<211> LENGTH: 51
<212> TYPE: DNA
<213> ORGANISM: Artificial
<220> FEATURE:
<223> OTHER INFORMATION: Synthetic primer sequence

<400> SEQUENCE: 15
accgcctcca ccggcggccg cttattaaca ctctcccctg ttgaagctct t         51

<210> SEQ ID NO 16
<211> LENGTH: 38
<212> TYPE: DNA
<213> ORGANISM: Artificial
<220> FEATURE:
<223> OTHER INFORMATION: Synthetic primer sequence

<400> SEQUENCE: 16
caaccagcgc tagccgacat ccagwtgacc cagtctcc                        38

<210> SEQ ID NO 17
<211> LENGTH: 38
<212> TYPE: DNA
<213> ORGANISM: Artificial
<220> FEATURE:
<223> OTHER INFORMATION: Synthetic primer sequence

<400> SEQUENCE: 17
caaccagcgc tagccgatgt tgtgatgact cagtctcc                        38

<210> SEQ ID NO 18
<211> LENGTH: 38
<212> TYPE: DNA
<213> ORGANISM: Artificial
<220> FEATURE:
<223> OTHER INFORMATION: Synthetic primer sequence

<400> SEQUENCE: 18
caaccagcgc tagccgaaat tgtgwtgacr cagtctcc                        38

<210> SEQ ID NO 19
<211> LENGTH: 38
<212> TYPE: DNA
<213> ORGANISM: Artificial
<220> FEATURE:
<223> OTHER INFORMATION: Synthetic primer sequence

<400> SEQUENCE: 19
caaccagcgc tagccgatat tgtgatgacc cacactcc                        38

<210> SEQ ID NO 20
<211> LENGTH: 38
<212> TYPE: DNA
<213> ORGANISM: Artificial
<220> FEATURE:
<223> OTHER INFORMATION: Synthetic primer sequence

<400> SEQUENCE: 20
caaccagcgc tagccgaaac gacactcacg cagtctcc                        38

<210> SEQ ID NO 21
<211> LENGTH: 38
<212> TYPE: DNA
<213> ORGANISM: Artificial
<220> FEATURE:
<223> OTHER INFORMATION: Synthetic primer sequence

<400> SEQUENCE: 21
```
caaccagcgc tagccgaaat tgtgctgact cagtctcc                           38

<210> SEQ ID NO 22
<211> LENGTH: 50
<212> TYPE: DNA
<213> ORGANISM: Artificial
<220> FEATURE:
<223> OTHER INFORMATION: Synthetic primer sequence

<400> SEQUENCE: 22
accgcctcca ccggcggccg cttattatga acattctgta ggggccactg              50

<210> SEQ ID NO 23
<211> LENGTH: 50
<212> TYPE: DNA
<213> ORGANISM: Artificial
<220> FEATURE:
<223> OTHER INFORMATION: Synthetic primer sequence

<400> SEQUENCE: 23
accgcctcca ccggcggccg cttattaaga gcattctgca ggggccactg              50

<210> SEQ ID NO 24
<211> LENGTH: 38
<212> TYPE: DNA
<213> ORGANISM: Artificial
<220> FEATURE:
<223> OTHER INFORMATION: Synthetic primer sequence

<400> SEQUENCE: 24
caaccagcgc tagcccagtc tgtgctgact cagccacc                           38

<210> SEQ ID NO 25
<211> LENGTH: 38
<212> TYPE: DNA
<213> ORGANISM: Artificial
<220> FEATURE:
<223> OTHER INFORMATION: Synthetic primer sequence

<400> SEQUENCE: 25
caaccagcgc tagcccagtc tgtgytgacg cagccgcc                           38

<210> SEQ ID NO 26
<211> LENGTH: 38
<212> TYPE: DNA
<213> ORGANISM: Artificial
<220> FEATURE:
<223> OTHER INFORMATION: Synthetic primer sequence

<400> SEQUENCE: 26
caaccagcgc tagcccagtc tgtcgtgacg cagccgcc                           38

<210> SEQ ID NO 27
<211> LENGTH: 36
<212> TYPE: DNA
<213> ORGANISM: Artificial
<220> FEATURE:
<223> OTHER INFORMATION: Synthetic primer sequence

<400> SEQUENCE: 27
caaccagcgc tagcccartc tgccctgact cagcct                             36

<210> SEQ ID NO 28
<211> LENGTH: 41
<212> TYPE: DNA
<213> ORGANISM: Artificial
<220> FEATURE:

<223> OTHER INFORMATION: Synthetic primer sequence

<400> SEQUENCE: 28
caaccagcgc tagccctttc ctatgwgctg actcagccac c         41

<210> SEQ ID NO 29
<211> LENGTH: 41
<212> TYPE: DNA
<213> ORGANISM: Artificial
<220> FEATURE:
<223> OTHER INFORMATION: Synthetic primer sequence

<400> SEQUENCE: 29
caaccagcgc tagccctttc ttctgagctg actcaggacc c         41

<210> SEQ ID NO 30
<211> LENGTH: 38
<212> TYPE: DNA
<213> ORGANISM: Artificial
<220> FEATURE:
<223> OTHER INFORMATION: Synthetic primer sequence

<400> SEQUENCE: 30
caaccagcgc tagcccacgt tatactgact caaccgcc              38

<210> SEQ ID NO 31
<211> LENGTH: 38
<212> TYPE: DNA
<213> ORGANISM: Artificial
<220> FEATURE:
<223> OTHER INFORMATION: Synthetic primer sequence

<400> SEQUENCE: 31
caaccagcgc tagcccaggc tgtgctgact cagccgtc              38

<210> SEQ ID NO 32
<211> LENGTH: 41
<212> TYPE: DNA
<213> ORGANISM: Artificial
<220> FEATURE:
<223> OTHER INFORMATION: Synthetic primer sequence

<400> SEQUENCE: 32
caaccagcgc tagcccttaa ttttatgctg actcagcccc a         41

<210> SEQ ID NO 33
<211> LENGTH: 38
<212> TYPE: DNA
<213> ORGANISM: Artificial
<220> FEATURE:
<223> OTHER INFORMATION: Synthetic primer sequence

<400> SEQUENCE: 33
caaccagcgc tagcccagrc tgtggtgacy caggagcc              38

<210> SEQ ID NO 34
<211> LENGTH: 38
<212> TYPE: DNA
<213> ORGANISM: Artificial
<220> FEATURE:
<223> OTHER INFORMATION: Synthetic primer sequence

<400> SEQUENCE: 34
caaccagcgc tagcccwgcc tgtgctgact cagccmcc              38

<210> SEQ ID NO 35

```
<211> LENGTH: 381
<212> TYPE: DNA
<213> ORGANISM: Homo Sapiens

<400> SEQUENCE: 35
gaggtgcagc tggtggagtc tgggggaggc ttggtacagc ctggagggtc cctgagactc      60
tcctgtgtag cctctggatt caccttcagg agttttgaca tgaactgggt ccgccaggct     120
ccagggaagg ggctggagtg ggtttcatac attaatagta ggggtagtac catatactac     180
gcagactctg tgaagggccg attcaccatc tccagagaga acgccaagaa ctcactgtat     240
ctgcaaatga acagcctgag agccgaggac acggctgttt attactgtgc gagagatttg     300
tacggtgact atgaccctaa gtcctactat tactacggta tgggcgtctg gggccaaggg     360
accacggtca ccgtctcgag t                                                381

<210> SEQ ID NO 36
<211> LENGTH: 375
<212> TYPE: DNA
<213> ORGANISM: Homo Sapiens

<400> SEQUENCE: 36
gaggtgcagc tggtggagac cggggggaggc gtggtccagc ctgggaggtc cctgagactc     60
tcctgtgcag cgtctggatt ctccttcagt aactttggct ccactggat ccgccagtct      120 ccaggcaagg ggctcgaatg ggtggcagtt atttggtatg atggaagcaa cagattctat     180
gcagattccg tgaagggccg attcaccatc tccagagata gttcgaagaa catgctgttt     240
ctgcaaatgg acagcctgag agccgaggac acggctgtgt attactgtgc gagagaaatt     300
tccatgaaag tagtgatccg cagacactac gttatggacg tctggggcca cgggaccacg     360
gtcaccgtct cgagt                                                       375

<210> SEQ ID NO 37
<211> LENGTH: 381
<212> TYPE: DNA
<213> ORGANISM: Homo sapiens

<400> SEQUENCE: 37
gaggtgcagc tggtggagac cggggggaggc ttagtacagc ctggagggtc cctgagactc    60
tcctgtgcag cctctggatt cagcttcagg agttatgaca tgaactgggt ccgccaggct    120
ccagggaagg ggctggagtg ggtgtcatac atcagtggca gaggtagtac aacatattac    180
gcagactctg tgaagggccg attcaccatc tccagagaca cgccaagaa ctcactgtat     240 ctgcaaatga acagtctgag agccgaggac acggctgttt attactgtgc gagagatttg    300
tacggtgact acgatcctaa gtcctactat tactacgcta tggacgtctg gggccacggg    360
accacggtca ccgtctcgag t                                               381

<210> SEQ ID NO 38
<211> LENGTH: 375
<212> TYPE: DNA
<213> ORGANISM: Homo Sapiens

<400> SEQUENCE: 38
gaggtgcagc tggtggagtc tgggggaggc gtggtccagc ctgggaggtc cctgagactc     60
tcctgtgcag cgtctggatt caccttcagt aattatggca tgcactgggt ccgccaggct    120
ccaggcaagg ggctggagtg ggtggcggtt atatggtatg atggaagtaa tagattctat    180
gcggactccg tgaagggccg attcaccatc tccagagaca attccaagaa tacgctgtat    240
```

```
ctgcaaatga acaacctgag agccgaggac acggctctct attcctgtgc gagagagatt      300
actacgacag tagtggtccg aagacactac cttatggaca tctggggcca agggaccacg      360
gtcaccgtct cgagt                                                       375
```

<210> SEQ ID NO 39
<211> LENGTH: 378
<212> TYPE: DNA
<213> ORGANISM: Homo Sapiens

<400> SEQUENCE: 39

```
gaggtgcagc tggtggagtc tgggggaggc gtggtccagt ctgggaggtc cctgagactc      60
tcatgtgcag cctctggatt caccttcagt aacaatggca tgcactgggt ccgccaggct     120
ccaggcaagg ggctggagtg ggtggcattt atttggtatg atggaagtaa taaatactat     180
gcagactccg tgaagggccg attcaccatc tccagagaca attccaagaa cacactgtat     240
ctgcaaatgg acgcctgag agccgaggac tcggctgtgt attactgtgc gagagaggaa      300
atagcagctc gtctttattc tcgctaccac tacgctatgg acgtctgggg ccaagggaca     360
atggtcaccg tctcgagt                                                   378
```

<210> SEQ ID NO 40
<211> LENGTH: 375
<212> TYPE: DNA
<213> ORGANISM: Homo Sapiens

<400> SEQUENCE: 40

```
caggtgcagc tggtggagtc tgggggaggc ctggtcaagc ctgggggtc cctgagactc       60 tcctgtgcag cctctggatt cggcttcagt gcttatagca tgaactgggt ccgccaggct     120
ccggggaagg ggctggagtg ggtctcatcc attactagca ctactacata ctacgcagac     180
tcagtgaagg gccgattcag catctccaga gacaacgcca agagcacact gtacctgcga     240
atgaacagcc tgagagccga ggacacggct gtatattatt gtgtgagaga aatcgccttt     300
agggggagca ttattctcg gtggtcgtac tactttgact tctggggcca gggaaccctg      360
gtcaccgtct cgagt                                                       375
```

<210> SEQ ID NO 41
<211> LENGTH: 384
<212> TYPE: DNA
<213> ORGANISM: Homo Sapiens

<400> SEQUENCE: 41

```
caggtgcagc tgcaggagtc gggcccagga ctggtgaagc cttcggagac cctgtccctc      60
acctgcactg tctctggtgg ctccatcagt agttactact ggagctgggt ccggcagccc     120
ccagggaagg gactggagtg gattgggtat atctattaca gtgggagcac caactacaac     180
ccctccctca agagtcgagt caccatagca ttagacacgt ccaagaacca gttcccctg      240 aagctgaggt ctgtgaccgc tgcggacacg gccgtgtatt tctgtacgag agactggagg     300
caatatgggt cggcgatccg aggttctcga tactactacg ggatggacgt ctggggccaa     360
gggaccacgg tcaccgtctc gagt                                             384
```

<210> SEQ ID NO 42
<211> LENGTH: 387
<212> TYPE: DNA
<213> ORGANISM: Homo Sapiens

<400> SEQUENCE: 42

```
caggtgcagc tggtggagtc tgggggaggc gtggtccagc ctggagggtc cctgagactc        60
tcctgtgcag cgtctggatt caccttcagt agctatggca tgcactgggt ccgccaggct       120
ccaggcaagg ggctggagtg ggtggcagtt atatggtatg atggaagtaa taaatactat       180
gcagactccg tgaagggccg attcaccatc tccagagaca attccaagaa cacgctgtat       240
ctgcaaatga acagcctgag agccgaggac acggctgtgt attactgtgc gagagacatg       300
gttactatgg ttcggggagc ctacagaaac tactactact acggtatgga cgtctggggc       360
aaagggacca cggtcaccgt ctcgagt                                            387

<210> SEQ ID NO 43
<211> LENGTH: 381
<212> TYPE: DNA
<213> ORGANISM: Homo Sapiens

<400> SEQUENCE: 43
gaggtgcagc tggtggagac cgggggaggc gtggtccagc ctggagggtc cctgagactc        60
tcctgtgcag cctctggatt cagcttcagt aactatggca tgcactgggt ccgccaggct       120
ccaggcaagg ggttggagtg ggtggcagtt atttggtttg atggaagtat taaatattat       180
gtagactccg tgaaggccg attcaccatc tccagagaca attccaagaa cacactctat       240
ctgcaaatga acagcctgag agccgaggag acggctatat atttctgtgc gagagaaaat       300
agtgttctag tcccaggtac tatacggagg cgatattatt tggactactg gggccaggga       360
accctggtca ccgtctcgag t                                                  381

<210> SEQ ID NO 44
<211> LENGTH: 381
<212> TYPE: DNA
<213> ORGANISM: Homo Sapiens

<400> SEQUENCE: 44
caggtgcagc tggtggagtc tgggggagac ctggtacagc ctggagggtc cctgagactc        60
tcctgtgcag cctctggatt caccttcagg agttatgaaa tgaactgggt ccgccaggct       120
ccagggaagg ggctggagtg ggtttcatac attaatagta gaggtaatac caaatactac       180
gcagactctg tgaagggccg attcaccatc tccagagaca acgccaagaa gtcactgtac       240
ctgcaaatga gcagcctgag agccgaggac acggctgttt attactgtgc gagaaatttg       300
ttcggtgact acgatcttaa gtcctactac tataacgcta tggacgtctg gggccaaggc       360
accctggtca ccgtctcgag t                                                  381

<210> SEQ ID NO 45
<211> LENGTH: 381
<212> TYPE: DNA
<213> ORGANISM: Homo Sapiens

<400> SEQUENCE: 45
caggtgcagc tggtggagtc tgggggaggc ctggtcaagc ctgggggtc cctgagactc         60 tcctgtgcag cctctggatt caccttcagt agttatgcca tgaactgggt ccgccaggct       120
ccagggaagg gactggagtg ggtctcatcc attagcggta ctagtagtta catatactat       180
gcagactcag tgaagggccg atttaccatt tcagagaca acgccaagag ctcagtttat       240
ctgcaaatga acagcctgag agtcgaggac acggctgtct attactgcgc gagagataga       300
tggtggggca tggttcggag agttttttccc acctatccct ttgactactg gggccaggga       360
accctggtca ccgtctcgag t                                                  381
```

<210> SEQ ID NO 46
<211> LENGTH: 375
<212> TYPE: DNA
<213> ORGANISM: Homo Sapiens

<400> SEQUENCE: 46

```
caggtgcagc tggtggagac cggggggaggc gtggtccagc ctggggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaagactat     180
gcagaccccg tgaagggccg attcaccatc tccagagaca attccaagaa cacgctgtat     240
ctgcaaatga acagcctcag agccgaggac acggctgtgt attactgtgc gagagagatc     300
gcctcccgtg atatagtcg ctacttatac tactttgact cctggggcca gggaaccctg     360
gtcaccgtct cgagt                                                      375
```

<210> SEQ ID NO 47
<211> LENGTH: 387
<212> TYPE: DNA
<213> ORGANISM: Homo Sapiens

<400> SEQUENCE: 47

```
caggtcacct tgaaggagtc tggtcctgtg ctggtgaaaac ccacagagac cctcacgctg      60
acctgcaccg tctctggggtt ctcactcagc aatgctagaa tgggtgtgag ctggatccgt     120
cagcccccag ggaaggccct ggagtggctt gcacacattt tttcgaatga cgaaaaatcc     180
tacagcacat ctctgaagag caggctcacc atctccaagg acacctccaa aagccaggtg     240
gtccttacca tgaccaacat ggaccctgtg gacacagcca catattactg tgcacggatg     300
aggcttacta tggttcgggg agttattacg tactactact acagtatgga cgtctggggc     360
caagggacca cggtcaccgt ctcgagt                                          387
```

<210> SEQ ID NO 48
<211> LENGTH: 381
<212> TYPE: DNA
<213> ORGANISM: Homo Sapiens

<400> SEQUENCE: 48

```
caggtgcagc tgcaggagtc gggcccagga ctggtgaagc cttcacagac cctgtccctc      60
acctgcactg tctctggtgg ctccatcagc agtggtagtt actactggag ctggatccgg     120
cagcccgccg ggaagggacc ggagtggatt gggcgtatct ataccagtgg gagtaccaac     180
tacaacccct ccctcaagag tcgactcacc atatcagtag acacgtccaa gaaccagttc     240
tccctgaagc tgacctctgt gaccgccgca gacacggccg tgtattactg tgcgagggcc     300
ccttcttact atgatagtag tggttatcgt tactggtaca tcgatctctg ggccgtggc      360
accctggtca ccgtctcgag t                                                381
```

<210> SEQ ID NO 49
<211> LENGTH: 378
<212> TYPE: DNA
<213> ORGANISM: Homo Sapiens

<400> SEQUENCE: 49

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaagactat     180
```

```
gcagactccg tgaagggccg attcaccatc tccagagaca actccaagaa cacgctgtat    240
ctgcaaatga acagcgtgag agccgaggac acggctgttt attactgtgc gagagaattg    300
agcacgcaac gtggatacag ccgctaccac tatgttatgg acgtctgggg ccaagggacc    360
acggtcaccg tctcgagt                                                  378

<210> SEQ ID NO 50
<211> LENGTH: 363
<212> TYPE: DNA
<213> ORGANISM: Homo Sapiens

<400> SEQUENCE: 50
caggtgcagc tggtggagtc tgggggaggc gtggtccagc ctggagggtc cctgagactc     60
tcctgtgcag cgtctggatt caccttcagt aactatggca tgcactgggt ccgccaggct    120
cctggcaagg ggctggaatg ggtggcagtt atctggtttg atggaagtaa tagagactat    180
gcagactccg tgaagggccg attcaccatc tccagagaca attccaagaa gacgctctat    240
ctgcaaatga acagcctgag agccgaggac acggctgttt attactgtgc gacagagttg    300
gccagagggc ggctacgagc cctagagtac tggggccagg gaaccctggt caccgtctcg    360
agt                                                                  363

<210> SEQ ID NO 51
<211> LENGTH: 378
<212> TYPE: DNA
<213> ORGANISM: Homo Sapiens

<400> SEQUENCE: 51
caggtgcagc tggtgcagtc tgggggaggc gtggtccagc ctgggaagtc cctgagactc     60
tcctgtgcag cgtctggatt caccttcagt acctatggca tgcactgggt ccgccaggct    120
ccaggcaagg ggctggagtg ggtggcagtt atatggtatg atggaagtaa taaatactat    180
gcagactccg tgaagggccg attcaccatc tccagagaca cttccaagaa cacgctgtat    240
ctgcaaatga acagcgtgag agtcgaggac acggctgttt attactgtgc gagagatttg    300
accacgcaac gtggatacag ccgctatcac tatgttatgg acgtctgggg ccaagggacc    360
acggtcaccg tctcgagt                                                  378

<210> SEQ ID NO 52
<211> LENGTH: 378
<212> TYPE: DNA
<213> ORGANISM: Homo Sapiens

<400> SEQUENCE: 52
caggtgcagc tggtggagtc tgggggaggc gtggtccagc ctgggaggtc cctgagactc     60
tcctgtgcag cgtctggatt caccttcagt agctatggca tgcactgggt ccgccaggct    120
ccaggcaagg ggctggagtg ggtggcagtt atatggtatg acggaagtaa taagtactat    180
gcagactccg tgaagggccg attcaccatc tccagagaca attccaagaa cacgctgcat    240
ctgcaaatga acagcctgag agccgaggac acggctgtgt attactgtgc gagagaagtg    300
ggttttggca gtggctggtc acgatactac tacggtatgg acgtctgggg ccaagggacc    360
acggtcaccg tctcgagt                                                  378

<210> SEQ ID NO 53
<211> LENGTH: 390
<212> TYPE: DNA
<213> ORGANISM: Homo Sapiens
```

<400> SEQUENCE: 53

```
gaggtgcagc tggtggagtc tggaggagga ggcgtggtcc agcctggag gtccctgagg      60 ctctcctgtg cagcgtctgg attcaccttc agtagctatg catgcactg gtccgccag      120 gctccaggca aggggctgga gtgggtggca gttatatggt atgatggaag taataaatac    180
tatgcagact ccgtgaaggg ccgattcacc atctccagag acaattccaa gaacacgctg    240
tatctgcaaa tgaacagcct gagagctgag gacacggctg tgtattactg tgcgagagag    300
agtactctgt atagcagcag ctggtacagg aggtactact actacggtat ggacgtctgg    360
ggccaaggga ccacggtcac cgtctcgagt                                     390
```

<210> SEQ ID NO 54
<211> LENGTH: 387
<212> TYPE: DNA
<213> ORGANISM: Homo Sapiens

<400> SEQUENCE: 54

```
caggtgcagc tggtggagtc tgggggaggc gtggtccagc ctggggaggtc cctgagactc    60 tcctgtgcag cctctggatt caccttcagt agctatgcta tgcactgggt ccgccaggct    120
ccaggcaagg ggctggagtg ggtggcagtt atatcatatg atggaagcaa taaatactac    180
gcagactccg tgaagggccg attcaccatc tccagagaca attccaagaa cacgctgtat    240
ctgcaaatga acagcctgag agctgaggac acggctgtgt attactgtgc gagagagagt    300
actctatata gcagcagctg gtacaggagg tactactact acagtatgga cgtctggggc    360
caagggacca cggtcaccgt ctcgagt                                        387
```

<210> SEQ ID NO 55
<211> LENGTH: 384
<212> TYPE: DNA
<213> ORGANISM: Homo Sapiens

<400> SEQUENCE: 55

```
caggtgcagc tggtggagtc tgggggaggc gtggtccagc ctggggaggtc cctgagactc    60 tcctgtgcgg cgtctggatt caccttcagt agctatggca tgcactgggt ccgccaggct    120
ccaggcaagg ggctggagtg ggtggcagtt atatggttcg atggaagtaa tagatactat    180
ggagactccg tgaagggccg agtcaccatc tccagagaca attccaagaa cacgctgtat    240
ctgcgaatga acagcctgag agccgaggac acggctgtgt attactgtgc gagagagttc    300
tatacacgta gcgggctatg gtcacaaggg tactcctatt acatgacgt ctggggcaaa     360 gggaccacgg tcaccgtctc gagt                                           384
```

<210> SEQ ID NO 56
<211> LENGTH: 387
<212> TYPE: DNA
<213> ORGANISM: Homo Sapiens

<400> SEQUENCE: 56

```
gaggtgcagc tggtggagtc tgggggaggc gtggtccagc ctggggaggtc cctgagactc    60 tcctgtgcag cgtctggatt caccttcagt aactatggca tgcactgggt ccgccaggct    120
ccaggcaagg ggctggagtg ggtggcagtt atatggtatg atggaagtaa taaatactat    180
gcagactccg tgaagggccg attcaccatc tccagagaca attccaagaa cacgctgtat    240
ctgcaaatga acagcctgag agccgaggac acggctgtgt attactgtgc gagagagatg    300
gtctcctata gcagcagctg gtaccgccgc tactactact acgttatgga cgtctggggc    360
```

```
aaagggacca cggtcaccgt ctcgagt                                         387
```

```
<210> SEQ ID NO 57
<211> LENGTH: 369
<212> TYPE: DNA
<213> ORGANISM: Homo Sapiens

<400> SEQUENCE: 57
gaggtgcagc tggtggagtc tggggggaggc gtggtccagc ctgggaggtc cctgagactc    60
tcctgtgcag cctctggatt cagcttcagt aactatggca tgcactgggt ccgccaggct   120
ccaggcaagg ggctggagtg ggtggcagtt atatcatatg atggaagtga aagtactat    180 gcagactccg tgaagggccg attcaccatc tccagagaca attccaagaa ggcgctgtat   240
ctgcaaatga acagcctgag agctgaggac acggctatgt attattgtaa gaataaagtg   300
ggagctaccc ggcgggcagt cgttgctttt gatatctggg gccaagggac cacggtcacc   360
gtctcgagt                                                            369
```

```
<210> SEQ ID NO 58
<211> LENGTH: 381
<212> TYPE: DNA
<213> ORGANISM: Homo Sapiens

<400> SEQUENCE: 58
gaggtgcagc tggtggagac cggggggaggc ctggtcaagc ctggggggtc cctgagactc    60
tcctgtgcag cctctggatt caccttcagg agttatagca tgaactgggt ccgccaggct   120
ccagggaagg ggctggagtg ggtctcatcc attggtagta gtagtactta cacatactcc   180
gcagactcag tgaagggccg attcaccatc tccagagaca acgccaagaa ctcactgtat   240
ctgcaaatga acagcctgag agccgaggac acggctgtgt attactgtgc gagaggagag   300
cctctaaact atgattacat ttggggaggg tatcgtttca ctatccactg ggccaggga    360 accctggtca ccgtctcgag t                                              381
```

```
<210> SEQ ID NO 59
<211> LENGTH: 387
<212> TYPE: DNA
<213> ORGANISM: Homo Sapiens

<400> SEQUENCE: 59
caggtgcagc tggtggagtc tggggggaggc gtggtccagc ctgggaggtc cctgagactc    60
tcctgtgcag cgtctggatt caccttcagt agttatggca tgcactgggt ccgccaggct   120
ccaggcaagg ggctggaatg ggtggcaatt atatggtttg atggaagtaa taaatactat   180
gcagactccg tgaagggccg attcaccatc tccagagaca attccaagaa cacgctgtat   240
ctgcaaataa acagcctgag agctgaggac acggctgtgt attactgtgc gaaagagcac   300
ggctattata gcagcagctg gtaccgaaac tactattact acgctatgga cgtctggggc   360
caagggacca cggtcaccgt ctcgagt                                         387
```

```
<210> SEQ ID NO 60
<211> LENGTH: 363
<212> TYPE: DNA
<213> ORGANISM: Homo Sapiens

<400> SEQUENCE: 60
gaggtgcagc tggtggagtc cggggggaggc gtggtccagc ctgggaggtc cctgagactc    60
tcctgtgcgg cgtctggatt caccttcagt agctatggca tgcactgggt ccgccaggct   120
```

| | |
|---|---|
| ccaggcaagg ggctggagtg ggtggcagtt atatggtatg atggaagtaa taaagactat | 180 |
| gtagactctg tgaagggccg attcaccatc tccagagaca attccaagaa cacgctgtat | 240 |
| ctgcaaatga acagtctgag agccgaggac acagctgtgt attactgtgc gagagagttg | 300 |
| gccaaagggc ggctacgaga cctagaccac tggggccagg gaaccctggt caccgtctcg | 360 |
| agt | 363 |

<210> SEQ ID NO 61
<211> LENGTH: 387
<212> TYPE: DNA
<213> ORGANISM: Homo Sapiens

<400> SEQUENCE: 61

| | |
|---|---|
| gaggtgcagc tggtggagtc tgggggaggc gtggtccagc ctgggaggtc cctgagactc | 60 |
| tcctgtgcag cctctggatt caccttcagg acttctgcca tgcactgggt ccgccaggct | 120 |
| ccaggcaagg ggctggagtg ggtggcagtt atatggtatg atggaagtaa taaatactat | 180 |
| gcagactccg tgaagggccg attcaccatc tccagagaca attccaagaa cacgctgtat | 240 |
| ctgcaaatga acagcctgag agccgaggac acggctgtgt attactgtgc gagagagatg | 300 |
| gtctcctata gcagcagctg gtaccgccgc tactactact acaatatgga cgtctggggc | 360 |
| aaagggacca cggtcaccgt ctcgagt | 387 |

<210> SEQ ID NO 62
<211> LENGTH: 375
<212> TYPE: DNA
<213> ORGANISM: Homo Sapiens

<400> SEQUENCE: 62

| | |
|---|---|
| caggtgcagc tggtggagtc tgggggaggc gtggtccagc ctgggacgtc cctgagattg | 60 |
| tcctgtgcag cgtctgggtt cacctttaga acctatggca tgcactgggt ccgccaggct | 120 |
| ccaggcaagg ggctggagtg ggtggcatat atatggtatg atggaagtaa taatactat | 180 |
| gcagactccg tgaagggccg attcaccatc tccagagaca attccaagag cacgctgaat | 240 |
| ctgcaaatga acagcctcag agccgaggac acggctgtgt attactgtgc gagagagatc | 300 |
| gcctcccgtg gatatagtcg ctacttatac tactttgact cctggggcca gggcaccctg | 360 |
| gtcaccgtct cgagt | 375 |

<210> SEQ ID NO 63
<211> LENGTH: 387
<212> TYPE: DNA
<213> ORGANISM: Homo Sapiens

<400> SEQUENCE: 63

| | |
|---|---|
| cagctgcagc tgcaggagtc gggcccagga ctggtgaagc cttcggggac cctgtccctc | 60 |
| acctgcgctg tctctggtgg ctccatgagg agtagtaact ggtggacttg ggtccgccag | 120 |
| cccccaggga aggggctgga atggattggg gaaatccatc atggtgggag caccaactac | 180 |
| aacccgtccc tccagagtcg agtcacgata tcagtagaca gtccaagaa ccggttctcc | 240 |
| ctgaagctga gctctgtgac cgccgcggac acggccgtat atcactgtgc gaggggagg | 300 |
| agttattatg atagtagtgg gcattccttt cgcggtctgg tacctttga tatctggggc | 360 |
| caagggacaa tggtcaccgt ctcgagt | 387 |

<210> SEQ ID NO 64
<211> LENGTH: 384
<212> TYPE: DNA

<213> ORGANISM: Homo Sapiens

<400> SEQUENCE: 64

```
caggtgcagc tgcaggagtc gggcccagga ctggtgaagc cttcggagac cctgtccctc      60
atctgcactg tctctggtgg ctccatcagt agtaactact ggagctggat ccggcagccc     120
ccagggaagg gactggagtg gattgggtat atctattaca gtgggaacac caactacaac     180
ccctccctca agagtcgagt caccatatca ttagacacgt ccaagaacca gttctccctg     240
aagctgagat ctgtgaccgc tgcggacacg gccgtgtatt actgtgcgag agagtggagg     300
cagtatggct cggggatccg aggttctcga tactactacg gtatggacgt ctggggccag     360
ggcaccctgg tcaccgtctc gagt                                             384
```

<210> SEQ ID NO 65
<211> LENGTH: 387
<212> TYPE: DNA
<213> ORGANISM: Homo Sapiens

<400> SEQUENCE: 65

```
gaggtgcagc tggtggagtc tgggggaggc gtggtccagc ctgggaggtc cctgagactc      60
tcctgtgcag cgtctggatt caccttcagt aaccatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag ggccgaggac acggctgtgt attactgtgc gagagagatg     300
gcctcctata gcagcagctg gtaccgccgc tactactact acgttatgga cgtctggggc     360
aaagggacca cggtcaccgt ctcgagt                                          387
```

<210> SEQ ID NO 66
<211> LENGTH: 375
<212> TYPE: DNA
<213> ORGANISM: Homo Sapiens

<400> SEQUENCE: 66

```
caggtgcagc tggtggagtc tgggggaggc gtggtccagc ctgggaggtc cctgagactc      60
tcctgtgcag cgtctggatt caccttcagt acctatggca tgcactgggt ccgccaggct     120
ccaggcaagg ggctggagtg ggtggcagtt atatggtatg atggaagtca gaaatactat     180
gtagactccg tgaagggccg attcaccatc tccagagaca attccaagaa cacgctgtat     240
ctgcaaatga acagcctgag agccgaggac acggctgtct attactgtgc gagagaggtt     300
gcggttcggg gagttattcg ctactactac ggtatggacg tctggggcca agggaccacg     360
gtcaccgtct cgagt                                                       375
```

<210> SEQ ID NO 67
<211> LENGTH: 384
<212> TYPE: DNA
<213> ORGANISM: Homo Sapiens

<400> SEQUENCE: 67

```
caggtgcagc tggtggagtc tgggggaggc gtggtccagc ctgggaggtc tctgagactc      60
tcctgtgcag cctcgggatt cagcttcagt agttatggca tgcactgggt ccgccaggct     120
ccaggcaagg gactggagtg ggtggcaatt atttggtatg atggagtaa caaactctat     180
gcagactccg tgaagggccg attcaccatc tccagagaca attccaggaa tacgttgtat     240
ctgcaaatga gcagtgtgag agccgaggac acggctgtgt attactgtgc gagagactct     300
```

```
gttcggggag tcagtagatg ggggactcag aaatattacg ctatggacgt ctggggccaa    360
gggaccacgg tcaccgtctc gagt                                          384
```

<210> SEQ ID NO 68
<211> LENGTH: 378
<212> TYPE: DNA
<213> ORGANISM: Homo Sapiens

<400> SEQUENCE: 68

```
gaggtgcagc tggtgcaatc tggggggaggc gtggtccagc ctgggaggtc cccgagactc    60
tcctgtgcag cgtctggatt caccttcagt agctatggca tgcactgggt ccgccaggct   120
ccaggcaagg ggctggagtg ggtggcattt atatggtatg atggaagtaa taaatactat   180
gcagactctg tgaagggccg attcaccatc tccagagaca attccaagaa cacgctgtat   240
ctgcaaatga acagcctgag agccgaggac acggctgtgt attactgtgc gagagatctc   300
cggaaccacg ttttttggag tggttattct acctcttttg actactgggg ccagggaacc   360
ctggtcaccg tctcgagt                                                 378
```

<210> SEQ ID NO 69
<211> LENGTH: 387
<212> TYPE: DNA
<213> ORGANISM: Homo Sapiens

<400> SEQUENCE: 69

```
gaggtgcagc tggtggagac cggggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagagagatg   300
gtctcctata gcagcagctg gtaccgccgc tactactact acaatatgga cgtctggggc   360
aaagggacca cggtcaccgt ctcgagt                                      387
```

<210> SEQ ID NO 70
<211> LENGTH: 387
<212> TYPE: DNA
<213> ORGANISM: Homo Sapiens

<400> SEQUENCE: 70

```
caggtgcagc tggtggagac cggggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatggtctg atggaagtaa taaatactat   180
gcagactccg tgaagggccg attcaccatc tccagagaca attccaggaa cacgctgtat   240
ctgcaaatga acagcctgag agccgaggac acggctgtgt tttactgtgc gagagagcaa   300 gggggggtata gcagcagttg gtaccgccgc tactactact actatatgga cgtctggggc   360
caagggacca cggtcaccgt ctcgagt                                      387
```

<210> SEQ ID NO 71
<211> LENGTH: 375
<212> TYPE: DNA
<213> ORGANISM: Homo Sapiens

<400> SEQUENCE: 71

```
gaggtgcagc tggtggagtc tgggggaggc gtggtccagc ctggaaggtc cctgagactc    60
```

```
tcctgtgcag cgtctggatt caccttcaat acctatggca tgcactgggt ccgccaggct      120
ccaggcaagg ggctggagtg ggtggcagtt atatggtatg atggaagtaa taaatactat      180
gcagactccg tgaagggccg attcaccatc tccagagaca attccaagaa cacgctgtat      240
ctgcaaatga acagcctgag agccgaggac acggctgtgt attactgtgc gagagaggtt      300
gcggttcggg gagttattcg ctactactac gctatggacg tctggggcca agggaccacg      360
gtcaccgtct cgagt                                                        375

<210> SEQ ID NO 72
<211> LENGTH: 369
<212> TYPE: DNA
<213> ORGANISM: Homo Sapiens

<400> SEQUENCE: 72
caggtgcagc tggtggagtc tgggggaggc gtggtccagc ctggagggtc tctgagactc       60
tcctgtgcag cctctggatt cagcttcagt aactatggca tgcactgggt ccgccaggct      120
ccaggcaagg ggctggagtg ggtggcagtt atatcatatg atggaagtga aagtactat       180 gcagactccg tgaagggccg attcaccatc tccagagaca attccaagaa aacgctgtat      240
ctgcaaatga acagcctgag agctgaggac acggctatgt attattgtaa gaataaagtg      300
ggagctaccc ggcgggcagt tgttgctgtt gatatttggg gccaagggac aatggtcacc      360
gtctcgagt                                                              369

<210> SEQ ID NO 73
<211> LENGTH: 381
<212> TYPE: DNA
<213> ORGANISM: Homo Sapiens

<400> SEQUENCE: 73
caggtgcagc tggtggagtc tgggggaggc ttggtacagc ctggagggtc cctgagactc       60
tcctgtgtag cctctggatt caccttcagg agttttgata tgaactgggt ccgccaggct      120
ccagggaagg ggctggagtg gatttcatat attaatagta gggggaacac cagatactat      180
gtagactctg tgaagggccg attcaccatc tccagagaca cgccaagaa ctcattgtat       240 ctgcaaatga acagcctgcg agccgaggac acggctgttt actactgtgc gagagatttg     300
tacggtgact acgatcctaa gtcctactat tactacggta tggacgtctg gggccaaggg      360
acaatggtca ccgtctcgag t                                                381

<210> SEQ ID NO 74
<211> LENGTH: 375
<212> TYPE: DNA
<213> ORGANISM: Homo Sapiens

<400> SEQUENCE: 74
gaggtgcagc tggtggagtc tgggggaggc gtggtccagc ctggagggtc cctgagactc       60
tcctgtgaag cgtctggatt caccttcagt aattatggca tgcactggtt ccgccaggct      120
ccaggcaagg ggctggagtg ggtggcaatt atatggtatg atggaagtaa taaacactat      180
gcagactccg tgaagggccg attcaccatc tccagagaca attcgaagaa cacgctgtat      240
ctgcaaatga acagcctcag agccgaggac acggctgtgt atttctgtgc gagagagatc      300
gcctcccgtg gatatagtcg ctacttatac tactttgact cctggggcca gggaaccctg      360
gtcaccgtct cgagt                                                        375

<210> SEQ ID NO 75
```

```
<211> LENGTH: 375
<212> TYPE: DNA
<213> ORGANISM: Homo Sapiens

<400> SEQUENCE: 75
caggtgcagc tggtggagtc tgggggaggc gtggtccagc ctgggaggtc cctgagactc      60
tcctgtgcag cgtctggatt caccttcagg acctatggca tgcactgggt ccgccaggct     120
ccaggcaagg ggctggagtg ggtggcagtt atatggtatg atggaagtaa taaagactat     180
gcagactccg tgaagggccg attcaccatc tccagagaca attccaagaa cacgctgcat     240
ctgcaaatga acagcctgag agccgaggac acggctgtgt attactgtgc gagagagatc     300
gcctcccgtg atatagtcg gtacttatac taccttgact ctggggcca gggcaccctg       360 gtcaccgtct cgagt                                                      375

<210> SEQ ID NO 76
<211> LENGTH: 378
<212> TYPE: DNA
<213> ORGANISM: Homo Sapiens

<400> SEQUENCE: 76
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatattat     180
gcagactccg tgaagggccg attcaccatc tccagagaca attccaagaa cacactatat     240
ctgcaaatga acagcgtgag agccgaggac acggctgttt attactgtgc gagagatttg     300
agcacgcaac gtggatacag ccgctactac tatgttatgg acgtctgggg ccaagggacc     360
acggtcaccg tctcgagt                                                   378

<210> SEQ ID NO 77
<211> LENGTH: 363
<212> TYPE: DNA
<213> ORGANISM: Homo Sapiens

<400> SEQUENCE: 77
caggtgcagc tggtggagtc tgggggaggc gtggtccagc ctgggaggtc cctgagactc      60
tcctgtgcag cgtctggatt caccttcagt aactttggca tgcactgggt ccgccaggct     120
ccaggcaagg ggctggagtg ggtggcagtt atatggtatg atggaagtaa taaagactat     180
gcagactccg tgaagggccg attcaccatc tccagagaca attccaagag gacgctgtat     240
ctgcaaatga acagcctgag agccgaggac acggctgtgt attactgtgc gagagagttg     300 gccgagggc ggctacgaga cctagactac tggggccagg gcaccctggt caccgtctcg      360
agt                                                                   363

<210> SEQ ID NO 78
<211> LENGTH: 384
<212> TYPE: DNA
<213> ORGANISM: Homo Sapiens

<400> SEQUENCE: 78
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
```

```
ctgcaaatga acagcctgag agccgaggac acggctgtgt attactgtgc gagagagttc    300
tatacacgta gcgggctatg gtcacaaggg tactcctatt acatggacgt ctggggcaaa    360
gggaccacgg tcaccgtctc gagt                                          384

<210> SEQ ID NO 79
<211> LENGTH: 387
<212> TYPE: DNA
<213> ORGANISM: Homo Sapiens

<400> SEQUENCE: 79
caggtgcagc tggtggagtc tgggggaggc gtggtccagc ctgggaggtc cctgagactc     60
tcctgtgcag cgtctggatt caccttcagt agctatggca tgcactgggt ccgccaggct    120
ccaggcaagg ggctggagtg ggtggcagtt atatggtttg atggaggtaa taaatactat    180
gcagactccg cgaagggccg attcaccatc tccagagaca attccaagaa cacgctgtat    240
ctgcaaatga acagcctgag agccgaggac acggctgtgt attactgtgc gagagatgcg    300
tcggtgcttt ctggattggt tactcgaagg ttagtctact acggtatgga cgtctggggc    360
caagggacca cggtcaccgt ctcgagt                                       387

<210> SEQ ID NO 80
<211> LENGTH: 387
<212> TYPE: DNA
<213> ORGANISM: Homo Sapiens

<400> SEQUENCE: 80
caggtgcagc tggtggagtc tgggggaggc gtggtccagc ctgggaggtc cctgagactc     60
tcctgtgcag cctctggatt caccttcagt agctatggca tgcactgggt ccgccaggct    120
ccaggcaagg ggctggagtg ggtggcgttt atatcatatg atggaagtaa taaatactat    180
gcagactccg tgaagggccg attcaccatc tccagagaca attccaagaa cacgctgtct    240
ctgcaaatga acagcctgag agctgaggac acggctgtgt attactgtgc gaaagagcac    300
ggctattatc gcagcagctg gtaccgaaac tactactact atgggatgga cgtctggggc    360
caagggacca cggtcaccgt ctcgagt                                       387

<210> SEQ ID NO 81
<211> LENGTH: 387
<212> TYPE: DNA
<213> ORGANISM: Homo Sapiens

<400> SEQUENCE: 81
caggtgcagc tggtggagtc tgggggaggc gtggtgcagc ctgagaggtc cctgagactc     60
tcctgtgcag cctctggatt caccttcagt tcctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gaaagatgaa    300
gtggggtata gcagcagctg gtacaggcgc tactactact acgctatgga cgtctggggc    360
caagggacca cggtcaccgt ctcgagt                                       387

<210> SEQ ID NO 82
<211> LENGTH: 384
<212> TYPE: DNA
<213> ORGANISM: Homo Sapiens

<400> SEQUENCE: 82
```

```
caggtgcagc tggtgcagtc tggggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagagagaca   300
gtggtggtag ctgccaaaat acgaaaccac tactactacg ctatggacgt ctggggccaa   360
gggaccacgg tcaccgtctc gagt                                          384

<210> SEQ ID NO 83
<211> LENGTH: 387
<212> TYPE: DNA
<213> ORGANISM: Homo Sapiens

<400> SEQUENCE: 83
caggtgcagc tggtggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcaggt atatggtatg atggaagtaa taaatactat   180
gcagactccg tgaagggccg attcaccatc tccagagaca attccaggaa cacgatgtat   240
ctgcaaatga acagcctgag agccgaggac acggctgtgt attactgtgc gagagagcaa   300 gggggggtata gcagcagttg gtaccgccgc tactactact acaatatgga cctctgggc   360 caagggacca cggtcaccgt ctcgagt                                       387

<210> SEQ ID NO 84
<211> LENGTH: 387
<212> TYPE: DNA
<213> ORGANISM: Homo Sapiens

<400> SEQUENCE: 84
caggtgcagc tggtggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga acaccctgag agacgacgac acggctgtgt attactgtgc gagagaggggt   300 actctgtata gcagcagctg gtacaggagg tactactact acggtatgga cgcctggggc   360
caagggacca cggtcaccgt ctcgagt                                       387

<210> SEQ ID NO 85
<211> LENGTH: 387
<212> TYPE: DNA
<213> ORGANISM: Homo Sapiens

<400> SEQUENCE: 85
caggtgcagc tggtggagac tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcaggt atatggtatg atggaagtaa taaatactat   180
ggagactccg tgaagggccg attcaccatc tccagagaca attccaggaa tacgctgtat   240
ctgcatatga acagcctcag agccgacgac acggctgtgt attactgtgc gagggaacac   300
ggcgggtcta ggagtggctg gtacactttta cgtctcgcgt actactttga ctactggggc   360
cagggcaccc tggtcaccgt ctcgagt                                       387
```

<210> SEQ ID NO 86
<211> LENGTH: 387
<212> TYPE: DNA
<213> ORGANISM: Homo Sapiens

<400> SEQUENCE: 86
caggtgcagc tgcaggagtc cggcccagga ctggtgaagc cttcgggac cctgtccctc    60 acctgcgctg tctctggtgg ctccatcagg ggtagtaatt ggtggagttg ggtccgccag   120
cccccaggga aggggctgga gtggattggg gaaatccatc atggtgggag caccaactac   180
aacccgtccc tcaagagtcg agtcacgata tcagtagaca gtccaagaa ccggttctcc    240 ctgaagctga gctctgtgac cgccgcggac acggccgtgt attactgtgc gaggggacg    300 tcttattatg atagtagtgg ttattccttt cgcggtctgg tagcttttga tatctggggc   360
caagggacaa tggtcaccgt ctcgagt                                       387

<210> SEQ ID NO 87
<211> LENGTH: 387
<212> TYPE: DNA
<213> ORGANISM: Homo Sapiens

<400> SEQUENCE: 87
caggtgcagc tggtggagtc tgggggaggc gtggtccagc ctgggaggtc cctgagactc    60
tcctgtgcag cgtctggatt caccttcagt acctatggca tgcactgggt ccgccaggct   120
ccaggcaagg ggctggagtg gtggcagtt atatggtatg atggaagtaa taaaaactat    180
gcagactccg tgaagggccg attcaccatc tccagagaca attccaagaa cacgctgtat   240
ctgcaaatga acagcctgag agccgaggac acggctgtgt attactgtgc gagagaccta   300
caagggtata gaagcagctg gtaccggatg tactactact acggtatgga cgtctggggc   360
caagggacca cggtcaccgt ctcgagt                                       387

<210> SEQ ID NO 88
<211> LENGTH: 381
<212> TYPE: DNA
<213> ORGANISM: Homo Sapiens

<400> SEQUENCE: 88
gaggtgcagc tggtggagtc tgggggaggc ctggtcaagc ctgggggtc cctgagactc     60 tcctgtgcag cctctggatt caccttcagg agttatagca tgaactgggt ccgccaggct   120
ccagggaagg ggctggagtg ggtctcatcc attggtagta gtagtattta cacatactcc   180
gcagactcag tgaagggccg attcaccatc tccagagaca acgccaagaa ctcactgtat   240
ctgcaaatga acagcctgag agccgaggac acggctgtgt attactgtgc gagaggagag   300 cctctaaaact atgattacat ttggggaagg tctcgtctca ctatccactg ggccaggga   360 accctggtca ccgtctcgag t                                             381

<210> SEQ ID NO 89
<211> LENGTH: 387
<212> TYPE: DNA
<213> ORGANISM: Homo Sapiens

<400> SEQUENCE: 89
caggtgcagc tggtggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taaatattat   180

```
gcagactccg tgaagggccg attcaccatc tcccgagaca attccaagaa cacgctgtat    240
ctgcaaatga acagcctgag agctgaggac acggctgtgt attactgtgc gagagattgg    300
gtcactcgca gcagcaactg gtacaggaac tactactact acggtatgga cgtctggggc    360
caagggacca cggtcaccgt ctcgagt                                        387

<210> SEQ ID NO 90
<211> LENGTH: 372
<212> TYPE: DNA
<213> ORGANISM: Homo Sapiens

<400> SEQUENCE: 90
gaggtgcagc tggtggagtc tgggggaggc ttagttcagc cggggaggtc cctgagactc     60
tcctgtgtag cctctggatt caccttcagt agctactgga tgcactgggt ccgccaagtt    120
ccagggaagg ggctggtgtg ggtctcacgt attaatgttg atgggaagag cacaagctac    180
gcggactccg tgaagggccg attcaccatc tccagagaca cgccaagaa cacgctgtac     240 ctgcaaatga acagtctgag agccgaggac acggctgtgt attactgtgc aagagatccc    300
cgacgatttt tggagtgggc ccgctacggt atggacgtct ggggccgagg gaccacggtc    360
accgtctcga gt                                                         372

<210> SEQ ID NO 91
<211> LENGTH: 654
<212> TYPE: DNA
<213> ORGANISM: Homo Sapiens

<400> SEQUENCE: 91
gaaattgtgt tgacgcagtc tccagccacc ctgtctttgt ctccagggga gagagccacc     60
ctctcctgca gggccagtca gagtgttagc agctacttag cctggtacca acagaaacgt    120
ggccaggctc ccaggctcct catctttaat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcagct ggcctccgat gtacactttt    300
ggccagggga ccaagctgga gatcaaacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata acgccctcca atcgggtaac    480
tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgtta ataa           654

<210> SEQ ID NO 92
<211> LENGTH: 648
<212> TYPE: DNA
<213> ORGANISM: Homo Sapiens

<400> SEQUENCE: 92
gacatccaga tgacccagtc tccatccccc ctgtctgcat ctgtaggaga cagagtctcc     60
atcacttgcc gggcgagtcg ggcattagc aattctttag cctggtatca gcagaaacca    120
gggaaagttc ctaagctcct catctatgct gcatccactt tgcaatcagg ggtcccatct    180
cggttcagtg gcggtggatc tgggacagat ttcactctca ccatcagcag cctgcagcct    240
gaagatgttg caacttatta ctgtcacacg tataacagtg ccccttcgc tttcggccct    300 gggaccaaag tggatatcaa acgaactgtg gctgcaccat ctgtcttcat cttcccgcca    360
```

```
tctgatgagc agttgaaatc tggaactgcc tctgttgtgt gcctgctgaa taacttctat    420
cccagagagg ccaaagtaca gtggaaggtg ataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttaataa               648

<210> SEQ ID NO 93
<211> LENGTH: 654
<212> TYPE: DNA
<213> ORGANISM: Homo Sapiens

<400> SEQUENCE: 93
gaaattgtga tgacacagtc tccaggcacc ctgtctttgt ctccagggga aagagccacc     60
ctctcctgca gggccagtca cactgtcagc agcggctact tagcctggta tcagcagaaa   120
cctggccagg ctcccaggct cctcatctat ggtgcatcca cagggccac tggcgtccca    180 gacaggttcg gtggcagtgg gtctgggaca gacttcactc tcaccatcag cagactggag   240
cctgaagatt ctgcagtgta ttttgtcag caatatggaa cctcaccggg ggtcactttc    300
ggccaaggga cacgactgga aattgaacga actgtggctg caccatctgt cttcatcttc    360
ccgccatctg atgagcagtt gaaatctggg actgcctctg ttgtgtgcct gctgaataac   420
ttctatccca gagaggccaa agtacagtgg aaggtggata acgccctcca atcgggtaac   480
tcccaggaga gtgtcacaga gcaggacagc aaggacagca cctacagcct cagcagcacc   540
ctgacgctga gcaaagcaga ctacgagaaa cacaaagtct acgcctgcga agtcacccat   600
cagggcctga gctcgcccgt cacaaagagc ttcaacaggg gagagtgtta ataa         654

<210> SEQ ID NO 94
<211> LENGTH: 648
<212> TYPE: DNA
<213> ORGANISM: Homo Sapiens

<400> SEQUENCE: 94
gacatccagt tgacccagtc tccatcctcc ctgtctgcat ctgtaggaga cagagtctcc     60
atcacttgcc gggcgagtca gggcattagc aattctttag cctggtatca gcagaaacca   120
gggaaagttc ctaagctcct catctatgct gcatccactt tgcaatcagg ggtcccatct   180
cggttcagtg gcggtggatc tgggacagat ttcactctca ccatcagcag cctgcagcct   240
gaagatgttg caacttatta ctgtcaaaag tataacagtg ccccttcgc tttcggccct    300 gggaccaaag tggatatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg ataacgccc tccaatcggg taactcccag    480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttaataa               648

<210> SEQ ID NO 95
<211> LENGTH: 651
<212> TYPE: DNA
<213> ORGANISM: Homo Sapiens

<400> SEQUENCE: 95
gacatccaga tgacccagtc tccatccttc ctgtctgcat ctgtaggaga cagagtcacc     60
```

```
atcacttgcc gggccagtca gggcattaga cgttatttag cctggtttca gcaaaaacca    120
gggaaagccc ctaaactcct gatcttttct gcatccactt tgcaaagtgg ggtcccatca    180
aggttcagcg gcagtggatc tgggacagaa ttcactctca caatcagcag cctgcagcct    240
gaggattttg caacttatta ctgtcaacag cttagtagtt accctccgta cacttttggc    300
caggggacca agctggagat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag acagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttaata a    651

<210> SEQ ID NO 96
<211> LENGTH: 648
<212> TYPE: DNA
<213> ORGANISM: Homo Sapiens

<400> SEQUENCE: 96
gacatccagt tgacccagtc tccatcttct gtgtctgctt ctgtagggga cagcgttacc     60
atcacttgtc gggcgagtca ggctgtgagc gggtgggtag cctggtatca gcagaaacca    120
gggaaagccc ctaaactcct gatctttggt ttgtccaatt tggaggatgg ggtcccatca    180
aggttcagcg gcagtggatc tgcgacagac ttcactctca ccatcaccgg cctgcagcct    240
gaagatttgg caacgtacta ctgtctacag gctaacaggt tcccctctc tttcggcgga    300 gggaccaggg tagagatcaa acgaactgtg ctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540 ctgagcaaag cagactacga gaaacacaaa gtctacgcct gcgaagtcac ccatcagggc    600
ctgagctcgc ccgtcacaaa gagcttcaac agggagagt gttaataa    648

<210> SEQ ID NO 97
<211> LENGTH: 654
<212> TYPE: DNA
<213> ORGANISM: Homo Sapiens

<400> SEQUENCE: 97
gaaattgtgt tgacgcagtc tccaggcacc ctgtctttgt ctccagggga aagagccacc     60
ctctcctgca gggccagtca gaatcctaga cgcaacttt tagcctggta ccaacagaaa    120
cctggccagg ctcccaggct tctcatctat gctgcatcca ccagggccac cggcatccca    180
gacaggttca gtggcagtgg gtctgggaca gacttcactc tcaccatcga cagactggag    240
cctgaagatt ctgcagtgta ttactgtcag gtctatggta gctcacctct gtacactttt    300
ggccagggga ccaaggtgga gatgaaacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata cgccctcca atcgggtaac    480 tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgtta ataa    654
```

<210> SEQ ID NO 98
<211> LENGTH: 654
<212> TYPE: DNA
<213> ORGANISM: Homo Sapiens

<400> SEQUENCE: 98

| | | | | | |
|---|---|---|---|---|---|
| gaaattgtga | tgacgcagtc | tccagccacc | ctgtctgtgt | ctccagggga | aagagccacc | 60 |
| ctctcctgca | gggccagtca | gagtgttagc | agcaacttag | cctggtacca | gcagaaacct | 120 |
| ggccaggctc | ccaggctcct | catctatggt | gcatccacca | gggccactgg | tatcccagcc | 180 |
| aggttcagtg | gcagtgggtc | tgggacagag | ttcactctca | ccatcagcag | cctgcagtct | 240 |
| gaagattttg | cagtttatta | ctgtcagcag | tataataact | ggccgaccct | gtacactttt | 300 |
| ggccagggga | ccaagctgga | gatcaaacga | actgtggctg | caccatctgt | cttcatcttc | 360 |
| ccgccatctg | atgagcagtt | gaaatctgga | actgcctctg | ttgtgtgcct | gctgaataac | 420 |
| ttctatccca | gagaggccaa | agtacagtgg | aaggtggata | acgccctcca | atcgggtaac | 480 |
| tcccaggaga | gtgtcacaga | gcaggacagc | aaggacagca | cctacagcct | cagcagcacc | 540 |
| ctgacgctga | gcaaagcaga | ctacgagaaa | cacaaagtct | acgcctgcga | agtcacccat | 600 |
| cagggcctga | gctcgcccgt | cacaaagagc | ttcaacaggg | gagagtgtta | ataa | 654 |

<210> SEQ ID NO 99
<211> LENGTH: 648
<212> TYPE: DNA
<213> ORGANISM: Homo Sapiens

<400> SEQUENCE: 99

| | | | | | |
|---|---|---|---|---|---|
| gacatccagt | tgacccagtc | tccatcctcc | ctgtctgcat | ctgtgggaga | cagagtcacc | 60 |
| atcacttgcc | gggcaagtca | gagcattagc | agctatttaa | attggtatca | gcagaaacca | 120 |
| ggggaagccc | ccaaactcct | gatctatgtt | gcatccactt | tgcaaagtgg | ggccccatca | 180 |
| aggttcagtg | gcagtggatc | tgggacagat | tacactctaa | ccattagcag | tctgcaacct | 240 |
| gaagattctg | caactttcta | ctgtcaacag | acttacagtc | cccctacac | ttttggccag | 300 |
| ggaaccaagc | tggagatcaa | acgaactgtg | gctgcaccat | ctgtcttcat | cttcccgcca | 360 |
| tctgatgagc | agttgaaatc | tggaactgcc | tctgttgtgt | gcctgctgaa | taacttctat | 420 |
| cccagagagg | ccaaagtaca | gtggaaggtg | gataacgccc | tccaatcggg | taactcccag | 480 |
| gagagtgtca | cagagcagga | cagcaaggac | agcacctaca | gcctcagcag | caccctgacg | 540 |
| ctgagcaaag | cagactacga | gaaacacaaa | gtctacgcct | gcgaagtcac | ccatcagggc | 600 |
| ctgagctcgc | ccgtcacaaa | gagcttcaac | aggggagagt | gttaataa | | 648 |

<210> SEQ ID NO 100
<211> LENGTH: 657
<212> TYPE: DNA
<213> ORGANISM: Homo Sapiens

<400> SEQUENCE: 100

| | | | | | |
|---|---|---|---|---|---|
| gaaattgtgc | tgactcagtc | tccaggcacc | ctgtcttcgt | ctccagggga | aagagccacc | 60 |
| ctctcctgca | gggccagtca | aagtgttact | agcagatact | tagcctggta | ccagcagaaa | 120 |
| catggccagg | ctcccaggct | cctcatctat | ggtacatcca | cgagggccac | tggcatccca | 180 |
| gacaggttca | gtggcggagg | gtctcagaca | gacttcactc | tcaccatcag | cagactggag | 240 |
| cctgaagatt | ttgcagtgta | ttattgtcag | cactatgatg | actcaatttc | gacgtacatt | 300 |
| tttggcccgg | ggaccgagct | ggagatcaag | cgaactgtgg | ctgcaccatc | tgtcttcatc | 360 |

```
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg ttaataa       657
```

```
<210> SEQ ID NO 101
<211> LENGTH: 648
<212> TYPE: DNA
<213> ORGANISM: Homo Sapiens

<400> SEQUENCE: 101
gacatccagt tgacccagtc tccatcttct gtgtctgctt ctgtaggaga cagagtgacc     60
atcacttgtc gggcgagtca gggtattaac aacttattag cctggtatca gcagaaacca    120
gggaaagccc ctaagctcct gatctacgct gcatccaatt tgcaaagtgg ggtcccatcg    180
aggttcagcg gcagtggatc tgggacagat ttcactctca ctatcaacag cctgcagcct    240
gaagattttg caacctacta ttgtcaacag gctaacagtt tccctctcac tttcggcgga    300
gggaccaagg tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540 ctgagcaaag cagactacga gaaacacaaa gtctacgcct gcgaagtcac ccatcagggc    600
ctgagctcgc ccgtcacaaa gagcttcaac aggggagagt gttaataa                 648
```

```
<210> SEQ ID NO 102
<211> LENGTH: 651
<212> TYPE: DNA
<213> ORGANISM: Homo Sapiens

<400> SEQUENCE: 102
gacatccaga tgacccagtc tccatcctcc ctgtctgcat ctgtaggaga cagagtcacc     60
atcacttgcc gggcaagtca gagcattagc agctatttaa attggtatca gcagaatcca    120
gggaaagccc ctaagctcct gatctatggt gcatccaatt tgcaaagtgg ggtcccatca    180
aggttcagtg gcagtggatc tgggacagat ttcactctca ccatcagcag tctgcaacct    240
gaagattttg caacttacta ctgtcaacag agttacagta ccctcgcgct cactttcggc    300
ggagggacca aggtggagat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttaata a             651
```

```
<210> SEQ ID NO 103
<211> LENGTH: 651
<212> TYPE: DNA
<213> ORGANISM: Homo Sapiens

<400> SEQUENCE: 103
gacatccaga tgacccagtc tccatcctcc ctgtctgcat ctgtaggaga cagagtcacc     60
```

| atcacttgcc gggcaagtca gagcattagc acctatttaa attggtatca gcagaaacca | 120 |
| gggaaagccc ctaagctcct gatctatgct gcatccactt tgcaaagtgg ggtcccatca | 180 |
| aggttcagtg gcagtggatc tgggacacat ttcactctca ccatcagctc tctgcaacgt | 240 |
| gaagattttg caacttacta ctgtcaacag acttacagaa cccccacgtg dacgttcggc | 300 |
| caagggacca aggtggaaat caaacgaact gtggctgcac catctgtctt catcttcccg | 360 |
| ccatctgatg agcagttgaa atctggaact gcctctgttg tgtgcctgct gaataacttc | 420 |
| tatcccagag aggccaaagt acagtggaag gtggataacg ccctccaatc gggtaactcc | 480 |
| caggagagtg tcacagagca ggacagcaag dacagcacct acagcctcag cagcaccctg | 540 |
| acgctgagca aagcagacta cgagaaacac aaagtctacg cctgcgaagt cacccatcag | 600 |
| ggcctgagct cgcccgtcac aaagagcttc aacaggggag agtgttaata a | 651 |

<210> SEQ ID NO 104
<211> LENGTH: 645
<212> TYPE: DNA
<213> ORGANISM: Homo Sapiens

<400> SEQUENCE: 104

| gacatccagt tgacccagtc tccatcctcc ctgtctgcat ctgtaggaga cagagtcacc | 60 |
| atcacttgcc gggcaagtca gaacattaac aggtatttaa attggtatca gcacaaacca | 120 |
| gggagagccc ctgagctcct gatctatgct gcgtccactt tacgaagggg ggtcccatca | 180 |
| aggttcagtg gcagtggatc tgggacagat ttcactctca ccatcagcag tctgcaacct | 240 |
| gaagattttg caacttacta ctgtcaacag agttacagta gagggacgtt cggccaaggg | 300 |
| actaaggtgg aaatcaaacg aactgtggct gcaccatctg tcttcatctt cccgccatct | 360 |
| gatgagcagt tgaaatctgg aactgcctct gttgtgtgcc tgctgaataa cttctatccc | 420 |
| agagaggcca agtacagtg gaaggtggat aacgccctcc aatcgggtaa ctcccaggag | 480 |
| agtgtcacag agcaggacag caaggacagc acctacagcc tcagcagcac cctgacgctg | 540 |
| agcaaagcag actacgagaa acacaaagtc tacgcctgcg aagtcaccca tcagggcctg | 600 |
| agctcgcccg tcacaaagag cttcaacagg ggagagtgtt aataa | 645 |

<210> SEQ ID NO 105
<211> LENGTH: 651
<212> TYPE: DNA
<213> ORGANISM: Homo Sapiens

<400> SEQUENCE: 105

| gacatccaga tgacccagtc tccatcctcc ctgtctgcat ctgtaggaga cagagtcacc | 60 |
| atcacttgcc gggcaagtca gagcattagc acctatttaa attggtatca gcagaaacca | 120 |
| gggaaagccc ctaagctcct gatctatgct gcatccactt tgcaaagtgg ggtcccatca | 180 |
| aggttcagtg gcagtggatc tgggacacat ttcactctca ccatcagcag tctgcaacgt | 240 |
| gaagattttg caacttacta ctgtcaacag agttacggaa cccccacgtg dacgttcggc | 300 |
| caagggacca aggtggaaat caagcgaact gtggctgcac catctgtctt catcttcccg | 360 |
| ccatctgatg agcagttgaa atctggaact gcctctgttg tgtgcctgct gaataacttc | 420 |
| tatcccagag aggccaaagt acagtggaag gtggataacg ccctccaatc gggtaactcc | 480 |
| caggagagtg tcacagagca ggacagcaag gacagcacct acagcctcag cagcaccctg | 540 |
| acgctgagca aagcagacta cgagaaacac aaagtctacg cctgcgaagt cacccatcag | 600 |
| ggcctgagct cgcccgtcac aaagagcttc aacaggggag agtgttaata a | 651 |

<210> SEQ ID NO 106
<211> LENGTH: 657
<212> TYPE: DNA
<213> ORGANISM: Homo Sapiens

<400> SEQUENCE: 106

| | | | | | |
|---|---|---|---|---|---|
| cagactgtgg | tgactcagga | gccctcactg | actgtgtccc | caggagggac | agtcaccctc | 60 |
| acctgtgctt | ccagcactgg | agcagtcacc | actggttact | atccaaactg | gttccagcag | 120 |
| aaacctggac | aagcacccag | gcactgatt | tatagtacaa | gcaagaaaca | ctcctggacc | 180 |
| cctgcccggt | tctcaggctc | cctccttggg | ggcaaagctg | ccctgacact | gtcaggtgtg | 240 |
| cagcctgagg | acgaggctga | gtattactgc | ctgctcttct | atggtggtgc | tcagctgggg | 300 |
| gtgttcggcg | gagggaccaa | gctgaccgtc | ctaggtcagc | ccaaggctgc | ccctcggtc | 360 |
| actctgttcc | cgccctcctc | tgaggagctt | caagccaaca | aggccacact | ggtgtgtctc | 420 |
| ataagtgact | tctacccggg | agccgtgaca | gtggcctgga | aggcagatag | cagccccgtc | 480 |
| aaggcgggag | tggagaccac | cacaccctcc | aaacaaagca | caacaagta | cgcggccagc | 540 |
| agctacctga | gcctgacgcc | tgagcagtgg | aagtcccaca | aaagctacag | ctgccaggtc | 600 |
| acgcatgaag | ggagcaccgt | ggagaagaca | gtggccccta | cagaatgttc | ataataa | 657 |

<210> SEQ ID NO 107
<211> LENGTH: 651
<212> TYPE: DNA
<213> ORGANISM: Homo Sapiens

<400> SEQUENCE: 107

| | | | | | |
|---|---|---|---|---|---|
| gacatccaga | tgacccagtc | tccatcctcc | ctgtctgcat | ctgtaggaga | cagagtcacc | 60 |
| atcacttgcc | gggcaagtca | gagcattggc | aactatttaa | attggtatca | gcagaaacca | 120 |
| ggaaaagccc | ctaagctcct | gatctctgct | gcatccagtt | tgcaaagtgg | ggtcccgtca | 180 |
| aggttcagtg | gcagtggatc | tgggacagat | ttcactctca | ccatcagcag | tctgcatcgt | 240 |
| gaagactatg | caacttacta | ctgtcaacag | agttacagta | ccccccgta | cacttttggc | 300 |
| caggggacca | agctggagat | caaacgaact | gtggctgcac | catctgtctt | catcttcccg | 360 |
| ccatctgatg | agcagttgaa | atctggaact | gcctctgttg | tgtgcctgct | gaataacttc | 420 |
| tatcccagag | aggccaaggt | acagtggaag | gtggataacg | ccctccaatc | gggtaactcc | 480 |
| caggagagtg | tcacagagca | ggacagcaag | gacagcacct | acagcctcag | cagcaccctg | 540 |
| acgctgagca | aagcagacta | cgagaaacac | aaagtctacg | cctgcgaagt | cacccatcag | 600 |
| ggcctgagct | cgcccgtcac | aaagagcttc | aacaggggag | agtgttaata | a | 651 |

<210> SEQ ID NO 108
<211> LENGTH: 651
<212> TYPE: DNA
<213> ORGANISM: Homo Sapiens

<400> SEQUENCE: 108

| | | | | | |
|---|---|---|---|---|---|
| gacatccaga | tgacccagtc | tccatcctcc | ctgtctgcat | ctgtaggaga | cagagtcacc | 60 |
| atcacttgcc | gggcaagtca | gagcattagc | agctatttaa | attggtatca | gcagaaacca | 120 |
| gggaaagccc | ctaagctcct | gatctatgct | gcatccagtt | tgcaaagtgg | ggtcccatca | 180 |
| aggttcagtg | gcagtggatc | tgggacagat | ttcactctca | ccatcagcag | tctgcaacct | 240 |
| gaagattttg | caacttacta | ctgtcaacag | agttacagta | cctccacgtg | gacgttcggc | 300 |
| caagggacca | aggtggaaat | caaacgaact | gtggctgcac | catctgtctt | catcttcccg | 360 |

```
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag acagcacct acagcctcag cagcaccctg       540
acgctgagca aagcagacta cgagaaacac aaagtctacg cctgcgaagt cacccatcag      600
ggcctgagct cgcccgtcac aaagagcttc aacaggggag agtgttaata a               651

<210> SEQ ID NO 109
<211> LENGTH: 648
<212> TYPE: DNA
<213> ORGANISM: Homo Sapiens

<400> SEQUENCE: 109
gacatccagt tgacccagtc tccatcctcc ctgtctgcat ctgtaggaga cagagtcacc       60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta cctcgtggac gttcggccaa      300
gggaccaagg tggaaatcaa acgaactgtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gttaataa                   648

<210> SEQ ID NO 110
<211> LENGTH: 654
<212> TYPE: DNA
<213> ORGANISM: Homo Sapiens

<400> SEQUENCE: 110
gaaattgtgt tgacgcagtc tccagccacc ctgtctgtgt ctccagggga aagagccacc       60
ctctcctgca gggccagtca gagtgttacc agcaacttag cctggtacca gcagaaacct      120
ggccaggctc ccaggctcct catctatggt gcatccacca gggccactgg tgtcccagcc      180
aggttcagtg gcagtgggtc tgggacagag ttcagtctca ccatcagcag cctgcagtct      240
gaagattttg cagtttatta ctgtcagcag tataataact ggcctcccat attcactttc      300
ggccctggga ccaaactgga tatcaaacga actgtggctg caccatctgt cttcatcttc      360
ccgccatctg atgagcagtt gaatctgga actgcctctg ttgtgtgcct gctgaataac      420
ttctatccca gagaggccaa agtacagtgg aaggtggata acgccctcca atcgggtaac      480
tcccaggaga gtgtcacaga gcaggacagc aaggacagca cctacagcct cagcagcacc      540
ctgacgctga gcaaagcaga ctacgagaaa cacaaagtct acgcctgcga agtcacccat      600
cagggcctga gctcgcccgt cacaaagagc ttcaacaggg gagagtgtta ataa            654

<210> SEQ ID NO 111
<211> LENGTH: 651
<212> TYPE: DNA
<213> ORGANISM: Homo Sapiens

<400> SEQUENCE: 111
gaaattgtgc tgactcagtc tccaggcacc ctgtctttgt ctccagggga aagagccacc       60
```

```
ctctcctgca gggccagtca gagtgttagc agcagctact tagcctggta ccagcataaa      120
cctggccagg ctcccaggct cctcatctac ggttcatcca acagggccac tggcatccca      180
gacaggttca gtggcagtgg gtctgggaca gacttcactg tcaccatcag cagactggag      240
cctgaagatt ttgcagtgta ttactgtcag cagtatggta ctgcacccta cacttttggc      300
caggggacca agctggagat caaacgaact gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag acagcacct acagcctcag cagcaccctg       540
acgctgagca aagcagacta cgagaaacac aaagtctacg cctgcgaagt cacccatcag      600
ggcctgagct cgcccgtcac aaagagcttc aacaggggag agtgttaata a               651

<210> SEQ ID NO 112
<211> LENGTH: 654
<212> TYPE: DNA
<213> ORGANISM: Homo Sapiens

<400> SEQUENCE: 112
cagtctgccc tgactcagcc tgcctccgtg tctgggtctc ctggacagtc gatcaccatc       60
tcctgcactg caaccagcag tgatattggg gcttataact atgtctcctg gtaccaacac      120
cacccaggta aagcccccaa agtcatcatt actgatgtta ataagcggcc ctcagggtc       180 cctgatcgct tctctggctc caagtctggc aacacggcct ccctgaccat ctcagggctc      240
cagcctgagg atgaggctga gtattcctgc tgctcatatg caggcaccta cagttatgtc      300
ttcggaactg ggaccaaggt caccgtcctg agtcagccca aggccaaccc cactgtcact      360
ctgttcccgc cctcctctga ggagctccaa gccaacaagg ccacactagt gtgtctgatc      420
agtgacttct acccgggagc tgtgacagtg gcctggaagg cagatggcag ccccgtcaag      480
gcgggagtgg agaccaccaa accctccaaa cagagcaaca caagtacgc ggccagcagc       540 tacctgagcc tgacgcccga gcagtggaag tcccacagaa gctacagctg ccaggtcacg      600
catgaaggga gcaccgtgga agagacagtg gcccctacag aatgttcata ataa            654

<210> SEQ ID NO 113
<211> LENGTH: 654
<212> TYPE: DNA
<213> ORGANISM: Homo Sapiens

<400> SEQUENCE: 113
ctttcttctg agctgactca ggaccctgct gtgtctgtgg ccttgggaca gacagtcagg       60
atcacatgcc aaggagacag cctcagaagt tattatgcaa actggtacca gcagaagcca      120
ggacaggccc ctctatcagt catctatggt aaaaacaacc ggccctcagg gatcccggac      180
cgattctctg gctccaactc aggaaacaca gcttttctga ccatcactgg gactcaggcg      240
gaagatgagg ctgactatta ctgtaactcc cgggacagca gtggtaatta tcgggagcta      300
ttcggcggag ggaccaagct gaccgtcctt ggtcagccca aggctgcccc ctcggtcact      360
ctgttcccgc cctcctctga ggagcttcaa gccaacaagg ccacactggt gtgtctcata      420
agtgacttct acccgggagc cgtgacagtg gcctggaagg cagatagcag ccccgtcaag      480
gcgggagtgg agaccaccac accctccaaa caaagcaaca caagtacgc ggccagcagc       540 tatctgagcc tgacgcctga gcagtggaag tcccacagaa gctacagctg ccaggtcacg      600
catgaaggga gcaccgtgga agagacagtg gcccctgcag aatgctctta ataa            654
```

<210> SEQ ID NO 114
<211> LENGTH: 651
<212> TYPE: DNA
<213> ORGANISM: Homo Sapiens

<400> SEQUENCE: 114

| | | | | | |
|---|---|---|---|---|---|
| gacatccagt | tgacccagtc | tccatccttc | ctgtctgcat | ctgtaggaga | cagagtcacc | 60 |
| atcacttgcc | gggccagtca | tggcattagc | agttatttag | cctggtatca | acagaaacca | 120 |
| gggaaagccc | ctaacctcct | gatctttcct | gcatccactt | tgcaaagtgg | ggtcccgtca | 180 |
| agattcagcg | gcagtggatc | tgggacagaa | ttcactctca | caatcagcag | cctgcggcct | 240 |
| gaagattttg | caacttatta | ctgtcaacaa | cttaatagtt | attccaggtg | ggcgttcggc | 300 |
| caagggacca | aggtggaagt | caaacgaact | gtggctgcac | catctgtctt | catcttcccg | 360 |
| ccatctgatg | agcagttgaa | atctggaact | gcctctgttg | tgtgcctgct | gaataacttc | 420 |
| tatcccagag | aggccaaagt | acagtggaag | gtggataacg | ccctccaatc | gggtaactcc | 480 |
| caggagagtg | tcacagagca | ggacagcaag | gacagcacct | acagcctcag | cagcaccctg | 540 |
| acgctgagca | aagcagacta | cgagaaacac | aaagtctacg | cctgcgaagt | cacccatcag | 600 |
| ggcctgagct | cgcccgtcac | aaagagcttc | aacaggggag | agtgttaata | a | 651 |

<210> SEQ ID NO 115
<211> LENGTH: 651
<212> TYPE: DNA
<213> ORGANISM: Homo Sapiens

<400> SEQUENCE: 115

| | | | | | |
|---|---|---|---|---|---|
| gacatccaga | tgacccagtc | tccatcctcc | ctgtctgcat | ctgtaggaga | cagagtcacc | 60 |
| atcacttgtc | gggcaagtca | gagcattagg | aggtatttaa | attggtatca | gaagaaacca | 120 |
| gggaaagccc | ctaagctcct | gatctatgct | gcatccagtt | tgcaaagtgg | ggtcccatca | 180 |
| aggttcagtg | gcagtggatc | tgggacagat | ttcactctca | ccatcagcag | tctgcaacct | 240 |
| gaagattttg | caacttacta | ctgtcaacag | agttaccgta | cccaaggtct | cactttcggc | 300 |
| ggagggacca | aggtggagat | caaacgaact | gtggctgcac | catctgtctt | catcttcccg | 360 |
| ccatctgatg | agcagttgaa | atctggaact | gcctctgttg | tgtgcctgct | gaataacttc | 420 |
| tatcccagag | aggccaaagt | acagtggaag | gtggataacg | ccctccaatc | gggtaactcc | 480 |
| caggagagtg | tcacagagca | ggacagcaag | gacagcacct | acagcctcag | cagcaccctg | 540 |
| acgctgagca | aagcagacta | cgagaaacac | aaagtctacg | cctgcgaagt | cacccatcag | 600 |
| ggcctgagct | cgcccgtcac | aaagagcttc | aacaggggag | agtgttaata | a | 651 |

<210> SEQ ID NO 116
<211> LENGTH: 657
<212> TYPE: DNA
<213> ORGANISM: Homo Sapiens

<400> SEQUENCE: 116

| | | | | | |
|---|---|---|---|---|---|
| caggctgtgg | tgactcagga | gccctcactg | actgtgtccc | caggagggac | agtcactctc | 60 |
| acctgtgctt | ccagcactgg | agcagtcacc | actggttact | atccaaactg | gttccagcag | 120 |
| aaacctggac | aagcacccag | gcactggtt | catagtacaa | gcagaaaca | ctcctggacc | 180 |
| cctgcccggt | tctcaggctc | cctccttggg | ggcaaagctg | ccctgacact | gtcaggtgtg | 240 |
| cagcctgagg | acgaggctga | gtattactgc | ctgctcttct | atggtggtgc | tcaactgggg | 300 |
| gtgttcggcg | gagggaccaa | actgaccgtc | ctaggtcagc | ccaaggctgc | ccctcggtc | 360 |

```
actctgttcc cgccctcctc tgaggagctt caagccaaca aggccacact ggtgtgtctc    420
ataagtgact tctacccggg agccgtgaca gtggcctgga aggcggatag cagcccgtc    480 aaggcgggag tggagaccac cacaccctcc aaacaaagca acaacaagta cgcggccagc    540
agctacctga gcctgacgcc tgagcagtgg aagtcccaca aaagctacag ctgccaggtc    600
acgcatgaag ggagcaccgt ggagaagaca gtggcccctg cagaatgctc ttaataa      657
```

<210> SEQ ID NO 117
<211> LENGTH: 657
<212> TYPE: DNA
<213> ORGANISM: Homo Sapiens

<400> SEQUENCE: 117

```
caggctgtgg tgactcagga gccctcactg actgtgtccc caggagggac agtcactctc     60
acctgtgctt ccagcactgg atcagtcacc agtggttact atccaaactg gttccagcag    120
aaacctggac aagcacccag gccactgatt tctggtacaa gcaacaaact ctcctggacc    180
cctgcccggt tctcaggctc cctccttggg ggcaaagctg ccctcacagt gtcaggtgtg    240
cagcctgagg acgaggctgt gtattactgc ctgctctact atggtgttcc tcagccagtg    300
gtattcggcg gagggaccaa gctgaccgtc ctaggtcagc ccaaggctgc cccctcggtc    360
actctgttcc cgccctcctc tgaggagctt caagccaaca aggccacact ggtgtgtctc    420
ataagtgact tctacccggg agccgtgaca gtggcctgga aggcagatag cagcccgtc    480 aaggcgggag tggagaccac cacaccctcc aaacaaagca acaacaagta cgcggccagc    540
agctacctga gcctgacgcc tgagcagtgg aagtcccaca gaagctacag ctgccaggtc    600
acgcatgaag ggagcaccgt ggagaagaca gtggccccta cagaatgttc ataataa       657
```

<210> SEQ ID NO 118
<211> LENGTH: 651
<212> TYPE: DNA
<213> ORGANISM: Homo Sapiens

<400> SEQUENCE: 118

```
gacatccagt tgacccagtc tccatcctcc ctgtctgcat ctgtaggaga cagagtcacc     60
atcacttgcc gggcaagtca gagcattagc agctatttaa attggtatca gcagaaacca    120
ggaaaagccc ctaagctcct gatctctgct gcatccagtt tgcaaagtgg ggtcccgtca    180
aggttcagtg gcagtggatc tgggacagat ttcactctca ccatcagcag tctgcaacgt    240
gaagactatg caacttacta ctgtcaacag agttacagta ccccccgta cacttttggc     300 caggggacca agctggagat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttaata a             651
```

<210> SEQ ID NO 119
<211> LENGTH: 648
<212> TYPE: DNA
<213> ORGANISM: Homo Sapiens

<400> SEQUENCE: 119

```
gacatccaga tgacccagtc tccttccacc ctgtctgcat ctgtaggaga cagagtcacc     60
```

```
atcacttgcc gggccagtca gagtattagc agttggttgg cctggtatca acagaaacca    120
gggaaagccc ctaagctcct ggtctataag acgtctagtt tagaaggtgg ggtcccatcc    180
aggttcagcg gcagtggatc tgggacagaa ttcagtctca caatcttcag actgcagtct    240
gatgattttg caacttatta ctgccaacag tataatagtt ttccgtacac ctttggccag    300
gggaccaagc tggagttcac acgaactgtg ctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg ataacgccc tccaatcggg taactcccag    480
gagagtgtca cagagcagga cagcaaggac agcacctaca gcctcagcag cacccctgacg   540 ctgagcaaag cagactacga gaaacacaaa gtctacgcct gcgaagtcac ccatcagggc   600
ctgagctcgc ccgtcacaaa gagcttcaac aggggagagt gttaataa                648

<210> SEQ ID NO 120
<211> LENGTH: 654
<212> TYPE: DNA
<213> ORGANISM: Homo Sapiens

<400> SEQUENCE: 120
gaaattgtgt tgacgcagtc tccagtcacc ctgtctttgt ctccagggga aagagccacc     60
ctctcctgta gggccagtca gagtgttagc agcggctact tagcctggta ccagcagaaa   120
cctggccagg ctcccaggct cctcatctat ggtacatcca tcagggccac tggcatccca   180
gacaggttca gtggcagtgg gtctgggaca gacttcactc tcaccatcag cagactggag   240
cctgaagatt ttgcagtgta ttactgtcag cagtatggta gctcacctct atactctttt   300
ggccagggga ccaaggtgga catcaaacga actgtggctg caccatctgt cttcatcttc   360
ccgccatctg atgagcagtt gaaatctgga actgcctctg ttgtgtgcct gctgaataac   420
ttctatccca gagaggccaa agtacagtgg aaggtggata acgccctcca atcgggtaac   480
tcccaggaga gtgtcacaga gcaggacagc aaggacagca cctacagcct cagcagcacc   540
ctgacgctga gcaaagcaga ctacgagaaa cacaaagtct acgcctgcga agtcacccat   600
cagggcctga gctcgcccgt cacaaagagc ttcaacaggg gagagtgtta ataa          654

<210> SEQ ID NO 121
<211> LENGTH: 651
<212> TYPE: DNA
<213> ORGANISM: Homo Sapiens

<400> SEQUENCE: 121
gaaattgtgt tgacgcagtc tccaggcacc ctgtctttgt ctccagggga aagagccacc     60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacggta cacttttggc   300
caggggacca agctggagat caaacgaact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca aagcagacta cgagaaacac aaagtctacg cctgcgaagt cacccatcag   600
ggcctgagct cgcccgtcac aaagagcttc aacagggag agtgttaata a               651
```

<210> SEQ ID NO 122
<211> LENGTH: 648
<212> TYPE: DNA
<213> ORGANISM: Homo Sapiens

<400> SEQUENCE: 122

| | | | | | |
|---|---|---|---|---|---|
| gacatccagt | tgacccagtc | tccgtcctcc | ctggctgcat | ctgtgggaga | cagagtcatt | 60 |
| attacttgcc | ggtcaggtca | gggcattagg | aactatttaa | attggtatca | gcagaaacct | 120 |
| gggaaagccc | ctaaactcct | gatctatgct | gcgtcctttt | tgcaaagtgg | ggtcccatca | 180 |
| aggttcagtg | gcagtggatc | tgggacagat | ttcactctca | ccatcagcag | tctgcaacct | 240 |
| gaggattttg | caacttacaa | ctgtcaacag | agttacagtg | acccgtggac | gttcggccaa | 300 |
| gggaccaagg | tggaaatcaa | acgaactgtg | gctgcaccat | ctgtcttcat | cttcccgcca | 360 |
| tctgatgagc | agttgaaatc | tggaactgcc | tctgttgtgt | gcctgctgaa | taacttctat | 420 |
| cccagagagg | ccaaagtaca | gtggaaggtg | gataacgccc | tccaatcggg | taactcccag | 480 |
| gagagtgtca | cagagcagga | cagcaaggac | agcacctaca | gcctcagcag | caccctgacg | 540 |
| ctgagcaaag | cagactacga | gaaacacaaa | gtctacgcct | gcgaagtcac | ccatcagggc | 600 |
| ctgagctcgc | ccgtcacaaa | gagcttcaac | aggggagagt | gttaataa | | 648 |

<210> SEQ ID NO 123
<211> LENGTH: 645
<212> TYPE: DNA
<213> ORGANISM: Homo Sapiens

<400> SEQUENCE: 123

| | | | | | |
|---|---|---|---|---|---|
| gacatccaga | tgacccagtc | tccatcttcc | ctgtctgcat | ctgtaggaga | cagagtcatt | 60 |
| atcacttgcc | gggcaagtca | gagcgttaac | aggtatttaa | attggtatca | gcagaaacca | 120 |
| gggaaagccc | ctaaactcct | catctatgct | gcatccagtt | tgcaaggtgg | ggtcccatca | 180 |
| aggttcagtg | gcagtggatc | tgggacagat | ttcactctca | ccatcagcag | tctgcaacgt | 240 |
| gaagattttg | caacttacta | ctgccaacag | agttacagaa | ctcggacgtt | cggccaaggg | 300 |
| accaaggtgg | aaatcaaacg | aactgtggct | gcaccatctg | tcttcatctt | cccgccatct | 360 |
| gatgagcagt | tgaaatctgg | aactgcctct | gttgtgtgcc | tgctgaataa | cttctatccc | 420 |
| agagaggcca | agtacagtg | gaaggtggat | aacgccctcc | aatcgggtaa | ctcccaggag | 480 |
| agtgtcacag | agcaggacag | caaggacagc | acctacagcc | tcagcagcac | cctgacgctg | 540 |
| agcaaagcag | actacgagaa | acacaaagtc | tacgcctgcg | aagtcaccca | tcagggcctg | 600 |
| agctcgcccg | tcacaaagag | cttcaacagg | ggagagtgtt | aataa | | 645 |

<210> SEQ ID NO 124
<211> LENGTH: 648
<212> TYPE: DNA
<213> ORGANISM: Homo Sapiens

<400> SEQUENCE: 124

| | | | | | |
|---|---|---|---|---|---|
| gacatccaga | tgacccagtc | tccatcctcc | ctgtctgcat | ctgtaggaga | cggaatcacc | 60 |
| atcacttgcc | gggcaagtca | aagcgttagg | agctatttaa | attggtatca | gcagaaacca | 120 |
| gggaaagccc | ctgagctcct | gatctatgct | gcatcccgtt | tgcaaagtgg | ggtcccatca | 180 |
| aggttcagtg | gcagtggatc | tgggacagat | ttcactctca | ccatcagcag | tctgcagcct | 240 |
| gaagattttg | caacttacta | ctgtcaacat | agttacagta | ccctgtcac | gttcggccaa | 300 |
| gggaccaagg | tggaagtcaa | gcgaactgtg | gctgcaccat | ctgtcttcat | cttcccgcca | 360 |

```
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttaataa                 648
```

<210> SEQ ID NO 125
<211> LENGTH: 651
<212> TYPE: DNA
<213> ORGANISM: Homo Sapiens

<400> SEQUENCE: 125

```
ctttcttctg agctgactca ggaccctgct gtgtctgtga ccttgggaca gacggtcaga     60
atcacatgcc aaggagacag cctcagacac tcttatgcaa gctggtacca gcagaagcca    120
gggcaggctc ctatacttgt catctatggt aaaaacatcc ggccctcagg gatcccagac    180
cgattctctg gctccacctc ggggaacaca gcttccttga ccatcactgg ggctcaggcg    240
gaagatggcg gtgactatta ctgtaactcc cgggacacca gtactgacca ttatgtcttc    300
ggagatggga ccagggtcac cgtcgtaggt cagcccaagg ccaaccccac tgtcactctg    360
ttcccgccct cctctgagga gctccaagcc aacaaggcca cactagtgtg tctgatcagt    420
gacttctacc cgggagctgt gacagtggcc tggaaggcag atggcagccc cgtcaaggcg    480
ggagtggaga ccaccaaacc ctccaaacag agcaacaaca gtacgcggc cagcagctac    540 ctgagcctga cgcccgagca gtggaagtcc cacagaagct acagctgcca ggtcacgcat    600
gaagggagca ccgtggagaa gacagtggcc cctacagaat gttcataata a             651
```

<210> SEQ ID NO 126
<211> LENGTH: 651
<212> TYPE: DNA
<213> ORGANISM: Homo Sapiens

<400> SEQUENCE: 126

```
gacatccaga tgacccagtc tccatcctcc ctgtctgcat ctgtaggaga cagagtcacc     60
atcacttgcc gggcaagtca gagcattagc agctggttaa attggtatca gcagaaacca    120
gggaaagccc ctaacctcct gatctttgct gcatccactt tgcaaagtgg ggtcccgtca    180
aggttcagtg gcagtggatc tgggacagat ttcactctca ccatcagcag tctgcaacct    240
gaagattttg caacttacta ctgtcaacag agttacagta gttctgtgta cacttttggc    300
caggggacca agctggagat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagcg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttaata a             651
```

<210> SEQ ID NO 127
<211> LENGTH: 648
<212> TYPE: DNA
<213> ORGANISM: Homo Sapiens

<400> SEQUENCE: 127

```
gacatccaga tgacccagtc tccatcctcc ctgtctgcat ctgtaggaga cagagtcacc     60
```

```
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggatagat ttcactctca ccatcagcag tctgcaacct    240
gaagattttg caacttacta ctgtcaacag agttacacta ccctctggac gttcggccaa    300
gggaccaagg tggaaatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540 ctgagcaaag cagactacga aaacacaaa gtctacgcct gcgaagtcac ccatcagggc    600
ctgagctcgc ccgtcacaaa gagcttcaac aggggagagt gttaataa    648
```

<210> SEQ ID NO 128
<211> LENGTH: 657
<212> TYPE: DNA
<213> ORGANISM: Homo Sapiens

<400> SEQUENCE: 128

```
gaaattgtgc tgactcagtc tccaggcacc ctgtctttgt ctccaaggga aagagccacc     60
ctctcctgca gggccaatca gtatgttaac agcaaccact agcctggta ccagcagaaa    120 cctggccagg ctcccaggct cctcctttat ggtgcatcaa ggagggccac tggcatccca    180
gacagattca gtggcagtgg gactgggaca gacttcactc tcatcatcag cagactggag    240
cctgaagatt ttgccgtata tttctgtcag ctgtatgatc actcacgtcc gatgtacact    300
tttggccagg ggactaagct ggagatcaaa cgaactgtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg ttaataa    657
```

<210> SEQ ID NO 129
<211> LENGTH: 654
<212> TYPE: DNA
<213> ORGANISM: Homo Sapiens

<400> SEQUENCE: 129

```
gaaattgtgc tgactcagtc tccaggcacc ctgtctttgt ctccagggga aagagccacc     60
ctctcctgca gggccagtca gagttttagc agcggctact agcctggta ccagcagaaa    120 cctggccagg ctcccaggct cctcatctat ggtgcatcca cagggccac tggcatccca    180 gacaggttca gtggcagtgg gtctggaaca gacttcactc tcaccatcag cagactggag    240
cctgaagatt ttgcagtgta ttactgtcag cactatggta gctcacctcc catcaccttc    300
ggccaaggga cacgactgga gattaaacga actgtggctg caccatctgt cttcatcttc    360
ccgccatctg atgagcagtt gaaatctgga actgcctctg ttgtgtgcct gctgaataac    420
ttctatccca gggaggccaa agtacagtgg aaggtggata cgccctcca atcgggtaac    480 tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgtta ataa    654
```

<210> SEQ ID NO 130
<211> LENGTH: 651
<212> TYPE: DNA
<213> ORGANISM: Homo Sapiens

<400> SEQUENCE: 130

```
gacatccaga tgacccagtc tccatcctcc ctgtctgcat ctgtaggaga cagagtcacc      60
atcacttgcc gggcaagtca gagcattagc agctatttaa attggtatca acagaaacca     120
gggaaagccc ctaagctcct gatctttgct gcatccagtt tgcaaagtgg ggtcccatca     180
aggttcagtg gcagtggatc tgggacagat ttcagtctca ccatcagcag tctgcaacct     240
gaagactttg caacttacta ctgtcaacag agttacagtt ccctcgcgct cactttcggc     300
ggagggacca aggtggagat caaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagacta cgagaaacac aaagtctacg cctgcgaagt cacccatcag     600
ggcctgagct cgcccgtcac aaagagcttc aacaggggag agtgttaata a              651
```

<210> SEQ ID NO 131
<211> LENGTH: 651
<212> TYPE: DNA
<213> ORGANISM: Homo Sapiens

<400> SEQUENCE: 131

```
gacatccagt tgacccagtc tccatcctcc ctgtctgcat ctgtaggaga cagagtcacc      60
atcacttgcc gggcaagtca gagcattagc agctatttaa attggtatca gcagaatcca     120
gggaaagccc ctaagctcct gatctatggt gcatccaatt tgcaaagtgg ggtcccatca     180
aggttcagtg gcagtggatc tgggacagat ttcactctca ccatcagcag tctgcaacct     240
gaagattttg caacttacta ctgtcaacag agttacagta ccctcgcgct cactttcggc     300
ggagggacca aggtggagat caaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagacta cgagaaacac aaagtctacg cctgcgaagt cacccatcag     600
ggcctgagct cgcccgtcac aaagagcttc aacaggggag agtgttaata a              651
```

<210> SEQ ID NO 132
<211> LENGTH: 651
<212> TYPE: DNA
<213> ORGANISM: Homo Sapiens

<400> SEQUENCE: 132

```
gacatccaga tgacccagtc tccatcctcc ctgtctgcat ctgtaggaga cagagtcacc      60
atcacttgcc gggcaagtca gagcattagc acctatttaa attggtatca gcagaaacca     120
ggaaaagccc ctaagctcct gatctctgct gcatccagtt tgcaaagtgg ggtcccgtca     180
aggttcagtg gcagtggatc tgggacagat ttcactctca ccatcagcag tctgcaacgt     240
gaagactatg cagcttacta ctgtcaacag agttacagta ccccccgta cacttttggc     300
caggggacca agctggagat caagcgaact gtggctgcac catctgtctt catcttcccg     360
```

```
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca aagcagacta cgagaaacac aaagtctacg cctgcgaagt cacccatcag      600
ggcctgagct cgcccgtcac aaagagcttc aacaggggag agtgttaata a               651
```

```
<210> SEQ ID NO 133
<211> LENGTH: 657
<212> TYPE: DNA
<213> ORGANISM: Homo Sapiens

<400> SEQUENCE: 133
caggctgtgg tgactcagga gccctcactg actgtgtccc caggagggac agtcactctc       60
acctgtgctt ccagcactgg agcagtcacc actggttact atccaaactg gttccagcag      120
aaacctggac aagcacccag gcactgatt tatagtacaa gcaagaaaca ctcctggacc       180
cctgcccggt tctcaggctc cctccttggg ggcaaagctg ccctgacact gtcaggtgtg      240
cagcctgagg acgaggctga gtattactgc ctgctcttct atggtggtgc tcagctgggg      300
gtgttcggcg agggaccaa gctgaccgtc ctaggtcagc ccaaggctgc cccctcggtc       360
actctgttcc cgcccctcctc tgaggagctt caagccaaca ggccacact ggtgtgtctc      420 ataagtgact tctacccggg agccgtgaca gtggcctgga aggcagatag cagccccgtc      480
aaggcgggag tggagaccac cacaccctcc aaacaaagca caacaagta cgcggccagc      540 agctacctga gcctgacgcc tgagcagtgg aagtcccaca aaagctacag ctgccaggtc      600
acgcatgaag ggagcaccgt ggagaagaca gtggccccta cagaatgttc ataataa        657
```

```
<210> SEQ ID NO 134
<211> LENGTH: 654
<212> TYPE: DNA
<213> ORGANISM: Homo Sapiens

<400> SEQUENCE: 134
cagactgtgg tgacccagga gccatcgttc tcagtgtccc ctggagggac ggtcacactc       60
acttgtggct tgagctctgg ctcagtctct gctcgttact accccagctg gtaccagcag      120
accccaggcc agcctccacg cacgctcatc acacagcacaa atactcggtc ttctggggtc    180
cctgatcgct tctctggctc catccttggg aacaaagctg ccctcaccat cacgggggcc     240
caggcagatg atgaatctga ttattactgt gtgctgtata tgggtagtgg cccttgggtg     300
ttcggcggag ggaccaagct gaccgtccta ggtcagccca aggctgcccc ctcggtcact     360
ctgttcccac cctcctctga ggagcttcaa gccaacaagg ccacactggt gtgtctcata    420
agtgacttct acccgggagc cgtgacagtg gcctggaagg cagatagcag ccccgtcaag    480
gcgggagtgg agaccaccac accctccaaa caaagcaaca caagtacgc ggccagcagc    540 tacctgagcc tgacgcctga gcagtggaag tcccacaaaa gctacagctg ccaggtcacg    600
catgaaggga gcaccgtgga agacagtg gcccctacag aatgttcata ataa              654
```

```
<210> SEQ ID NO 135
<211> LENGTH: 663
<212> TYPE: DNA
<213> ORGANISM: Homo Sapiens

<400> SEQUENCE: 135
gatgttgtga tgactcagtc tccactctcc ctgcccgtca cccctggaga gccggcctcc       60
```

```
atctcctgca ggtctagtca gagcctcctg cataggaatg gatacaacta tttgaattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcggagtgg aggctgagga tgttgcgttt tattactgca tgcaaggtct acgaactccg    300
tacactttcg gccaggggac caagctggag atcaagcgaa ctgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttaa    660
taa                                                                 663
```

<210> SEQ ID NO 136
<211> LENGTH: 648
<212> TYPE: DNA
<213> ORGANISM: Homo Sapiens

<400> SEQUENCE: 136

```
gacatccagt tgacccagtc tccatcctcc ctgtctgcat ctgtaggaga cagagtcacc     60
atcacttgcc gggcaagtca gagtatcagc agctatttaa attggtataa gcagagacca    120
gggaaagccc ctaagctcct gatctatgct gcatccactt tgcagagtgg ggtcccatca    180
aggttcagtg gcagtggatc tgggacagat ttcgctctca ccatcagcag tctgcaagct    240
gaagattttg caacttacta ctgtcaacag acttacagta cccttttggac gttcggccaa    300 gggaccaagg tggaaatcac acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttaataa                648
```

<210> SEQ ID NO 137
<211> LENGTH: 651
<212> TYPE: DNA
<213> ORGANISM: Homo Sapiens

<400> SEQUENCE: 137

```
gaaattgtgt tgacacagtc tccaggtacc ttgtctctgt ctccagggga aacagccacc     60
ctgtcctgca gggccagtca gagtgtcagt gatcgcgact ggcctggta tcaacaaaag    120 tctggccagt ctcccagact tctcatgtat ggtggatcca ccaggccccc tggtataccg    180
gtcaggttca gtggcagtgg gtctgggaca gagttcactc tcaccatcag cagcctgcag    240
tctgaagatt ttgcaatttta ttactgtcaa cactatcatg actggcctcc gaccttcggc    300
caagggacac gactggagat aaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
```

-continued

| | |
|---|---|
| ggcctgagct cgcccgtcac aaagagcttc aacaggggag agtgttaata a | 651 |

<210> SEQ ID NO 138
<211> LENGTH: 648
<212> TYPE: DNA
<213> ORGANISM: Homo Sapiens

<400> SEQUENCE: 138

| | |
|---|---|
| gacatccaga tgacccagtc tccatcctcc ctgtctgcat ctttagggggg cacggtcacc | 60 |
| ctcacttgcc ggtcaagtca gttcattagt cgctatttaa attggtatca acaacaccca | 120 |
| gggaaagtcc ctagactcct catttctggc gcatcaagat tgcaaagggg ggtcccgtca | 180 |
| aggttcactg gcggcgggtc tgggacagac ttcacactca ccataaagaa tgtacagcct | 240 |
| gacgatattg caacatactt ctgtcagcac tcttacagaa gtgggcgggc gttcggccaa | 300 |
| gggaccacgg tggaggtgaa acgaactgtg gctgcaccat ctgtcttcat cttcccgcca | 360 |
| tctgatgagc agttgaaatc tggaactgcc tccgttgtgt gcctgctgaa taacttctat | 420 |
| cccagagagg ccaaagtaca gtggaaggtg ataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gttaataa | 648 |

<210> SEQ ID NO 139
<211> LENGTH: 651
<212> TYPE: DNA
<213> ORGANISM: Homo Sapiens

<400> SEQUENCE: 139

| | |
|---|---|
| gaaattgtgt tgacgcagtc tccaggcagc ctgtctttgt ctccagggga aagagccacc | 60 |
| ctctcctgca gggccagtca gagtgttagc agcagctact tagcctggta ccagcagaaa | 120 |
| cctggccagg ctcccaggct cctcatctat ggtccatcca gcagggccac tggcatccca | 180 |
| gacaggttca gtggcagtgg gtctgggaca gacttcactc tcaccatcag cagactggag | 240 |
| cctgaagatt ttgcagtgta ttactgtcag cattttggta actcacgggg aacgttcggc | 300 |
| caagggacca aggtggaaat cagacgaact gtggctgcac catctgtctt catcttcccg | 360 |
| ccatctgatg agcagttgaa atctggaact gcctctgttg tgtgcctgct gaataacttc | 420 |
| tatcccagag aggccaaagt acagtggaag gtggataacg ccctccaatc gggtaactcc | 480 |
| caggagagtg tcacagagca ggacagcaag gacagcacct acagcctcag cagcaccctg | 540 |
| acgctgagca aagcagacta cgagaaacac aaagtctacg cctgcgaagt cacccatcag | 600 |
| ggcctgagct cgcccgtcac aaagagcttc aacaggggag agtgttaata a | 651 |

<210> SEQ ID NO 140
<211> LENGTH: 654
<212> TYPE: DNA
<213> ORGANISM: Homo Sapiens

<400> SEQUENCE: 140

| | |
|---|---|
| gaaattgtgt tgacgcagtc tccaggcacc ctgtctttgt ctccagggga aagagtcaca | 60 |
| ctctcctgca ggcccagtcg gtatattgcc agcgactact tagcctggta ccaactaaga | 120 |
| cctggccagg ctcccaaact cctcatctat ggtgcctcca gcagggccac tggcatccca | 180 |
| gacaggttca gtggcgttgg gtctccgaca gacttcactc tcaccatcag cagactggag | 240 |
| cctgaagatt ttgcgatgta ttactgtcac tattctggtg gctcacctcc gtaccctttt | 300 |

```
ggccagggga ccaggctgga catcaaacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata acgccctcca atcgggtaac    480
tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgtta ataa          654

<210> SEQ ID NO 141
<211> LENGTH: 648
<212> TYPE: DNA
<213> ORGANISM: Homo Sapiens

<400> SEQUENCE: 141
gacatccagt tgacccagtc tccatcctcc ctgtctgcat ctgtaggaga cagagtcacc     60
atcacttgcc gggcaagtca gtacattaac gtctacttaa attggtatca gcacaaagca    120
gggagagccc ctaagctcct gatctatgct gcatccaatt tgcaaagtgg ggtcccacca    180
aggttcattg gcagtggatc tgggacagat ttcactctta ccatcagcag tctgcaatct    240
gaagatttcg caacttacta ctgtctccag agtttcactg tccctcggac tttcggccct    300
gggaccaaag tggatgtcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca gagcagga cagcaaggac agcacctaca gcctcagcag caccctgacg    540
ctgagcaaag cagactacga gaacacaaa gtctacgcct gcgaagtcac ccatcagggc    600
ctgagctcgc ccgtcacaaa gagcttcaac aggggagagt gttaataa                648

<210> SEQ ID NO 142
<211> LENGTH: 651
<212> TYPE: DNA
<213> ORGANISM: Homo Sapiens

<400> SEQUENCE: 142
gaaattgtgt tgacacagtc tccaggcacc ctgtctttgt ctccagggga gagagccacc     60
ctctcctgca gggccagtca gagtgttagc agcgccttct tagcctggta ccagcagaaa    120
cctggccagg ctcccagact cctcatctat ggtgcctcca gcagggccac tggcatccca    180
gacaggttca gtggcagtgg gtctgggaca gacttcactc tcaccatcag cagactggag    240
cctgaagatt ttgcagtgta ttactgtcag cagtatggca gcttttcgat caccttcggc    300
caagggacac gactggagat taaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacagggagag tgttaata a              651

<210> SEQ ID NO 143
<211> LENGTH: 657
<212> TYPE: DNA
<213> ORGANISM: Homo Sapiens

<400> SEQUENCE: 143
```

```
cagactgtgg tgacccagga gccctcactg actgtgtccc caggagggac agtcactctc    60
acctgtgctt ccagcactgg agcagtcacc agtggttact atccaaactg gttccagcag   120
aaacctggac aagcacccag ggcactgatt tatagtacaa gcaacaaaca ctcctggacc   180
cctgcccggt tctcaggctc cctccttggg ggcaaagctg ccctgacact gtcaggtgtg   240
cagcctgagg acgaggctga gtattactgc tgctctact atggtggtgc tcagcgttgg   300
gtgttcggcg gagggaccat cctgaccgtc ctaggtcagc ccaaggctgc ccctcggtc    360 actctgttcc cgccctcctc tgaggagctt caagccaaca ggccacact ggtgtgtctc    420 ataagtgact tctacccggg agccgtgaca gtggcctgga aggcagatag cagccccgtc   480
aaggcgggag tggagaccac cacaccctcc aaacaaagca caacaagta cgcggccagc    540 agctacctga gcctgacgcc tgagcagtgg aagtcccaca aaagctacag ctgccaggtc   600
acgcatgaag ggagcaccgt ggagaagaca gtggccccta cagaatgttc ataataa      657

<210> SEQ ID NO 144
<211> LENGTH: 657
<212> TYPE: DNA
<213> ORGANISM: Homo Sapiens

<400> SEQUENCE: 144 cttaattttta tgctgactca gccccactct gtgtcggagt ctccggggaa gacggtaacc    60
atctcctgca cccgcagcag tggcagcatt gccagcaact atatgcagtg gtaccagcag   120
cgcccgggca gttccccac cactgtgatc tatgaggata tcggagacc ctctggggtc     180 cctgatcgct tctctggctc catcgacagc tcctccaact ctgcctccct caccatctct   240
ggactgaaga ctgaggacga ggctgactac tactgtcagt cttatgatag taacaattgg   300
gtgttcggcg gagggaccaa gctgaccgtc ctaggtcagc ccaaggctgc ccctcggtc    360 actctgttcc cgccctcctc tgaggagctt caagccaaca ggccacact ggtgtgtctc    420 ataagtgact tctacccggg agccgtgaca gtggcctgga aggcagatag cagccccgtc   480
aaggcgggag tggagaccac cacaccctcc aaacaaagca caacaagta cgcggccagc    540 agctacctga gcctgacgcc tgagcagtgg aagtcccaca aaagctacag ctgccaggtc   600
acgcatgaag ggagcaccgt ggagaagaca gtggccccta cagaatgttc ataataa      657

<210> SEQ ID NO 145
<211> LENGTH: 651
<212> TYPE: DNA
<213> ORGANISM: Homo Sapiens

<400> SEQUENCE: 145
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccactt tgcaaagtgg ggtcccatca   180
aggttcagtg gcagtggatc tgggacagat ttcactctca ccatcagcag tctgcaacct   240
gaagattttg caacttacta ctgtcaacag tattacagaa cgcccacgtg acgttcggc    300 caagggacca aggtggaaat caaacgaact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca aagcagacta cgagaaacac aaagtctacg cctgcgaagt cacccatcag   600
```

```
                                        -continued ggcctgagct cgcccgtcac aaagagcttc aacaggggag agtgttaata a           651

<210> SEQ ID NO 146
<211> LENGTH: 651
<212> TYPE: DNA
<213> ORGANISM: Homo Sapiens

<400> SEQUENCE: 146
gaaattgtgt tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact ggccccggta cacttttggc   300
caggggacca agctggagat caaacgaact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacac aaagtctacg cctgcgaagt cacccatcag   600
ggcctgagct cgcccgtcac aaagagcttc aacaggggag agtgttaata a             651

<210> SEQ ID NO 147
<211> LENGTH: 127
<212> TYPE: PRT
<213> ORGANISM: Homo Sapiens

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Arg Ser Phe
            20                  25                  30

Asp Met Asn Trp Val Arg Gln Ala Pro Gly Lys Gly Leu Glu Trp Val
        35                  40                  45

Ser Tyr Ile Asn Ser Arg Gly Ser Thr Ile Tyr Tyr Ala Asp Ser Val
    50                  55                  60

Lys Gly Arg Phe Thr Ile Ser Arg Glu Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Tyr Gly Asp Tyr Asp Pro Lys Ser Tyr Tyr Tyr Tyr
            100                 105                 110

Gly Met Gly Val Trp Gly Gln Gly Thr Thr Val Thr Val Ser Ser
        115                 120                 125

<210> SEQ ID NO 148
<211> LENGTH: 125
<212> TYPE: PRT
<213> ORGANISM: Homo Sapiens

<400> SEQUENCE: 148

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Ser Phe Ser Asn Phe
            20                  25                  30

Gly Phe His Trp Ile Arg Gln Ser Pro Gly Lys Gly Leu Glu Trp Val
        35                  40                  45
```

Ala Val Ile Trp Tyr Asp Gly Ser Asn Arg Phe Tyr Ala Asp Ser Val
            50                  55                  60

Lys Gly Arg Phe Thr Ile Ser Arg Asp Ser Ser Lys Asn Met Leu Phe
 65                  70                  75                  80

Leu Gln Met Asp Ser Leu Arg Ala Glu Asp Thr Ala Val Tyr Tyr Cys
                85                  90                  95

Ala Arg Glu Ile Ser Met Lys Val Val Ile Arg Arg His Tyr Val Met
            100                 105                 110

Asp Val Trp Gly His Gly Thr Thr Val Thr Val Ser Ser
            115                 120                 125

<210> SEQ ID NO 149
<211> LENGTH: 127
<212> TYPE: PRT
<213> ORGANISM: Homo Sapiens

<400> SEQUENCE: 149

Glu Val Gln Leu Val Glu Thr Gly Gly Gly Leu Val Gln Pro Gly Gly
 1               5                  10                  15

Ser Leu Arg Leu Ser Cys Ala Ala Ser Gly Phe Ser Phe Arg Ser Tyr
            20                  25                  30

Asp Met Asn Trp Val Arg Gln Ala Pro Gly Lys Gly Leu Glu Trp Val
            35                  40                  45

Ser Tyr Ile Ser Gly Arg Gly Ser Thr Thr Tyr Tyr Ala Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Leu Tyr Gly Asp Tyr Asp Pro Lys Ser Tyr Tyr Tyr Tyr
            100                 105                 110

Ala Met Asp Val Trp Gly His Gly Thr Thr Val Thr Val Ser Ser
            115                 120                 125

<210> SEQ ID NO 150
<211> LENGTH: 125
<212> TYPE: PRT
<213> ORGANISM: Homo Sapiens

<400> SEQUENCE: 150

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Arg Phe Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Asn Leu Arg Ala Glu Asp Thr Ala Leu Tyr Ser Cys
                85                  90                  95

Ala Arg Glu Ile Thr Thr Thr Val Val Val Arg Arg His Tyr Leu Met
            100                 105                 110

Asp Ile Trp Gly Gln Gly Thr Thr Val Thr Val Ser Ser
            115                 120                 125

-continued

```
<210> SEQ ID NO 151
<211> LENGTH: 126
<212> TYPE: PRT
<213> ORGANISM: Homo Sapiens

<400> SEQUENCE: 151

Glu Val Gln Leu Val Glu Ser Gly Gly Gly Val Val Gln Ser Gly Arg
1               5                   10                  15

Ser Leu Arg Leu Ser Cys Ala Ala Ser Gly Phe Thr Phe Ser Asn Asn
            20                  25                  30

Gly Met His Trp Val Arg Gln Ala Pro Gly Lys Gly Leu Glu Trp Val
        35                  40                  45

Ala Phe Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Gly Leu Arg Ala Glu Asp Ser Ala Val Tyr Tyr Cys
                85                  90                  95

Ala Arg Glu Glu Ile Ala Ala Arg Leu Tyr Ser Arg Tyr His Tyr Ala
            100                 105                 110

Met Asp Val Trp Gly Gln Gly Thr Met Val Thr Val Ser Ser
        115                 120                 125

<210> SEQ ID NO 152
<211> LENGTH: 125
<212> TYPE: PRT
<213> ORGANISM: Homo Sapiens

<400> SEQUENCE: 152

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Gly Phe Ser Ala Tyr
            20                  25                  30

Ser Met Asn Trp Val Arg Gln Ala Pro Gly Lys Gly Leu Glu Trp Val
        35                  40                  45

Ser Ser Ile Thr Ser Thr Thr Thr Tyr Tyr Ala Asp Ser Val Lys Gly
    50                  55                  60

Arg Phe Ser Ile Ser Arg Asp Asn Ala Lys Ser Thr Leu Tyr Leu Arg
65                  70                  75                  80

Met Asn Ser Leu Arg Ala Glu Asp Thr Ala Val Tyr Tyr Cys Val Arg
                85                  90                  95

Glu Ile Ala Phe Arg Gly Ser Thr Tyr Ser Arg Trp Ser Tyr Tyr Phe
            100                 105                 110

Asp Phe Trp Gly Gln Gly Thr Leu Val Thr Val Ser Ser
        115                 120                 125

<210> SEQ ID NO 153
<211> LENGTH: 128
<212> TYPE: PRT
<213> ORGANISM: Homo Sapiens

<400> SEQUENCE: 153

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Val Arg Gln Pro Pro Gly Lys Gly Leu Glu Trp Ile
        35                  40                  45
```

```
Gly Tyr Ile Tyr Tyr Ser Gly Ser Thr Asn Tyr Asn Pro Ser Leu Lys
        50                  55                  60

Ser Arg Val Thr Ile Ala Leu Asp Thr Ser Lys Asn Gln Phe Ser Leu
 65                  70                  75                  80

Lys Leu Arg Ser Val Thr Ala Ala Asp Thr Ala Val Tyr Phe Cys Thr
                    85                  90                  95

Arg Asp Trp Arg Gln Tyr Gly Ser Ala Ile Arg Gly Ser Arg Tyr Tyr
            100                 105                 110

Tyr Gly Met Asp Val Trp Gly Gln Gly Thr Thr Val Thr Val Ser Ser
            115                 120                 125

<210> SEQ ID NO 154
<211> LENGTH: 129
<212> TYPE: PRT
<213> ORGANISM: Homo Sapiens

<400> SEQUENCE: 154

Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Met Val Thr Met Val Arg Gly Ala Tyr Arg Asn Tyr Tyr
            100                 105                 110

Tyr Tyr Gly Met Asp Val Trp Gly Lys Gly Thr Thr Val Thr Val Ser
            115                 120                 125

Ser

<210> SEQ ID NO 155
<211> LENGTH: 127
<212> TYPE: PRT
<213> ORGANISM: Homo Sapiens

<400> SEQUENCE: 155

Glu Val Gln Leu Val Glu Thr Gly Gly Gly Val Val Gln Pro Gly Arg
 1               5                   10                  15

Ser Leu Arg Leu Ser Cys Ala Ala Ser Gly Phe Ser Phe Ser Asn Tyr
                20                  25                  30

Gly Met His Trp Val Arg Gln Ala Pro Gly Lys Gly Leu Glu Trp Val
            35                  40                  45

Ala Val Ile Trp Phe Asp Gly Ser Ile Lys Tyr Tyr Val Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Glu Thr Ala Ile Tyr Phe Cys
                85                  90                  95

Ala Arg Glu Asn Ser Val Leu Val Pro Gly Thr Ile Arg Arg Arg Tyr
            100                 105                 110

Tyr Leu Asp Tyr Trp Gly Gln Gly Thr Leu Val Thr Val Ser Ser
```

<210> SEQ ID NO 156
<211> LENGTH: 127
<212> TYPE: PRT
<213> ORGANISM: Homo Sapiens

<400> SEQUENCE: 156

Gln Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Arg Ser Tyr
            20                  25                  30

Glu Met Asn Trp Val Arg Gln Ala Pro Gly Lys Gly Leu Glu Trp Val
        35                  40                  45

Ser Tyr Ile Asn Ser Arg Gly Asn Thr Lys Tyr Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Ser Ser Leu Arg Ala Glu Asp Thr Ala Val Tyr Tyr Cys
                85                  90                  95

Ala Arg Asn Leu Phe Gly Asp Tyr Asp Leu Lys Ser Tyr Tyr Tyr Asn
            100                 105                 110

Ala Met Asp Val Trp Gly Gln Gly Thr Leu Val Thr Val Ser Ser
        115                 120                 125

<210> SEQ ID NO 157
<211> LENGTH: 127
<212> TYPE: PRT
<213> ORGANISM: Homo Sapiens

<400> SEQUENCE: 157

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ser Ile Ser Gly Thr Ser Ser Tyr Ile Tyr Tyr Ala Asp Ser Val
    50                  55                  60

Lys Gly Arg Phe Thr Ile Phe Arg Asp Asn Ala Lys Ser Ser Val Tyr
65                  70                  75                  80

Leu Gln Met Asn Ser Leu Arg Val Glu Asp Thr Ala Val Tyr Tyr Cys
                85                  90                  95

Ala Arg Asp Arg Trp Trp Gly Met Val Arg Arg Val Phe Pro Thr Tyr
            100                 105                 110

Pro Phe Asp Tyr Trp Gly Gln Gly Thr Leu Val Thr Val Ser Ser
        115                 120                 125

<210> SEQ ID NO 158
<211> LENGTH: 125
<212> TYPE: PRT
<213> ORGANISM: Homo Sapiens

<400> SEQUENCE: 158

Gln Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Asp Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ile Ala Ser Arg Gly Tyr Ser Arg Tyr Leu Tyr Tyr Phe
                100                 105                 110

Asp Ser Trp Gly Gln Gly Thr Leu Val Thr Val Ser Ser
        115                 120                 125

<210> SEQ ID NO 159
<211> LENGTH: 129
<212> TYPE: PRT
<213> ORGANISM: Homo Sapiens

<400> SEQUENCE: 159

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Met Arg Leu Thr Met Val Arg Gly Val Ile Thr Tyr Tyr
                100                 105                 110

Tyr Tyr Ser Met Asp Val Trp Gly Gln Gly Thr Thr Val Thr Val Ser
        115                 120                 125

Ser

<210> SEQ ID NO 160
<211> LENGTH: 127
<212> TYPE: PRT
<213> ORGANISM: Homo Sapiens

<400> SEQUENCE: 160

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ser Tyr Tyr Trp Ser Trp Ile Arg Gln Pro Ala Gly Lys Gly Pro Glu
        35                  40                  45

Trp Ile Gly Arg Ile Tyr Thr Ser Gly Ser Thr Asn Tyr Asn Pro Ser
    50                  55                  60

Leu Lys Ser Arg Leu Thr Ile Ser Val Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Ala Pro Ser Tyr Tyr Asp Ser Ser Gly Tyr Arg Tyr Trp
                100                 105                 110

Tyr Ile Asp Leu Trp Gly Arg Gly Thr Leu Val Thr Val Ser Ser
        115                 120                 125

<210> SEQ ID NO 161
<211> LENGTH: 126
<212> TYPE: PRT
<213> ORGANISM: Homo Sapiens

<400> SEQUENCE: 161

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Val Arg Ala Glu Asp Thr Ala Val Tyr Tyr Cys
                85                  90                  95

Ala Arg Glu Leu Ser Thr Gln Arg Gly Tyr Ser Arg Tyr His Tyr Val
            100                 105                 110

Met Asp Val Trp Gly Gln Gly Thr Thr Val Thr Val Ser Ser
        115                 120                 125

<210> SEQ ID NO 162
<211> LENGTH: 121
<212> TYPE: PRT
<213> ORGANISM: Homo Sapiens

<400> SEQUENCE: 162

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Phe Asp Gly Ser Asn Arg Asp Tyr Ala Asp Ser Val
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Leu Ala Arg Gly Arg Leu Arg Ala Leu Glu Tyr Trp Gly
            100                 105                 110

Gln Gly Thr Leu Val Thr Val Ser Ser
        115                 120

<210> SEQ ID NO 163
<211> LENGTH: 126
<212> TYPE: PRT
<213> ORGANISM: Homo Sapiens

<400> SEQUENCE: 163

Gln Val Gln Leu Val Gln Ser Gly Gly Gly Val Val Gln Pro Gly Lys
1               5                   10                  15

Ser Leu Arg Leu Ser Cys Ala Ala Ser Gly Phe Thr Phe Ser Thr Tyr

```
                    20                  25                  30
Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Thr Ser Lys Asn Thr Leu Tyr
65                  70                  75                  80

Leu Gln Met Asn Ser Val Arg Val Glu Asp Thr Ala Val Tyr Tyr Cys
                85                  90                  95

Ala Arg Asp Leu Thr Thr Gln Arg Gly Tyr Ser Arg Tyr His Tyr Val
            100                 105                 110

Met Asp Val Trp Gly Gln Gly Thr Thr Val Thr Val Ser Ser
        115                 120                 125

<210> SEQ ID NO 164
<211> LENGTH: 126
<212> TYPE: PRT
<213> ORGANISM: Homo Sapiens

<400> SEQUENCE: 164

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Val Tyr Tyr Cys
                85                  90                  95

Ala Arg Glu Val Gly Phe Gly Ser Gly Trp Ser Arg Tyr Tyr Tyr Gly
            100                 105                 110

Met Asp Val Trp Gly Gln Gly Thr Thr Val Thr Val Ser Ser
        115                 120                 125

<210> SEQ ID NO 165
<211> LENGTH: 130
<212> TYPE: PRT
<213> ORGANISM: Homo Sapiens

<400> SEQUENCE: 165

Glu Val Gln Leu Val Glu Ser Gly Gly Gly Val Val Gln Pro Gly
1               5                   10                  15

Arg Ser Leu Arg Leu Ser Cys Ala Ala Ser Gly Phe Thr Phe Ser Ser
            20                  25                  30

Tyr Gly Met His Trp Val Arg Gln Ala Pro Gly Lys Gly Leu Glu Trp
        35                  40                  45

Val Ala Val Ile Trp Tyr Asp Gly Ser Asn Lys Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Glu Ser Thr Leu Tyr Ser Ser Ser Trp Tyr Arg Arg Tyr
            100                 105                 110
```

Tyr Tyr Tyr Gly Met Asp Val Trp Gly Gln Gly Thr Thr Val Thr Val
        115                 120                 125

Ser Ser
    130

<210> SEQ ID NO 166
<211> LENGTH: 129
<212> TYPE: PRT
<213> ORGANISM: Homo Sapiens

<400> SEQUENCE: 166

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Thr Leu Tyr Ser Ser Ser Trp Tyr Arg Arg Tyr Tyr
            100                 105                 110

Tyr Tyr Ser Met Asp Val Trp Gly Gln Gly Thr Thr Val Thr Val Ser
        115                 120                 125

Ser

<210> SEQ ID NO 167
<211> LENGTH: 128
<212> TYPE: PRT
<213> ORGANISM: Homo Sapiens

<400> SEQUENCE: 167

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Ser Asn Arg Tyr Tyr Gly Asp Ser Val
    50                  55                  60

Lys Gly Arg Val Thr Ile Ser Arg Asp Asn Ser Lys Asn Thr Leu Tyr
65                  70                  75                  80

Leu Arg Met Asn Ser Leu Arg Ala Glu Asp Thr Ala Val Tyr Tyr Cys
                85                  90                  95

Ala Arg Glu Phe Tyr Thr Arg Ser Gly Leu Trp Ser Gln Gly Tyr Ser
            100                 105                 110

Tyr Tyr Met Asp Val Trp Gly Lys Gly Thr Thr Val Thr Val Ser Ser
        115                 120                 125

<210> SEQ ID NO 168
<211> LENGTH: 129
<212> TYPE: PRT
<213> ORGANISM: Homo Sapiens

<400> SEQUENCE: 168

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Met Val Ser Tyr Ser Ser Trp Tyr Arg Arg Tyr Tyr
            100                 105                 110

Tyr Tyr Val Met Asp Val Trp Gly Lys Gly Thr Thr Val Thr Val Ser
        115                 120                 125

Ser
```

<210> SEQ ID NO 169
<211> LENGTH: 123
<212> TYPE: PRT
<213> ORGANISM: Homo Sapiens

<400> SEQUENCE: 169

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Glu Lys Tyr Tyr Ala Asp Ser Val
    50                  55                  60

Lys Gly Arg Phe Thr Ile Ser Arg Asp Asn Ser Lys Lys Ala Leu Tyr
65                  70                  75                  80

Leu Gln Met Asn Ser Leu Arg Ala Glu Asp Thr Ala Met Tyr Tyr Cys
                85                  90                  95

Lys Asn Lys Val Gly Ala Thr Arg Arg Ala Val Val Ala Phe Asp Ile
            100                 105                 110

Trp Gly Gln Gly Thr Thr Val Thr Val Ser Ser
        115                 120
```

<210> SEQ ID NO 170
<211> LENGTH: 127
<212> TYPE: PRT
<213> ORGANISM: Homo Sapiens

<400> SEQUENCE: 170

```
Glu Val Gln Leu Val Glu Thr Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Ser Met Asn Trp Val Arg Gln Ala Pro Gly Lys Gly Leu Glu Trp Val
        35                  40                  45

Ser Ser Ile Gly Ser Ser Ser Thr Tyr Thr Tyr Ser Ala Asp Ser Val
    50                  55                  60

Lys Gly Arg Phe Thr Ile Ser Arg Asp Asn Ala Lys Asn Ser Leu Tyr
```

```
                65                  70                  75                  80
Leu Gln Met Asn Ser Leu Arg Ala Glu Asp Thr Ala Val Tyr Tyr Cys
                        85                  90                  95

Ala Arg Gly Glu Pro Leu Asn Tyr Asp Tyr Ile Trp Gly Gly Tyr Arg
                100                 105                 110

Phe Thr Ile His Trp Gly Gln Gly Thr Leu Val Thr Val Ser Ser
                115                 120                 125

<210> SEQ ID NO 171
<211> LENGTH: 129
<212> TYPE: PRT
<213> ORGANISM: Homo Sapiens

<400> SEQUENCE: 171

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ile Ile Trp Phe Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Ile Asn Ser Leu Arg Ala Glu Asp Thr Ala Val Tyr Tyr Cys
                    85                  90                  95

Ala Lys Glu His Gly Tyr Tyr Ser Ser Ser Trp Tyr Arg Asn Tyr Tyr
                100                 105                 110

Tyr Tyr Ala Met Asp Val Trp Gly Gln Gly Thr Thr Val Thr Val Ser
            115                 120                 125

Ser

<210> SEQ ID NO 172
<211> LENGTH: 121
<212> TYPE: PRT
<213> ORGANISM: Homo Sapiens

<400> SEQUENCE: 172

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Asp Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Glu Leu Ala Lys Gly Arg Leu Arg Asp Leu Asp His Trp Gly
                100                 105                 110

Gln Gly Thr Leu Val Thr Val Ser Ser
            115                 120

<210> SEQ ID NO 173
<211> LENGTH: 129
```

```
<212> TYPE: PRT
<213> ORGANISM: Homo Sapiens

<400> SEQUENCE: 173

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Thr Ser
            20                  25                  30

Ala Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Met Val Ser Tyr Ser Ser Trp Tyr Arg Tyr Arg Tyr Tyr
            100                 105                 110

Tyr Tyr Asn Met Asp Val Trp Gly Lys Gly Thr Thr Val Thr Val Ser
        115                 120                 125

Ser

<210> SEQ ID NO 174
<211> LENGTH: 125
<212> TYPE: PRT
<213> ORGANISM: Homo Sapiens

<400> SEQUENCE: 174

Gln Val Gln Leu Val Glu Ser Gly Gly Gly Val Val Gln Pro Gly Thr
1               5                   10                  15

Ser Leu Arg Leu Ser Cys Ala Ala Ser Gly Phe Thr Phe Arg Thr Tyr
            20                  25                  30

Gly Met His Trp Val Arg Gln Ala Pro Gly Lys Gly Leu Glu Trp Val
        35                  40                  45

Ala Tyr Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Ser Thr Leu Asn
65                  70                  75                  80

Leu Gln Met Asn Ser Leu Arg Ala Glu Asp Thr Ala Val Tyr Tyr Cys
                85                  90                  95

Ala Arg Glu Ile Ala Ser Arg Gly Tyr Ser Arg Tyr Leu Tyr Tyr Phe
            100                 105                 110

Asp Ser Trp Gly Gln Gly Thr Leu Val Thr Val Ser Ser
        115                 120                 125

<210> SEQ ID NO 175
<211> LENGTH: 129
<212> TYPE: PRT
<213> ORGANISM: Homo Sapiens

<400> SEQUENCE: 175

Gln Leu Gln Leu Gln Glu Ser Gly Pro Gly Leu Val Lys Pro Ser Gly
1               5                   10                  15

Thr Leu Ser Leu Thr Cys Ala Val Ser Gly Gly Ser Met Arg Ser Ser
            20                  25                  30

Asn Trp Trp Thr Trp Val Arg Gln Pro Pro Gly Lys Gly Leu Glu Trp
        35                  40                  45
```

```
Ile Gly Glu Ile His His Gly Gly Ser Thr Asn Tyr Asn Pro Ser Leu
 50                  55                  60

Gln Ser Arg Val Thr Ile Ser Val Asp Lys Ser Lys Asn Arg Phe Ser
 65                  70                  75                  80

Leu Lys Leu Ser Ser Val Thr Ala Ala Asp Thr Ala Val Tyr His Cys
                 85                  90                  95

Ala Arg Gly Arg Ser Tyr Tyr Asp Ser Ser Gly His Ser Phe Arg Gly
                100                 105                 110

Leu Val Pro Phe Asp Ile Trp Gly Gln Gly Thr Met Val Thr Val Ser
                115                 120                 125

Ser
```

<210> SEQ ID NO 176
<211> LENGTH: 128
<212> TYPE: PRT
<213> ORGANISM: Homo Sapiens

<400> SEQUENCE: 176

```
Gln Val Gln Leu Gln Glu Ser Gly Pro Gly Leu Val Lys Pro Ser Glu
  1               5                  10                  15

Thr Leu Ser Leu Ile Cys Thr Val Ser Gly Gly Ser Ile Ser Ser Asn
                 20                  25                  30

Tyr Trp Ser Trp Ile Arg Gln Pro Pro Gly Lys Gly Leu Glu Trp Ile
                 35                  40                  45

Gly Tyr Ile Tyr Tyr Ser Gly Asn Thr Asn Tyr Asn Pro Ser Leu Lys
                 50                  55                  60

Ser Arg Val Thr Ile Ser Leu Asp Thr Ser Lys Asn Gln Phe Ser Leu
 65                  70                  75                  80

Lys Leu Arg Ser Val Thr Ala Ala Asp Thr Ala Val Tyr Tyr Cys Ala
                 85                  90                  95

Arg Glu Trp Arg Gln Tyr Gly Ser Gly Ile Arg Gly Ser Arg Tyr Tyr
                100                 105                 110

Tyr Gly Met Asp Val Trp Gly Gln Gly Thr Leu Val Thr Val Ser Ser
                115                 120                 125
```

<210> SEQ ID NO 177
<211> LENGTH: 129
<212> TYPE: PRT
<213> ORGANISM: Homo Sapiens

<400> SEQUENCE: 177

```
Glu Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Asn His
                 20                  25                  30

Gly Met His Trp Val Arg Gln Ala Pro Gly Lys Gly Leu Glu Trp Val
                 35                  40                  45

Ala Val Ile Trp Tyr Asp Gly Ser Asn Lys Tyr Tyr Ala Asp Ser Val
                 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Met Ala Ser Tyr Ser Ser Ser Trp Tyr Arg Arg Tyr Tyr
                100                 105                 110

Tyr Tyr Val Met Asp Val Trp Gly Lys Gly Thr Thr Val Thr Val Ser
                115                 120                 125
```

Ser

<210> SEQ ID NO 178
<211> LENGTH: 125
<212> TYPE: PRT
<213> ORGANISM: Homo Sapiens

<400> SEQUENCE: 178

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Thr Tyr
            20                  25                  30
Gly Met His Trp Val Arg Gln Ala Pro Gly Lys Gly Leu Glu Trp Val
        35                  40                  45
Ala Val Ile Trp Tyr Asp Gly Ser Gln Lys Tyr Tyr Val Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Val Ala Val Arg Gly Val Ile Arg Tyr Tyr Gly Met
            100                 105                 110
Asp Val Trp Gly Gln Gly Thr Thr Val Thr Val Ser Ser
        115                 120                 125

<210> SEQ ID NO 179
<211> LENGTH: 128
<212> TYPE: PRT
<213> ORGANISM: Homo Sapiens

<400> SEQUENCE: 179

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Ser Phe Ser Ser Tyr
            20                  25                  30
Gly Met His Trp Val Arg Gln Ala Pro Gly Lys Gly Leu Glu Trp Val
        35                  40                  45
Ala Ile Ile Trp Tyr Asp Gly Ser Asn Lys Leu Tyr Ala Asp Ser Val
    50                  55                  60
Lys Gly Arg Phe Thr Ile Ser Arg Asp Asn Ser Arg Asn Thr Leu Tyr
65                  70                  75                  80
Leu Gln Met Ser Ser Val Arg Ala Glu Asp Thr Ala Val Tyr Tyr Cys
                85                  90                  95
Ala Arg Asp Ser Val Arg Gly Val Ser Arg Trp Gly Thr Gln Lys Tyr
            100                 105                 110
Tyr Ala Met Asp Val Trp Gly Gln Gly Thr Thr Val Thr Val Ser Ser
        115                 120                 125

<210> SEQ ID NO 180
<211> LENGTH: 126
<212> TYPE: PRT
<213> ORGANISM: Homo Sapiens

<400> SEQUENCE: 180

Glu Val Gln Leu Val Gln Ser Gly Gly Gly Val Val Gln Pro Gly Arg
1               5                   10                  15
Ser Pro Arg Leu Ser Cys Ala Ala Ser Gly Phe Thr Phe Ser Ser Tyr
            20                  25                  30

```
Gly Met His Trp Val Arg Gln Ala Pro Gly Lys Gly Leu Glu Trp Val
            35                  40                  45

Ala Phe Ile Trp Tyr Asp Gly Ser Asn Lys Tyr Tyr Ala Asp Ser Val
 50                      55                  60

Lys Gly Arg Phe Thr Ile Ser Arg Asp Asn Ser Lys Asn Thr Leu Tyr
 65                      70                  75                  80

Leu Gln Met Asn Ser Leu Arg Ala Glu Asp Thr Ala Val Tyr Tyr Cys
                    85                  90                  95

Ala Arg Asp Leu Arg Asn His Val Phe Trp Ser Gly Tyr Ser Thr Ser
                100                 105                 110

Phe Asp Tyr Trp Gly Gln Gly Thr Leu Val Thr Val Ser Ser
                115                 120                 125

<210> SEQ ID NO 181
<211> LENGTH: 129
<212> TYPE: PRT
<213> ORGANISM: Homo Sapiens

<400> SEQUENCE: 181

Glu Val Gln Leu Val Glu Thr Gly Gly Gly Val Val Gln Pro Gly Arg
 1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
 50                      55                  60

Lys Gly Arg Phe Thr Ile Ser Arg Asp Asn Ser Lys Asn Thr Leu Tyr
 65                      70                  75                  80

Leu Gln Met Asn Ser Leu Arg Ala Glu Asp Thr Ala Val Tyr Tyr Cys
                    85                  90                  95

Ala Arg Glu Met Val Ser Tyr Ser Ser Ser Trp Tyr Arg Ala Tyr Tyr
                100                 105                 110

Tyr Tyr Asn Met Asp Val Trp Gly Lys Gly Thr Thr Val Thr Val Ser
            115                 120                 125

Ser

<210> SEQ ID NO 182
<211> LENGTH: 129
<212> TYPE: PRT
<213> ORGANISM: Homo Sapiens

<400> SEQUENCE: 182

Gln Val Gln Leu Val Glu Thr Gly Gly Gly Val Val Gln Pro Gly Arg
 1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Ser Asp Gly Ser Asn Lys Tyr Tyr Ala Asp Ser Val
 50                      55                  60

Lys Gly Arg Phe Thr Ile Ser Arg Asp Asn Ser Arg Asn Thr Leu Tyr
 65                      70                  75                  80

Leu Gln Met Asn Ser Leu Arg Ala Glu Asp Thr Ala Val Phe Tyr Cys
                    85                  90                  95

Ala Arg Glu Gln Gly Gly Tyr Ser Ser Ser Trp Tyr Arg Arg Tyr Tyr
```

```
                100             105             110
Tyr Tyr Tyr Met Asp Val Trp Gly Gln Gly Thr Thr Val Thr Val Ser
        115                 120                 125

Ser

<210> SEQ ID NO 183
<211> LENGTH: 125
<212> TYPE: PRT
<213> ORGANISM: Homo Sapiens

<400> SEQUENCE: 183

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Val Ala Val Arg Gly Val Ile Arg Tyr Tyr Tyr Ala Met
            100                 105                 110

Asp Val Trp Gly Gln Gly Thr Thr Val Thr Val Ser Ser
        115                 120                 125

<210> SEQ ID NO 184
<211> LENGTH: 123
<212> TYPE: PRT
<213> ORGANISM: Homo Sapiens

<400> SEQUENCE: 184

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Glu Lys Tyr Tyr Ala Asp Ser Val
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Met Tyr Tyr Cys
                85                  90                  95

Lys Asn Lys Val Gly Ala Thr Arg Ala Val Val Ala Val Asp Ile
            100                 105                 110

Trp Gly Gln Gly Thr Met Val Thr Val Ser Ser
        115                 120

<210> SEQ ID NO 185
<211> LENGTH: 127
<212> TYPE: PRT
<213> ORGANISM: Homo Sapiens

<400> SEQUENCE: 185

Gln Val Gln Leu Val Glu Ser Gly Gly Gly Leu Val Gln Pro Gly Gly
```

-continued

```
                1               5                  10                 15
        Ser Leu Arg Leu Ser Cys Val Gly Ser Gly Phe Thr Phe Arg Ser Phe
                        20                  25                 30

Asp Met Asn Trp Val Arg Gln Ala Pro Gly Lys Gly Leu Glu Trp Ile
                        35                  40                 45

Ser Tyr Ile Asn Ser Arg Gly Asn Thr Arg Tyr Tyr Val Asp Ser Val
         50                     55                  60

Lys Gly Arg Phe Thr Ile Ser Arg Asp Asn Ala Lys Asn Ser Leu Tyr
         65                     70                  75                 80

Leu Gln Met Asn Ser Leu Arg Ala Glu Asp Thr Ala Val Tyr Tyr Cys
                        85                  90                 95

Ala Arg Asp Leu Tyr Gly Asp Tyr Asp Pro Lys Ser Tyr Tyr Tyr Tyr
                        100                 105                110

Gly Met Asp Val Trp Gly Gln Gly Thr Met Val Thr Val Ser Ser
                        115                 120                125
```

<210> SEQ ID NO 186
<211> LENGTH: 125
<212> TYPE: PRT
<213> ORGANISM: Homo Sapiens

<400> SEQUENCE: 186

```
        Glu Val Gln Leu Val Glu Ser Gly Gly Gly Val Val Gln Pro Gly Arg
         1                      5                   10                 15

Ser Leu Arg Leu Ser Cys Glu Ala Ser Gly Phe Thr Phe Ser Asn Tyr
                        20                  25                 30

Gly Met His Trp Phe Arg Gln Ala Pro Gly Lys Gly Leu Glu Trp Val
                        35                  40                 45

Ala Ile Ile Trp Tyr Asp Gly Ser Asn Lys His Tyr Ala Asp Ser Val
         50                     55                  60

Lys Gly Arg Phe Thr Ile Ser Arg Asp Asn Ser Lys Asn Thr Leu Tyr
         65                     70                  75                 80

Leu Gln Met Asn Ser Leu Arg Ala Glu Asp Thr Ala Val Tyr Phe Cys
                        85                  90                 95

Ala Arg Glu Ile Ala Ser Arg Gly Tyr Ser Arg Tyr Leu Tyr Tyr Phe
                        100                 105                110

Asp Ser Trp Gly Gln Gly Thr Leu Val Thr Val Ser Ser
                        115                 120                125
```

<210> SEQ ID NO 187
<211> LENGTH: 125
<212> TYPE: PRT
<213> ORGANISM: Homo Sapiens

<400> SEQUENCE: 187

```
        Gln Val Gln Leu Val Glu Ser Gly Gly Gly Val Val Gln Pro Gly Arg
         1                      5                   10                 15

Ser Leu Arg Leu Ser Cys Ala Ala Ser Gly Phe Thr Phe Arg Thr Tyr
                        20                  25                 30

Gly Met His Trp Val Arg Gln Ala Pro Gly Lys Gly Leu Glu Trp Val
                        35                  40                 45

Ala Val Ile Trp Tyr Asp Gly Ser Asn Lys Asp Tyr Ala Asp Ser Val
         50                     55                  60

Lys Gly Arg Phe Thr Ile Ser Arg Asp Asn Ser Lys Asn Thr Leu His
         65                     70                  75                 80

Leu Gln Met Asn Ser Leu Arg Ala Glu Asp Thr Ala Val Tyr Tyr Cys
                        85                  90                 95
```

```
Ala Arg Glu Ile Ala Ser Arg Gly Tyr Ser Arg Tyr Leu Tyr Tyr Leu
            100                 105                 110

Asp Phe Trp Gly Gln Gly Thr Leu Val Thr Val Ser Ser
        115                 120                 125

<210> SEQ ID NO 188
<211> LENGTH: 126
<212> TYPE: PRT
<213> ORGANISM: Homo Sapiens

<400> SEQUENCE: 188

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Val Arg Ala Glu Asp Thr Ala Val Tyr Tyr Cys
                85                  90                  95

Ala Arg Asp Leu Ser Thr Gln Arg Gly Tyr Ser Arg Tyr Tyr Tyr Val
            100                 105                 110

Met Asp Val Trp Gly Gln Gly Thr Thr Val Thr Val Ser Ser
        115                 120                 125

<210> SEQ ID NO 189
<211> LENGTH: 121
<212> TYPE: PRT
<213> ORGANISM: Homo Sapiens

<400> SEQUENCE: 189

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Asp Tyr Ala Asp Ser Val
    50                  55                  60

Lys Gly Arg Phe Thr Ile Ser Arg Asp Asn Ser Lys Arg Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ala Arg Gly Arg Leu Arg Asp Leu Asp Tyr Trp Gly
            100                 105                 110

Gln Gly Thr Leu Val Thr Val Ser Ser
        115                 120

<210> SEQ ID NO 190
<211> LENGTH: 128
<212> TYPE: PRT
<213> ORGANISM: Homo Sapiens

<400> SEQUENCE: 190

Gln Val Gln Leu Val Glu Ser Gly Gly Gly Val Val Gln Pro Gly Arg
```

```
                1               5              10              15
Ser Leu Arg Leu Ser Cys Ala Ala Ser Gly Phe Thr Phe Ser Ser Tyr
                20                      25                      30

Gly Met His Trp Val Arg Gln Ala Pro Gly Lys Gly Leu Glu Trp Val
            35                      40                      45

Ala Val Ile Trp Tyr Asp Gly Ser Asn Lys Tyr Tyr Ala Asp Ser Val
        50                      55                      60

Lys Gly Arg Phe Thr Ile Ser Arg Asp Asn Ser Lys Asn Thr Leu Tyr
65                      70                      75                  80

Leu Gln Met Asn Ser Leu Arg Ala Glu Asp Thr Ala Val Tyr Tyr Cys
                    85                      90                      95

Ala Arg Glu Phe Tyr Thr Arg Ser Gly Leu Trp Ser Gln Gly Tyr Ser
                100                     105                     110

Tyr Tyr Met Asp Val Trp Gly Lys Gly Thr Thr Val Thr Val Ser Ser
            115                     120                     125
```

<210> SEQ ID NO 191
<211> LENGTH: 129
<212> TYPE: PRT
<213> ORGANISM: Homo Sapiens

<400> SEQUENCE: 191

```
Gln Val Gln Leu Val Glu Ser Gly Gly Val Val Gln Pro Gly Arg
1               5              10              15

Ser Leu Arg Leu Ser Cys Ala Ala Ser Gly Phe Thr Phe Ser Ser Tyr
                20                      25                      30

Gly Met His Trp Val Arg Gln Ala Pro Gly Lys Gly Leu Glu Trp Val
            35                      40                      45

Ala Val Ile Trp Phe Asp Gly Asn Lys Tyr Tyr Ala Asp Ser Ala
        50                      55                      60

Lys Gly Arg Phe Thr Ile Ser Arg Asp Asn Ser Lys Asn Thr Leu Tyr
65                      70                      75                  80

Leu Gln Met Asn Ser Leu Arg Ala Glu Asp Thr Ala Val Tyr Tyr Cys
                    85                      90                      95

Ala Arg Asp Ala Ser Val Leu Ser Gly Leu Val Thr Arg Arg Leu Val
                100                     105                     110

Tyr Tyr Gly Met Asp Val Trp Gly Gln Gly Thr Thr Val Thr Val Ser
            115                     120                     125

Ser
```

<210> SEQ ID NO 192
<211> LENGTH: 129
<212> TYPE: PRT
<213> ORGANISM: Homo Sapiens

<400> SEQUENCE: 192

```
Gln Val Gln Leu Val Glu Ser Gly Gly Gly Val Val Gln Pro Gly Arg
1               5              10              15

Ser Leu Arg Leu Ser Cys Ala Ala Ser Gly Phe Thr Phe Ser Ser Tyr
                20                      25                      30

Gly Met His Trp Val Arg Gln Ala Pro Gly Lys Gly Leu Glu Trp Val
            35                      40                      45

Ala Phe Ile Ser Tyr Asp Gly Ser Asn Lys Tyr Tyr Ala Asp Ser Val
        50                      55                      60

Lys Gly Arg Phe Thr Ile Ser Arg Asp Asn Ser Lys Asn Thr Leu Ser
65                      70                      75                  80
```

-continued

Leu Gln Met Asn Ser Leu Arg Ala Glu Asp Thr Ala Val Tyr Tyr Cys
                85                  90                  95

Ala Lys Glu His Gly Tyr Tyr Arg Ser Ser Trp Tyr Arg Asn Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 193
<211> LENGTH: 129
<212> TYPE: PRT
<213> ORGANISM: Homo Sapiens

<400> SEQUENCE: 193

Gln Val Gln Leu Val Glu Ser Gly Gly Val Val Gln Pro Glu Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Glu Val Gly Tyr Ser Ser Ser Trp Tyr Arg Arg Tyr Tyr
            100                 105                 110

Tyr Tyr Ala Met Asp Val Trp Gly Gln Gly Thr Thr Val Thr Val Ser
        115                 120                 125

Ser

<210> SEQ ID NO 194
<211> LENGTH: 128
<212> TYPE: PRT
<213> ORGANISM: Homo Sapiens

<400> SEQUENCE: 194

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Val Val Val Ala Ala Lys Ile Arg Asn His Tyr Tyr
            100                 105                 110

Tyr Ala Met Asp Val Trp Gly Gln Gly Thr Thr Val Thr Val Ser Ser
        115                 120                 125

<210> SEQ ID NO 195
<211> LENGTH: 129

```
<212> TYPE: PRT
<213> ORGANISM: Homo Sapiens

<400> SEQUENCE: 195

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Gly Ile Trp Tyr Asp Gly Ser Asn Lys Tyr Tyr Ala Asp Ser Val
        50                  55                  60

Lys Gly Arg Phe Thr Ile Ser Arg Asp Asn Ser Arg Asn Thr Met Tyr
65                  70                  75                  80

Leu Gln Met Asn Ser Leu Arg Ala Glu Asp Thr Ala Val Tyr Tyr Cys
                85                  90                  95

Ala Arg Glu Gln Gly Gly Tyr Ser Ser Ser Trp Tyr Arg Tyr Arg Tyr
            100                 105                 110

Tyr Tyr Asn Met Asp Leu Trp Gly Gln Gly Thr Thr Val Thr Val Ser
        115                 120                 125

Ser

<210> SEQ ID NO 196
<211> LENGTH: 129
<212> TYPE: PRT
<213> ORGANISM: Homo Sapiens

<400> SEQUENCE: 196

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Asp Asp Asp Thr Ala Val Tyr Tyr Cys
                85                  90                  95

Ala Arg Glu Gly Thr Leu Tyr Ser Ser Ser Trp Tyr Arg Arg Tyr Tyr
            100                 105                 110

Tyr Tyr Gly Met Asp Ala Trp Gly Gln Gly Thr Thr Val Thr Val Ser
        115                 120                 125

Ser

<210> SEQ ID NO 197
<211> LENGTH: 129
<212> TYPE: PRT
<213> ORGANISM: Homo Sapiens

<400> SEQUENCE: 197

Gln Val Gln Leu Val Glu Thr Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
```

```
                35                  40                  45
Ala Gly Ile Trp Tyr Asp Gly Ser Asn Lys Tyr Gly Asp Ser Val
 50                  55                  60

Lys Gly Arg Phe Thr Ile Ser Arg Asp Asn Ser Arg Asn Thr Leu Tyr
 65                  70                  75                  80

Leu His Met Asn Ser Leu Arg Ala Asp Asp Thr Ala Val Tyr Tyr Cys
                 85                  90                  95

Ala Arg Glu His Gly Gly Ser Arg Ser Gly Trp Tyr Thr Leu Arg Leu
                100                 105                 110

Ala Tyr Tyr Phe Asp Tyr Trp Gly Gln Gly Thr Leu Val Thr Val Ser
                115                 120                 125

Ser
```

```
<210> SEQ ID NO 198
<211> LENGTH: 129
<212> TYPE: PRT
<213> ORGANISM: Homo Sapiens

<400> SEQUENCE: 198

Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Arg Gly Ser
                20                  25                  30

Asn Trp Trp Ser Trp Val Arg Gln Pro Pro Gly Lys Gly Leu Glu Trp
                35                  40                  45

Ile Gly Glu Ile His His Gly Ser Thr Asn Tyr Asn Pro Ser Leu
 50                  55                  60

Lys Ser Arg Val Thr Ile Ser Val Asp Lys Ser Lys Asn Arg Phe Ser
 65                  70                  75                  80

Leu Lys Leu Ser Ser Val Thr Ala Ala Asp Thr Ala Val Tyr Tyr Cys
                 85                  90                  95

Ala Arg Gly Thr Ser Tyr Tyr Asp Ser Ser Gly Tyr Ser Phe Arg Gly
                100                 105                 110

Leu Val Ala Phe Asp Ile Trp Gly Gln Gly Thr Met Val Thr Val Ser
                115                 120                 125

Ser
```

```
<210> SEQ ID NO 199
<211> LENGTH: 129
<212> TYPE: PRT
<213> ORGANISM: Homo Sapiens

<400> SEQUENCE: 199

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
                35                  40                  45

Ala Val Ile Trp Tyr Asp Gly Ser Asn Lys Asn Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Gln Gly Tyr Arg Ser Ser Trp Tyr Arg Met Tyr Tyr
```

```
            100                 105                 110
Tyr Tyr Gly Met Asp Val Trp Gly Gln Gly Thr Thr Val Thr Val Ser
        115                 120                 125
Ser
```

<210> SEQ ID NO 200
<211> LENGTH: 127
<212> TYPE: PRT
<213> ORGANISM: Homo Sapiens

<400> SEQUENCE: 200

```
Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Arg Ser Tyr
            20                  25                  30
Ser Met Asn Trp Val Arg Gln Ala Pro Gly Lys Gly Leu Glu Trp Val
        35                  40                  45
Ser Ser Ile Gly Ser Ser Ser Ile Tyr Thr Tyr Ser Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Gly Glu Pro Leu Asn Tyr Asp Tyr Ile Trp Gly Arg Ser Arg
            100                 105                 110
Leu Thr Ile His Trp Gly Gln Gly Thr Leu Val Thr Val Ser Ser
        115                 120                 125
```

<210> SEQ ID NO 201
<211> LENGTH: 129
<212> TYPE: PRT
<213> ORGANISM: Homo Sapiens

<400> SEQUENCE: 201

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Trp Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Trp Val Thr Arg Ser Ser Asn Trp Tyr Arg Asn Tyr Tyr
            100                 105                 110
Tyr Tyr Gly Met Asp Val Trp Gly Gln Gly Thr Thr Val Thr Val Ser
        115                 120                 125
Ser
```

<210> SEQ ID NO 202
<211> LENGTH: 124
<212> TYPE: PRT
<213> ORGANISM: Homo Sapiens

<400> SEQUENCE: 202

```
Glu Val Gln Leu Val Glu Ser Gly Gly Leu Val Gln Pro Gly Arg
1               5                   10                  15

Ser Leu Arg Leu Ser Cys Val Ala Ser Gly Phe Thr Phe Ser Ser Tyr
            20                  25                  30

Trp Met His Trp Val Arg Gln Val Pro Gly Lys Gly Leu Val Trp Val
            35                  40                  45

Ser Arg Ile Asn Val Asp Gly Lys Ser Thr Ser Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Arg Phe Leu Glu Trp Ala Arg Tyr Gly Met Asp
                100                 105                 110

Val Trp Gly Arg Gly Thr Thr Val Thr Val Ser Ser
            115                 120
```

<210> SEQ ID NO 203
<211> LENGTH: 216
<212> TYPE: PRT
<213> ORGANISM: Homo Sapiens

<400> SEQUENCE: 203

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Arg Gly Gln Ala Pro Arg Leu Leu Ile
            35                  40                  45

Phe Asn Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Ser Trp Pro Pro
                85                  90                  95

Met Tyr Thr Phe Gly Gln Gly Thr Lys Leu Glu Ile Lys Arg Thr Val
                100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
            195                 200                 205

Lys Ser Phe Asn Arg Gly Glu Cys
    210                 215
```

<210> SEQ ID NO 204
<211> LENGTH: 214
<212> TYPE: PRT
<213> ORGANISM: Homo Sapiens

<400> SEQUENCE: 204

Asp Ile Gln Met Thr Gln Ser Pro Ser Pro Leu Ser Ala Ser Val Gly
1               5                   10                  15

Asp Arg Val Ser Ile Thr Cys Arg Ala Ser Arg Gly Ile Ser Asn Ser
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Gly Gly Ser Gly Thr Asp Phe Thr Leu Thr Ile Ser Ser Leu Gln Pro
65                  70                  75                  80

Glu Asp Val Ala Thr Tyr Tyr Cys His Thr Tyr Asn Ser Ala Pro Phe
                85                  90                  95

Ala Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 205
<211> LENGTH: 216
<212> TYPE: PRT
<213> ORGANISM: Homo Sapiens

<400> SEQUENCE: 205

Glu Ile Val Met Thr Gln Ser Pro Gly Thr Leu Ser Leu Ser Pro Gly
1               5                   10                  15

Glu Arg Ala Thr Leu Ser Cys Arg Ala Ser His Thr Val Ser Ser Gly
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Val Pro Asp Arg Phe Gly
50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Phe Cys Gln Gln Tyr Gly Thr Ser Pro
                85                  90                  95

Gly Val Thr Phe Gly Gln Gly Thr Arg Leu Glu Ile Glu Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

```
Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 206
<211> LENGTH: 214
<212> TYPE: PRT
<213> ORGANISM: Homo Sapiens

<400> SEQUENCE: 206

Asp Ile Gln Leu Thr Gln Ser Pro Ser Ser Leu Ser Ala Ser Val Gly
1               5                   10                  15

Asp Arg Val Ser Ile Thr Cys Arg Ala Ser Gln Gly Ile Ser Asn Ser
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Phe
                85                  90                  95

Ala Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 207
<211> LENGTH: 215
<212> TYPE: PRT
<213> ORGANISM: Homo Sapiens

<400> SEQUENCE: 207

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Arg Arg Tyr
            20                  25                  30

Leu Ala Trp Phe Gln Gln Lys Pro Gly Lys Ala Pro Lys Leu Leu Ile
```

```
            35                  40                  45
Phe Ser Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Ser Ser Tyr Pro Pro
                 85                  90                  95

Tyr Thr Phe Gly Gln Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 208
<211> LENGTH: 214
<212> TYPE: PRT
<213> ORGANISM: Homo Sapiens

<400> SEQUENCE: 208

Asp Ile Gln Leu Thr Gln Ser Pro Ser Ser Val Ser Ala Ser Val Gly
  1               5                  10                  15

Asp Ser Val Thr Ile Thr Cys Arg Ala Ser Gln Ala Val Ser Gly Trp
                 20                  25                  30

Val Ala Trp Tyr Gln Gln Lys Pro Gly Lys Ala Pro Lys Leu Leu Ile
             35                  40                  45

Phe Gly Leu Ser Asn Leu Glu Asp Gly Val Pro Ser Arg Phe Ser Gly
 50                  55                  60

Ser Gly Ser Ala Thr Asp Phe Thr Leu Thr Ile Thr Gly Leu Gln Pro
 65                  70                  75                  80

Glu Asp Leu Ala Thr Tyr Tyr Cys Leu Gln Ala Asn Arg Phe Pro Leu
                 85                  90                  95

Ser Phe Gly Gly Gly Thr Arg Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

Phe Asn Arg Gly Glu Cys
    210

<210> SEQ ID NO 209
<211> LENGTH: 216
<212> TYPE: PRT
<213> ORGANISM: Homo Sapiens

<400> SEQUENCE: 209

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Asn Pro Arg Arg Asn
            20                  25                  30

Phe Leu Ala Trp Tyr Gln Gln Lys Pro Gly Gln Ala Pro Arg Leu Leu
        35                  40                  45

Ile Tyr Ala Ala Ser Thr Arg Ala Thr Gly Ile Pro Asp Arg Phe Ser
50                  55                  60

Gly Ser Gly Ser Gly Thr Asp Phe Thr Leu Thr Ile Asp Arg Leu Glu
65                  70                  75                  80

Pro Glu Asp Ser Ala Val Tyr Tyr Cys Gln Val Tyr Gly Ser Ser Pro
                85                  90                  95

Leu Tyr Thr Phe Gly Gln Gly Thr Lys Val Glu Met Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 210
<211> LENGTH: 216
<212> TYPE: PRT
<213> ORGANISM: Homo Sapiens

<400> SEQUENCE: 210

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Thr
                85                  90                  95

-continued

```
Leu Tyr Thr Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 211
<211> LENGTH: 214
<212> TYPE: PRT
<213> ORGANISM: Homo Sapiens

<400> SEQUENCE: 211

Asp Ile Gln Leu Thr Gln Ser Pro Ser Ser Leu Ser Ala Ser Val Gly
1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Glu Ala Pro Lys Leu Leu Ile
        35                  40                  45

Tyr Val Ala Ser Thr Leu Gln Ser Gly Ala Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ser Ala Thr Phe Tyr Cys Gln Gln Thr Tyr Ser Pro Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 212
<211> LENGTH: 217
<212> TYPE: PRT
<213> ORGANISM: Homo Sapiens
```

<400> SEQUENCE: 212

```
Glu Ile Val Leu Thr Gln Ser Pro Gly Thr Leu Ser Ser Ser Pro Gly
1               5                   10                  15

Glu Arg Ala Thr Leu Ser Cys Arg Ala Ser Gln Ser Val Thr Ser Arg
            20                  25                  30

Tyr Leu Ala Trp Tyr Gln Gln Lys His Gly Gln Ala Pro Arg Leu Leu
        35                  40                  45

Ile Tyr Gly Thr Ser Thr Arg Ala Thr Gly Ile Pro Asp Arg Phe Ser
    50                  55                  60

Gly Gly Gly Ser Gln Thr Asp Phe Thr Leu Thr Ile Ser Arg Leu Glu
65                  70                  75                  80

Pro Glu Asp Phe Ala Val Tyr Tyr Cys Gln His Tyr Asp Asp Ser Ile
                85                  90                  95

Ser Thr Tyr Ile Phe Gly Pro Gly Thr Glu Leu Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 213
<211> LENGTH: 214
<212> TYPE: PRT
<213> ORGANISM: Homo Sapiens

<400> SEQUENCE: 213

```
Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Asn Asn Leu
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 214
<211> LENGTH: 215
<212> TYPE: PRT
<213> ORGANISM: Homo Sapiens

<400> SEQUENCE: 214

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Asn Pro Gly Lys Ala Pro Lys Leu Leu Ile
            35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Ala
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 215
<211> LENGTH: 215
<212> TYPE: PRT
<213> ORGANISM: Homo Sapiens

<400> SEQUENCE: 215

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
                20                  25                  30

Leu Asn Trp Tyr Gln Gln Lys Pro Gly Lys Ala Pro Lys Leu Leu Ile
```

```
                35                  40                  45
Tyr Ala Ala Ser Thr Leu Gln Ser Gly Val Pro Ser Arg Phe Ser Gly
 50                  55                  60

Ser Gly Ser Gly Thr His Phe Thr Leu Thr Ile Ser Ser Leu Gln Arg
 65                  70                  75                  80

Glu Asp Phe Ala Thr Tyr Tyr Cys Gln Gln Thr Tyr Arg Thr Pro Thr
                 85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 216
<211> LENGTH: 213
<212> TYPE: PRT
<213> ORGANISM: Homo Sapiens

<400> SEQUENCE: 216

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Asn Ile Asn Arg Tyr
                20                  25                  30

Leu Asn Trp Tyr Gln His Lys Pro Gly Arg Ala Pro Glu Leu Leu Ile
             35                  40                  45

Tyr Ala Ala Ser Thr Leu Arg Arg Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Arg Gly Thr
                 85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
```

Asn Arg Gly Glu Cys
    210

<210> SEQ ID NO 217
<211> LENGTH: 215
<212> TYPE: PRT
<213> ORGANISM: Homo Sapiens

<400> SEQUENCE: 217

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr His Phe Thr Leu Thr Ile Ser Ser Leu Gln Arg
65                  70                  75                  80

Glu Asp Phe Ala Thr Tyr Tyr Cys Gln Gln Ser Tyr Gly Thr Pro Thr
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 218
<211> LENGTH: 217
<212> TYPE: PRT
<213> ORGANISM: Homo Sapiens

<400> SEQUENCE: 218

Gln Thr Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Thr Gly
            20                  25                  30

Tyr Tyr Pro Asn Trp Phe Gln Gln Lys Pro Gly Gln Ala Pro Arg Ala
        35                  40                  45

Leu Ile Tyr Ser Thr Ser Lys Lys His Ser Trp Thr Pro Ala Arg Phe
50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Phe Tyr Gly Gly
                85                  90                  95

```
Ala Gln Leu Gly Val Phe Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Lys Ser Tyr Ser Cys Gln Val Thr His Glu Gly Ser Thr Val Glu
                195                 200                 205

Lys Thr Val Ala Pro Thr Glu Cys Ser
        210                 215
```

<210> SEQ ID NO 219
<211> LENGTH: 215
<212> TYPE: PRT
<213> ORGANISM: Homo Sapiens

<400> SEQUENCE: 219

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Asn Tyr
            20                  25                  30

Leu Asn Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu His Arg
65                  70                  75                  80

Glu Asp Tyr Ala Thr Tyr Tyr Cys Gln Gln Ser Tyr Ser Thr Pro Pro
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
        210                 215
```

<210> SEQ ID NO 220
<211> LENGTH: 215
<212> TYPE: PRT
<213> ORGANISM: Homo Sapiens

<400> SEQUENCE: 220

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Ser Thr
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 221
<211> LENGTH: 214
<212> TYPE: PRT
<213> ORGANISM: Homo Sapiens

<400> SEQUENCE: 221

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Ser Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210
```

<210> SEQ ID NO 222
<211> LENGTH: 216
<212> TYPE: PRT
<213> ORGANISM: Homo Sapiens

<400> SEQUENCE: 222

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Thr Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Thr Glu Phe Ser Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Ile Phe Thr Phe Gly Pro Gly Thr Lys Leu Asp Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 223
<211> LENGTH: 215
<212> TYPE: PRT
<213> ORGANISM: Homo Sapiens

<400> SEQUENCE: 223

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln His Lys Pro Gly Gln Ala Pro Arg Leu Leu
```

```
                35                  40                  45
Ile Tyr Gly Ser Ser Asn Arg Ala Thr Gly Ile Pro Asp Arg Phe Ser
 50                  55                  60

Gly Ser Gly Ser Gly Thr Asp Phe Thr Val Thr Ile Ser Arg Leu Glu
 65                  70                  75                  80

Pro Glu Asp Phe Ala Val Tyr Tyr Cys Gln Gln Tyr Gly Thr Ala Pro
                 85                  90                  95

Tyr Thr Phe Gly Gln Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
                130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
                210                 215

<210> SEQ ID NO 224
<211> LENGTH: 216
<212> TYPE: PRT
<213> ORGANISM: Homo Sapiens

<400> SEQUENCE: 224

Gln Ser Ala Leu Thr Gln Pro Ala Ser Val Ser Gly Ser Pro Gly Gln
 1                   5                  10                  15

Ser Ile Thr Ile Ser Cys Thr Ala Thr Ser Ser Asp Ile Gly Ala Tyr
                 20                  25                  30

Asn Tyr Val Ser Trp Tyr Gln His His Pro Gly Lys Ala Pro Lys Val
                 35                  40                  45

Ile Ile Thr Asp Val Asn Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Pro Glu Asp Glu Ala Glu Tyr Ser Cys Cys Ser Tyr Ala Gly Thr
                 85                  90                  95

Tyr Ser Tyr Val Phe Gly Thr Gly Thr Lys Val Thr Val Leu Ser Gln
                100                 105                 110

Pro Lys Ala Asn Pro Thr Val Thr Leu Phe Pro Pro Ser Ser Glu Glu
                115                 120                 125

Leu Gln Ala Asn Lys Ala Thr Leu Val Cys Leu Ile Ser Asp Phe Tyr
                130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
```

```
                    195                 200                 205

Thr Val Ala Pro Thr Glu Cys Ser
    210                 215

<210> SEQ ID NO 225
<211> LENGTH: 216
<212> TYPE: PRT
<213> ORGANISM: Homo Sapiens

<400> SEQUENCE: 225

Leu Ser Ser Glu Leu Thr Gln Asp Pro Ala Val Ser Val Ala Leu Gly
1               5                   10                  15

Gln Thr Val Arg Ile Thr Cys Gln Gly Asp Ser Leu Arg Ser Tyr Tyr
            20                  25                  30

Ala Asn Trp Tyr Gln Gln Lys Pro Gly Gln Ala Pro Leu Ser Val Ile
        35                  40                  45

Tyr Gly Lys Asn Asn Arg Pro Ser Gly Ile Pro Asp Arg Phe Ser Gly
    50                  55                  60

Ser Asn Ser Gly Asn Thr Ala Phe Leu Thr Ile Thr Gly Thr Gln Ala
65                  70                  75                  80

Glu Asp Glu Ala Asp Tyr Tyr Cys Asn Ser Arg Asp Ser Ser Gly Asn
                85                  90                  95

Tyr Arg Glu Leu Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215

<210> SEQ ID NO 226
<211> LENGTH: 215
<212> TYPE: PRT
<213> ORGANISM: Homo Sapiens

<400> SEQUENCE: 226

Asp Ile Gln Leu Thr Gln Ser Pro Ser Phe Leu Ser Ala Ser Val Gly
1               5                   10                  15

Asp Arg Val Thr Ile Thr Cys Arg Ala Ser His Gly Ile Ser Ser Tyr
            20                  25                  30

Leu Ala Trp Tyr Gln Gln Lys Pro Gly Lys Ala Pro Asn Leu Leu Ile
        35                  40                  45

Phe Pro Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Arg Pro
65                  70                  75                  80

Glu Asp Phe Ala Thr Tyr Tyr Cys Gln Gln Leu Asn Ser Tyr Ser Arg
                85                  90                  95
```

```
Trp Ala Phe Gly Gln Gly Thr Lys Val Glu Val Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 227
<211> LENGTH: 215
<212> TYPE: PRT
<213> ORGANISM: Homo Sapiens

<400> SEQUENCE: 227

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Arg Tyr
            20                  25                  30

Leu Asn Trp Tyr Gln Lys Lys Pro Gly Lys Ala Pro Lys Leu Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Thr Gln Gly
            85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 228
<211> LENGTH: 217
<212> TYPE: PRT
<213> ORGANISM: Homo Sapiens
```

<400> SEQUENCE: 228

```
Gln Ala Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Thr Gly
            20                  25                  30

Tyr Tyr Pro Asn Trp Phe Gln Gln Lys Pro Gly Gln Ala Pro Arg Ala
        35                  40                  45

Leu Val His Ser Thr Ser Lys Lys His Ser Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Phe Tyr Gly Gly
                85                  90                  95

Ala Gln Leu Gly Val Phe Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Lys Ser Tyr Ser Cys Gln Val Thr His Glu Gly Ser Thr Val Glu
        195                 200                 205

Lys Thr Val Ala Pro Ala Glu Cys Ser
    210                 215
```

<210> SEQ ID NO 229
<211> LENGTH: 217
<212> TYPE: PRT
<213> ORGANISM: Homo Sapiens

<400> SEQUENCE: 229

```
Gln Ala Val Val Thr Gln Glu Pro Ser Leu Thr Val Ser Pro Gly Gly
1               5                   10                  15

Thr Val Thr Leu Thr Cys Ala Ser Ser Thr Gly Ser Val Thr Ser Gly
            20                  25                  30

Tyr Tyr Pro Asn Trp Phe Gln Gln Lys Pro Gly Gln Ala Pro Arg Pro
        35                  40                  45

Leu Ile Ser Gly Thr Ser Asn Lys Leu Ser Trp Thr Pro Ala Arg Phe
    50                  55                  60

Ser Gly Ser Leu Leu Gly Gly Lys Ala Ala Leu Thr Ser Gly Val
65                  70                  75                  80

Gln Pro Glu Asp Glu Ala Val Tyr Tyr Cys Leu Leu Tyr Tyr Gly Val
                85                  90                  95

Pro Gln Pro Val Val Phe Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140
```

```
Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
            165                 170                 175

Tyr Ala Ala Ser Ser Tyr Leu Ser Leu Thr Pro Glu Gln Trp Lys Ser
        180                 185                 190

His Arg Ser Tyr Ser Cys Gln Val Thr His Glu Gly Ser Thr Val Glu
    195                 200                 205

Lys Thr Val Ala Pro Thr Glu Cys Ser
    210                 215

<210> SEQ ID NO 230
<211> LENGTH: 215
<212> TYPE: PRT
<213> ORGANISM: Homo Sapiens

<400> SEQUENCE: 230

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Arg
65                  70                  75                  80

Glu Asp Tyr Ala Thr Tyr Tyr Cys Gln Gln Ser Tyr Ser Thr Pro Pro
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 231
<211> LENGTH: 214
<212> TYPE: PRT
<213> ORGANISM: Homo Sapiens

<400> SEQUENCE: 231

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Val
```

```
                35                  40                  45
Tyr Lys Thr Ser Ser Leu Glu Gly Gly Val Pro Ser Arg Phe Ser Gly
 50                  55                  60

Ser Gly Ser Gly Thr Glu Phe Ser Leu Thr Ile Phe Arg Leu Gln Ser
 65                  70                  75                  80

Asp Asp Phe Ala Thr Tyr Tyr Cys Gln Gln Tyr Asn Ser Phe Pro Tyr
                 85                  90                  95

Thr Phe Gly Gln Gly Thr Lys Leu Glu Phe Thr Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 232
<211> LENGTH: 216
<212> TYPE: PRT
<213> ORGANISM: Homo Sapiens

<400> SEQUENCE: 232

Glu Ile Val Leu Thr Gln Ser Pro Val Thr Leu Ser Leu Ser Pro Gly
 1               5                  10                  15

Glu Arg Ala Thr Leu Ser Cys Arg Ala Ser Gln Ser Val Ser Ser Gly
                20                  25                  30

Tyr Leu Ala Trp Tyr Gln Gln Lys Pro Gly Gln Ala Pro Arg Leu Leu
             35                  40                  45

Ile Tyr Gly Thr Ser Ile Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Tyr Ser Phe Gly Gln Gly Thr Lys Val Asp Ile Lys Arg Thr Val
                100                 105                 110

Ala Ala Pro Ser Val Phe Ile Phe Pro Pro Ser Asp Glu Gln Leu Lys
                115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
```

<210> SEQ ID NO 233
<211> LENGTH: 215
<212> TYPE: PRT
<213> ORGANISM: Homo Sapiens

<400> SEQUENCE: 233

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Arg
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 234
<211> LENGTH: 214
<212> TYPE: PRT
<213> ORGANISM: Homo Sapiens

<400> SEQUENCE: 234

Asp Ile Gln Leu Thr Gln Ser Pro Ser Ser Leu Ala Ala Ser Val Gly
1               5                   10                  15

Asp Arg Val Ile Ile Thr Cys Arg Ser Gly Gln Gly Ile Arg Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Phe Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Asn Cys Gln Gln Ser Tyr Ser Asp Pro Trp
                85                  90                  95

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 235
<211> LENGTH: 213
<212> TYPE: PRT
<213> ORGANISM: Homo Sapiens

<400> SEQUENCE: 235

Asp Ile Gln Met Thr Gln Ser Pro Ser Ser Leu Ser Ala Ser Val Gly
1               5                   10                  15

Asp Arg Val Ile Ile Thr Cys Arg Ala Ser Gln Ser Val Asn Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Arg
65                  70                  75                  80

Glu Asp Phe Ala Thr Tyr Tyr Cys Gln Gln Ser Tyr Arg Thr Arg Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 236
<211> LENGTH: 214
<212> TYPE: PRT
<213> ORGANISM: Homo Sapiens
```

<400> SEQUENCE: 236

Asp Ile Gln Met Thr Gln Ser Pro Ser Ser Leu Ser Ala Ser Val Gly
1               5                   10                  15

Asp Gly Ile Thr Ile Thr Cys Arg Ala Ser Gln Ser Val Arg Ser Tyr
            20                  25                  30

Leu Asn Trp Tyr Gln Gln Lys Pro Gly Lys Ala Pro Glu Leu Leu Ile
        35                  40                  45

Tyr Ala Ala Ser Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Ser Tyr Ser Thr Pro Val
                85                  90                  95

Thr Phe Gly Gln Gly Thr Lys Val Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 237
<211> LENGTH: 215
<212> TYPE: PRT
<213> ORGANISM: Homo Sapiens

<400> SEQUENCE: 237

Leu Ser Ser Glu Leu Thr Gln Asp Pro Ala Val Ser Val Thr Leu Gly
1               5                   10                  15

Gln Thr Val Arg Ile Thr Cys Gln Gly Asp Ser Leu Arg His Ser Tyr
            20                  25                  30

Ala Ser Trp Tyr Gln Gln Lys Pro Gly Gln Ala Pro Ile Leu Val Ile
        35                  40                  45

Tyr Gly Lys Asn Ile Arg Pro Ser Gly Ile Pro Asp Arg Phe Ser Gly
50                  55                  60

Ser Thr Ser Gly Asn Thr Ala Ser Leu Thr Ile Thr Gly Ala Gln Ala
65                  70                  75                  80

Glu Asp Gly Gly Asp Tyr Tyr Cys Asn Ser Arg Asp Thr Ser Thr Asp
                85                  90                  95

His Tyr Val Phe Gly Asp Gly Thr Arg Val Thr Val Val Gly Gln Pro
            100                 105                 110

Lys Ala Asn Pro Thr Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
130                 135                 140

```
Gly Ala Val Thr Val Ala Trp Lys Ala Asp Gly Ser Pro Val Lys Ala
145                 150                 155                 160

Gly Val Glu Thr Thr Lys Pro Ser Lys Gln Ser Asn Asn Lys Tyr Ala
            165                 170                 175

Ala Ser Ser Tyr Leu Ser Leu Thr Pro Glu Gln Trp Lys Ser His Arg
        180                 185                 190

Ser Tyr Ser Cys Gln Val Thr His Glu Gly Ser Thr Val Glu Lys Thr
    195                 200                 205

Val Ala Pro Thr Glu Cys Ser
    210                 215

<210> SEQ ID NO 238
<211> LENGTH: 215
<212> TYPE: PRT
<213> ORGANISM: Homo Sapiens

<400> SEQUENCE: 238

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Asn Trp Tyr Gln Gln Lys Pro Gly Lys Ala Pro Asn Leu Leu Ile
        35                  40                  45

Phe Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Ser Val
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 239
<211> LENGTH: 214
<212> TYPE: PRT
<213> ORGANISM: Homo Sapiens

<400> SEQUENCE: 239

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
```

```
                35                  40                  45
Tyr Ala Ala Ser Ser Leu Gln Ser Gly Val Pro Ser Arg Phe Ser Gly
    50                  55                  60
Ser Gly Ser Gly Ile Asp Phe Thr Leu Thr Ile Ser Ser Leu Gln Pro
65                  70                  75                  80
Glu Asp Phe Ala Thr Tyr Tyr Cys Gln Gln Ser Tyr Thr Thr Leu Trp
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 240
<211> LENGTH: 217
<212> TYPE: PRT
<213> ORGANISM: Homo Sapiens

<400> SEQUENCE: 240

Glu Ile Val Leu Thr Gln Ser Pro Gly Thr Leu Ser Leu Ser Pro Arg
1               5                   10                  15
Glu Arg Ala Thr Leu Ser Cys Arg Ala Asn Gln Tyr Val Asn Ser Asn
                20                  25                  30
His Leu Ala Trp Tyr Gln Gln Lys Pro Gly Gln Ala Pro Arg Leu Leu
            35                  40                  45
Leu Tyr Gly Ala Ser Arg Arg Ala Thr Gly Ile Pro Asp Arg Phe Ser
        50                  55                  60
Gly Ser Gly Thr Gly Thr Asp Phe Thr Leu Ile Ile Ser Arg Leu Glu
65                  70                  75                  80
Pro Glu Asp Phe Ala Val Tyr Phe Cys Gln Leu Tyr Asp His Ser Arg
                85                  90                  95
Pro Met Tyr Thr Phe Gly Gln Gly Thr Lys Leu Glu Ile Lys Arg Thr
            100                 105                 110
Val Ala Ala Pro Ser Val Phe Ile Phe Pro Pro Ser Asp Glu Gln Leu
        115                 120                 125
Lys Ser Gly Thr Ala Ser Val Val Cys Leu Leu Asn Asn Phe Tyr Pro
    130                 135                 140
Arg Glu Ala Lys Val Gln Trp Lys Val Asp Asn Ala Leu Gln Ser Gly
145                 150                 155                 160
Asn Ser Gln Glu Ser Val Thr Glu Gln Asp Ser Lys Asp Ser Thr Tyr
                165                 170                 175
Ser Leu Ser Ser Thr Leu Thr Leu Ser Lys Ala Asp Tyr Glu Lys His
            180                 185                 190
Lys Val Tyr Ala Cys Glu Val Thr His Gln Gly Leu Ser Ser Pro Val
```

```
                    195                 200                 205

Thr Lys Ser Phe Asn Arg Gly Glu Cys
    210                 215

<210> SEQ ID NO 241
<211> LENGTH: 216
<212> TYPE: PRT
<213> ORGANISM: Homo Sapiens

<400> SEQUENCE: 241

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Ser Ser Gly
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Ser Pro
                85                  90                  95

Pro Ile Thr Phe Gly Gln Gly Thr Arg Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 242
<211> LENGTH: 215
<212> TYPE: PRT
<213> ORGANISM: Homo Sapiens

<400> SEQUENCE: 242

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Phe Ala Ala Ser Ser Leu Gln Ser Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln Gln Ser Tyr Ser Ser Leu Ala
                85                  90                  95
```

```
Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 243
<211> LENGTH: 215
<212> TYPE: PRT
<213> ORGANISM: Homo Sapiens

<400> SEQUENCE: 243

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Asn Pro Gly Lys Ala Pro Lys Leu Leu Ile
            35                  40                  45

Tyr Gly Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Ala
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 244
<211> LENGTH: 215
<212> TYPE: PRT
<213> ORGANISM: Homo Sapiens
```

```
<400> SEQUENCE: 244

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Arg
65                  70                  75                  80

Glu Asp Tyr Ala Ala Tyr Tyr Cys Gln Gln Ser Tyr Ser Thr Pro Pro
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 245
<211> LENGTH: 217
<212> TYPE: PRT
<213> ORGANISM: Homo Sapiens

<400> SEQUENCE: 245

Gln Ala Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Thr Gly
            20                  25                  30

Tyr Tyr Pro Asn Trp Phe Gln Gln Lys Pro Gly Gln Ala Pro Arg Ala
        35                  40                  45

Leu Ile Tyr Ser Thr Ser Lys Lys His Ser Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Phe Tyr Gly Gly
                85                  90                  95

Ala Gln Leu Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140
```

```
Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Lys Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 246
<211> LENGTH: 216
<212> TYPE: PRT
<213> ORGANISM: Homo Sapiens

<400> SEQUENCE: 246

```
Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Ala Arg
            20                  25                  30

Tyr Tyr Pro Ser Trp Tyr Gln Gln Thr Pro Gly Gln Pro Pro Arg Thr
        35                  40                  45

Leu Ile His Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Pro Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 247
<211> LENGTH: 219
<212> TYPE: PRT
<213> ORGANISM: Homo Sapiens

<400> SEQUENCE: 247

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Asn Gly Tyr Asn Tyr Leu Asn Trp Tyr Leu Gln Lys Pro Gly Gln Ser
```

```
                    35                  40                  45
Pro Gln Leu Leu Ile Tyr Leu Gly Ser Asn Arg Ala Ser Gly Val Pro
                50                  55                  60

Asp Arg Phe Ser Gly Ser Gly Ser Gly Thr Asp Phe Thr Leu Lys Ile
65                  70                  75                  80

Ser Gly Val Glu Ala Glu Asp Val Ala Phe Tyr Tyr Cys Met Gln Gly
                85                  90                  95

Leu Arg Thr Pro Tyr Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 248
<211> LENGTH: 214
<212> TYPE: PRT
<213> ORGANISM: Homo Sapiens

<400> SEQUENCE: 248

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Lys Gln Arg Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Ala Leu Thr Ile Ser Ser Leu Gln Ala
65                  70                  75                  80

Glu Asp Phe Ala Thr Tyr Tyr Cys Gln Gln Thr Tyr Ser Thr Leu Trp
                85                  90                  95

Thr Phe Gly Gln Gly Thr Lys Val Glu Ile Thr Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

-continued

Phe Asn Arg Gly Glu Cys
    210

<210> SEQ ID NO 249
<211> LENGTH: 215
<212> TYPE: PRT
<213> ORGANISM: Homo Sapiens

<400> SEQUENCE: 249

Glu Ile Val Leu Thr Gln Ser Pro Gly Thr Leu Ser Leu Ser Pro Gly
1               5                   10                  15

Glu Thr Ala Thr Leu Ser Cys Arg Ala Ser Gln Ser Val Ser Asp Arg
            20                  25                  30

Asp Leu Ala Trp Tyr Gln Gln Lys Ser Gly Ser Pro Arg Leu Leu
        35                  40                  45

Met Tyr Gly Gly Ser Thr Arg Ala Pro Gly Ile Pro Val Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Ile Tyr Tyr Cys Gln His Tyr His Asp Trp Pro
                85                  90                  95

Pro Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 250
<211> LENGTH: 214
<212> TYPE: PRT
<213> ORGANISM: Homo Sapiens

<400> SEQUENCE: 250

Asp Ile Gln Met Thr Gln Ser Pro Ser Ser Leu Ser Ala Ser Leu Gly
1               5                   10                  15

Gly Thr Val Thr Leu Thr Cys Arg Ser Ser Gln Phe Ile Ser Arg Tyr
            20                  25                  30

Leu Asn Trp Tyr Gln Gln His Pro Gly Lys Val Pro Arg Leu Leu Ile
        35                  40                  45

Ser Gly Ala Ser Arg Leu Gln Arg Gly Val Pro Ser Arg Phe Thr Gly
    50                  55                  60

Gly Gly Ser Gly Thr Asp Phe Thr Leu Thr Ile Lys Asn Val Gln Pro
65                  70                  75                  80

Asp Asp Ile Ala Thr Tyr Phe Cys Gln His Ser Tyr Arg Ser Gly Arg
                85                  90                  95

```
Ala Phe Gly Gln Gly Thr Thr Val Glu Val Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 251
<211> LENGTH: 215
<212> TYPE: PRT
<213> ORGANISM: Homo Sapiens

<400> SEQUENCE: 251

Glu Ile Val Leu Thr Gln Ser Pro Gly Ser Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Pro Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Phe Gly Asn Ser Arg
                85                  90                  95

Gly Thr Phe Gly Gln Gly Thr Lys Val Glu Ile Arg Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 252
<211> LENGTH: 216
<212> TYPE: PRT
<213> ORGANISM: Homo Sapiens
```

<400> SEQUENCE: 252

Glu Ile Val Leu Thr Gln Ser Pro Gly Thr Leu Ser Leu Ser Pro Gly
1               5                   10                  15

Glu Arg Val Thr Leu Ser Cys Arg Pro Ser Arg Tyr Ile Ala Ser Asp
            20                  25                  30

Tyr Leu Ala Trp Tyr Gln Leu Arg Pro Gly Gln Ala Pro Lys Leu Leu
        35                  40                  45

Ile Tyr Gly Ala Ser Ser Arg Ala Thr Gly Ile Pro Asp Arg Phe Ser
    50                  55                  60

Gly Val Gly Ser Pro Thr Asp Phe Thr Leu Thr Ile Ser Arg Leu Glu
65                  70                  75                  80

Pro Glu Asp Phe Ala Met Tyr Tyr Cys His Tyr Ser Gly Gly Ser Pro
                85                  90                  95

Pro Tyr Pro Phe Gly Gln Gly Thr Arg Leu Asp Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 253
<211> LENGTH: 214
<212> TYPE: PRT
<213> ORGANISM: Homo Sapiens

<400> SEQUENCE: 253

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Tyr Ile Asn Val Tyr
            20                  25                  30

Leu Asn Trp Tyr Gln His Lys Ala Gly Arg Ala Pro Lys Leu Leu Ile
        35                  40                  45

Tyr Ala Ala Ser Asn Leu Gln Ser Gly Val Pro Pro Arg Phe Ile Gly
    50                  55                  60

Ser Gly Ser Gly Thr Asp Phe Thr Leu Thr Ile Ser Ser Leu Gln Ser
65                  70                  75                  80

Glu Asp Phe Ala Thr Tyr Tyr Cys Leu Gln Ser Phe Thr Val Pro Arg
                85                  90                  95

Thr Phe Gly Pro Gly Thr Lys Val Asp Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 254
<211> LENGTH: 215
<212> TYPE: PRT
<213> ORGANISM: Homo Sapiens

<400> SEQUENCE: 254

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ala
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Phe Ser
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 255
<211> LENGTH: 217
<212> TYPE: PRT
<213> ORGANISM: Homo Sapiens

<400> SEQUENCE: 255

Gln Thr Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Tyr Tyr Pro Asn Trp Phe Gln Gln Lys Pro Gly Gln Ala Pro Arg Ala

```
                35                  40                  45
Leu Ile Tyr Ser Thr Ser Asn Lys His Ser Trp Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Leu Leu Tyr Tyr Gly Gly
                 85                  90                  95

Ala Gln Arg Trp Val Phe Gly Gly Gly Thr Ile Leu Thr Val Leu Gly
                100                 105                 110

Gln Pro Lys Ala Ala Pro Ser Val Thr Leu Phe Pro Pro Ser Ser Glu
                115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Lys Ser Tyr Ser Cys Gln Val Thr His Glu Gly Ser Thr Val Glu
                195                 200                 205

Lys Thr Val Ala Pro Thr Glu Cys Ser
210                 215

<210> SEQ ID NO 256
<211> LENGTH: 217
<212> TYPE: PRT
<213> ORGANISM: Homo Sapiens

<400> SEQUENCE: 256

Leu Asn Phe Met Leu Thr Gln Pro His Ser Val Ser Glu Ser Pro Gly
 1               5                  10                  15

Lys Thr Val Thr Ile Ser Cys Thr Arg Ser Ser Gly Ser Ile Ala Ser
                 20                  25                  30

Asn Tyr Met Gln Trp Tyr Gln Gln Arg Pro Gly Ser Ser Pro Thr Thr
                 35                  40                  45

Val Ile Tyr Glu Asp Asn Arg Arg Pro Ser Gly Val Pro Asp Arg Phe
 50                  55                  60

Ser Gly Ser Ile Asp Ser Ser Ser Asn Ser Ala Ser Leu Thr Ile Ser
 65                  70                  75                  80

Gly Leu Lys Thr Glu Asp Glu Ala Asp Tyr Tyr Cys Gln Ser Tyr Asp
                 85                  90                  95

Ser Asn Asn Trp Val Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
                115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Lys Ser Tyr Ser Cys Gln Val Thr His Glu Gly Ser Thr Val Glu
```

Lys Thr Val Ala Pro Thr Glu Cys Ser
    210             215

<210> SEQ ID NO 257
<211> LENGTH: 215
<212> TYPE: PRT
<213> ORGANISM: Homo Sapiens

<400> SEQUENCE: 257

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Arg Thr Pro Thr
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210             215

<210> SEQ ID NO 258
<211> LENGTH: 215
<212> TYPE: PRT
<213> ORGANISM: Homo Sapiens

<400> SEQUENCE: 258

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

```
Tyr Thr Phe Gly Gln Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 259
<211> LENGTH: 23
<212> TYPE: DNA
<213> ORGANISM: Artificial
<220> FEATURE:
<223> OTHER INFORMATION: Synthetic primer sequence

<400> SEQUENCE: 259
cgttcttttt cgcaacgggt ttg                                            23

<210> SEQ ID NO 260
<211> LENGTH: 23
<212> TYPE: DNA
<213> ORGANISM: Artificial
<220> FEATURE:
<223> OTHER INFORMATION: Synthetic primer sequence

<400> SEQUENCE: 260
aagaccgatg ggcccttggt gga                                            23
```